US011679187B2

(12) United States Patent
Suljevic et al.

(10) Patent No.: US 11,679,187 B2
(45) Date of Patent: Jun. 20, 2023

(54) MEDICAL TREATMENT SYSTEMS, METHODS, AND APPARATUSES USING A PLURALITY OF FLUID LINES

(71) Applicant: DEKA Products Limited Partnership, Manchester, NH (US)

(72) Inventors: Adnan Suljevic, Bedford, NH (US); Daniel Scott Karol, Southborough, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 408 days.

(21) Appl. No.: 16/823,758

(22) Filed: Mar. 19, 2020

(65) Prior Publication Data

US 2020/0297909 A1    Sep. 24, 2020

Related U.S. Application Data

(60) Provisional application No. 62/820,551, filed on Mar. 19, 2019.

(51) Int. Cl.
*A61M 1/28* (2006.01)

(52) U.S. Cl.
CPC ..... *A61M 1/288* (2014.02); *A61M 2205/3306* (2013.01); *A61M 2205/3327* (2013.01);
(Continued)

(58) Field of Classification Search
CPC .......... A61M 1/288; A61M 2205/3306; A61M 2205/3327; A61M 2205/3379;
(Continued)

(56) References Cited

U.S. PATENT DOCUMENTS 5,350,357 A    9/1994  Kamen et al.
6,210,361 B1   4/2001  Kamen et al.
(Continued)

FOREIGN PATENT DOCUMENTS

WO    WO 1999010830 A1    3/1999
WO    WO 2014090746 A1    6/2014

OTHER PUBLICATIONS

International Search Report and Written Opinion dated Jul. 3, 2020 received in International patent application PCT/US2020/023556 from European Patent Office as International Searching Authority, European Patent Office, P.B. 5818 Patentlaan 2 NL—2280 HV Rijswijk (12pgs).

*Primary Examiner* — Nathan R Price
*Assistant Examiner* — Anh Bui
(74) *Attorney, Agent, or Firm* — Toohey Law Group, LLC; Kevin D. Mandro

(57) ABSTRACT

A fluid pumping system may comprise a pump and a fluid line state detector having, a receptacle, at sensor, and an illuminator. The system may further comprise a fluid transfer set including an output line for mating into the receptacle. The system may further comprise a controller in data communication with the fluid line state detector configured to power the illuminator and monitor an output signal of the sensor when the outlet line is in the receptacle to determine a dry tube light intensity value. The controller may be further configured to govern operation of the pump to prime the output line with fluid. The controller may be further configured to power the illuminator, monitor the output signal, and halt operation of the pump when the output signal indicates the light intensity value has dropped below a primed line threshold which is dependent upon the dry tube intensity value.

29 Claims, 84 Drawing Sheets

(52) U.S. Cl.
CPC ............... *A61M 2205/3379* (2013.01); *A61M 2205/366* (2013.01); *A61M 2205/52* (2013.01); *A61M 2205/581* (2013.01); *A61M 2205/583* (2013.01); *A61M 2205/702* (2013.01)

(58) Field of Classification Search
CPC ...... A61M 2205/366; A61M 2205/702; A61M 2205/583; A61M 2205/581; A61M 2205/52
See application file for complete search history.

(56) References Cited

U.S. PATENT DOCUMENTS

| | | |
|---|---|---|
| 6,806,947 B1 | 10/2004 | Ekdahl et al. |
| 7,461,968 B2 | 12/2008 | Demers et al. |
| 7,498,563 B2 | 3/2009 | Mandro et al. |
| 7,632,080 B2 | 12/2009 | Tracey et al. |
| 7,794,141 B2 | 9/2010 | Perry et al. |
| 7,892,197 B2 | 2/2011 | Folden et al. |
| 8,158,102 B2 | 4/2012 | Demers et al. |
| 8,512,553 B2 | 8/2013 | Cicchello et al. |
| 9,677,555 B2 | 6/2017 | Kamen et al. |
| 10,576,197 B2 | 3/2020 | Fujiwara et al. |
| 10,682,450 B2 | 6/2020 | Wilt et al. |
| 2005/0209563 A1 | 9/2005 | Hopping et al. |
| 2007/0276328 A1 | 11/2007 | Childers et al. |
| 2009/0294359 A1 | 12/2009 | Hopping et al. |
| 2011/0306931 A1 | 12/2011 | Kamen et al. |
| 2015/0238681 A1 | 8/2015 | Vasta et al. |
| 2016/0101227 A1* | 4/2016 | Norris ................... G01V 8/20 604/29 |
| 2017/0268495 A1 | 9/2017 | Overson et al. |
| 2018/0110914 A1* | 4/2018 | Fujiwara ............. A61M 1/3638 |
| 2018/0296746 A1 | 10/2018 | Van der Merwe et al. |
| 2019/0328964 A1 | 10/2019 | Desch et al. |

\* cited by examiner

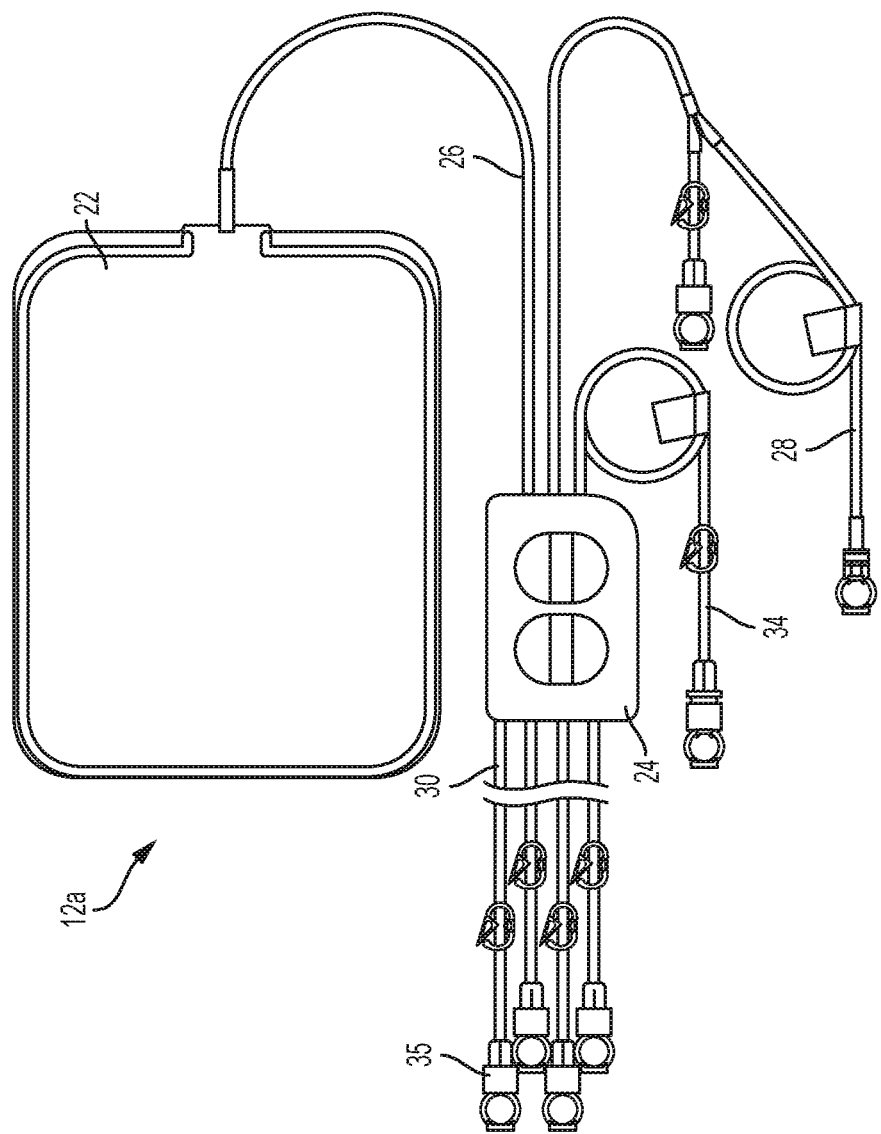

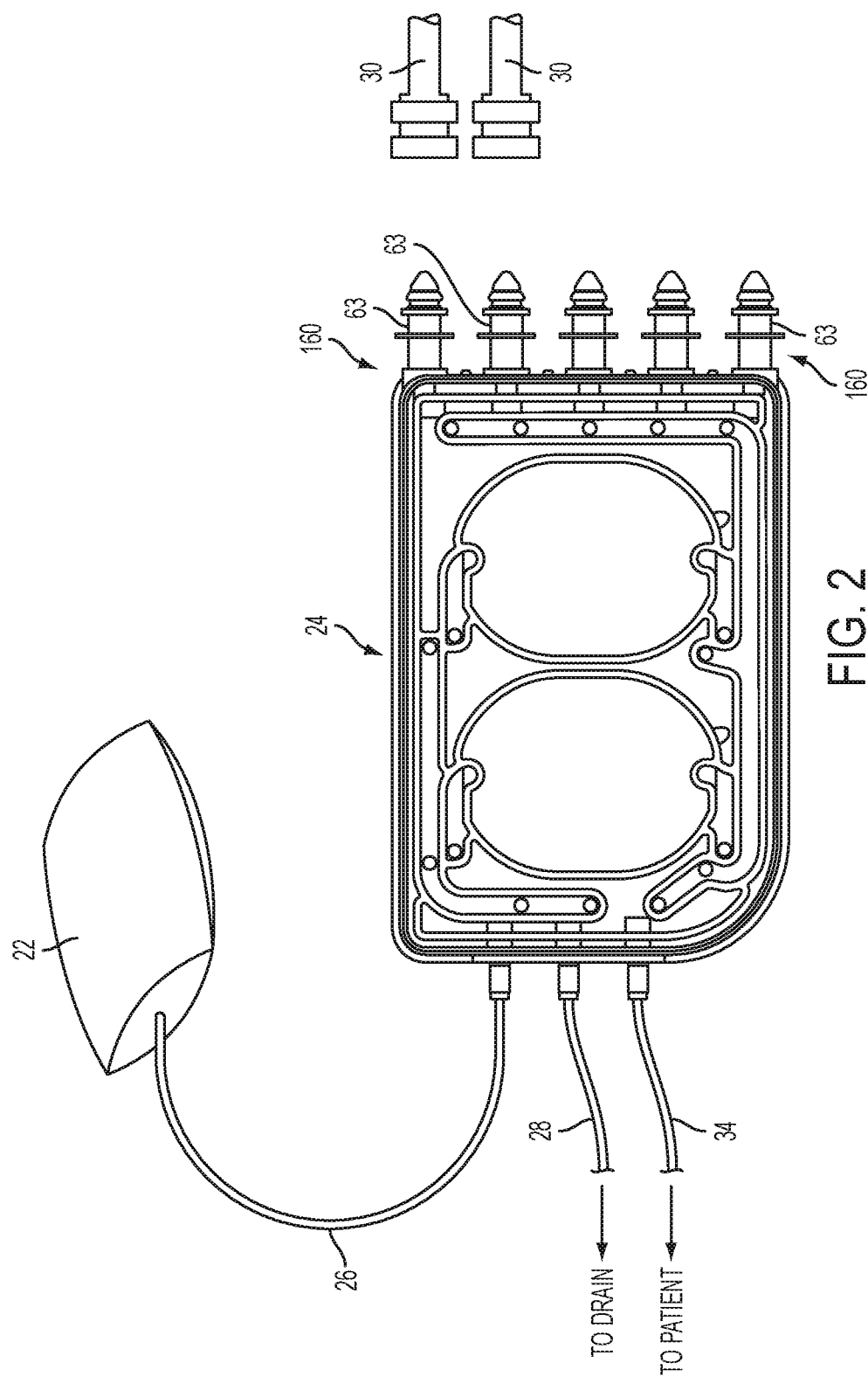

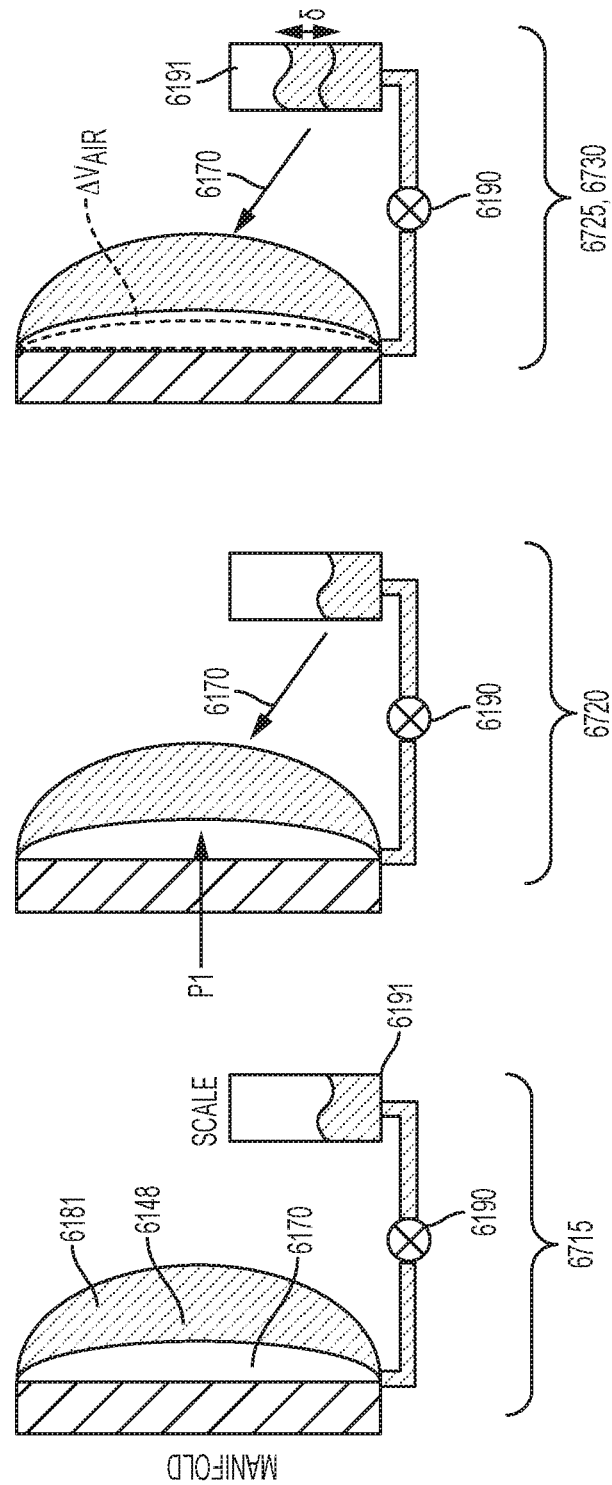

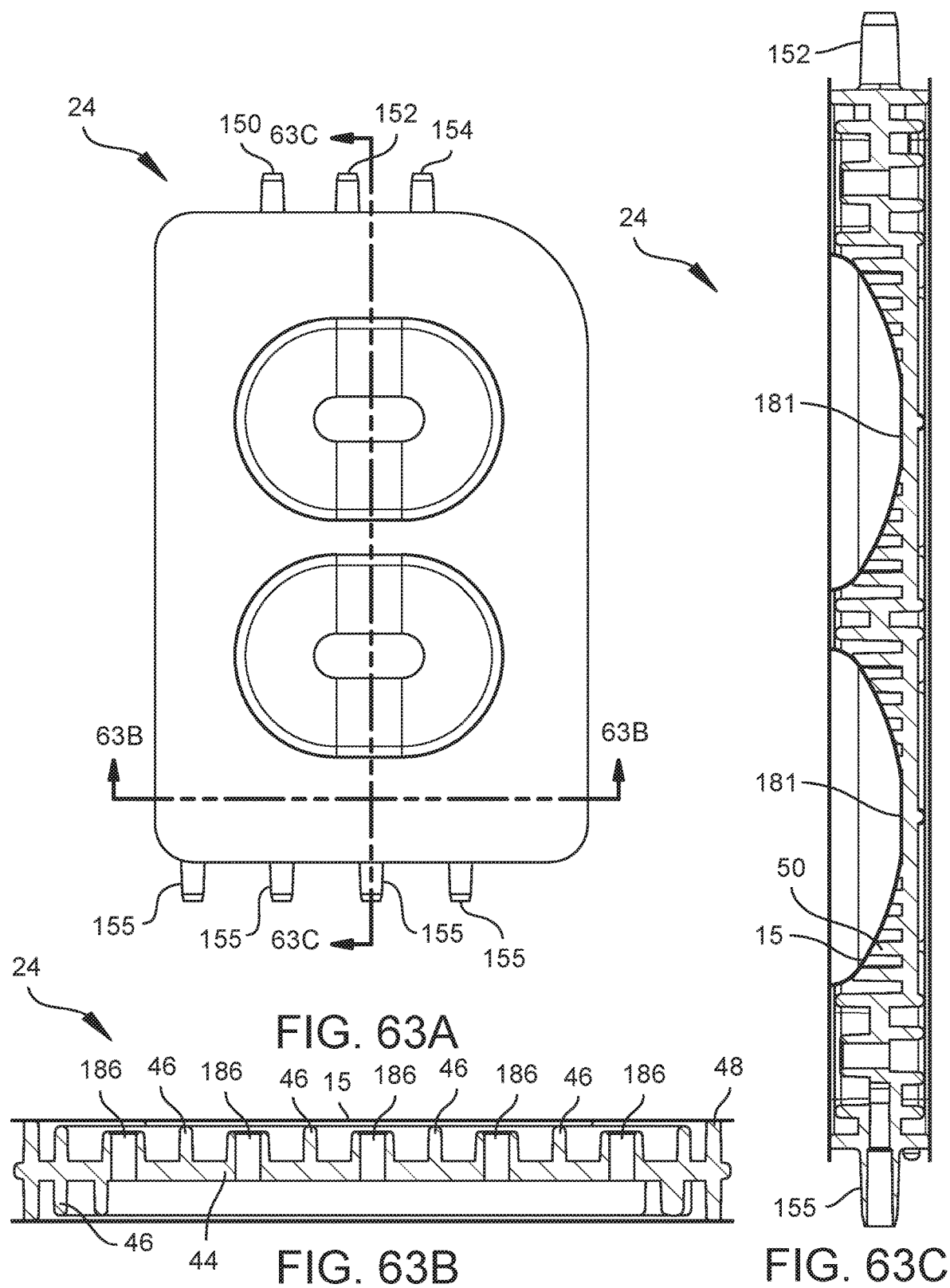

MEDICAL TREATMENT SYSTEMS, METHODS, AND APPARATUSES USING A PLURALITY OF FLUID LINES

CROSS-REFERENCE TO RELATED APPLICATIONS

The present application claims the benefit of U.S. Provisional Application Ser. No. 62/820,551 filed Mar. 19, 2019 and entitled VOLUMETRIC CALIBRATION CASSETTES, FLUID PUMPING SYSTEM CALIBRATION, AND RELATED METHODS, which is hereby incorporated herein by reference in its entirety.

BACKGROUND

Peritoneal Dialysis (PD) involves the periodic infusion of sterile aqueous solution (called peritoneal dialysis solution, or dialysate) into the peritoneal cavity of a patient. Diffusion and osmosis exchanges take place between the solution and the bloodstream across the natural body membranes. These exchanges transfer waste products to the dialysate that the kidneys normally excrete. The waste products typically consist of solutes like sodium and chloride ions, and other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During a drain/fill procedure for CAPD, the patient initially drains spent peritoneal dialysis solution from his/her peritoneal cavity, and then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically lasts for several hours. It often begins with an initial drain phase to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a period of time. This is called the dwell phase. During the drain phase, the cycler removes the spent dialysate from the peritoneal cavity.

The number of fill/dwell/drain cycles that are required during a given APD session depends upon the total volume of dialysate prescribed for the patient's APD regimen, and is either entered as part of the treatment prescription or calculated by the cycler.

APD can be and is practiced in different ways.

Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 4-8 fill/dwell/drain cycles to achieve a prescribed therapy volume.

After the last prescribed fill/dwell/drain cycle in CCPD, the cycler infuses a final fill volume. The final fill volume dwells in the patient for an extended period of time. It is drained either at the onset of the next CCPD session in the evening, or during a mid-day exchange. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home.

Like CCPD, IPD involves a series of fill/dwell/drain cycles. Unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse and then drain a replacement volume on top of the base volume. The last drain phase removes all dialysate from the peritoneal cavity.

There is a variation of TPD that includes cycles during which the patient is completely drained and infused with a new full base volume of dialysis.

TPD can include a final fill cycle, like CCPD. Alternatively, TPD can avoid the final fill cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

SUMMARY

In accordance with an embodiment of the present disclosure a volumetric standard cassette or cycler substantially as shown and described herein.

In accordance with another embodiment of the present disclosure a volumetric standard cassette for calibration of a cassette based pumping system may comprise a rigid body configured to be sealing installed within the cassette based pumping system. The rigid body may have a midbody and a number of solid pump chambers regions each having a predefined geometry defining a known volume of the pump chamber region. The rigid body may be flow path and orifice free.

In some embodiments, the volumetric standard cassette may be metal. In some embodiments, the volumetric standard cassette may be machined. In some embodiments, the volumetric standard cassette may be made from a list of materials consisting of aluminum, steel, and plastic. In some embodiments, the volumetric standard cassette may be constructed via a material additive process. In some embodiments, the midbody may have a thickness equivalent to at least half that of the thickest portion of the rigid body. In some embodiments, the midbody may have a thickness equivalent to at least 60% that of the thickest portion of the rigid body. In some embodiments, the midbody may have a thickness equivalent to a range of one half to three fourths that of the thickest portion of the rigid body. In some embodiments, the volumetric standard cassette includes no cassette sheeting.

In accordance with another embodiment of the present disclosure a volumetric standard cassette for calibration of a cassette based pumping system may comprise a midbody which may be completely solid and includes a first face and opposing second face. The volumetric standard cassette may further comprise a number of walls extending from at least the first face of the midbody and including a peripheral wall located at a peripheral edge of the midbody as well as a number of interior walls. The volumetric standard cassette may further comprise a number of solid pump chambers regions each having a predefined geometry defining a known volume of the pump chamber region. The volumetric standard cassette may be incapable of pumping fluid.

In some embodiments, no sheeting may be coupled to any of the number of walls of the volumetric standard cassette. In some embodiments, the first face of the midbody may be uncovered by cassette sheeting and may include the pump chamber regions. In some embodiments, both the first and opposing face of the midbody may be uncovered by cassette sheeting. In some embodiments, the volumetric standard cassette may be made from a list of processes consisting of a material additive process, machining, and molding. In some embodiments, the volumetric standard cassette may be made from a list of materials consisting of aluminum, steel, and plastic. In some embodiments, the opposing face of the volumetric standard cassette may be flat. In some embodiments, the first face of the volumetric standard cassette may include a number of projections which may be surrounded by the walls of the interior walls. In some embodiments, the walls may be draft free.

In accordance with another embodiment of the present disclosure a cassette analog of a disposable pumping cassette for calibration of a cassette based pumping system may comprise a midbody having a first face and opposing second face. The cassette analog may further comprise a number of sealing ribs on at least the first face. The cassette analog may further comprise a first pump chamber region and a second pump chamber region. Each of the first and second pump chamber region may have a defined, dimensionally stable geometry representative of a selected fill volume of corresponding pump chambers in the disposable pumping cassette. The first face and opposing face may be open faced or have no overlaying cassette sheeting. The cassette analog may be incapable of pumping fluid.

In some embodiments, the cassette analog may be formed of metal. In some embodiments, the midbody may be completely solid. In some embodiments, the midbody may be devoid of any pass-throughs. In some embodiments, the selected fill volume may be a full pump chamber volume of the corresponding pump chambers in the disposable pumping cassette. In some embodiments, the selected fill volume may be an empty pump chamber volume of the corresponding pump chambers in the disposable pumping cassette. In some embodiments, the selected fill volume may be and intermediate volume between a full pump chamber volume and an empty pump chamber volume of the corresponding pump chambers in the disposable pumping cassette. In some embodiments, the opposing face of the volumetric standard cassette may be flat. In some embodiments, the first face of the volumetric standard cassette may include a number of projections which are surrounded by the sealing ribs. The number of projections may be disposed at locations corresponding to a number valve seats in the disposable pumping cassette. In some embodiments, the cassette analog may be devoid of ports, spikes, and attached fluid lines.

In accordance with another embodiment of the present disclosure a method for calibrating a cassette based pumping system may comprise serially installing a number of volumetric calibration cassettes in the cassette based pumping system. Each of the number of volumetric calibration cassettes may include a pump chamber region having a known volume. The method may further comprise measuring, with the cassette based pumping system, the known volume of the pump chamber region in each of the volumetric calibration cassettes. The method may further comprise generating a calibration curve for volume measurements conducted with the cassette based pumping system based at least in part on the known volumes for each of the number of volumetric calibration cassettes and a corresponding measured volume of the pump chamber region for each volumetric calibration cassette.

In some embodiments, measuring the known volume of the pump chamber region in each of the volumetric calibration cassettes may comprise taking a plurality of measurements of the known volume of the pump chamber region of each of the volumetric calibration cassettes and analyzing the plurality of measurements to determine a single value for the volume of the pump chamber region which serves as the corresponding measured volume. In some embodiments, analyzing the plurality of measurements may comprise averaging the plurality of measurements. In some embodiments, generating the calibration curve may comprise generating a best fit equation. In some embodiments, generating the calibration curve may comprise generating a best fit polynomial. In some embodiments, the best fit polynomial may be a third order polynomial. In some embodiments, generating the calibration curve may comprise conducting a least squares regression. In some embodiments, generating the calibration curve may comprise constraining at least one region of the curve to at least one limit. In some embodiments, the limit may be an allowable range of derivative values for points along the at least one region. In some embodiments, generating the calibration curve may comprise enforcing a constraint on the allowable derivative value at the zero crossing of the calibration curve. In some embodiments, measuring the known volume of the pump chamber region in each of the volumetric calibration cassettes may comprise taking a plurality of measurements of the known volume of the pump chamber region of each of the volumetric calibration cassettes, determining their conformance to a predefined criteria, and analyzing the plurality of measurements to determine a single value for the volume of the pump chamber region which serves as the corresponding measured volume. In some embodiments, the predefined criteria may be a predefined allowed variability. In some embodiments, the predefined criteria may be an allowed standard deviation. In some embodiments, the method further may comprise refining the calibration curve to a second calibration curve which accounts for volume measurement error attributable to a disposable pumping cassette. In some embodiments, the method may further comprise refining the calibration curve to another calibration curve which accounts for volume measurement error attributable to the head height of a fluid source or destination.

In accordance with another embodiment of the present disclosure a cassette based pumping system may comprise a fluid handling set including a pumping cassette having a flexible membrane overlaying at least one pumping chamber. The system may further comprise a cycler. The cycler may comprise a mounting location sized to receive the pumping cassette and position the cassette against a control surface. The cycler may further comprise a plurality of pressure reservoirs. The cycler may further comprise a pressure delivery assembly for applying pressure from the pressure reservoirs to the pumping cassette to pump fluid through the cassette. The pressure delivery assembly may have the control surface, pneumatic channels, and control chambers for actuating the flexible membrane in addition to pressure sensors as well as at least one reference chamber of known volume for measuring pump chamber volume. The pneumatic channels may be in selective communication with the pressure reservoirs via a number of valves. The cycler may further comprise a controller configured receive data from the pressure sensors, determine a raw measured volume of fluid pumped via the data, and adjust the raw measured volume of fluid pumped based at least in part upon a cycler specific calibration equation.

In some embodiments, wherein the controller may be configured to adjust the raw measured volume of fluid pumped based at least in part upon a cycler specific calibration equation and a pumping cassette volumetric error calibration equation. In some embodiments, the controller may be configured to adjust the raw measured volume of fluid pumped based at least in part upon a cycler specific calibration equation, a pumping cassette volumetric error calibration equation, and a head height error calibration equation. In some embodiments, the cycler specific calibration equation may be a best fit polynomial through a data set of test measurements of a series of volumetric standard cassettes. In some embodiments, the controller may be configured to adjust the raw measured volume of fluid pumped based a second calibration equation which may be a function of the cycler specific calibration equation. In some embodiments, the second equation may be a pumping cassette volumetric error calibration equation. In some embodiments, the controller may be configured to adjust the raw measured volume of fluid pumped based a third calibration equation which may be a function of second calibration equation. In some embodiments, the second equation may be a pumping cassette volumetric error calibration equation and the third equation may be a head height error calibration equation. In some embodiments, the second equation may be a head height error calibration equation and the third equation may be a pumping cassette volumetric error calibration equation. In some embodiments, wherein the controller may be configured to adjust the raw measured volume of fluid pumped based at least in part upon a cycler specific calibration equation and a second calibration equation. In some embodiments, the system may further comprise a database of pumping cassette volumetric error calibration equations associated with cassette related unique identifiers. In some embodiments, the cycler may further comprise a user interface and the controller may be configured to receive a cassette related unique identifier input through the user interface. The controller may be configured to communicate with the database to acquire the pumping cassette volumetric error calibration equation associated with the cassette related unique identifier input. The pumping cassette volumetric error calibration equation associated with the cassette related unique identifier input may be used as the second calibration equation. In some embodiments, the cycler may further comprise an imager. The controller may be configured to determine cassette related unique identifier data via imager data, and communicate with the database to acquire the pumping cassette volumetric error calibration equation associated with the cassette related unique identifier data. The pumping cassette volumetric error calibration equation associated with the cassette related unique identifier data may be used as the second calibration equation. In some embodiments, the fluid handling set may comprise a coded cassette related unique identifier.

In accordance with another embodiment of the present disclosure a cassette based pumping system may comprise a fluid handling set including a pumping cassette having a flexible membrane overlaying at least one pumping chamber and at least one cassette valve gating fluid communication to a fluid reservoir. The system may further comprise a cycler comprising a pressure delivery assembly having at least one pump control chamber for actuating a portion of the flexible membrane overlaying the at least one pump chamber. The pressure delivery assembly may further comprise at least one valve control chamber for actuating a portion of the flexible membrane overlaying the at least one cassette valve. The pressure delivery assembly may further comprise at least one pressure sensor in communication with the at least one pump control chamber. The cycler may further comprise a pressure reservoir in selective communication with the at least one pump control chamber and the at least one valve control chamber via a number of pressure delivery valves. The cycler may further comprise a controller configured receive data from the at least one pressure sensor. The controller may be further configured to command the at least one cassette valve to an open state, monitor data from the at least one pressure sensor to identify a first and second pressure peak, and calculate a head height of the fluid reservoir based upon the first and second pressure peak.

In some embodiments, the controller may be further configured to determine a length of a fluid line coupling the fluid reservoir to the cassette based on temporal data related to the first and second peak. In some embodiments, the first peak may be an overshoot peak and the second peak may be an undershoot peak. In some embodiments, the controller may be further configured to adjust an operating parameter based on the calculated head height. In some embodiments, the operating parameter may be at least one pumping pressure. In some embodiments, the controller may be further configured to refine a calibration curve based upon the head height. In some embodiments, the fluid reservoir may be a dialysate solution reservoir. In some embodiments, the fluid reservoir may be a body cavity of a patient. In some embodiments, the controller may be further configured to displace the portion of the flexible membrane overlaying the at least one pump chamber to a midstroke position prior to commanding the at least one cassette valve to the open state. In some embodiments, the controller may be further configured to determine a number of extension lines included in a fluid line coupling the fluid reservoir to the cassette based on temporal data related to the first and second peak. In some embodiments, the controller may be further configured to generate an error when the head height is in breach of a threshold. In some embodiments, the controller may be further configured to compare the head height to a predefined allowed head height threshold.

In accordance with another embodiment of the present disclosure a method of selecting a pumping pressure for a cassette based pumping system may comprise priming a fluid handling set installed in the pumping system. The method may further comprise placing a pump chamber of a cassette of the fluid handling set into communication with a reservoir. The method may further comprise detecting a first pressure peak in a control chamber separated from the pump chamber by a membrane. The method may further comprise detecting a second pressure peak in the control chamber. The method may further comprise predicting a final pressure using the first and second pressure peaks. The method may further comprise calculating the pump pressure based upon the predicted final pressure.

In some embodiments, the method may further comprise calculating a head height of the reservoir based on the predicted final pressure. In some embodiments, the method may further comprise determining a length characteristic of a fluid line coupling the reservoir to the cassette based temporal data related to the first and second peaks. In some embodiments, the method may further comprise determining a number of extensions included in a fluid path coupling the cassette to the reservoir based on temporal data related to the first and second peaks. In some embodiments, the method may further comprise generating an error if the predicted final pressure is in breach of a predetermined threshold. In some embodiments, the method may further comprise displacing the membrane to a predetermined initial position. In some embodiments, the predetermined initial position may be a position which biases a head height detection range toward detection of positive head heights. In some embodiments, the predetermined initial position may be a position which biases a head height detection range toward detection of negative head heights. In some embodiments, the predetermined initial position may be a midstroke position. In some embodiments, the method may further comprise adjusting a calibration curve of the cassette based pumping system based on the predicted final pressure. In some embodiments, detecting the first peak may comprise calculating a difference between a set of consecutive data points from at least one pressure sensor in communication with the control chamber. In some embodiments, detecting the first peak may further comprise applying data smoothing to the set of consecutive data points form the at least one pressure sensor. In some embodiments, the method may further comprise identifying the first peak when the difference between the set of consecutive data points is less than a predefined limit. In some embodiments, predicting the final pressure may comprise determining an overshoot percent based on the first and second peaks.

In accordance with another embodiment of the present disclosure a method of checking a head height of a reservoir coupled to a cassette based pumping system may comprise placing a pump chamber of a cassette of the fluid handling set installed in the cassette based pumping system into communication with a reservoir. The method may further comprise detecting a first pressure peak in a control chamber separated from the pump chamber by a membrane. The method may further comprise detecting a second pressure peak in the control chamber. The method may further comprise predicting a final pressure using the first and second pressure peaks. The method may further comprise comparing the predicted final pressure to at least one predetermined threshold. The method may further comprise generating a notification when the predicted final pressure is in breach in at least one of the at least one predetermined threshold.

In some embodiments, generating the notification may comprise generating an error. In some embodiments, generating the notification may comprise generating a screen for display on a user interface of the cassette based pumping system. In some embodiments, generating the notification may comprise generating an audible noise. In some embodiments, the method may further comprise calculating a head height of the reservoir based on the predicted final pressure. In some embodiments, the method may further comprise determining an overshoot percentage based on the first and second pressure peak. In some embodiments, the method may further comprise determining a length characteristic of a fluid line coupling the reservoir to the cassette based on temporal data related to the first and second peaks. In some embodiments, the method may further comprise determining a number of extensions included in a fluid path coupling the cassette to the reservoir based on temporal data related to the first and second peaks. In some embodiments, the method may further comprise displacing the membrane to a predetermined initial position. In some embodiments, the predetermined initial position may be a position which biases a head height detection range toward detection of positive head heights. In some embodiments, the predetermined initial position may be a position which biases a head height detection range toward detection of negative head heights. In some embodiments, the predetermined initial position may be a midstroke position. In some embodiments, the method may further comprise adjusting a calibration curve of the cassette based pumping system based on the predicted final pressure. In some embodiments, detecting the first peak may comprise calculating a difference between a set of consecutive data points from at least one pressure sensor in communication with the control chamber. In some embodiments, detecting the first peak further may comprise applying data smoothing to the set of consecutive data points from the at least one pressure sensor. In some embodiments, the method may further comprise identifying the first peak when the difference between the set of consecutive data points is less than a predefined limit.

In accordance with another embodiment of the present disclosure, a cassette based pumping system may comprise a fluid handling set including a pumping cassette having a flexible membrane overlaying at least one pumping chamber and at least one cassette valve gating fluid communication to a fluid reservoir. The system may further comprise a cycler comprising at least one pump control chamber. The cycler may further comprise at least one valve control chamber. The cycler may further comprise at least one pressure sensor in communication with the at least one pump control chamber. The cycler may further comprise a pressure reservoir in selective communication with the at least one pump control chamber and the at least one valve control chamber via a number of pressure delivery valves. The cycler may further comprise a controller in data communication with the pressure sensor. The controller may be configured to command the at least one cassette valve to an open state, monitor data from the at least one pressure sensor and identify a first and second pressure peak, and predict a final pressure based on the first and second pressure peak.

In some embodiments, the controller may be further configured to determine a length of a fluid line coupling the fluid reservoir to the cassette based on temporal data related to the first and second peak. In some embodiments, the first peak may be an overshoot peak and the second peak is an undershoot peak. In some embodiments, the controller may be further configured to adjust an operating parameter based on the calculated head height. In some embodiments, the operating parameter may be at least one pumping pressure. In some embodiments, the controller may be further configured to refine a calibration curve based upon the head height. In some embodiments, the fluid reservoir may be a dialysate solution reservoir. In some embodiments, the fluid reservoir may be a body cavity of a patient. In some embodiments, the controller may be further configured to displace the portion of the flexible membrane overlaying the at least one pump chamber to a midstroke position prior to commanding the at least one cassette valve to the open state. In some embodiments, the controller may be further configured to determine a number of extension lines included in a fluid line coupling the fluid reservoir to the cassette based on temporal data related to the first and second peak. In some embodiments, the controller may be further configured to generate an error when the predicted final pressure is in breach of a threshold. In some embodiments, the controller may be further configured to compare the predicted final pressure to a predefined allowed head height pressure threshold.

In accordance with another embodiment of the present disclosure, a fluid line state detector may comprise a receptacle configured to retain a fluid line opaque to ultraviolet light. The fluid line state detector may further comprise a light sensor. The fluid line state detector may further comprise an infrared light emitting LED. The fluid line state detector may further comprise an ultraviolet light emitting LED. The fluid line state detector may further comprise a third LED. The fluid line state detector may further comprise a controller in data communication with the light sensor. The controller may be configured determine an appropriate tube is present in the fluid line state detector when intensity of infrared light sensed by light sensor from the infrared light emitting LED is above a predetermined first threshold and when the intensity of ultraviolet light sensed by the light sensor from the ultraviolet light emitting LED is below a predetermined second threshold. An axis of the infrared light emitting LED and an axis of the ultraviolet light emitting LED may be parallel to one another as well as to an axis of the light sensor.

In some embodiments, the axis of the infrared light emitting LED may be an optical axis of the infrared light emitting LED and the axis of the ultraviolet light emitting LED may be an optical axis of the ultraviolet light emitting LED. In some embodiments, the axis of the infrared light emitting LED may be a mechanical axis of the infrared light emitting LED and the axis of the ultraviolet light emitting LED may be a mechanical axis of the ultraviolet light emitting LED. In some embodiments, the axis of the light sensor may be an optical axis of the light sensor. In some embodiments, the axis of the light sensor is a mechanical axis of the light sensor. In some embodiments, the third LED may be an infrared light emitting LED. In some embodiments, an axis of the third LED may be at an angle other than parallel to the axis of the infrared light emitting LED and the axis of the ultraviolet light emitting LED. In some embodiments, the axis of the ultraviolet light emitting LED may be configured to pass through a central portion of a fluid line installed within the receptacle. In some embodiments, the receptacle may include a retainer for holding the fluid line. In some embodiments, the controller may be further configured to determine that the fluid line is dry when light intensity from the third LED is above a predetermined dry threshold. In some embodiments, the controller may be further configured to determine that the fluid line is primed when light intensity from the third LED is below a predetermined primed threshold. The predetermined prime threshold may be lower than the predetermined dry threshold. In some embodiments, the controller may be further configured to determine that the fluid line is primed when light intensity from the infrared light emitting LED is below a predetermined infrared light threshold and when light intensity from the third LED is below a predetermined primed threshold. The predetermined prime threshold may be lower than the predetermined dry threshold. In some embodiments, the controller may be configured to determine an appropriate tube is present in the fluid line state detector when the intensity of infrared light sensed by the light sensor from the infrared light emitting LED is above a predetermined first threshold, when the intensity of ultraviolet light sensed by the light sensor from the ultraviolet light emitting LED is below a predetermined second threshold and when the intensity of light emitted by the third LED is below a predetermined third threshold. In some embodiments, the controller may be further configured to govern provision of power to the infrared light emitting LED, the ultraviolet light emitting LED, and the third LED.

In accordance with an embodiment of the present disclosure a fluid line state detector for detecting presence of a fluid line opaque to light in a first spectrum and at least translucent to light in a second spectrum may comprise a receptacle configured to retain the fluid line. The fluid line state detector may further comprise a light sensor. The fluid line state detector may further comprise a first LED configured to emit light in the first spectrum. The fluid line state detector may further comprise a second LED configured to emit light in the second spectrum. The fluid line state detector may further comprise a third LED. The fluid line state detector may further comprise a controller in data communication with the light sensor. The controller may be configured to determine the fluid line is present in the fluid line state detector when the intensity of light in the first spectrum sensed by the light sensor from first LED is below a predetermined first threshold and when the intensity of light in the second spectrum sensed by the light sensor from the second LED is above a predetermined second threshold. An axis of the first LED and an axis of the second LED may be parallel to one another as well as to an axis of the light sensor.

In some embodiments, the axis of first LED may be an optical axis of the first LED and the axis of the second LED may be an optical axis of the second LED. In some embodiments, the axis of the first LED may be a mechanical axis of the first LED and the axis of the second LED may be a mechanical axis of the second LED. In some embodiments, the axis of the light sensor may be an optical axis of the light sensor. In some embodiments, the axis of the light sensor may be a mechanical axis of the light sensor. In some embodiments, the third LED may be configured to emit light in the second spectrum. In some embodiments, an axis of the third LED may be at an angle other than parallel to the axis of the first LED and the axis of the second LED. In some embodiments, the axis of the first LED may be configured to pass through a central portion of the fluid line when the fluid line is installed within the receptacle. In some embodiments, the receptacle may include a retainer for holding the fluid line. In some embodiments, the controller may be further configured to determine that the fluid line is dry when light intensity from the third LED is above a predetermined dry threshold. In some embodiments, the controller may be further configured to determine that the fluid line is primed when light intensity from the third LED is below a predetermined primed threshold. The predetermined prime threshold may be lower than the predetermined dry threshold. In some embodiments, the controller may be further configured to determine that the fluid line is primed when light intensity from the second LED is below a predetermined second light spectrum threshold and when light intensity from the third LED is below a predetermined primed threshold, the predetermined prime threshold being lower than the predetermined dry threshold. In some embodiments, the controller may be configured determine the fluid line is present in the fluid line state detector when the intensity of light in the first spectrum sensed by the light sensor from the first LED is below a predetermined first threshold, when the intensity of light in the second spectrum sensed by the light sensor from the second LED is above a predetermined second threshold and when the intensity of light sensed by the light sensor from the third LED is below a predetermined third threshold. In some embodiments, the controller may be further configured to govern provision of power to the first, second, and third LED. In some embodiments, the first spectrum may be an ultraviolet spectrum. In some embodiments, the second spectrum may be an infrared spectrum. In some embodiments, the fluid line may be transparent to light in the second spectrum.

In accordance with an embodiment of the present disclosure a method of detecting the presence of an appropriate fluid line in a receptacle of a detector may comprise emitting light in a first spectrum from a first LED. The fluid line may be opaque to light in the first spectrum. The method may further comprise emitting light in a second spectrum from a second LED. The fluid line may be at least translucent to light in the second spectrum. The method may further comprise monitoring an intensity of received light with a light sensor disposed on an opposing side of the receptacle than the first and second LED. The method may further comprise comparing the intensity of light received in the first spectrum to a first threshold. The method may further comprise comparing the intensity of light received in the second spectrum to a second threshold. The method may further comprise determining the presence of the appropriate fluid line when the intensity of light in the first spectrum is less than the first threshold and the intensity of light in the second spectrum is greater than the second threshold.

In some embodiments, the first threshold may correspond to substantially no light transmission from the first LED to the light sensor. In some embodiments, the first spectrum may be an ultraviolet spectrum. In some embodiments, the second spectrum may be a higher wavelength spectrum than the first spectrum. In some embodiments, the second spectrum may be an infrared spectrum. In some embodiments, the fluid line may be transparent to light in the second spectrum. In some embodiments, the method may further comprise generating a notification when the intensity of light in the first spectrum is above than the first threshold and the intensity of light in the second spectrum is greater than the second threshold. In some embodiments, generating the notification may comprise displaying a notice to reload the fluid line on a graphical user interface. In some embodiments, an axis of the first LED and second LED may be parallel to one another and to an axis of the light sensor.

In accordance with an embodiment of the present disclosure, a fluid pumping system may comprise a pump. The fluid pumping system may further comprise a displaced volume sensing assembly. The fluid pumping system may further comprise a fluid line state detector having a receptacle for retaining a fluid line, at least one light sensor, and at least one LED. The fluid pumping system may further comprise a fluid transfer set including an output line configured to mate into the receptacle. The fluid pumping system may further comprise at least one fluid source. The fluid pumping system may further comprise a controller in data communication with the fluid line state detector. The controller may be configured to power the at least one LED and monitor an output signal of the at least one light sensor when the outlet line is installed in the receptacle to determine a dry tube light intensity value. The controller may be further configured to govern operation of the pump to prime the output line with fluid from the at least one fluid source. The controller may be further configured to power the at least one LED, monitor the output signal, and halt operation of the pump when the output signal indicates the light intensity value has dropped below a primed line threshold. The primed line threshold may be calculated by the controller based upon the dry tube intensity reading.

In some embodiments, the primed line threshold may be calculated by adding a constant to a percentage of the dry tube intensity value. In some embodiments, the controller may be further configured to power the at least one LED a plurality of times. The dry tube intensity value may be based on a maximum light intensity value output from the light sensor over the plurality of times. In some embodiments, the controller may be configured to power the at least one LED a plurality of times and monitor the output signal to determine a maximum light intensity value. The dry tube intensity value may be based on the maximum light intensity value and at least one limit. In some embodiments, the limit may be a minimum value for the dry tube intensity value. In some embodiments, the controller may be further configured to generate a notification when displaced volume sensing assembly indicates that the volume of fluid displaced is greater than a predefined threshold. In some embodiments, controller may be configured to continue pumping upon receipt of a user input from a user interface of the system indicating that the output line has yet to fully prime. In some embodiments, the pump may be a diaphragm pump. In some embodiments, the pump may be a pneumatic diaphragm pump. In some embodiments, a portion of the pump may be included in the fluid transfer set. In some embodiments, the portion of the pump may be included in a fluid handling cassette of the fluid transfer set. In some embodiments, the fluid transfer set may include a fluid handling cassette with at least one pump chamber, each of the at least one pump chamber forming part of the pump. In some embodiments, the at least one fluid source may be a dialysate reservoir. In some embodiments, the at least one LED may include a first LED disposed at an angle to the optical axis of the light sensor. In some embodiments, the at least on LED may include a second LED and a third LED. In some embodiments, an axis of the second LED and an axis of the third LED may be parallel to the optical axis of the light sensor.

In accordance with another embodiment of the present disclosure a method of priming a fluid line may comprise installing the fluid line in a receptacle of a fluid line state detector. The method may further comprise emitting light from at least one LED of the fluid line state detector a first plurality of times. The method may further comprise monitoring an output signal of a light sensor of the fluid line state detector and determining a maximum light intensity value based on the output signal during the first plurality of times. The method may further comprise determining a primed line threshold based on the maximum light intensity value. The method may further comprise pumping fluid through the fluid line. The method may further comprise emitting light from the at least one LED of the fluid line state detector a second plurality of times. The method may further comprise determining that the fluid line is primed when the output signal of the light sensor indicates that the light intensity from the LED is in breach of the primed tube threshold.

In some embodiments, installing the fluid line in the receptacle may comprise seating the fluid line within a channel of the fluid line state detector. In some embodiments, the method may further comprise comparing the maximum light intensity to a limit and over writing the maximum light intensity value with the value of the limit when the maximum light intensity value does not conform to the limit. In some embodiments, determining the maximum light intensity value based on the output signal may comprise comparing the light intensity values indicated by the output signal during the first plurality of times to a calibrated value to determine a ratio. In some embodiments, the calibrated value may be a light intensity value from the at least one LED output from the light sensor when no tube is installed in the receptacle. In some embodiments, determining the primed line threshold may comprise adding a constant to a percentage of the maximum light intensity value. In some embodiments, the second plurality of times may occur over the course of pumping fluid through the line. In some embodiments, emitting light from the at least one LED during the second plurality of times may comprise emitting light from a first, second, and third LED. In some embodiments, the method may further comprise halting pumping of fluid through the line upon determining that the fluid line has been primed. In some embodiments, the method may further comprise monitoring a volume of fluid pumped via a displaced volume sensing assembly. In some embodiments, the method may further comprise pausing pumping of fluid when the volume of fluid pumped exceeds a first volume threshold. In some embodiments, the method may further comprise resuming pumping upon receipt of a user input indicating that the line is yet to be fully primed. In some embodiments, the method may further comprise prohibiting resumption of pump when the volume of fluid pumped exceeds a second volume threshold.

In accordance with another embodiment of the present disclosure a fluid pumping system may comprise a pump. The fluid pumping system may further comprise a fluid line state detector having a receptacle, at least one sensor, and at least one illuminator. The fluid pumping system may further comprise a fluid transfer set including an output line configured to mate into the receptacle. The fluid pumping system may further comprise a controller in data communication with the fluid line state detector. The controller may be configured to power the at least one illuminator and monitor an output signal of the at least one sensor when the outlet line is installed in the receptacle to determine a dry tube light intensity value. The controller may be further configured to govern operation of the pump to prime the output line with fluid from at least one fluid source. The controller may be further configured to power the at least one illuminator, monitor the output signal, and halt operation of the pump when the output signal indicates the light intensity value has dropped below a primed line threshold which is dependent upon the dry tube intensity value.

In some embodiments, the primed line threshold may be calculated by adding a constant to a percentage of the dry tube light intensity value. In some embodiments, the controller may be configured to power the at least one illuminator a plurality of times and the dry tube light intensity value is based on a maximum light intensity value output from the sensor over the plurality of times. In some embodiments, the controller may be configured to power the at least one illuminator a plurality of times and monitor the output signal to determine a maximum light intensity value, the dry tube light intensity value being based on the maximum light intensity value and at least one limit. In some embodiments, the limit may be a minimum value for the dry tube light intensity value. In some embodiments, the system may further comprise a displaced volume sensing assembly. The controller may be further configured to generate a notification when the displaced volume sensing assembly indicates that the volume of fluid displaced is greater than a predefined threshold. In some embodiments, the controller may be configured to continue pumping upon receipt of a user input from a user interface of the system indicating that the output line has yet to fully prime. In some embodiments, the pump may be a diaphragm pump. In some embodiments, the pump may be a pneumatic diaphragm pump. In some embodiments, a portion of the pump may be included in the fluid transfer set. In some embodiments, the at least one fluid source may be a dialysate reservoir. In some embodiments, the at least one illuminator may include a first LED disposed at an angle to the optical axis of the sensor. In some embodiments, the at least one illuminator may include a second LED and a third LED. In some embodiments an axis of the second LED and an axis of the third LED may be parallel to the optical axis of the sensor.

BRIEF DESCRIPTION OF THE DRAWINGS

These and other aspects will become more apparent from the following detailed description of the various embodiments of the present disclosure with reference to the drawings in which like numerals reference like elements, and wherein:

FIG. 1B shows an alternative arrangement for a dialysate delivery set shown in FIG. 1;

FIG. 2 is a schematic view of an illustrative set for use with the APD system of FIG. 1;

FIG. 54 is a depiction of process used for calibrating partial stroke volumes in the diaphragm pump;

FIG. 63A depicts a top down view of an exemplary disposable fluid pumping cassette;

FIG. 63B depicts a cross-sectional view taken at line 63B-63B of FIG. 63A;

FIG. 63C depicts a cross-sectional view taken at line 63C-63C of FIG. 63A;

DETAILED DESCRIPTION

Automated Peritoneal Dialysis System

Figure 1A:
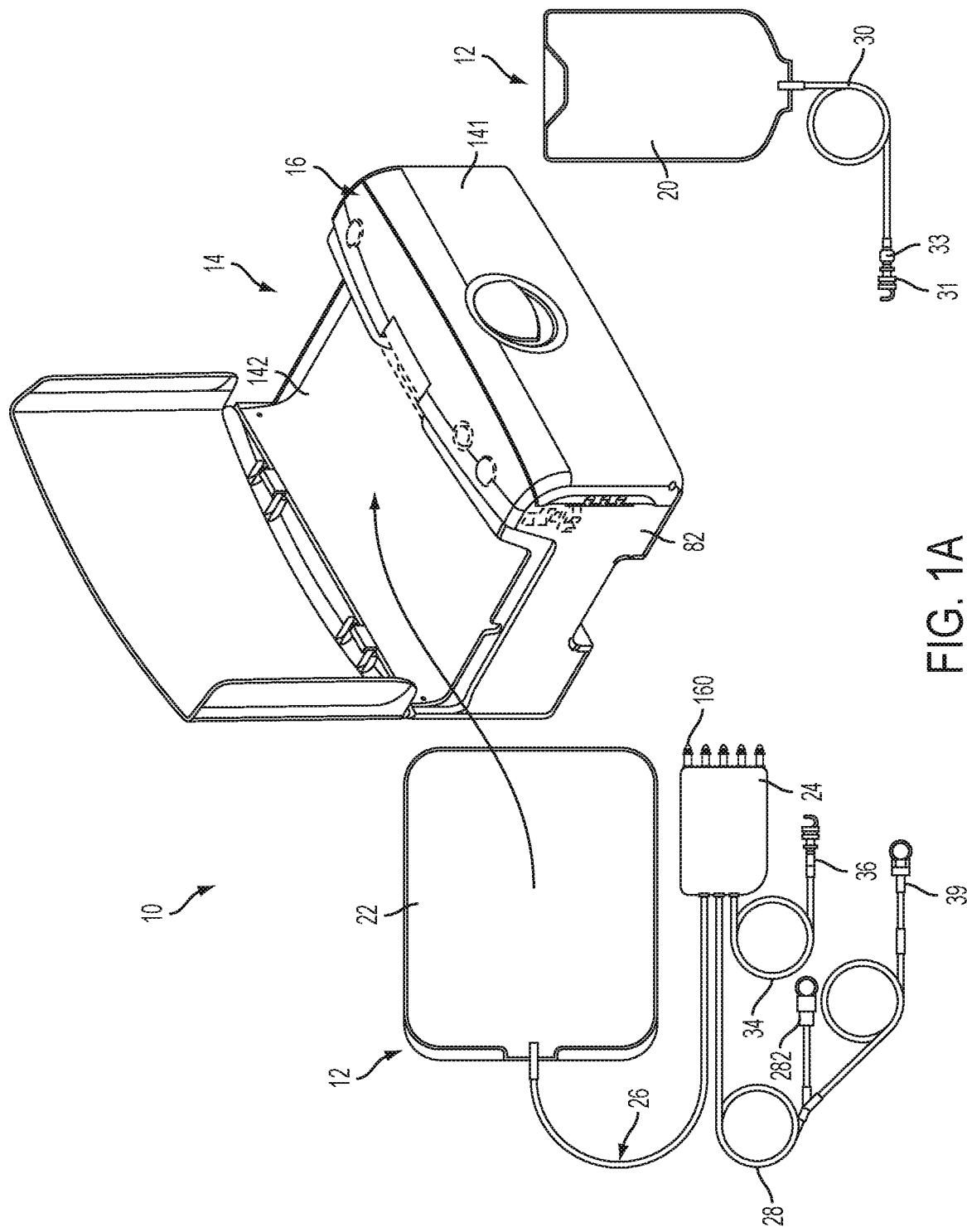
FIG. 1A shows a schematic view of an automated peritoneal dialysis (APD) system that incorporates one or more aspects of the disclosure.

FIG. 1A shows an automated peritoneal dialysis (APD) system 10 that encompasses one or more aspects of the disclosure. Other APD systems or components thereof such as those shown and described in U.S. Pat. No. 10,058,694, to Norris et al., entitled Medical Treatment System and Methods Using a Plurality of Fluid Lines, filed Jun. 5, 2015, which is incorporated herein by reference in its entirety may also be used with the various aspects of the disclosure detailed herein.

As shown in FIG. 1A, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 that governs the process to perform an APD procedure. The control system 16 may, for example, include a programmed computer or other data processor, computer memory, an interface to provide information to and receive input from a user or other device, one or more sensors, actuators, relays, pneumatic pumps, tanks, a power supply, and/or other suitable components such as buttons for receiving user control input are (shown in FIG. 1A). Further details regarding the control system 16 components are provided below. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14, which interacts with the cassette 24 to pump and control fluid flow in the various lines of the set 12. For example, dialysate may be pumped both to and from the patient to effect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette with a patient line 34 sized for use with an adult patient, and a second type of cassette with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. The lines 26, 28, 30, 34 may include a flexible tubing and/or suitable connectors and other components (such as pinch valves, etc.) as desired. The containers 20 may contain sterile peritoneal dialysis solution for infusion, or other materials (e.g., materials used by the cycler 14 to formulate dialysate by mixing with water, or admixing different types of dialysate solutions). The lines 30 may be connected to spikes 160 of the cassette 24, which are shown in FIG. 1A covered by removable caps.

In one aspect of the disclosure, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

In another aspect, a dialysate delivery set 12A may not have cassette spikes 160. Instead, one or more solution lines 30 may be permanently affixed to the inlet ports of cassette 24, as shown in FIG. 1B. In this case, each solution line 30 may have a capped spike connector 35 for manual connection to a solution container or dialysate bag 20.

With various connections made, the control system 16 may pace the cycler 14 through a series of fill, dwell, and/or drain cycles typical of an APD procedure. For example, during a fill phase, the cycler 14 may pump dialysate by way of the cassette 24 from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler 14, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the disclosure, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the disclosure, a cassette 24 may include patient and drain lines 34, 28 that are separately occludable with respect to solution supply lines 30. That is, safety critical flow to and from patient line 34 may be controlled, e.g., by pinching the lines to stop flow, without the need to occlude flow through one or more solution supply lines 30. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines 34, 28 may be occluded. However, the solution supply and/or heater bag lines 30, 26 may remain open for flow, allowing the cycler 14 to prepare for a next dialysis cycle. For example, separate occlusion of patient and drain lines 34, 28 may help ensure patient safety while permitting the cycler 14 to continue to pump dialysate from one or more containers 20 to the heater bag 22 or to other solution containers 20.

In another aspect of the disclosure, the cassette 24 may have patient, drain and heater bag lines 34, 28, 26 at one side or portion of the cassette 24 and one or more solution supply lines 30 at another side or portion of the cassette 24, e.g., an opposite side of the cassette 24. Such an arrangement may allow for separate occlusion of patient, drain or heater bag lines 34, 28, 26 with respect to solution lines 30 as discussed above. Physically separating the lines attached to the cassette 24 by type or function allows for more efficient control of interaction with lines of a certain type or function. For example, such an arrangement may allow for a simplified occluder design because less force is required to occlude one, two or three of these lines than all lines leading to or away from the cassette 24. Alternately, this arrangement may allow for more effective automated connection of solution supply lines 30 to the cassette 24, as discussed in more detail below. That is, with solution supply lines 30 and their respective connections located apart from patient, drain and/or heater bag lines 34, 28, 26, an automated de-capping and connection device may remove caps from spikes on the cassette 24 as well as caps on solution supply lines 30, and connect the lines to respective spikes without interference by the patient, drain or heater bag lines 34, 28, 26.

FIG. 2 shows an illustrative embodiment of a cassette 24 that incorporates aspects of the disclosure described above. In this embodiment, the cassette 24 has a generally planar body and the heater bag line 26, the drain line 28 and the patient line 34 are connected at respective ports on the left end of the cassette body 18, while the right end of the cassette body 18 may include five spikes 160 to which solution supply lines 30 may be connected. In the arrangement shown in FIG. 2, each of the spikes 160 is covered by a spike cap 63, which may be removed, exposing the respective spike 160 and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
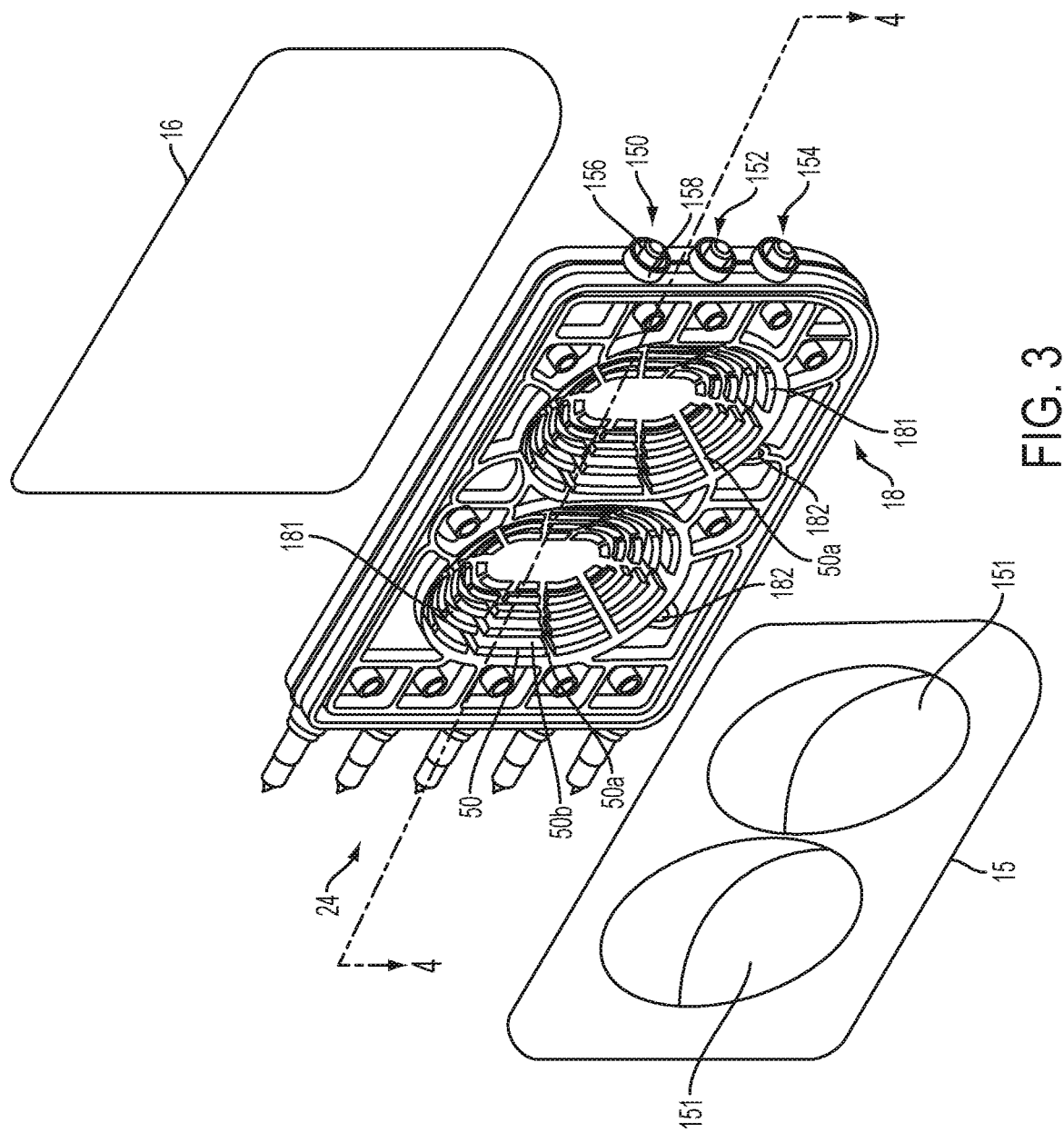
FIG. 3 is an exploded perspective view of a cassette in a first embodiment.
Figure 4:
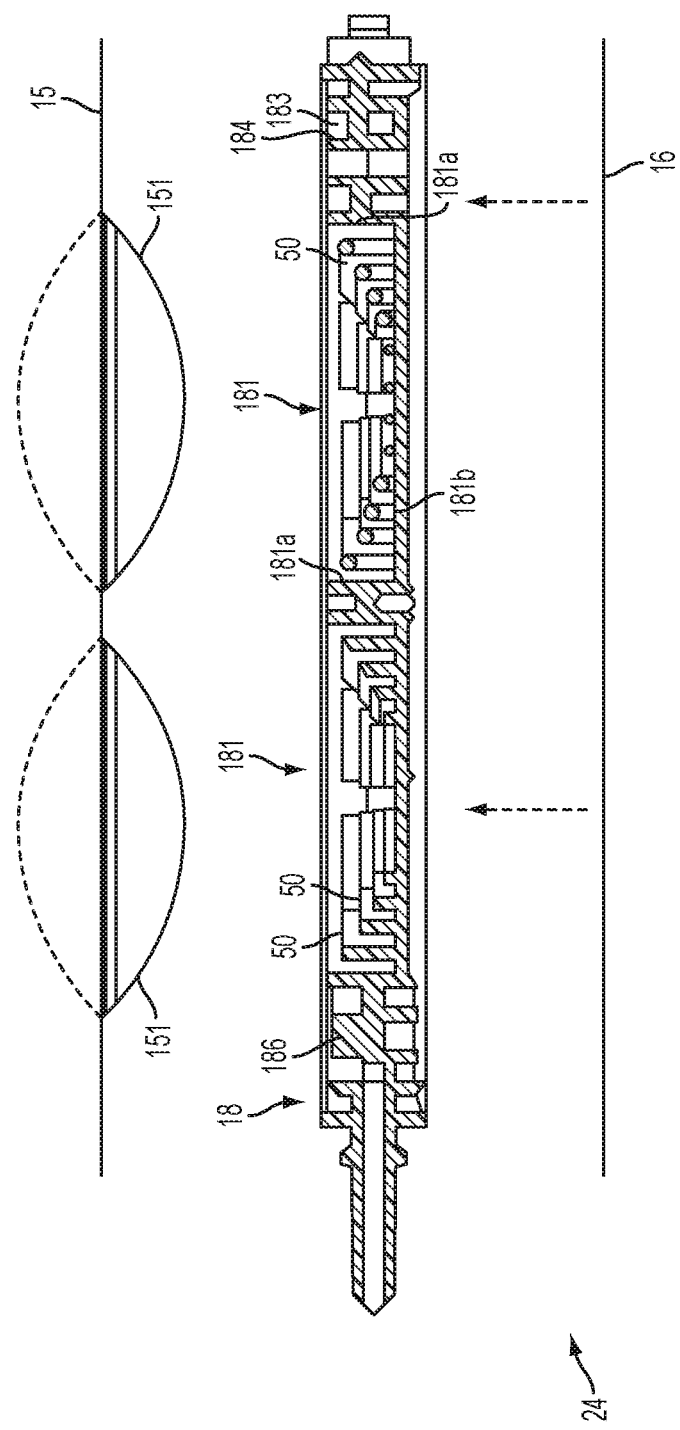
FIG. 4 is a cross sectional view of the cassette along the line 4-4 in FIG. 3.

FIGS. 3 and 4 show exploded views (respectively a perspective and cross sectional view taken at the indicated plane of FIG. 3) of the cassette 24 in this illustrative embodiment. The cassette 24 is formed as a relatively thin and flat member having a generally planar shape. The cassette 24 may, for example, include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports 150, 152, 154 may be arranged in any suitable way, such as, for example, a central tube 156 extending from an outer ring or skirt 158, or a central tube 156 alone. Flexible tubing for each of the heater bag, drain and patient lines 26, 28, 34 may be connected to a respective central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet 15, 16 may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane 15, 16 thickness may be in the range of approximately 0.002 to 0.020 inches thick. In a preferred embodiment, the thickness of a PVC—based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flow paths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flow paths of the cassette 24. It is also possible that the cassette 24 may not include the membrane 16 or the membrane 15, e.g., where the cycler 14 includes a suitable member to seal pathways of the cassette, control valve and pump function, etc.

Figure 5:
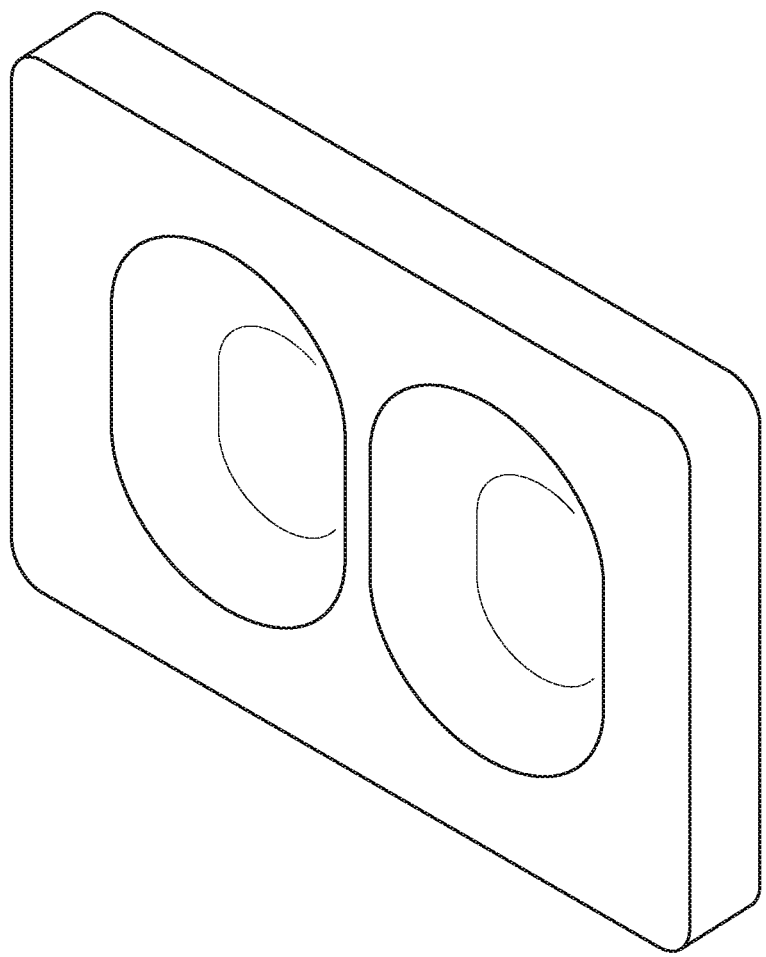
FIG. 5 is a perspective view of a vacuum mold that may be used to form a membrane having pre-formed pump chamber portions in an illustrative embodiment.

In accordance with another aspect of the disclosure, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane 15 over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane 15. In one example, the molded membrane sheet 15 is trimmed while attached to the vacuum form mold. The vacuum form mold then presses the trimmed membrane sheet 15 against the cassette body 18 and bonds them together. In one embodiment the membrane sheets 15, 16 are heat-welded to the cassette body 18. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181. For example, if the pump chamber portions 151 define a volume that is about 100% of the pump chamber 181 volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain phase of a cycle. A patient may experience discomfort during the drain phase of a treatment in part because of the negative pressure being applied by the pumps during a fill stroke. The added control that a pre-formed membrane can provide to the negative pressure being applied during a fill stroke may help to reduce the patient's discomfort.

A number of other benefits may be realized by using pump membranes 151 pre-formed to the contour of the cassette 24 pump chamber 181. For example, the flow rate of liquid through the pump chamber 181 can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane 15, as well as the accuracy of measuring pressures within the pump chambers 181. In addition, pressure spikes within the fluid lines can be minimized. Also, correlating the pressures measured by pressure transducers on the control (e.g. pneumatic) side of the membrane 15 with the actual pressure of the liquid on the pump chamber 181 side of the membrane 15 may be simpler. This in turn may permit more accurate head height measurements of the patient and fluid source bags prior to therapy, improve the sensitivity of detecting air in the pump chamber 181, and improve the accuracy of volumetric measurements. Furthermore, eliminating the need to stretch the membrane 15 may allow for the construction and use of pump chambers 181 having greater volumes.

In this embodiment, the cassette 24 includes a pair of pump chambers 181 that are formed in the base member 18, although one pump chamber 181 or more than two pump chambers 181 are possible. In accordance with an aspect of the disclosure, the inner wall of pump chambers 181 includes spacer elements 50 that are spaced from each other and extend from the inner wall of pump chamber 18 to help prevent portions of the membrane 15 from contacting the inner wall of pump chamber 181. As shown on the right-side pump chamber 181 in FIG. 4, the inner wall is defined by side portions 181A and a bottom portion 181B. The spacers 50 extend upwardly from the bottom portion 181B in this embodiment, but could extend from the side portions 181A or be formed in other ways. By preventing contact of the membrane 15 with the pump chamber 181 inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber 181 inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheeting 15 happens to contact the pump chamber 181 inner wall in a non-uniform manner. Further details regarding the arrangement and/or function of spacers 50 are provided in U.S. Pat. Nos. 6,302,653 and 6,382,923, both of which are incorporated herein by reference.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181B of the inner wall with distance away from the center of the pump chamber 181 to form a semi-elliptical domed shaped region. Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50A in the elliptical pattern. Breaks (or aisles) 50A help to maintain an equal gas level throughout the rows (voids or dead space) 50B between spacer elements 50 as fluid is delivered from the pump chamber 181. For example, if the spacer elements 50 were arranged in the stadium seating arrangement shown in FIG. 6 without breaks (or aisles) 50A or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50A or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the disclosure, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements 50 are outside of, or adjacent to, the domed region intended to be swept by the flexible membrane 15 provides a dead space between the spacers 50 and the membrane 15, such as described above, while minimizing any reduction to the intended stroke capacity of pump chambers 181.

Figure 6:
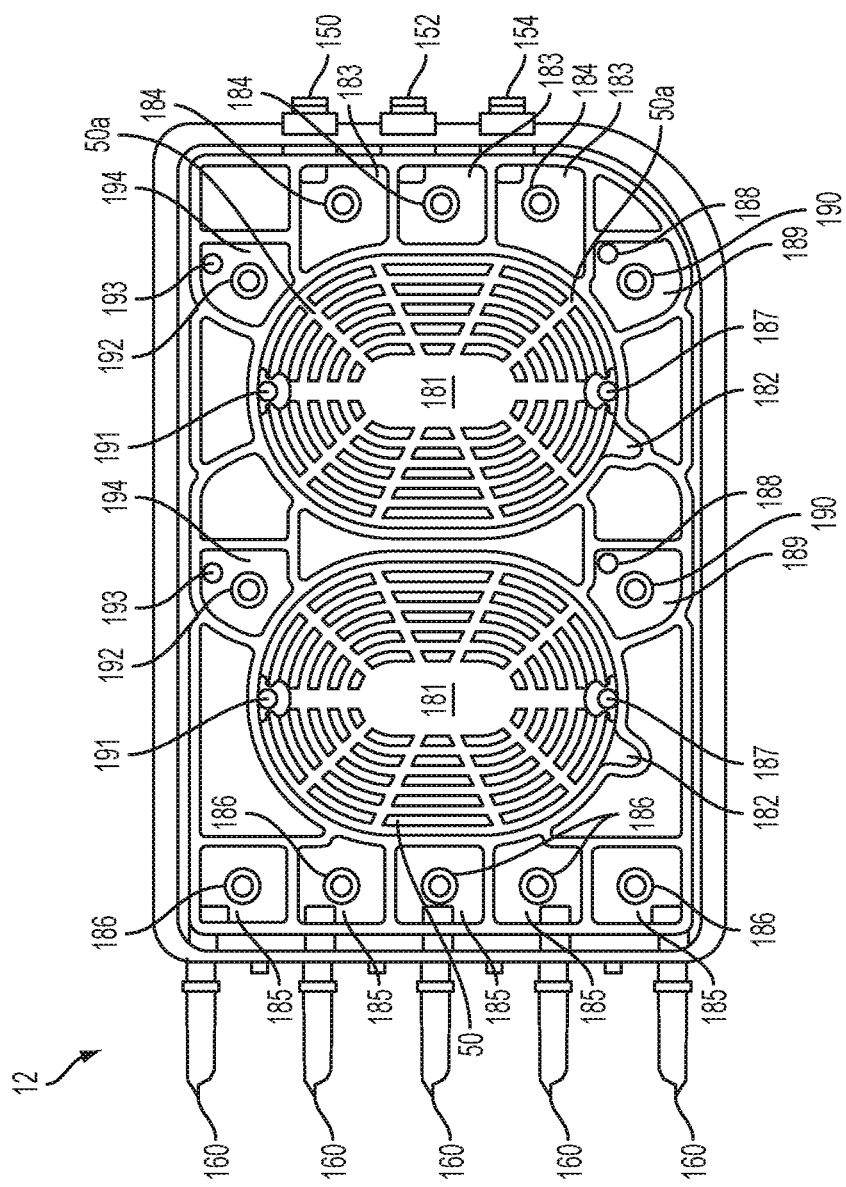
FIG. 6 shows a front view of the cassette body of FIG. 3.
Figure 7:
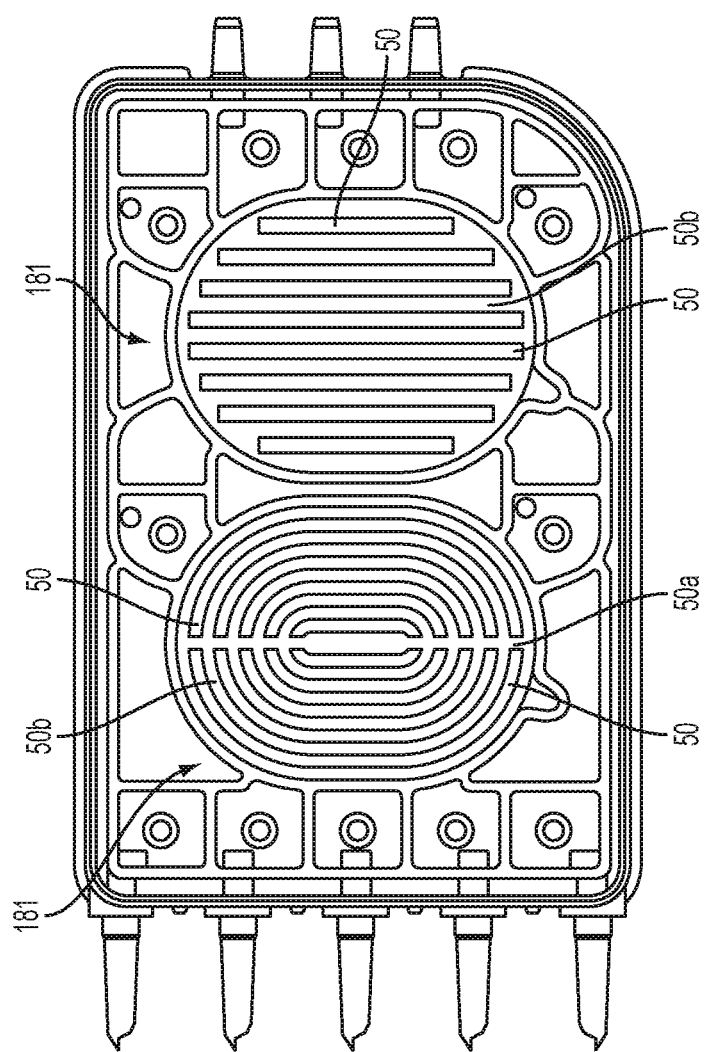
FIG. 7 is a front view of a cassette body including two different spacer arrangements in an illustrative embodiment.

It should be understood that the spacer elements 50, if present, in a pump chamber 181 may be arranged in any other suitable way, such as for example, shown in FIG. 7. The left side pump chamber 181 in FIG. 7 includes spacers 50 arranged similarly to that in FIG. 6, but there is only one break or aisle 50A that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50B between spacers 50 also arranged vertically. As with the left-side pump chamber 181, the spacers 50 in the right-side pump chamber 181 may define a semi-elliptical, spherical, box-like or any other suitably shaped depression. It should be understood, however, that the spacer elements 50 may have a fixed height, a different spatial pattern than those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
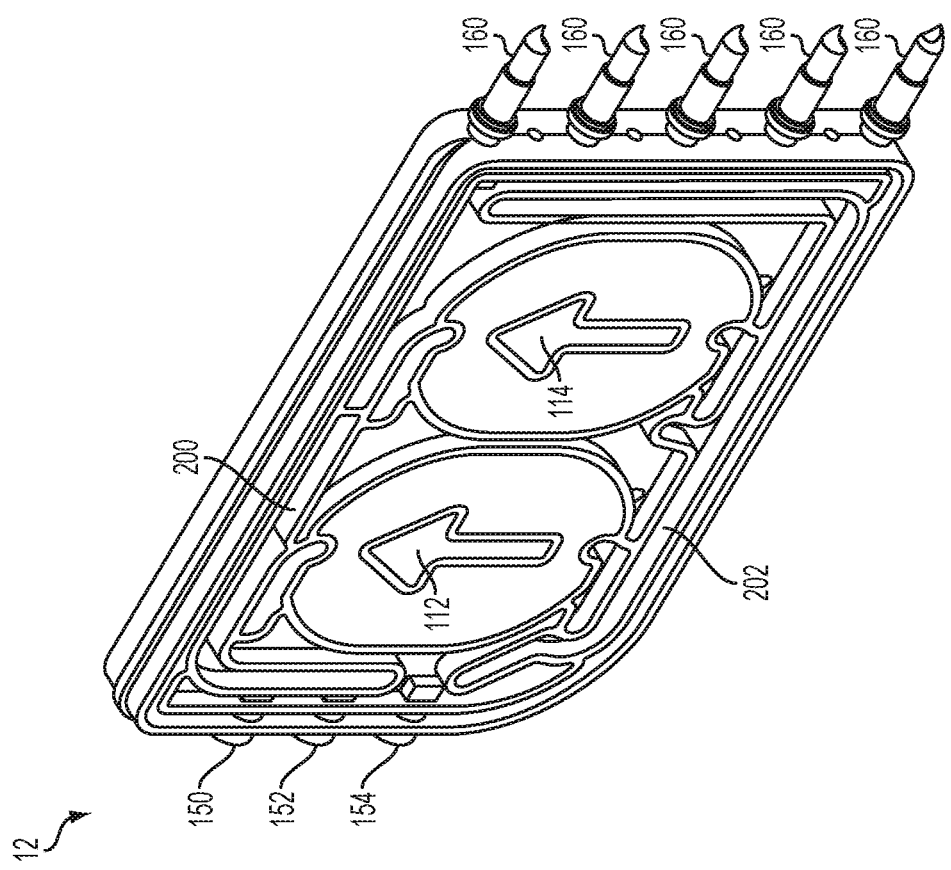
FIG. 8 is a rear perspective view of the cassette body of FIG. 3.
Figure 9:
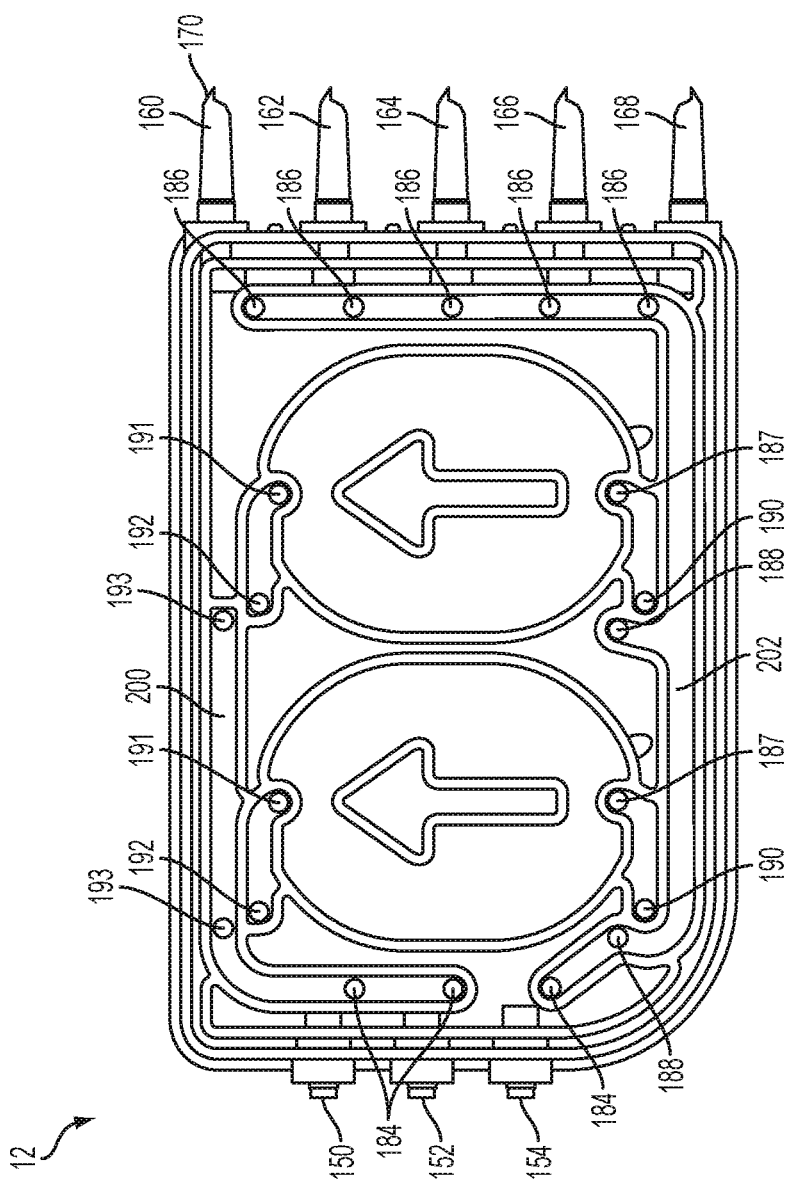
FIG. 9 is a rear view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well or chamber 183 that is formed in the base member 18. The valve wells or chambers 183 are fluidly isolated from each other by walls surrounding each valve well or chamber 183 and by sealing engagement of the membrane 15 with the walls around the wells or chambers 183. Similarly, valve wells 185 can be sealed from ports 186 by operation of the cassette membrane 15. The pump inlet or outlet valves have wells 189, 194 that can be sealed from ports 190, 192 by operation of the cassette membrane 15. As mentioned above, the membrane 15 may sealingly engage the walls around each valve well or chamber 183, 185, 189 and 194 (and other walls of the base member 18) by being pressed into contact with the walls, e.g., when loaded into the cycler 14. Fluid in the valve wells or chambers 183, 185, 189 and 194 may flow into or out of a respective valve port or orifice 184, 186, 190 and 192, if the membrane 15 is not pressed into sealing engagement with the valve port or orifice 184, 186, 190 and 192. Thus, each valve port or orifice 184, 186, 190 and 192 defines a valve (e.g., a "volcano valve") that can be opened and closed by selectively moving a portion of the membrane 15 associated with the valve port or orifice 184, 186, 190 and 192. The cassette valve port or orifice seat can be defined by a raised circumferential wall 196, forming a valve seat (see, e.g., FIG. 3), so that occlusion of the port by the cassette membrane 15 and associated valve control region of gasket 148 can be achieved more reliably. But in other embodiments, a cassette valve port seat may not comprise a raised wall 196 if the cassette membrane 15 is sufficiently flexible or appropriately shaped, and the applied pressure is sufficient to seal the valve port 184, 186, 190 and 192 from the valve well or chamber 183, 185, 189 and 194.

As will be described in more detail below, the cycler 14 may selectively control the position of portions of the membrane 15 so that cassette valve ports or orifices (such as ports 184) may be opened or closed so as to control flow through the various fluid channels and other pathways in the cassette 24. Flow through the valve ports or orifices 184, 186, 190 and 192 leads to the back side of the base member 18. For the valve ports 184 associated with the heater bag and the drain (ports 150 and 152), the valve ports 184 lead to a common channel 200 formed at the back side of the base member 18. As with the valve wells or chambers 183, 185, 189 and 194, the channel 200 is isolated from other channels and pathways of the cassette 24 by the sheet 16 making sealing contact with the walls of the base member 18 that form the channel 200. For the valve port or orifice 184 associated with the patient line port 154, flow through the port 184 leads to a common channel 202 on the back side of the base member 18. Common channel 200 may also be referred to herein as an upper fluidic bus and common channel 202 may also be referred to herein as a lower fluidic bus.

Returning to FIG. 6, each of the spikes 160 (shown uncapped in FIG. 6) fluidly communicates with a respective valve well 185, which are isolated from each other by walls and sealing engagement of the membrane 15 with the walls that form the wells 185. Fluid in the valve wells 185 may flow into a respective valve port 186, if the membrane 15 is not in sealing engagement with the port 186. Again, the position of portions of the membrane 15 over each valve port 186 can be controlled by the cycler 14 to open and close the valve ports 186. Flow through the valve ports 186 leads to the back side of the base member 18 and into the common channel 202. Thus, in accordance with one aspect of the disclosure, a cassette 24 may have a plurality of solution supply lines (or other lines that provide materials for providing dialysate) that are connected to a common manifold or channel of the cassette 24, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 (and possibly closing other valve ports 186 for other spikes 160). Also, the lower pump valve ports 190 may be opened and the upper pump valve ports 192 may be closed. Thereafter, the portion of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. Of course, only one pump chamber 181 need be operable to draw fluid into itself. The other pump chamber 181 may be left inoperable and closed off to flow by closing the appropriate lower pump valve port 190.

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 (and into the corresponding heater bag line 26 or drain line 28) by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray 142 for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line 28 for disposal or for sampling into a drain or collection container. Alternatively, fluid may also be routed to one or more spikes 160/lines 30 for sampling or drain purposes. This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient.

In accordance with an aspect of the disclosure, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient—"are you asleep?" and control system operation based on the patient's response (or lack of response).

Patient Line State Detection Apparatus

In one aspect of the disclosure, a fluid line state detector may detect when a fluid line to a patient, such as patient line 34, is adequately primed with fluid before it is connected to the patient. It should be understood that although a fluid line state detector is described in connection with a patient line 34, aspects of the disclosure include the detection of the presence any suitable tubing segment or other conduit and/or a fill state of that tubing segment or other conduit. Thus, aspects of the disclosure are not limited to use with a patient line 34, as a tubing state detector may be used with any suitable conduit. In some embodiments, a fluid line state detector can be used to detect adequate priming of a tubing segment of the patient-connecting end of a fluid line. The patient line 34 may be connected to an indwelling catheter in a patient's blood vessel, in a body cavity, subcutaneously, or in another organ. In one embodiment, the patient line 34 may be a component of a peritoneal dialysis system 10, delivering dialysate to and receiving fluid from a patient's peritoneal cavity. A tubing segment near the distal end of the line may be placed in an upright position in a cradle within which the sensor elements of the detector are located.

Figure 10:
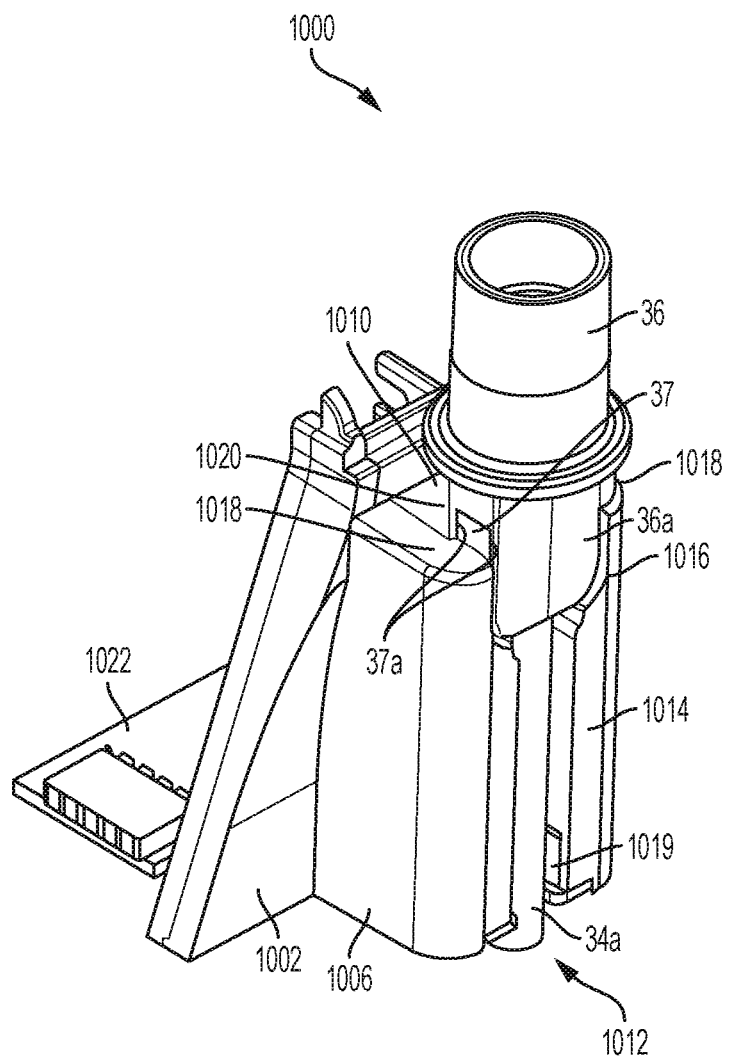
FIG. 10 is a front perspective view of an exemplary configuration of a fluid line state detector or liquid level detector.

FIG. 10 shows a front perspective view of an exemplary configuration of a fluid line state detector 1000, which may be mounted on, or otherwise exposed at, the left side exterior of the housing 82, e.g., to the left of the front door 141. The fluid line state detector will be described as a patient line state detector 1000, for purposes of example. The patient line 34 should preferably be primed prior to being connected to the patient, because air could otherwise be delivered into the patient, raising the risk of complications. It may be permissible in some settings to allow up to 1 mL of air to be present in the patient line 34 prior to being connected to a patient's peritoneal dialysis catheter. The exemplary configurations of the patient line state detector 1000 described below will generally meet or exceed this standard, as they are capable of detecting a liquid level in a properly positioned tubing segment of line 34 so that at most about 0.2 mL of air remains in the distal end of line 34 after priming.

In one aspect, a first configuration patient line state detector 1000 may include a base member 1002. There may also be a patient line state detector housing 1006 affixed to (or commonly molded with) the base member 1002, such that the detector housing 1006 may extend outwardly from the base member 1002. The detector housing 1006 defines a tube or connector holding channel 1012 within which a tubing segment 34a near the distal end of a patient line 34, or its associated connector 36 may be positioned. The portion of the detector housing 1006 facing the base member 1002 may be substantially hollow, and as a result an open cavity 1008 (shown in FIG. 11 and FIG. 13) may be created behind the detector housing 1006. The open cavity 1008 may accommodate the placement and positioning of sensor elements (1026, 1028, 1030 and 1032 shown in FIG. 13) next to the channel 1012 within which tubing segment 34a may be positioned. In an alternative embodiment, there may also optionally be a stabilizing tab 1010 extending outwardly from the base member 1002. The stabilizing tab 1010 may have a concave outer shape, so that it may substantially conform to the curvature of the patient line connector 36 when the patient line 34 is placed in the patient line state detector housing 1006. The stabilizing tab 1010 may help to prevent the connector 36 from moving during priming of the patient line 34, increasing the accuracy and efficiency of the priming process. The detector housing 1006 may have a shape that generally helps to define the tube or connector holding channel 1012, which in turn may have dimensions that vary to accommodate the transition from tubing segment 34a to tube connector 36.

In this illustrative embodiment, the channel 1012 may substantially conform to the shape of the patient line connector 36. As a result, the channel 1012 may be "U-shaped" so as to encompass a portion of the connector 36 when it is placed into the channel 1012. The channel 1012 may be made up of two distinct features; a tube portion 1014 and a cradle 1016. In another aspect, the tube portion 1014 may be positioned below the cradle 1016. Additionally, the cradle 1016 may be formed by a pair of side walls 1018 and a back wall 1020. Both of the side walls 1018 may be slightly convex in shape, while the back wall 1020 may be generally flat or otherwise may have a contour generally matching the shape of the adjacent portion of connector 36. A generally convex shape of the side walls 1018 helps to lock the patient line connector 36 into place when positioned in the cradle 1016.

In an illustrative embodiment for a first configuration of patient line state detector 1000, a region 36a of the patient line connector 36 may have a generally planar surface that can rest securely against the opposing back wall 1020 of channel 1012. Additionally, this region 36a of the connector 36 may have recesses 37 on opposing sides, which can be positioned adjacent to the opposing side walls 1018 of channel 1012 when the connector 36 is positioned within the detector housing 1006. The recesses 37 can be defined by flanking raised elements 37a of connector 36. One of these recesses 37 is partially visible in FIG. 10. The two side walls 1018 may have a generally mating shape (such as, e.g. a convex shape) to engage recesses 37 and to help lock connector 36 into place within cradle 1016. This helps to prevent the connector 36 and tubing segment 34a from being inadvertently removed from the detector housing 1006 during priming of the patient line 34. If the raised elements 37a of connector 36 are made of sufficiently flexible material (such as, e.g., polypropylene, polyethylene, or other similar polymer-based material) a threshold pulling force against connector 36 will be capable of disengaging connector 36 and tubing segment 34a from the detector housing 1006.

In another aspect, the tube portion 1014 of the cavity 1012 may surround a majority of tubing segment 34a at a point just before tubing segment 34a attaches to the connector 36. The tube portion 1014 may contain a majority of tubing segment 34a using three structures: the two side walls 1018 and the back wall 1020. In an embodiment, the two side walls 1018 and back wall 1020 may be transparent or sufficiently translucent (constructed from, e.g. plexiglass) so as to allow the light from a plurality of LED's (such as, e.g., LED's 1028, 1030, and 1032 in FIG. 13) to be directed through the walls without being significantly blocked or diffused. An optical sensor 1026 (shown in FIG. 12), may also be positioned along one of the walls 1018, and can detect the light being emitted by the LED's. In the illustrated embodiment, a transparent or translucent plastic insert 1019 may be constructed to snap into the main detector housing 1006 in the region where the LED's have been positioned in the housing.

Figure 12:
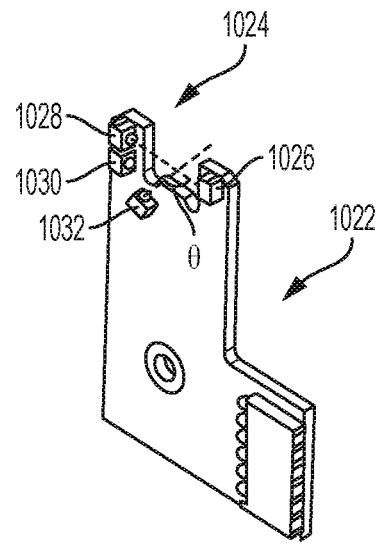
FIG. 12 is a perspective layout view of three LEDs and an optical detector surface-mounted on a printed circuit board.
Figure 13:
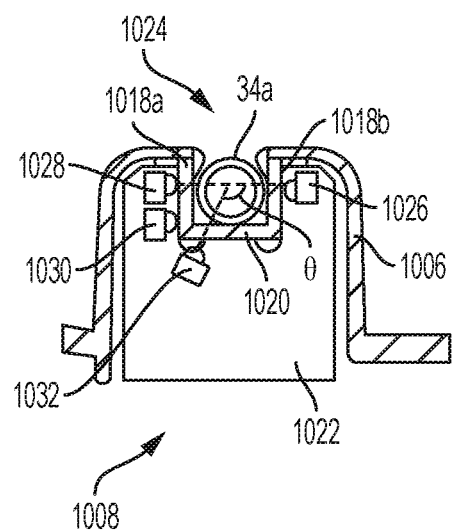
FIG. 13 is a plan view of three LEDs and an optical detector mounted on a detector circuit board.
Figure 14:
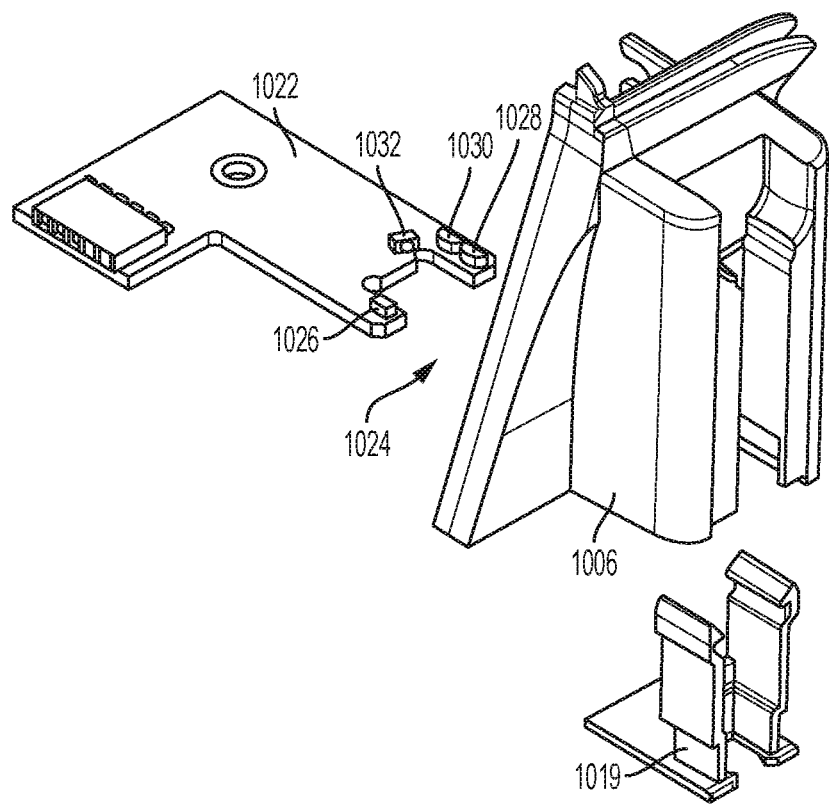
FIG. 14 is an exploded perspective view of the detector of FIG. 10 showing the printed circuit board and transparent or translucent plastic insert.

FIG. 12 shows a perspective layout view with LED's 1028, 1030, and 1032 and optical sensor 1026 surface-mounted on a patient line state detector printed circuit board 1022. FIG. 13 shows a plan view of LED's 1028, 1030, and 1032 and optical sensor 1026 mounted on detector circuit board 1022, where the detector circuit board 1022 can be positioned adjacent the back wall 1020 and side walls 1018 of detector housing 1006. FIG. 14 is an exploded perspective view of detection assembly 1000 showing the relative positions of the printed circuit board 1022 and the translucent or transparent plastic insert 1019 with respect to the housing 1006.

Figure 11:
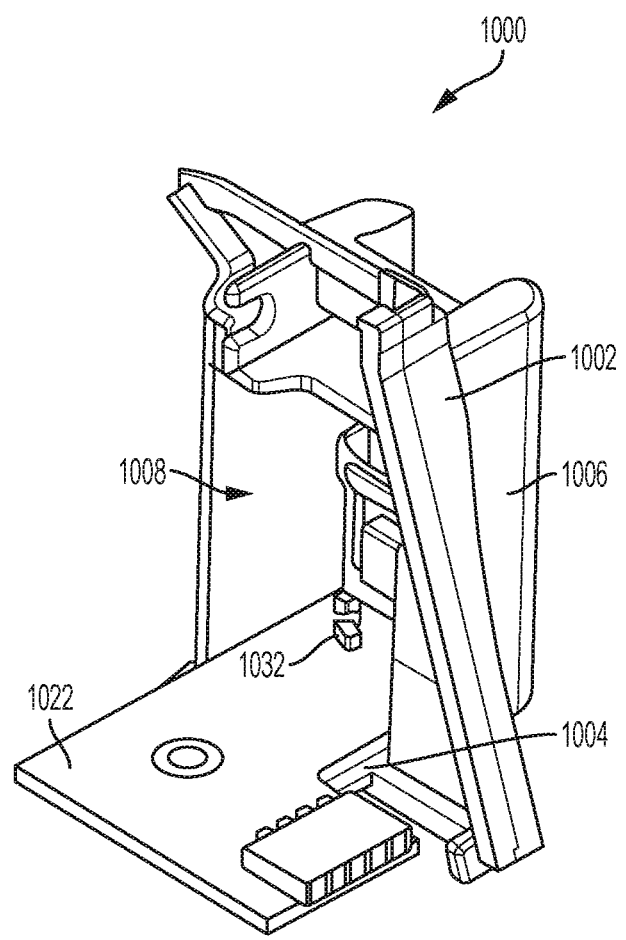
FIG. 11 is a rear perspective view of a fluid line state detector or liquid level detector.

Referring also to the illustrative embodiment of FIG. 11, the detector circuit board 1022 may be positioned on a support structure 1004 and inside open cavity 1008, which was formed from detector housing 1006 extending outwardly from base member 1002. The base member 1002 and support structure 1004 may be affixed to one another, or may be commonly molded, so that the base member 1002 is generally perpendicular to the support structure 1004. This orientation generally permits the plane of the detector circuit board 1022 to be generally perpendicular to the long axis of tubing segment 34a when secured within channel 1012. The detector circuit board 1022 may conform generally to the cross-sectional shape of open cavity 1008, and it may also include a cutout 1024 (FIG. 12, 13) generally matching the cross-sectional shape of channel 1012 formed by back wall 1020 and side walls 1018 (FIG. 10). The detector circuit board 1022 may then be positioned within open cavity 1008 with cutout 1024 nearly adjacent to side walls 1018 and back wall 1020 of detector housing 1006 in order to ensure proper alignment of the detector circuit board 1022 with tubing segment 34a or connector 36.

The detector circuit board 1022 may include a plurality of LED's and at least one optical sensor, which may be attached to circuit board 1022, and in one embodiment, the LED's and optical sensor may be surface-mounted to circuit board 1022. In one aspect, the detector circuit board 1022 may include a first LED 1028, a second LED 1030, a third LED 1032, and an optical sensor 1026. A first LED 1028 and a second LED 1030 may be positioned so as to direct light through the same side wall 1018a of channel 1012. The light emitted by the first LED 1028 and the second LED 1030 may be directed in a generally parallel direction, generally perpendicular to the side wall 1018a to which they are nearest. An optical sensor 1026 may be positioned along the opposite side wall 1018b of channel 1012. Furthermore, a third LED 1032 may be positioned along the back wall 1020 of channel 1012. In this illustrative embodiment, such a configuration of the LED's and the optical sensor 1026 allows the patient line state detector 1000 to detect three different states during the course of priming the patient line 34; a tubing segment 34a or connector 36 nearly completely filled with fluid (primed state), an incompletely filled tubing segment 34a or connector 36 (non-primed state), or the absence of a tubing segment 34a and/or connector 36 from channel 1012 (line-absent state).

When used in a peritoneal dialysis system such as, for example peritoneal dialysis system 10, configuring the detector circuit board 1022 in this fashion allows the appropriate control signal to be sent to the PD cycler controller system 16. Controller system 16 may then inform the user, via user interface 144, to position the distal end of line 34 in the patient line state detector 1000 prior to making a connection to the peritoneal dialysis catheter. The controller system 16 may then monitor for placement of tubing segment 34a within patient line state detector 1000. The controller system 16 may then proceed to direct the priming of line 34, to direct termination of priming once line 34 is primed, and then to instruct the user to disengage the distal end of line 34 from the patient line state detector 1000 and connect it to the user's peritoneal dialysis catheter.

Surface mounting the LED's 1028, 1030, and 1032 and the optical sensor 1026 to the circuit board 1022 can simplify manufacturing processes for the device, can allow the patient line state detector 1000 and circuit board 1022 to occupy a relatively small amount of space, and can help eliminate errors that may arise from movement of the LED's or the optical sensor relative to each other or to the channel 1012. Were it not for surface mounting of the sensor components, misalignment of the components could occur either during assembly of the device, or during its use.

In one aspect, the optical axis (or central optical axis or in alternative embodiments the mechanical axis) of LED 1032 may form an oblique angle with the optical axis of optical sensor 1026. In the illustrated embodiment, the optical axis (or mechanical axis) of a first LED 1028, a second LED 1030, and an optical sensor 1026 are each generally parallel to each other and to back wall 1020 of channel 1012. Thus, the amount of light directed toward optical sensor 1026 from the LED's may vary depending on the presence or absence of (a) a translucent or transparent conduit within channel 1012 and/or (b) the presence of liquid within the conduit (which, for example, may be tubing segment 34a). Preferably, LED 1032 may be positioned near the side wall (e.g., 1018a) that is farthest from optical sensor 1026 in order for some of the light emitted by LED 1032 to be refracted by the presence of a translucent or transparent tubing segment 34a within channel 1012. The degree of refraction away from or toward optical sensor 1026 may depend on the presence or absence of fluid in tubing segment 34a.

In various embodiments, the oblique angle of LED 1032 with respect to optical sensor 1026 creates a more robust system for determining the presence or absence of liquid with a translucent or transparent conduit in channel 1012. LED 1032 may be positioned so that its optical axis can form any angle between 91° and 179° with respect to the optical axis of optical sensor 1026. Preferably the angle may be set within the range of about 95° to about 135° with respect to the optical sensor's 1026 optical axis. More preferably, LED 1032 may be set to have an optical axis of about 115°+/−5° with respect to the optical axis of optical sensor 1026. In an illustrative embodiment shown in FIG. 13, the angle θ of the optical axis of LED 1032 with respect to the optical axis of optical sensor 1026 was set to approximately 115°, +/−5°. The optical axis of optical sensor 1026 in this particular embodiment is roughly parallel to back wall 1020, and roughly perpendicular to side wall 1018b. The advantage of angling LED 1032 with respect to the optical axis of optical sensor 1026 was confirmed in a series of tests comparing the performance of the optical sensor 1026 in distinguishing a fluid filled tube segment (wet tube) from an air filled tube segment (dry tube) using an LED 1032 oriented at about a 115° angle vs. an LED whose optical axis was directed either perpendicularly or parallel to the optical axis of optical sensor 1026. The results showed that an angled LED-based system was more robust in distinguishing the presence or absence of liquid in tubing segment 34a. Using an angled LED 1032, it was possible to select an optical sensor signal strength threshold above which an empty tubing segment 34a could reliably be detected. It was also possible to select an optical sensor signal strength threshold below which a liquid-filled tubing segment 34a could reliably be detected.

Figure 15:
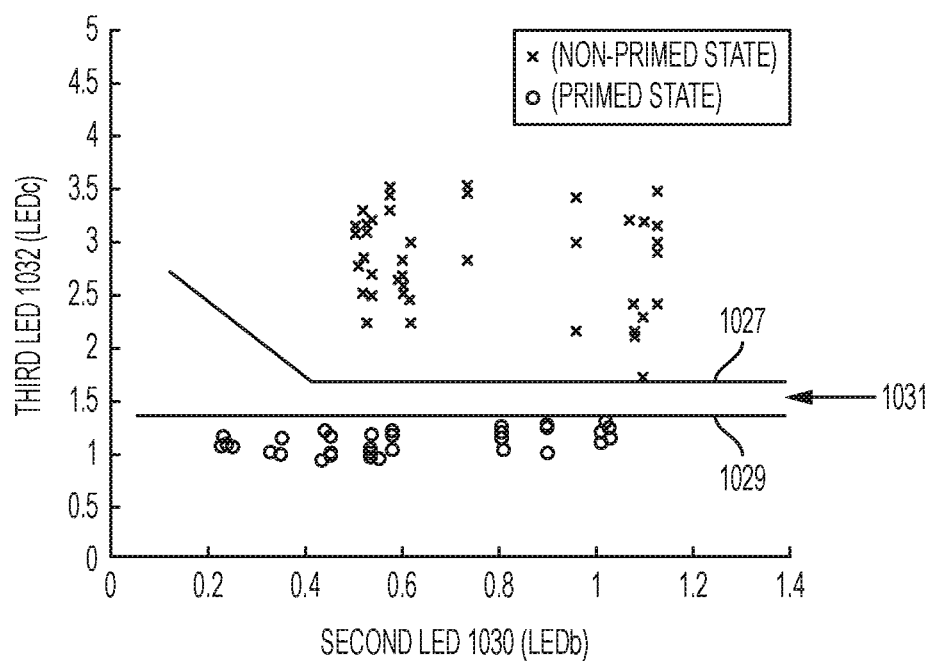
FIG. 15 is a graph showing the ability of the liquid level detector of FIG. 10 to distinguish between a primed and a non-primed fluid line.

FIG. 15 shows a graph of test results demonstrating the ability of patient line state detector 1000 to distinguish between a liquid-filled tubing segment 34a (primed state) and an empty tubing segment 34a (non-primed state). The results were recorded with LED 1032 (third LED) oriented at an angle of about 115° with respect to the optical axis of optical sensor 1026, and LED 1030 (second LED) oriented roughly parallel to the optical axis of optical sensor 1026. The results plotted in FIG. 15 demonstrate that patient line state detector 1000 can reliably discriminate between a primed state and a non-primed state. When the relative signal strength associated with light received from LED 1030 was approximately 0.4 or above, it was possible to resolve an upper signal detection threshold 1027 and a lower signal detection threshold 1029 for a non-primed vs. primed state using only the light signal received from LED 1032. The upper threshold 1027 can be used to identify the non-primed state, and the lower threshold 1029 can be used to identify the primed state. The data points located above the upper-threshold 1027 are associated with an empty tubing segment 34*a* (non-primed state), and the data points located below the lower-threshold 1029 are associated with a liquid-filled tubing segment 34*a* (primed state). A relatively narrow region 1031 between these two threshold values defines a band of relative signal strength associated with light received from LED 1032 in which an assessment of the priming state of tubing segment 34*a* may be indeterminate. A controller (such as, e.g., control system 16) may be programmed to send the user an appropriate message whenever a signal strength associated with light received from LED 1032 falls within this indeterminate range. For example, the user may be instructed to assess whether tubing segment 34*a* and/or connector 36 are properly mounted in patient line state detector 1000. In the context of a peritoneal dialysis system, if optical sensor 1026 generates a signal corresponding with an empty tubing segment 34*a*, the controller can direct the cycler 14 to continue to prime patient line 34 with dialysate. A signal corresponding to a liquid-filled tubing segment 34*a* can be used by the controller to stop further priming and instruct the user that the fluid line 34 is ready to be connected to a dialysis catheter.

In an embodiment, the cycler 14 controller may continuously monitor the received signal from one of the LED's at the initiation of the priming procedure. Upon detection of a change in the received signal, the controller may halt further fluid pumping to carry out a full measurement using all of the LED's. If the received signals are well within the range indicating a wet tube, then further priming may be halted. However, if the received signals are within the indeterminate region 1031 or within the 'dry' region, then the cycler 14 may command a series of small incremental pulses of fluid into the patient line 34 by the pumping cassette, with a repeat reading of the LED signal strengths after each pulse of fluid. The priming can then be halted as soon as a reading is achieved that indicates a fluid-filled line at the level of the sensor. Incremental pulses of fluid may be accomplished by commanding brief pulses of the valve connecting the pressure reservoir to the pump actuation or control chamber. Alternatively, the controller may command the application of continuous pressure to the pump actuation or control chamber, and command the pump's outlet valve to open briefly and close to generate the series of fluid pulses.

Figure 16:
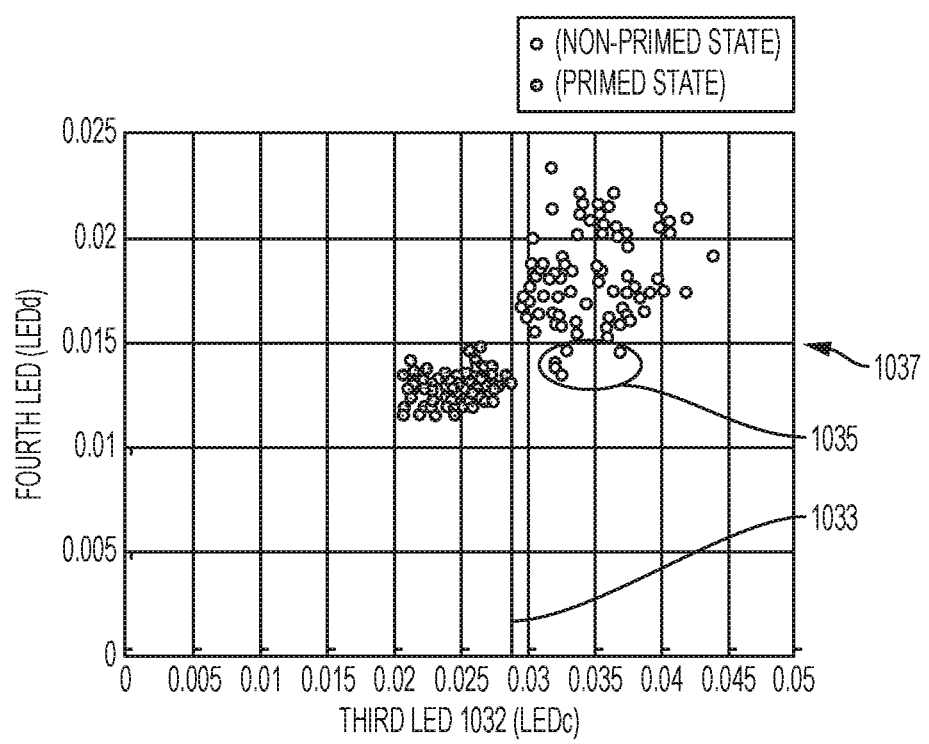
FIG. 16 is a graph showing measurements collected by an optical sensor comparing liquid detection using an orthogonally oriented LED vs. an angled LED.

FIG. 16 shows a graph of test results demonstrating the superiority of an angled LED 1032 (LEDc) when compared with an LED (LEDd not shown) whose optical axis is roughly perpendicular to the optical axis of optical sensor 1026. In this case, the relative signal strength generated by optical sensor 1026 in response to light from LEDc 1032 was plotted against the signal strength associated with light from LEDd. Although some separation between a liquid-filled ('primed') and empty ('non-primed') tubing segment 34*a* was apparent at an LEDd relative signal strength of about 0.015, there remained a substantial number of 'non-primed' data points 1035 that cannot be distinguished from 'primed' data points based on this threshold value. On the other hand, a relative signal strength 1033 associated with light from LEDc 1032 of 0.028-0.03 can effectively discriminate between 'primed' tubing segment 34*a* (primed state) and 'non-primed' tubing segment 34*a* (non-primed state). Thus an angled LED (1032) can generate more reliable data than a generally perpendicularly oriented LED.

In another embodiment, a patient line state detector 1000 can also determine whether a tubing segment 34*a* is present in channel 1012. In one aspect, a first LED 1028 and a second LED 1030 may be positioned next to one another. One LED (e.g., LED 1028) may be positioned so that its optical axis passes through approximately the center of a properly positioned translucent or transparent conduit or tubing segment 34*a* in channel 1012. The second LED (e.g. LED 1030) may be positioned so that its optical axis is shifted slightly off center with respect to conduit or tubing segment 34*a* in channel 1012. Such an on-center/off-center pairing of LED's on one side of channel 1012, with an optical sensor 1026 on the opposing side of channel 1012, has been shown to increase the reliability of determining whether a liquid conduit or tubing segment 34*a* is present or absent within channel 1012. In a series of tests in which a tubing segment 34*a* was alternately absent, present but improperly positioned, or present and properly positioned within channel 1012, signal measurements were taken by the optical sensor 1026 from the first LED 1028 and the second LED 1030. The signals received from each LED were plotted against each other, and the results are shown in FIG. 17.

Figure 17:
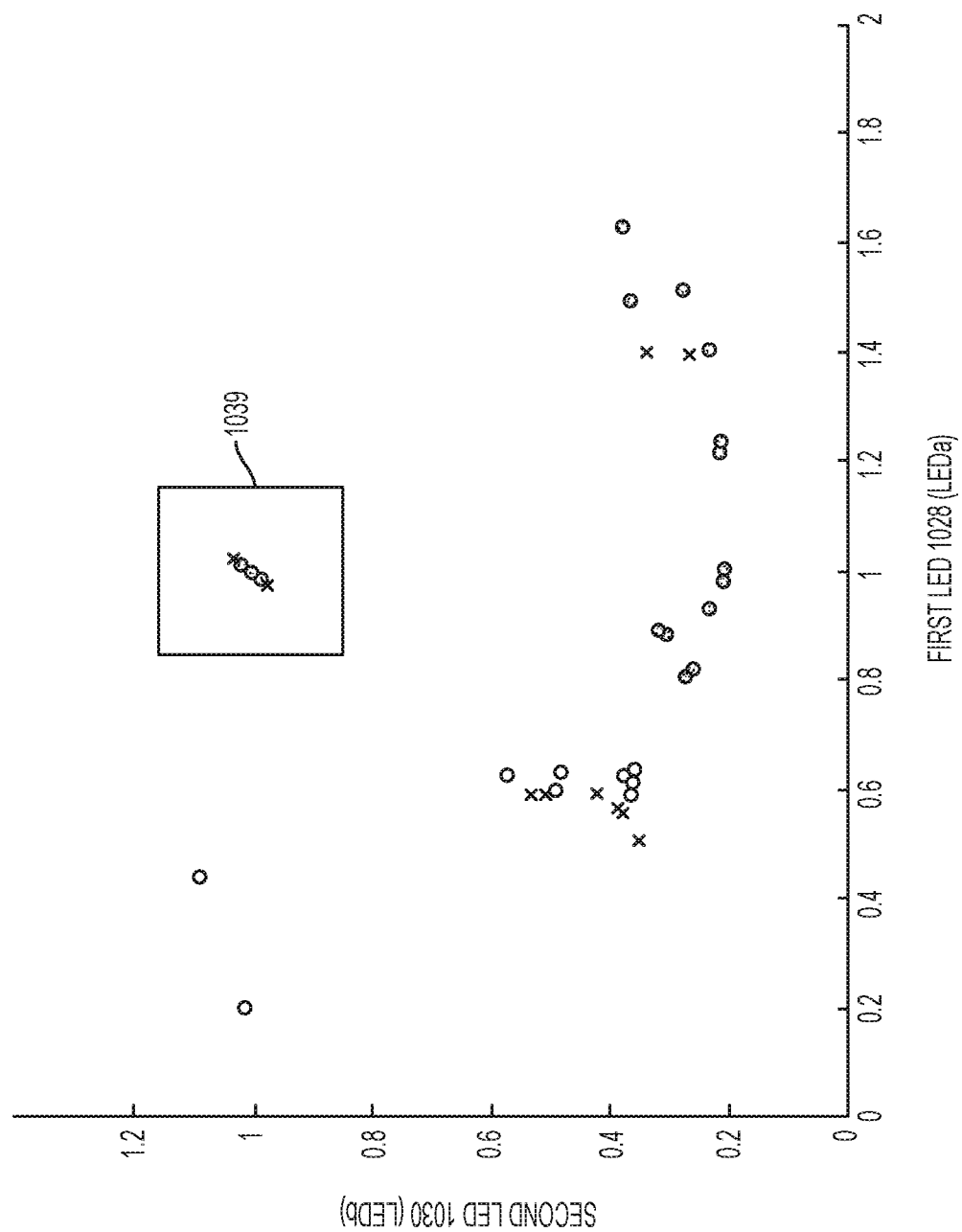
FIG. 17 is a graph showing the ability of the liquid level detector of FIG. 10 to distinguish between the presence and absence of a tubing segment within the detector.

As shown in FIG. 17, in the majority of cases in which tubing segment 34*a* was absent from channel 1012 (region 1039), the signal strength received by optical sensor 1026 attributable to LEDa 1028 (LEDa reception strength) was found not to be significantly different from the signal strength received from LEDa 1028 during a calibration step in which LEDa 1028 was illuminated in a known absence of any tubing in channel 1012. Similarly, the signal strength associated with LEDb 1030 (LEDb reception strength), was found not to be significantly different from LEDb 1030 during a calibration step in which LEDb 1030 was illuminated in a known absence of any tubing in channel 1012. Patient line state detector 1000 can reliably determine that no tube is present within channel 1012 if the ratio of LEDa 1028 to its calibration value, and the ratio of LEDb 1030 to its calibration value are each approximately 1+20%. In a preferred embodiment, the threshold ratio can be set at 1+15%. In an embodiment in which patient line state detector 1000 is used in conjunction with a peritoneal dialysis cycler 14, LEDa 1028 and LEDb 1030 values within region 1039 of FIG. 17, for example, can be used to indicate the absence of tube segment 34*a* from channel 1012. The cycler 14 controller can be programmed to pause further pumping actions and inform the user via user interface 144 of the need to properly position the distal end of patient line 34 within patient line state detector 1000.

The configuration and alignment of the three LED's and the optical sensor 1026 described above is capable of generating the required data using translucent or transparent fluid conduits (e.g. tubing segment 34*a*) having a wide range of translucence. In additional testing, patient line state detector 1000 was found to be capable of providing reliable data to distinguish liquid from air in a fluid conduit, or the presence or absence of a fluid conduit, using samples of tubing having significantly different degrees of translucence. It was also capable of providing reliable data regardless of whether the PVC tubing being used was unsterilized, or sterilized (e.g., EtOx-sterilized).

In certain embodiments, the fluid conduit or patient line 34 may be transparent or translucent to light in a first spectrum or spectrums. The fluid conduit may also be opaque to light in a second spectrum or spectrums. The LEDs used in the patient line state detector 1000 may be selected based on the light transmission characteristics of the fluid conduit. For example, a first of the LEDs may be selected to emit light in the first spectrum or at least one of the first spectrums. A second of the LEDs may be selected to emit light in the second spectrum or spectrums. For example, a fluid conduit may be transparent or translucent at least to light in the infrared spectrum while being opaque to light in at least the ultraviolet spectrum. A first of the LEDs (e.g. LED 1030) may emit light in the infrared spectrum while a second of the LEDs (e.g. LED 1028) may be selected to emit light in the ultraviolet spectrum. The optical sensor 1026 may be capable of sensing light emitted from each of the LEDs or multiple sensors may be included in the optical sensor 1026 may be included with one for each LED wavelength. Filters or the like may be included as part of the optical sensor 1026 to filter out light of undesired wavelengths. Trim (short and long pass) and band pass filters may for example be used.

In embodiments where LED 1028 emits ultraviolet light and LED 1030 emits infrared light, the optical sensor 1026 may sense light from both LEDs 1028, 1030 when tubing is absent from the channel 1012. When tubing (e.g. patient line 34) is installed in the channel 1012, light from the ultraviolet LED 1028 may be blocked by the presence of the tubing. Light from the infrared LED may be registered by the optical sensor 1026 as the tubing may be translucent or transparent to that light spectrum. Thus the control system 16 may declare tubing to be present when the intensity of light from the ultraviolet LED 1028 drops below a predefined threshold (which may be set to be indicative of light being totally or near totally obscured) and light from the infrared emitting LED 1030 is above at least a certain threshold. This may additionally be beneficial as the patient line state detector 1000 may be capable of discriminating between tubing of an expected type or composition and undesired or unauthorized tubing types. The patient line state detector 1000 may also have greater robustness in discriminating between various scenarios. For example, use of an ultraviolet and infrared LED may aid a patient line state detector 1000 in determining whether a foreign object or detritus is present instead of an improperly positioned tube. Thus any troubleshooting and prompting generated for display on the user interface may be streamlined and the cycler 14 may provide a better patient experience. This may be particularly desirable as patients typically set up therapy as they are preparing for bed every night and prolonged troubleshooting may result in lost sleep which can be source of frustration.

In some embodiments, matching the light sources to characteristics of the tubing may allow one of the LEDs 1028, 1030 used for tubing detection to be omitted. An infrared emitting LED 1030 may be omitted and the control system 16 may only monitor for light from the ultraviolet emitting LED to be blocked (e.g. decreasing below some predefined threshold) to determine whether tubing is present or appropriately installed in the channel 1012.

The measurements taken by the optical sensor 1026 from the LED's 1028, 1030, 1032 can be used as inputs to a patient line state detector algorithm in order to detect the state (or presence) of tubing segment 34*a*. Besides detecting a full, empty, or absent tubing segment 34*a*, the result of the algorithm may be indeterminate, possibly indicate movement or improper positioning of the tubing segment 34*a* within the patient line state detector 1000, or possibly the presence of a foreign object in channel 1012 of patient line state detector 1000. Manufacturing variations may cause the output from the LED's 1028, 1030, 1032 and the sensitivity of optical sensor 1026 to vary among different assemblies. Therefore, it may be advantageous to perform an initial calibration of the patient line state detector 1000. For example, the following procedure may be used to obtain calibration values of the LED's and sensor:

(1) Ensure that no tubing segment 34*a* is loaded in the patient line state detector 1000.

(2) Poll the optical sensor 1026 in four different states:
  (a) no LED illuminated
  (b) first LED 1028 (LEDa) illuminated
  (c) second LED 1030 (LEDb) illuminated
  (d) third LED 1032 (LEDc) illuminated (3) Subtract the 'no LED illuminated' signal value from each of the other signal values to determine their ambient corrected values, and store these three readings as 'no-tube' calibration values.

Once calibration values for the LED's and sensor are obtained, the state of tubing segment 34*a* may then be detected. In this illustrative embodiment, the patient line state detector algorithm performs a state detection in a test as follows:

(1) Poll the optical sensor 1026 in four different states:
  (a) no LED illuminated
  (b) first LED 1028 (LEDa) illuminated
  (c) second LED 1030 (LEDb) illuminated
  (d) third LED 1032 (LEDc) illuminated (2) Subtract the 'no LED illuminated' value from each of the other values to determine their ambient corrected values.

(3) Calculate the relative LED values by dividing the test values associated with each LED by their corresponding calibration ('no-tube') values.

Results:
  If the ambient corrected LEDa 1028 value is less than 0.10, then there may be a foreign object in the detector, or an indeterminate result can be reported to the user.
  If the ambient corrected LEDa 1028 and LEDb 1030 values fall within ±15% of their respective stored calibration (no-tube) values, then report to the user that no tubing segment is present in the detector.
  If the ambient corrected LEDb 1030 value is equal to or greater than about 40% of its stored calibration ('no-tube') value,
    (a) check the signal associated with LEDc 1032
    (i) if the ambient corrected signal associated with LEDc 1032 is equal or greater than about 150% of its calibration ('no-tube') value, then report to the user that the tubing segment is empty.
    (ii) If the ambient corrected signal associated with LEDc 1032 is equal to or less than about 125% of its calibration ('no-tube') value, then report to the user that the tubing segment is filled with liquid.
    (iii) Otherwise, the result is indeterminate, and either repeat the measurement (e.g., the tubing segment may be moving, may be indented, or otherwise obscured), or report to the user that the tubing segment should be checked to ensure that it is properly inserted in the detector.
  If the ambient corrected LEDb 1030 value is less than about 40% of its stored calibration ('no-tube') value, then the LEDc 1032 threshold for determining the presence of a dry tube may be greater. In an embodiment, for example, the LEDc 1032 empty tube threshold was found empirically to follow the relationship: [LEDc 1032 empty tube threshold]=−3.75×[LEDb 1030 value]+3.

Once it is determined that the tubing segment 34a has been loaded in the patient line state detector 1000, the patient line state detector algorithm can perform the following:

a) Poll the optical sensor 1026 with no LED illuminated and store this as the no LED value.

b) Illuminate LEDc 1032 c) Poll the optical sensor 1026, subtract the no LED value from the LEDc 1032 value, and store this as the initial value.

d) Begin pumping e) Poll the optical sensor 1026 and subtract the no LED value from the subsequent LEDc 1032 value.

f) If this value is less than 75% of the initial value, then conclude that tubing segment 34a is filled with liquid, stop pumping, confirm the detector state using the above procedure, and when indicated, report to the user that priming is complete. Otherwise, keep repeating the poll, calculation, and comparison. In an embodiment, the system controller can be programmed to perform the polling protocol as frequently as desired, such as, for example, every 0.005 to 0.01 seconds. In an embodiment, the entire polling cycle can conveniently be performed every 0.5 seconds.

Figure 18:
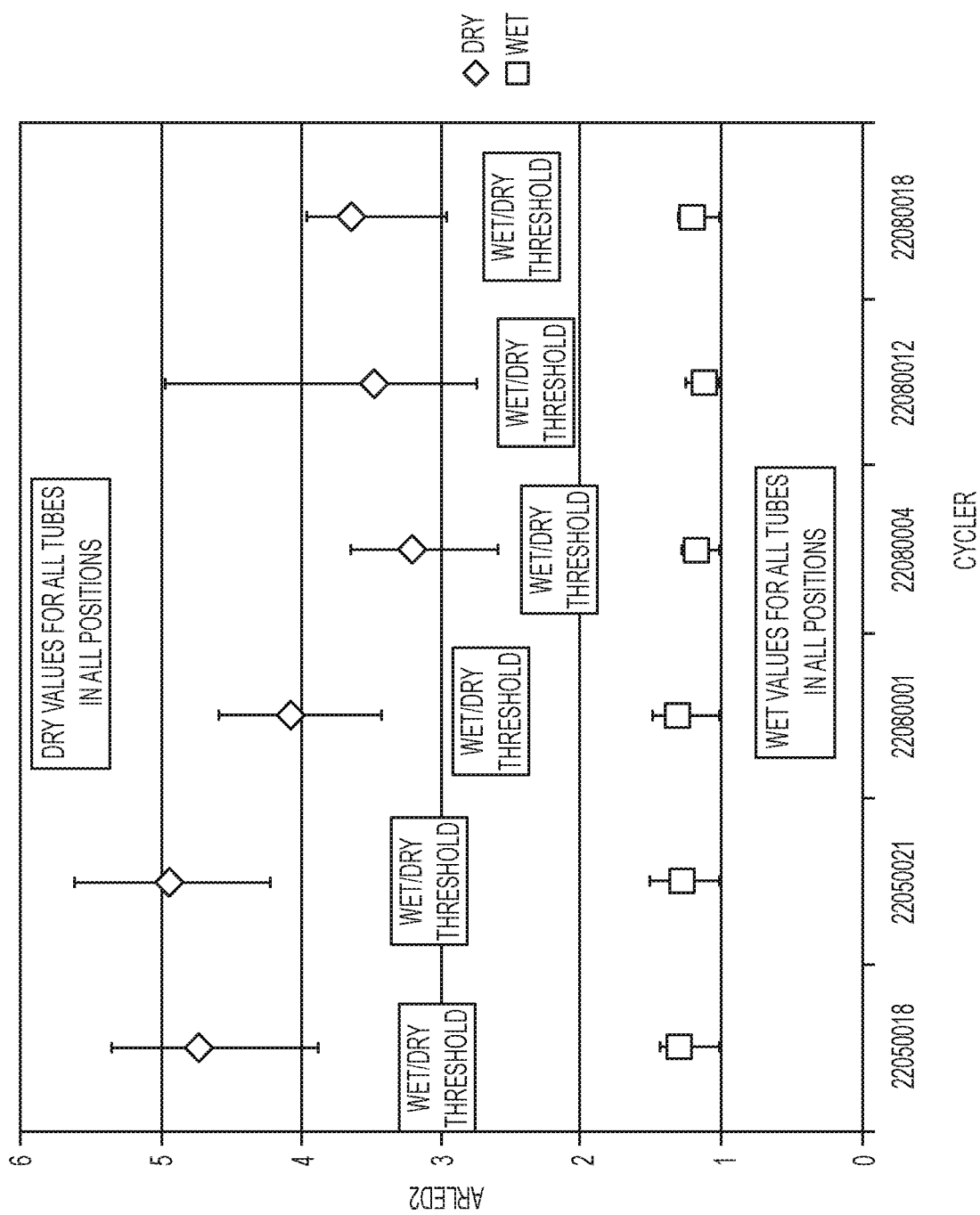
FIG. 18 is a graph showing the range of signals corresponding to a primed and a non-primed fluid line for different cyclers using the liquid detector of FIG. 10.

FIG. 18 shows the results of sample calibration procedures for six cyclers. The signal strength range that distinguishes a dry tube from a wet tube ('wet/dry threshold' ranges) is noted to vary among the different cyclers. The variations in these ranges may be due to minor variations in manufacturing, assembly and positioning of the various components. Thus at calibration, each cycler 14 may be assigned a wet/dry threshold signal strength range that optimally separates the data points generated with a dry tube from the data points generated with a wet tube.

Figure 19:
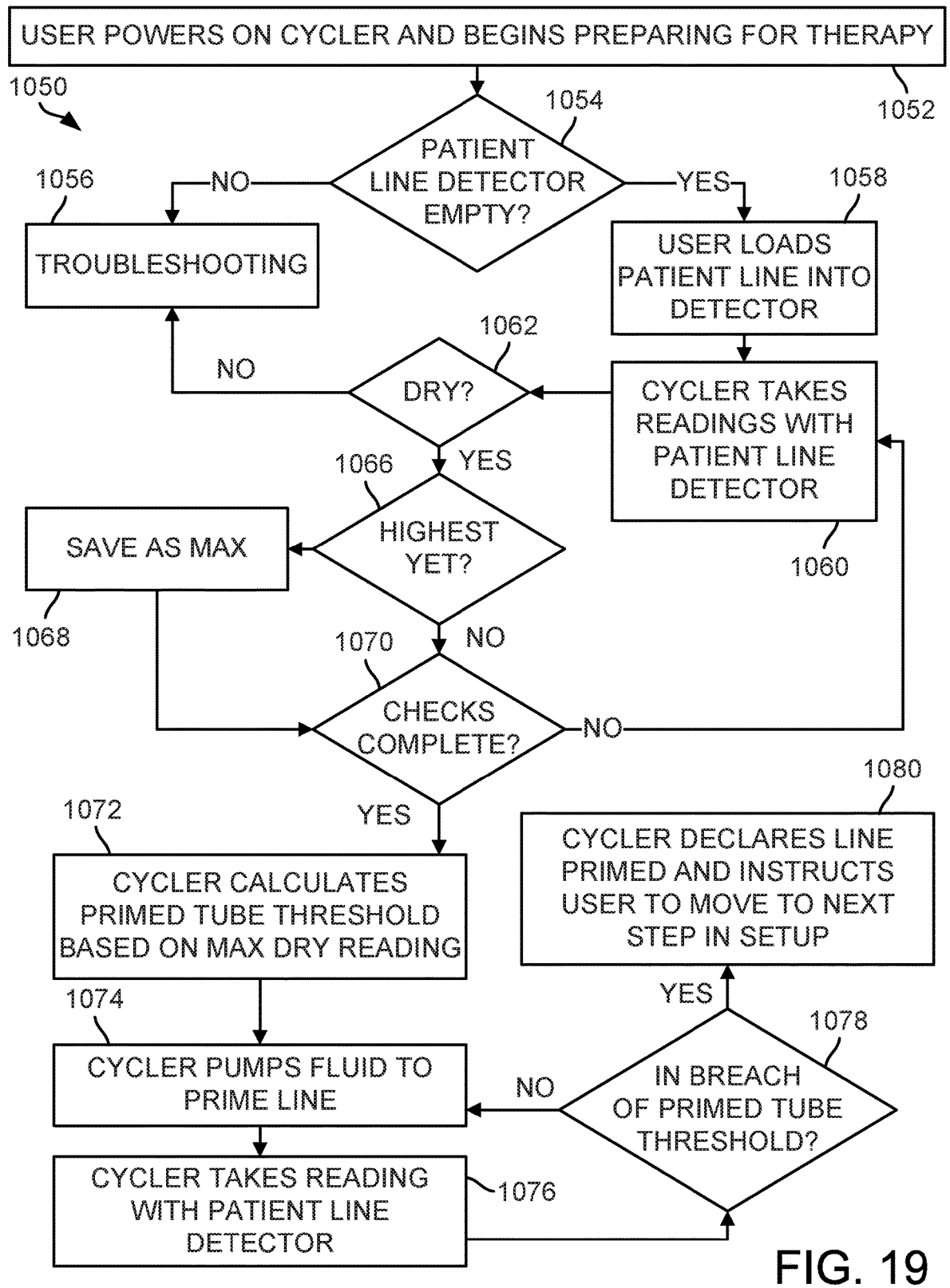
FIG. 19 is a flowchart detailing a number of example actions which may be executed to prime a fluid line.

In some examples, the threshold at which the control system 16 may register a wet or liquid filled tube may differ. For example, in some embodiments and as shown in FIG. 19, the threshold may be dependent upon a previously collected value when the tubing segment 34a was determined to be dry. This may aid the patient line state detector 1000 in more robustly determining when a transition from a dry line to a primed line occurs. Additionally, this may aid in making the patient line state detector 1000 more resistant to drift which may occur after repeated use and over time.

FIG. 19 depicts a flowchart 1050 detailing a number of actions which may be executed to prime a fluid line. As shown, in block 1052, a user may power on their cycler 14 and begin preparations for therapy. If, in block 1054, the patient line state detector 1000 is not empty, the control system 16 of the cycler 14 may enter a troubleshooting mode in block 1056. During troubleshooting, the control system 16 of the cycler 14 may generate an alert or warning and one or more message for display on a user interface of the cycler 14 suggesting actions the user may take to resolve the problem. The user may, for example be requested to remove an old line, clean the patient line state detector 1000, or check for detritus. If, in block 1054, the patient line state detector 1000 is empty, the user may load a patient line into the patient line state detector 1000 in block 1058. The cycler 14 may display a prompt instructing the user to do so. The control system 16 may use the patient line state detector 1000 to determine whether or not the patient line state detector 1000 is empty as described elsewhere herein.

The control system 16 of the cycler 14 may orchestrate collection of a state reading on the patient line 34 with the patient line state detector 1000 in block 1060. To collect this reading the control system 16 may, for example, power on LEDc 1032 and check light intensity with the optical sensor 1026. If, in block 1062, the reading is indicative that the patient line is not dry, the control system 16 of the cycler 14 may proceed to troubleshooting in block 1056. During troubleshooting, the control system 16 of the cycler 14 may generate an alert or warning and one or more message for display on a user interface of the cycler 14 suggesting actions the user may take to resolve the problem. For example, the user may be asked to remove and reload the line. In the event that the patient line state detector 1000 continues to determine a wet line is present, therapy with that set 12 may be prohibited. The user may be requested to discard the set 12 and restart with a new fresh set 12. Various guidance graphics may be generated for display on the user interface during troubleshooting.

The reading may be determined to indicate the line is dry in the event that the ratio of the reading value, to a "no tube" calibrated value conforms to a predefined range or threshold. If, in block 1062, the reading indicates that the line is dry, the control system 16 may check a characteristic of that reading against one or more criteria. For example, in the embodiment shown in FIG. 19, the control system 16 may check whether the ratio of the reading value to the "no tube" value is greater than a threshold (e.g. 1.7). The control system 16 may also check if that ratio is the largest seen for that patient line. If, in block 1066, the reading (or ratio) is the highest yet, it may be saved as a maximum value in block 1068. Alternatively, if the reading (or ratio) is not higher than the threshold (e.g. 1.7), the maximum value may be saved as the value of the threshold in block 1068.

In some embodiments, the control system 16 may require multiple readings (e.g. consecutive readings) indicative of the patient line being dry before commanding the cycler 14 to prime the patient line. If, in block 1070, a predefined number of checks have not been completed the control system 16 may return to block 1060 and collect another reading. If, in block 1070, the prerequisite number of check have been completed, the control system 16 of the cycler 14 may calculate a primed patient line threshold value in block 1072. In alternative embodiments, this primed tube threshold may be calculated at a different point in time, for example after the first reading in block 1060. In such embodiments, the primed tube threshold may be updated with each subsequent pass through block 1060.

As indicated in FIG. 19, the primed line threshold may be based on the maximum value saved in block 1068. In certain examples, the primed tube threshold may be calculated as the greater of a predefined value (e.g. 1.7) and the output of a predefined equation. For instance, an equation using a constant added to a percentage of the maximum value from block 1068 may be used. In a specific embodiment, the equation may be Primed_tube_threshold=1.1+(Max Dry Tube [from block 1068]*0.2).

In block 1074, the control system 16 of the cycler 14 may command the cycler 14 to pump fluid through the patient line 34. In block 1076, the control system 16 of the cycler 14 may command a reading to be collected with the patient line state detector 1000. If, in block 1078, the reading indicates that the primed tube threshold has not been breached, the control system 16 of the cycler 14 may return to block 1074 and command additional pumping. Alternatively, readings may be collected while pumping is occurring. If, in block 1078, the reading indicates that the primed tube threshold has been breached, the control system 16 of the cycler 14 may declare that the line is primed in block 1080. The control system 16 of the cycler 14 may also orchestrate communication to the user to indicate to the user (e.g. via a screen or prompt generated on the user interface) to move on to the next step in setup of the therapy in block 1080. The reading may be determined to indicate that the threshold has been breached when the ratio of the reading to the "no tube" value is greater than the primed tube threshold calculated in block 1072.

In some embodiments, the control system 16 of the cycler 14 may limit the volume of fluid which is acceptable to displace during priming of a patient line 34. For example, there may be a volume threshold (e.g. line volume in a nominal patient line 34) imposed on the volume displaced to prime the patient line 24 and the control system 16 may generate a notification or alert when this volume is breached. The user may be instructed (via a GUI) to check the line to ensure that the line is not completely primed and is properly seated in the patient line state detector 1000. The control system 16 of the cycler 14 may allow the cycler 14 to return to block 1074 and continue priming upon receipt of a user input that the line is properly seated and not completely primed. In some embodiments, there may be a cap to the number of times continued pumping may be allowed. If this cap is reached or exceeded, the control system 16 of the cycler 14 may trigger an alert or error and prevent the cycler 14 from conducting a therapy with that set 12.

Figure 20:
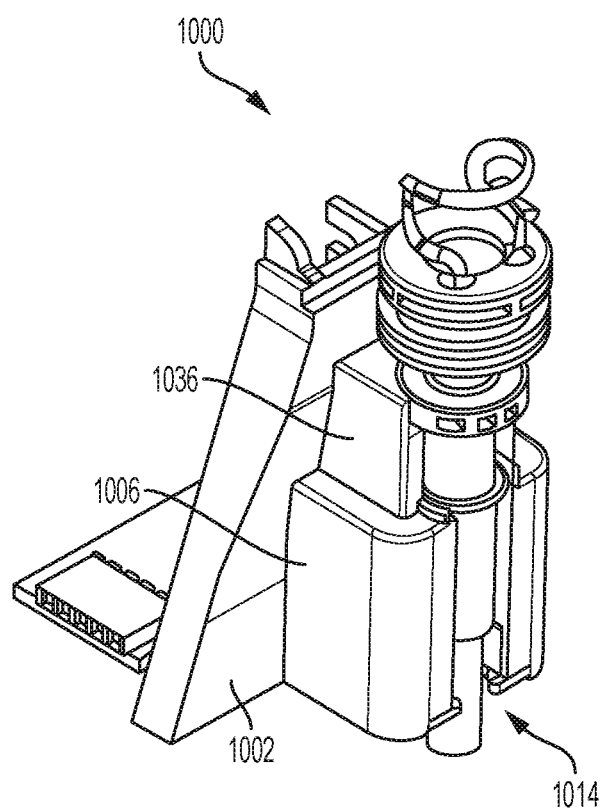
FIG. 20 is a perspective view of an alternative configuration of a liquid level detector.

FIG. 20 shows a perspective view of a second configuration of a patient line state detector 1000. Two or more different patient line state detector configurations may be necessary to accommodate varying types of patient connectors. In this illustrative embodiment, the second configuration patient line state detector 1000 may include most of the same components as in the first configuration patient line state detector 1000. However, in order to accommodate a different type of connector, the second configuration may include a raised element 1036 above housing 1006, rather than the stabilizing tab 1010 found in the first configuration patient line state detector 1000. The raised element 1036 may generally conform to the shape of a standard patient line connector cap or connector flange.

In accordance with an aspect of the disclosure, detector housing 1006 may not include a tube portion 1014. Therefore, open cavity 1008 may be arranged to allow placement of detector circuit board 1022 so that the LED's and optical sensor may be positioned next to a translucent or transparent patient line connector 36 rather than a section of tubing. Channel 1012 consequently may be shaped differently to accommodate the transmission of LED light through connector 36.

In some embodiments, the fluid line detector 1000, rather than being used to detect the prime state of a segment of tubing, may use one or more LED's simply to detect the presence of the line segment in the fluid line detector 1000. The presence and proper seating of the line segment may be determined using fewer LED's than the embodiments described above.

In other embodiments, another type of sensor may be used to detect one or more condition of interest related to a fluid line such as a fluid line 30 or patient line 34. For example, a fluid line detector 1000 may include an electrical or magnetic contact switch or physically actuated switch such as a microswitch. The fluid line detector 1000 may detect the presence of a fluid line connector 36 or tubing segment 34a with actuation of such a switch. In some embodiments, two or more such switches may be used in a fluid line detector 1000. This may provide some redundancy or may be used to detect that multiple line segments of interest are properly seated. In an embodiment, a microswitch may, for example, be disposed in the channel 1012 so as to be actuated when the tubing segment 34a is seated in the channel 1012. Alternatively or additionally, a microswitch may be disposed, for example in a cradle 1016, to be actuated when a fluid line connector 36 is positioned in the fluid line detector 1000. In such embodiments, a cycler 14 controller (e.g. control system 16) may not allow priming of the tubing until all of the one or more switches indicate that the line and/or connector are properly seated in the fluid line detector 1000.

In another embodiment, the fluid line detector 1000 may sense the presence and state of a tube segment using a split ring resonator-based sensor. Such a detector is shown and described, for example, in U.S. patent application Ser. No. 14/341,207, filed Jul. 25, 2014, and entitled System, Method and Apparatus for Bubble Detection in a Fluid Line Using a Split-Ring Resonator, the contents of which are hereby incorporated by reference.

In some embodiments, the sensor(s) in the fluid line detector 1000 may be configured to detect the type of fluid line 34 installed in the fluid line detector 1000 (e.g., adult vs. pediatric size, opaque vs. translucent, etc.). The fluid line connector 36 and/or tubing segment 34a may, for example, have different differentiating features (e.g. different geometries) depending on the type of line being used. The sensor(s) in the fluid line detector 1000 may be configured to discern which type of line is present based upon sensing the presence or absence of such differentiating features.

For example, if a fluid line detector 1000 is configured to use microswitches, the switches may be configured to detect the presence of a particular type of fluid line connector 36. The fluid line connectors 36 on each type of line may include different features (e.g. different projections or voids, or differently disposed projections or voids). When installed in the fluid line detector 1000, the fluid line connector 36 may trip a specific switch or group of switches to detect the presence of the particular type of fluid line connector 36. If an invalid or unexpected combination of switches are actuated, or if a combination of switches is actuated that does not correspond to a fluid line geometry intended for use with the cycler or medical device, the controller may be programmed to notify the user of the incompatible or improper line. This arrangement of switches may also be used to detect improperly seated lines or connectors.

In other embodiments, the completion of priming of a fluid line 34 with a liquid can be inferred by detecting when liquid flow has replaced air flow in the lumen of the distal end of the line 34 or in a connector 36 at the distal end of the line 34. The difference in resistance to flow between air and liquid in a lumen of a given caliber can be detected by monitoring the flow rate of the liquid when under a predetermined force (by gravity or by active pumping). The caliber of the lumen may be chosen to optimize the differentiation between air flow and liquid flow. In most cases, this will involve introducing a flow restriction near or at the end of the fluid line 34 or a distal connector. A properly chosen flow restriction at the distal end of the line 34 or connector 36 will permit relatively unrestricted air flow out of the line 34, while impeding liquid flow enough to slow the advance of a liquid column through the line 34. This increased liquid flow resistance or change in pressure drop across the restriction zone can be detected by the use of a flow meter in the liquid flow path, or by measurement of the change in volume of liquid in an upstream pumping chamber over a predetermined time interval. In an embodiment in which a membrane-based positive displacement pump is used, the rate of change of liquid volume in a pumping chamber can be calculated by monitoring the pressure in an actuation chamber of the pump (through the application of Boyle's Law or other pressure-volume relationships of an ideal gas in a closed space, for example), the pressure in the actuation chamber providing an indication of the pressure in the pumping chamber of the pump. A controller receiving liquid flow data from the fluid line, or computing liquid flow out of the pumping chamber through measurement of pressure changes in the pumping chamber, can compare the liquid flow to a pre-determined value. Alternatively, the controller can calculate a drop in liquid flow rate, and compare the change in flow rate to an expected value to declare that the fluid line has been primed with liquid.

The flow-impeded zone may comprise a constriction, obstruction, partial blockage, or restriction (e.g. orifice) which allows for the easy passage of air, but impedes the passage of a liquid such as dialysate solution. The feature may comprise a short segment of distal tubing or fluid connector 36 that includes a region having a smaller cross-sectional area than that of the fluid conduit in the upstream or proximal section of the fluid line. The term 'restriction' as used herein is meant to encompass any feature that increases resistance to flow differentially between air and liquid in a fluid conduit.

In an embodiment, the restriction may be removable from the distal end of the fluid line or an associated connector. For instance, the restriction may be included in a plug or cap which remains in place on the fluid line 34 during priming of the fluid line 34. The restriction may, for example, be molded as part of the plug or cap during manufacture. This restriction may be a recess, void, channel or other flow path in the plugging portion of the cap. The plugging portion of the cap may be inserted into the fluid conduit directly, or into the lumen of an attached connector 36. Alternatively, the plug or plugging portion of the cap may be sized to have a diameter which is smaller than the diameter of the fluid conduit or its associated connector lumen. When the cap is installed the plug portion may obstruct part of the fluid conduit, creating a small gap between the outer surface of the plug and the inner wall of the conduit, and thereby generate the restriction.

When pumping fluid to prime a fluid line 34, fluid will move at a relatively high flow rate as air is freely displaced out of the fluid line 34 through the restriction. The increase in impedance when liquid reaches the restriction will slow the flow rate. Flow rate may be monitored by a controller receiving input from one or more sensors as priming occurs. When the flow rate drops, it may be inferred that the air has been pushed out of the line beyond the restriction, and that a given applied force is now attempting to push liquid through the restriction. In some embodiments, the controller may employ additional logic to discern between a number of possible causes for reduced liquid flow rates in the fluid line.

In embodiments in which the restriction is an orifice (positioned either at the distal end of the fluid line or within an attached connector), the cross-sectional area of the orifice opening may be selected so as to generate a desired amount of impedance to liquid flow. Additionally, the pumping pressure chosen may be selected such that the flow rates when pumping air and when pumping liquid are detectably different.

It may be desirable to place the restriction slightly upstream of the point at which a fluid line 34 would be fully primed. This would allow for some liquid to flow through the restriction during a determination or recognition period over which a controller is determining whether the impedance to liquid flow has changed. Having a line volume downstream from the restriction provides a fluid buffer to accumulate additional liquid while the controller makes a determination of priming and stops the fluid pump, thus helping to prevent overflow of liquid out of the distal end of the fluid line. Preferably, the delay characteristics of the pumping system in responding to a change in liquid flow impedance are determined empirically for the system once the system parameters have been selected. These parameters may include, for example, the force or pressure applied by the pump, the frequency of pumping volume determinations or flow rate measurements, the caliber and length of the tubing, the properties of the flow restriction, and the response times of the controller and pump. Once the system characteristics are determined, the post-restriction tubing or connector buffer volume needed to prevent overflow can be determined empirically. For illustrative purposes, if the flow rate through a restriction is 30 mL/min, and it takes about 5 seconds for the controller and pump to recognize and respond to the impedance change, a hysteretic fluid volume of about 2.5 mL would be moved while the system responds to the impedance change. In such an embodiment, the downstream volume beyond the restriction may be set to approximately 2.5 mL or slightly more than 2.5 mL. This may serve to help minimize the amount of air left in the fluid line 34 during priming without over-priming the line and causing fluid to overflow the line and spill out.

Alternatively, the restriction may extend along the line axis for a distance that allows the restriction flow pathway volume to approximately the flow volume anticipated while the impedance change is being detected. This embodiment may be desirable when the restriction is included in a fluid line cap.

In some embodiments, an air permeable, but substantially liquid impermeable material may be used to restrict liquid flow. Such a material may allow for relatively unrestricted passage of air, but restrict or prevent passage of liquid. This material may be placed at the end of the fluid line 34 and may allow for air to be pumped out of the line 34, but prevent overflowing and spilling when the line 34 reaches primed state. The material may then, for example, be removed along with a fluid line cap when a user uncaps the line. In some specific embodiments, the material used may be Goretex or another similar material (e.g., breathable materials that may be either microporous or macroporous). As above, a drop in flow rate when the liquid reaches the material would signal that the fluid line 34 has reached a primed state.

Figure 21:
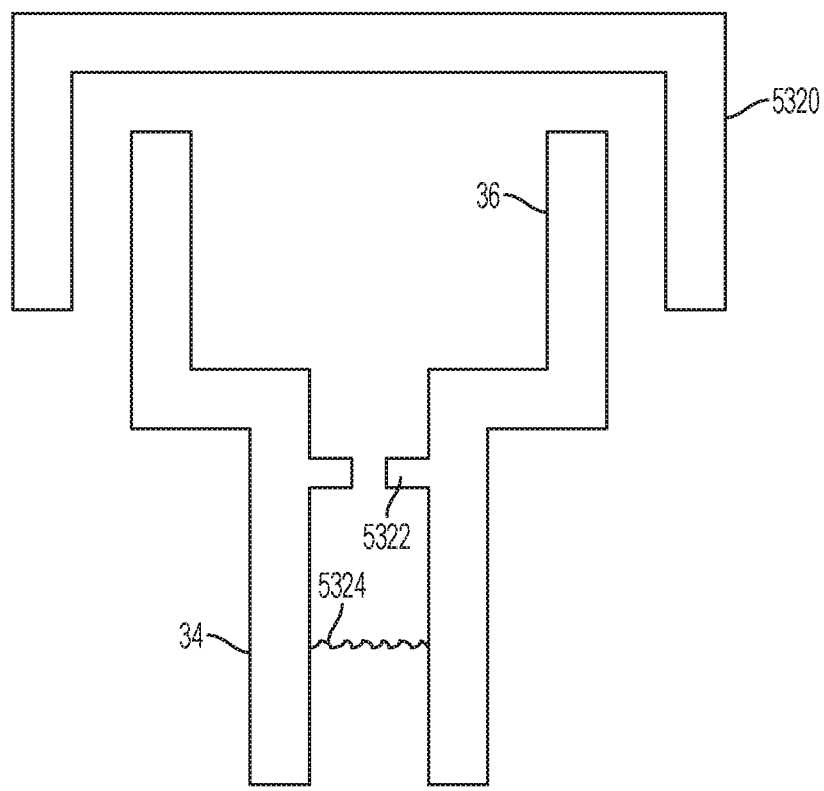
FIG. 21 and FIG. 22 show an embodiment of a fluid line cap, fluid line, and a fluid line connector.
Figure 22:
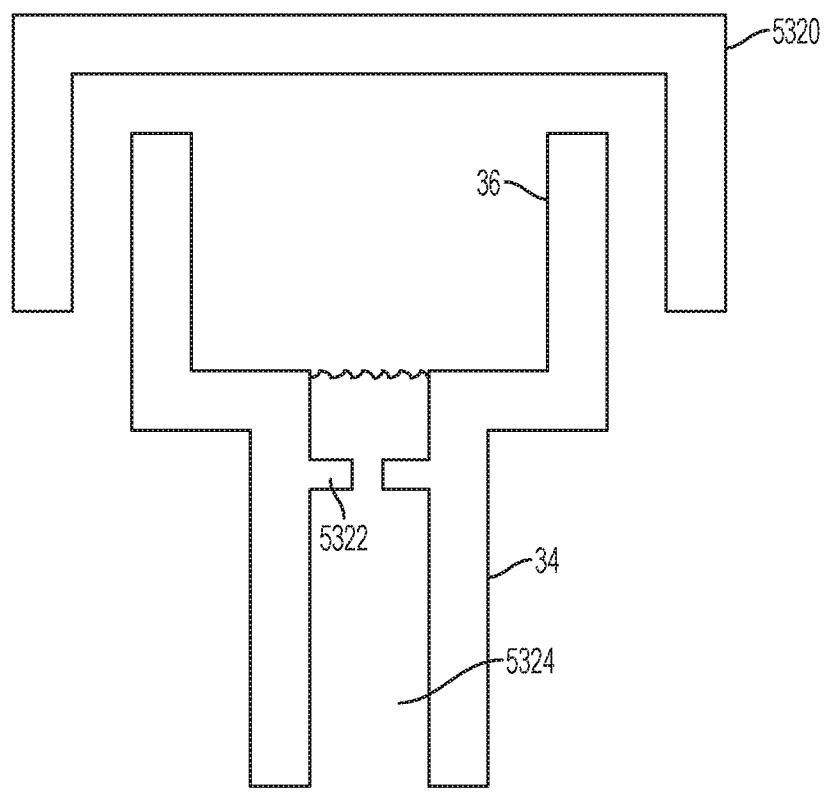

FIG. 21 and FIG. 22 depict an example representative embodiment of a fluid line cap 5320, fluid line 34 and a fluid line connector 36. As shown, a restriction 5322 is included in the fluid line 34. In other examples, the cap 5320 may have inside surface features that incorporate restriction similar to the restriction 5322 shown. In this example, the restriction 5322 is optionally positioned such that there is some fluid line 34 volume downstream of the restriction 5322. The restriction 5322 in the example embodiment is a section in the fluid path with a reduced cross sectional area. In other examples, the restriction 5322 may be an orifice or a membrane which is slit, perforated, or otherwise has one or more pores to increase the resistance to the passage of liquid.

As illustrated in FIG. 21 the liquid 5324 in the fluid line 34 has not yet reached the restriction 5322. At this point, the flow rate of fluid through the fluid line 34 (e.g. a stratified column of air and liquid) may be relatively high. Once the air column has been evacuated, liquid 5324 in the fluid line 34 will have reached the restriction 5322. At this point, the flow rate will drop due to an impedance change. Some liquid 5324 will continue to flow as the cycler determines that the impedance has changed. Once detected, the cycler may be programmed to stop the flow of liquid through the line. At this point, and as shown in FIG. 22, the liquid 5324 will have substantially primed the entire line 34 including the line 34 volume downstream of the restriction 5322. The controller may be programmed to notify a user that the line 34 has been primed and is ready for connection to a catheter or other device in preparation for treatment.

Figure 23:
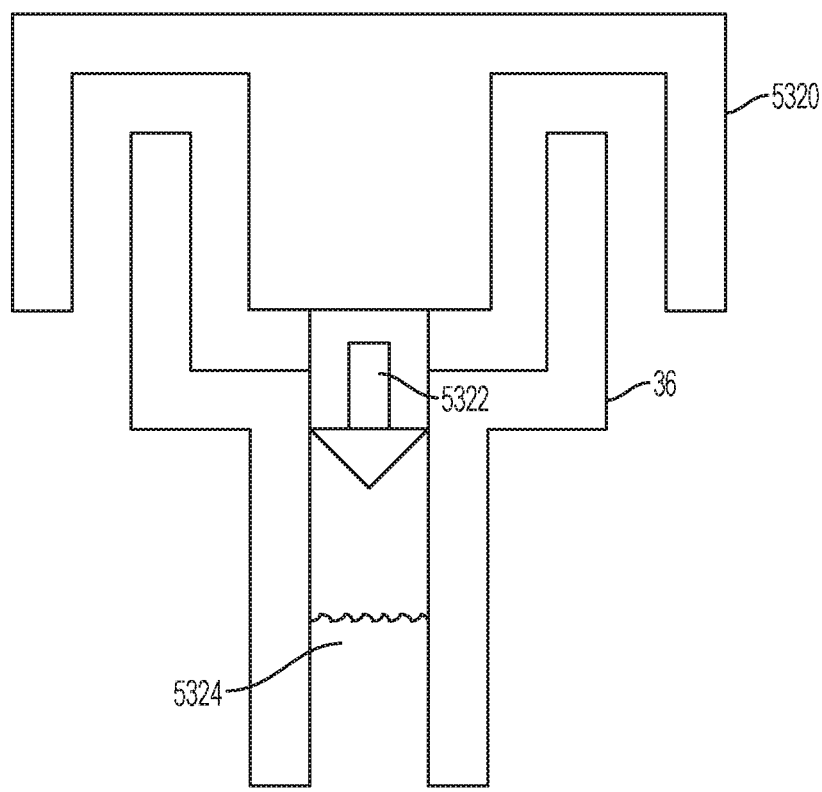
FIG. 23 and FIG. 24 show another embodiment of a fluid line cap, fluid line, and a fluid line connector.
Figure 24:
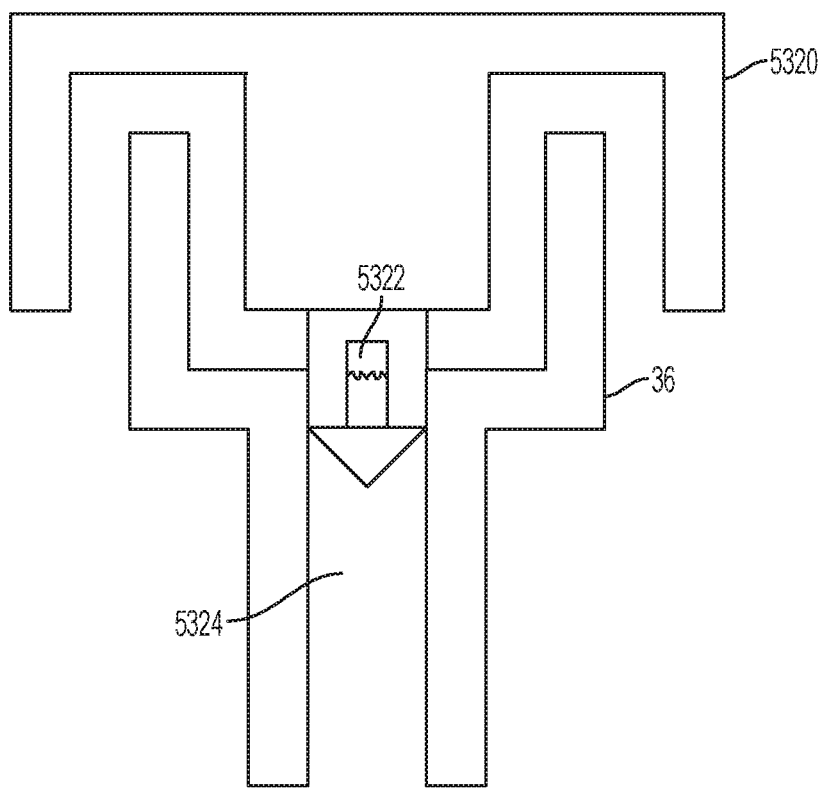

FIG. 23 and FIG. 24 depict another example embodiment of a fluid line 34, fluid line connector 36, and a fluid line cap 5320. As shown, there is no restriction in the fluid line 34 or fluid line connector 36. The fluid line cap 5320 acts as plug for the fluid line 34 and includes a restriction 5322. In the example embodiment, the restriction 5322 may comprise a notch, groove, or channel recessed into the circumference of the plugging portion of the fluid line cap 5320. The restriction 5322 may be sized to allow air to be pumped out of the line at relatively little resistance during priming, but impede the flow of liquid when the air column has been fully expelled. When the controller determines that the line 34 is primed, the controller may then instruct a user to remove line cap 5320 and attach the fluid line connector 36 to an indwelling catheter or other similar device.

As illustrated in FIG. 23 the liquid 5324 in the fluid line 34 has not yet reached the restriction 5322. At this point, the flow rate of fluid (gas plus liquid) through the fluid line 34 may be relatively high. Once the liquid 5324 in the fluid line 34 reaches the restriction 5322, the flow rate will drop due to an impedance change between gas flow and liquid flow through the restriction 5322. Some liquid 5324 will continue to flow as the controller determines that the impedance has changed. Once detected, the controller will stop the flow of liquid 5324 through the line. At this point, and as shown in FIG. 24, the liquid 5324 will have substantially primed the entire line 34. The controller may then notify a user that the line 34 has been primed and that the line cap 5320 may be removed. With the cap 5320 removed, any excess liquid 5324 pumped may fill the volume of the fluid line 34 which was previously occupied by the plugging portion of the fluid line cap 5320. Alternatively, the controller may be programmed to receive a signal from the user that the cap 5320 has been removed, and the controller may be programmed to cause the cycler or pump to advance a small quantity of liquid down the fluid line 34 to top off the distal end of the line 34 or connector 36 prior to its use.

Figure 25:
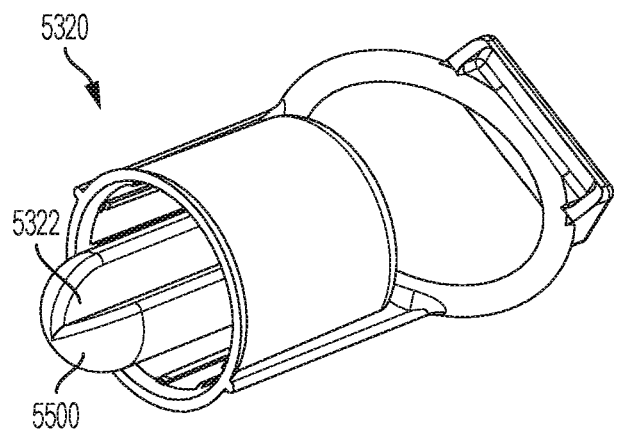
FIG. 25 shows an example of a fluid line cap including a notch.

FIG. 25 depicts a representative example of a fluid line cap 5320 with a plug or plug portion 5500. As shown, the fluid line cap 5320 includes a plug portion 5500 which may be sized to project into and snuggly fit in the fluid conduit of the fluid line 34. A notch is recessed into the plug portion 5500 of the fluid line cap 5320 and serves to create a restriction 5322 when the fluid line cap 5320 is installed on the end of the fluid line 34 or a line connector 36. In the illustration, the notch is substantially triangular in cross-section. In other embodiments, any suitable cross sectional geometry may be used. Other arrangements may be used; such as, for example, a narrow lumen through the length of an otherwise solid plug 5500. Also as shown in FIG. 25, the end of the plug portion 5500 which extends into the fluid flow path may optionally be rounded (or tapered). This may facilitate placing a fluid line cap 5320 onto a fluid line 34.

Figure 26:
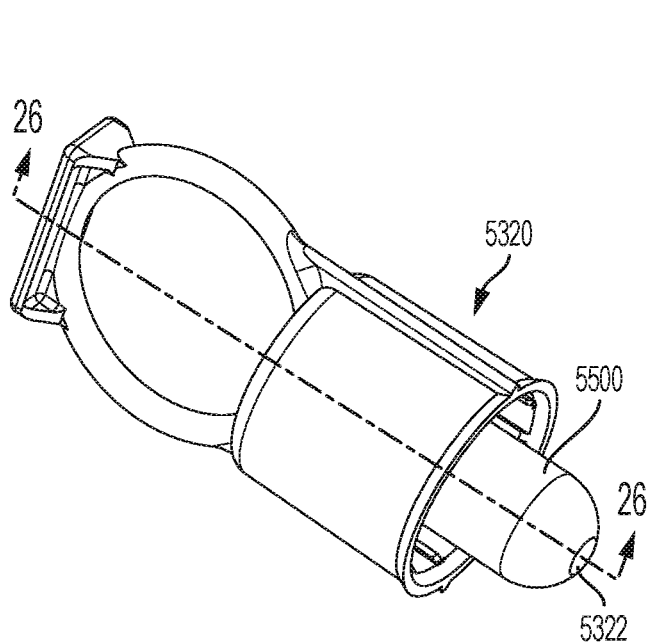
FIG. 26 shows an example of a fluid line cap including a restriction.
Figure 27:
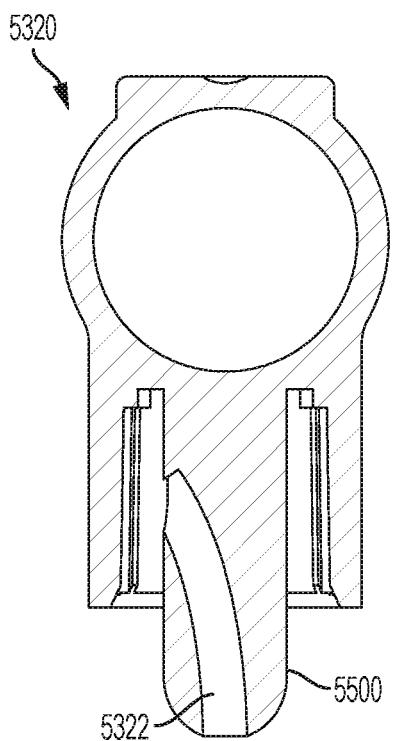
FIG. 27 shows a cross section of a fluid line cap taken at line 26-26 of FIG. 26.

FIG. 26 depicts another embodiment of a fluid line cap 5320. Similar to FIG. 25, the fluid line cap 5320 includes a plug portion 5500 which may be sized to project into and snuggly fit in the fluid conduit of the fluid line 34. The restriction 5322 in FIG. 26 is a flow path which allows for fluid to flow from the fluid conduit of the fluid line 34, through the interior of the plug portion 5500 and into an inner volume of a fluid line connector 36. A cross-sectional view taken on a longitudinal plane of the example fluid line cap 5320 is shown in FIG. 27. The cross-sectional area of the flow path is less than that of the fluid line 34 fluid conduit.

Figure 28:
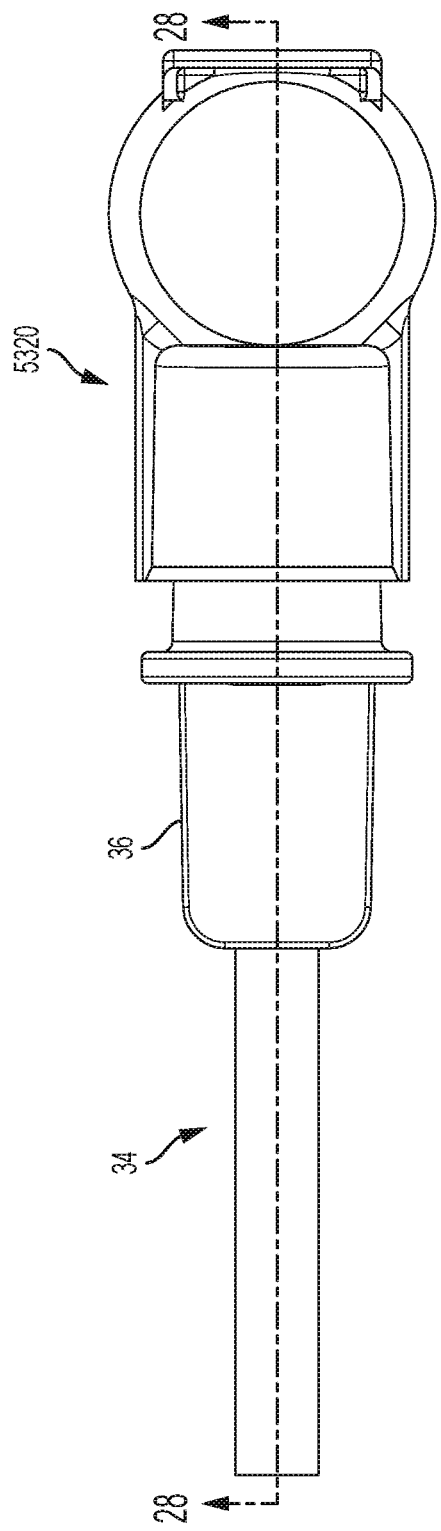
FIG. 28 shows an example of a fluid line cap installed on a fluid line connector of fluid line.
Figure 29:
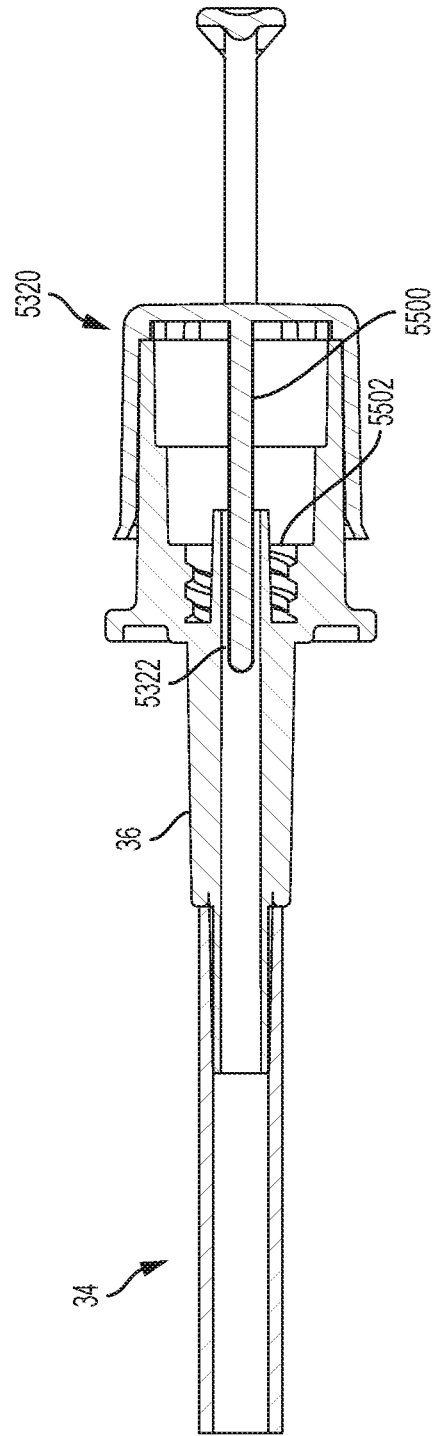
FIG. 29 shows a cross section of the fluid line cap, fluid line, and fluid line connector of FIG. 27 taken at line 28-28 of FIG. 28.

FIG. 28 shows another embodiment of a fluid line cap 5320 installed on the fluid line connector 36 of a fluid line 34. As shown in FIG. 29 a cross-section taken at line 28-28 of FIG. 28, the fluid line connector 36 includes a segment which extends into the fluid conduit of the fluid line 34. The tube of the fluid line 34 may be fixed (e.g. glued, bonded, welded, etc.) to the fluid line connector 36. The fluid line connector 36 includes a flow path which leads from the fluid conduit of the fluid line 34 to a connector fitting 5502 included as part of the fluid line connector 36. The connector fitting 5502 may mate with a cooperating feature on a complementary connector (e.g., of a patient's indwelling catheter) to allow for fluid to be delivered and/or withdrawn from a site (e.g., peritoneal cavity or another body cavity). In the example embodiment, a Luer lock is shown; however, any of a number of other suitable connectors or fittings may be used.

The cap in the example embodiment includes a plug portion 5500. The plug portion 5500 is sized so as to extend into the fluid pathway of the fluid line connector 36. In the example embodiment, the diameter of the plug portion 5500 is smaller than the diameter of the flow path in the fluid line connector 36. When the plug portion 5500 of the fluid line cap 5320 is installed into the flow path of the fluid line connector 36, a small gap remains between the outer surface of the plug portion 5500 and the inner wall of the flow path. Thus, the plug portion 5500 serves to reduce the cross-sectional area of the flow path and creates a restriction 5322.

As described above, in some embodiments, a small gap between the outer surface of the plug portion 5500 and the inner wall of the flow path need not be present. Instead, the plug portion 5500 may fit snuggly in the flow path. A notch may be recessed into the outer surface of the plug portion 5500 to reduce the cross sectional area of the flow path and create the restriction, or an otherwise solid plug inserted in the connector lumen may include a narrow flow path to create a restricted flow path.

In one aspect, the change in fluid flow impedance may be determined based on a flow rate estimation during the progression of a pumping stroke from a pumping cassette. Additionally, a stroke displacement estimation may be used to discriminate between a change in flow rate due to an empty pumping chamber and a change in flow rate due to liquid 5324 reaching the restriction 5322 in the fluid line 34. Estimation of flow rate and stroke displacement during the progression of a pumping stroke will be further described below.

In some embodiments, a controller algorithm to estimate stroke displacement may be used to stop a stroke prior to the full chamber being delivered to a fluid line. That is, a controller may be programmed to instruct a pump to perform partial delivery strokes during priming so as to avoid having the pump diaphragm reach an end-of-stroke position. This may help to ensure that any drop in flow rate is not attributable to a pump diaphragm having reached the rigid pumping chamber wall at the end of a pump stroke. When the controller determines that the volume of fluid pumped per unit of time has decreased beyond a predetermined threshold value, the liquid 5324 in the fluid line 34 may be assumed to have reached the restriction 5322, and the line may be deemed to have been primed.

In other embodiments, a controller may direct the pump to pump fluid until a flow rate discontinuity is detected. At this point, the controller may direct the pumping apparatus (e.g., cycler) to attempt to deliver a small volume of fluid from another pump chamber of a dual pump cassette. In the event that the flow discontinuity was due to the pump diaphragm reaching end-of-stroke, flow from the other chamber should be greater than the ending flow rate from the first chamber. If the discontinuity is due to a primed line condition, flow rate from the other chamber will be similar to that of the ending flow rate from the first chamber. Thus the device controller may determine that the line has been primed.

In some embodiments, a nominal interior tubing volume for a fluid line 34 may be determined. A controller may then direct a pump to move fluid down the line 34 until the volume of the fluid primed down the line 34 is within one chamber volume of the nominal tubing volume. Once the remaining volume of the line 34 is determined to be less than the volume of a full pump stroke, the controller may register the next flow rate discontinuity as indicative of a primed condition.

The nominal interior volume of the line 34 may be determined based on the type of set being used. For example, a pediatric set may have a smaller interior tubing volume than an adult set. In some embodiments, a device controller may determine this information via an optical sensor. In some embodiments the set may include a bar code or data matrix that can be read by a camera on the pumping device or cycler, the encoded information allowing the controller to determine the type of set installed. A controller receiving input from a camera may also be capable of detecting different features or geometries of a portion of a set. For example, the fluid line connector 36 may have unique, detectable geometries detectable by a fluid line detector 1000 as described above. Alternatively, a user may manually enter information on a user interface of the pumping device about the type of tubing or pump cassette in use.

Line Priming

To reduce the time needed to prime a line, it may be preferable to have the pumping device actively prime the line rather than allowing gravity-based flow to accomplish the task. In Gravity-based priming, which is a standard procedure, fluid flow through the line depends on the head height of the reservoir in which the priming fluid is stored. The flow rate of the fluid through the line during prime will increase with an increase in head height of the prime fluid reservoir. Actively priming the line through the use of one or more pumps may allow a pumping device or cycler to simulate various head heights for a reservoir while the reservoir remains in a fixed position. If the fluid pump includes pumping chamber(s) which are actuated pneumatically, the amount of pneumatic pressure applied to the pumping chamber(s) via a diaphragm can control the flow rate to a desired value without relocating the priming reservoir. Avoiding having to relocate a fluid reservoir helps to keep the pumping or dialysis system compact, reduces the setup burden on a user, and allows for relative fast priming of fluid lines.

In some embodiments in which flow paths and chambers of a pump cassette are to be primed with fluid, priming may be performed in two or more phases. In the first phase, the line may be primed with a lower effective head height (e.g., lower pump pressure or by passive gravity flow) than in a second or subsequent phase. Turbulence of a higher flow rate may lead to introduction or trapping of air bubbles or pockets in various locations or recesses of a pump cassette. This problem can be mitigated by allowing the pump cassette to be primed slowly, and subsequently proceeding to a more rapid priming process once the fluid reaches a fluid line downstream of the cassette. The length of the first phase may be predetermined empirically through testing, or by measurement of the amount of fluid volume moved from the priming reservoir to the cassette or attached fluid line.

Reducing air bubble formation or trapping is desirable for a number of reasons, including that a line priming sensor may detect the air bubbles and lead the controller to stop the process and issue a user alert.

The duration of the first priming phase may depend on the type of cassette being used (number of pumps and valves, and complexity of flow paths), and the volume of its interior fluid paths and pump chambers. Preferably, the priming is performed to allow fluid to displace air from the cassette from bottom to top, and at a sufficiently slow rate to ensure that most or all of the enclosed air is forced into the attached fluid line and then expelled into the environment.

Figure 30:
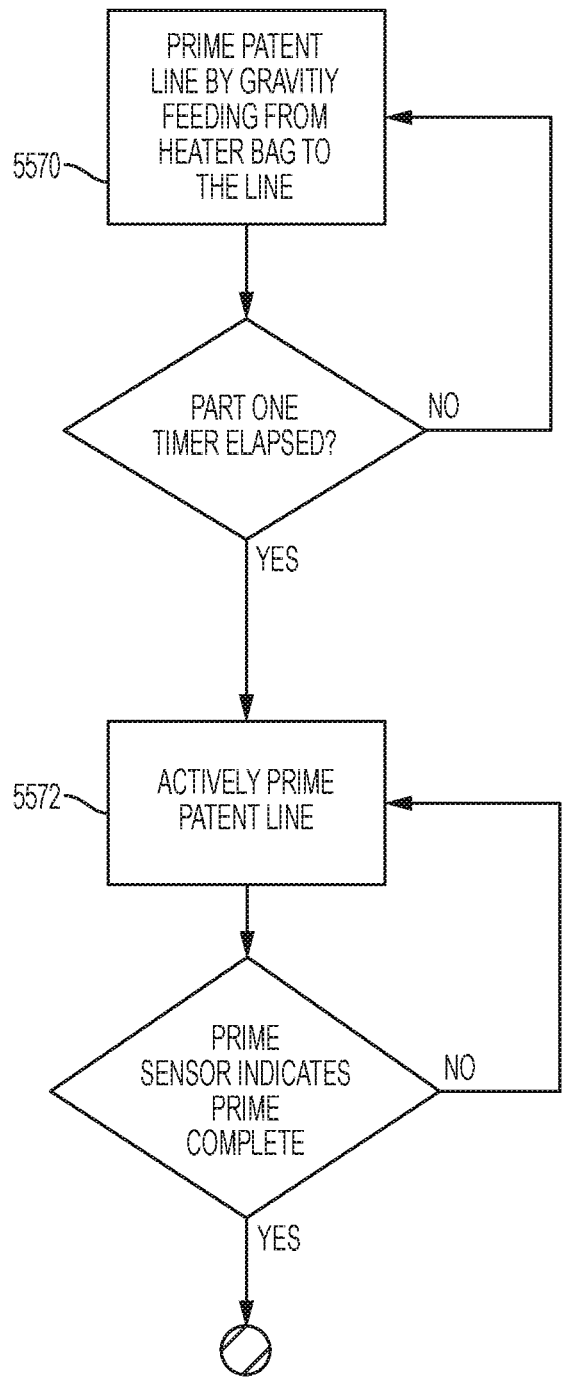
FIG. 30 shows a flowchart outlining a number of steps which may be used by a cycler to prime a line with a two part prime.

FIG. 30 depicts a flowchart detailing a number of steps a controller may use to control the priming of a cassette and attached line using two phases. In the example, the line primed is a patient line extending from a pump cassette to a patient. The steps shown may readily be generalized for priming of other fluid lines. As shown, in step 5570, the cycler begins priming the patient line by gravity feeding fluid into the line through the cassette. In the example embodiment, the priming reservoir is a heater bag. Free flow may be accomplished by controlling valves of the cassette so that an open flow path between the patient line and the heater bag is created.

When the priming operation begins in step 5570, the controller may initiate a timer for the first priming phase. The duration of the first priming phase can be determined empirically through testing so that it is sufficient to ensure that any air in the cassette has been flushed out of the cassette and into the patient line. Using the example of the cassette depicted in FIG. 3, this duration may range from 1-3 seconds. In one embodiment, the timer may be set to about 1.6 seconds. In control system embodiments that do not use a timer, but rather transition out of the first priming phase when a pre-determined volume of fluid has been transferred out of the priming reservoir, the pre-determined volume may amount to approximately 1-3 ml, given the example cassette shown in FIG. 3.

When the timer has elapsed (or the pre-determined volume has been transferred), the pumping apparatus or cycler may proceed to step 5572 and begin actively priming the line. Preferably step 5572 primes the line at a faster flow rate than step 5570. The cycler may continue to actively prime the patient line until a prime sensor indicates that the line has reached a fully primed state. In some embodiments, the controller may then signal a user on a user interface that the priming has completed and the primed line is ready to be connected.

Set Loading and Operation

Figure 31:
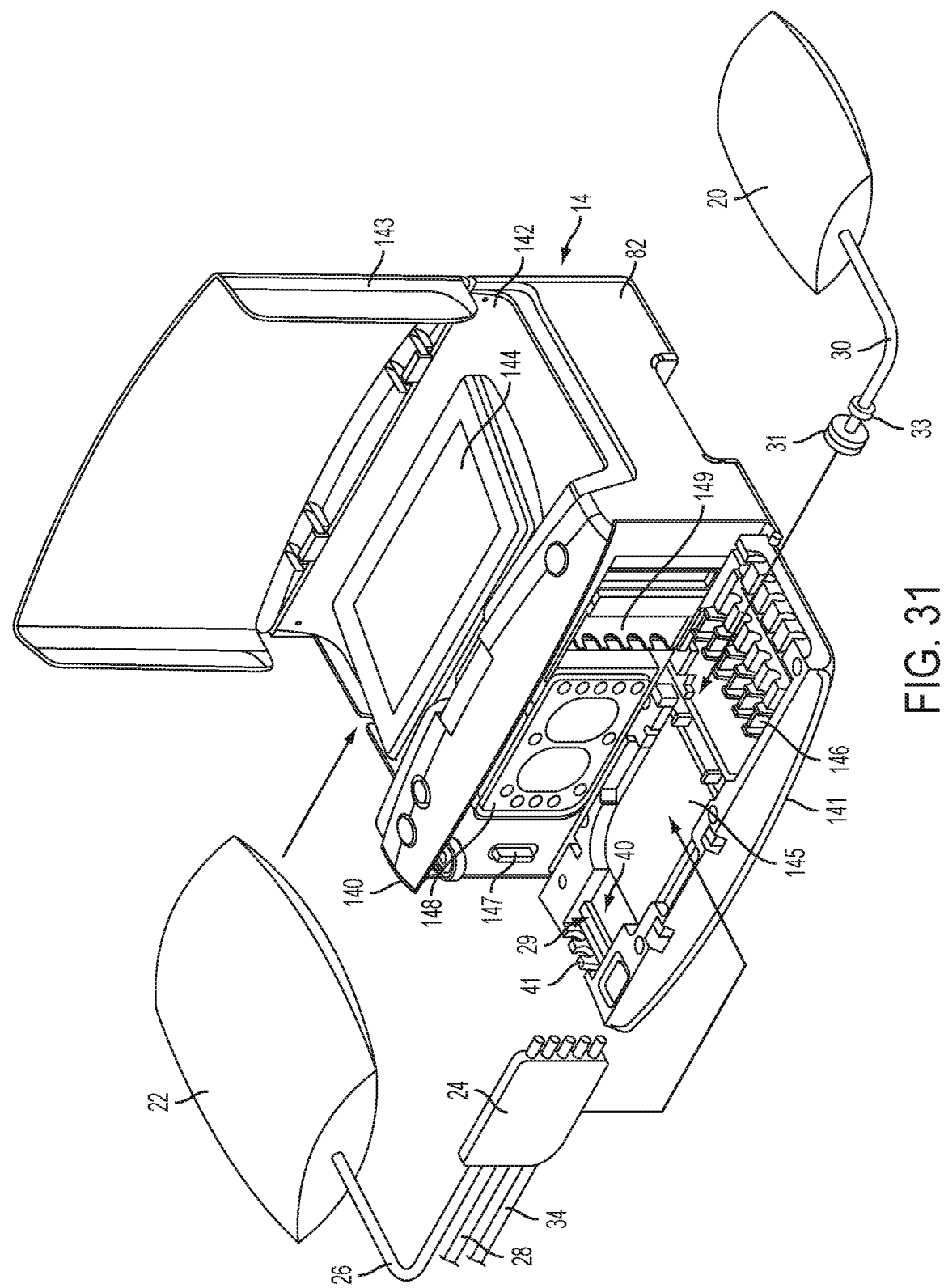
FIG. 31 is a perspective view of the APD system of FIG. 1 with the door of the cycler in an open position.

FIG. 31 shows a perspective view of the APD system 10 of FIG. 1A with the door 141 of the cycler 14 lowered into an open position, exposing a mounting location 145 for the cassette 24 and a carriage 146 for the solution lines 30. In this embodiment, the door 141 is mounted by a hinge at a lower part of the door 141 to the cycler housing 82. When loading the set 12, the cassette 24 is placed in the mounting location 145 with the membrane 15 and the pump chamber side of the cassette 24 facing upwardly, allowing the portions of the membrane 15 associated with the pump chambers and the valve ports to interact with a control surface or gasket 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the disclosure, when the cassette 24 is placed in the mounting location 145, the patient, drain and heater bag lines 34, 28 and 26 are routed through a channel 40 in the door 141 to the left as shown in FIG. 31. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating, yet occlude the lines when the cycler 14 is powered down (and/or not operating properly). Occlusion of the lines may be performed by pressing on the lines, or otherwise pinching the lines to close off the flow path in the lines. Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface 148 e.g., by an air bladder, spring or other suitable arrangement in the door 141 behind the mounting location 145 that squeezes the cassette 24 between the mounting location 145 and the control surface 148. The control surface 148 may be a membrane or gasket. This containment of the cassette 24 may press the membranes 15 and 16 into contact with walls and other features of the base member 18, thereby isolating channels and other flow paths of the cassette 24. The control surface or gasket 148 may include a flexible or elastomeric material, e.g., a sheet of silicone rubber or other material, either involving the entire gasket, or at least portions of the gasket that serve as pump or valve control regions. The gasket 148 is positioned adjacent the membrane 15 and can selectively move portions of the membrane 15 to cause pumping action in the pump chambers 181 and opening/closing of valve ports of the cassette 24. The control gasket 148 may be associated with the various portions of the membrane 15, e.g., the two may be placed into intimate contact with each other, so that portions of the membrane 15 move in response to movement of corresponding portions of the control gasket 148. For example, the membrane 15 and control gasket 148 may be positioned close together, and a suitable vacuum (or pressure that is lower relative to ambient) may be introduced through vacuum ports suitably located in the control gasket 148 (preferably near the respective pump and valve control regions to evacuate air from between the gasket 148 and cassette membrane 15 at least specifically in the control regions) A negative pressure is maintained between the membrane 15 and the control gasket 148 so that the membrane 15 and the control gasket 148 are essentially stuck together, at least in regions of the membrane 15 that require movement to open/close valve ports and/or to cause pumping action. In another embodiment, the membrane 15 and control gasket 148 may be adhered together, or otherwise suitably associated.

In some embodiments, the surface of the control gasket 148 facing the corresponding cassette membrane overlying the pump chambers and/or valves is textured or roughened. The texturing creates a plurality of small passages horizontally or tangentially along the surface of the gasket when the gasket is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, ideal gas law calculations), by minimizing trapped pockets of air between the gasket and the membrane. It may also improve the detection of any liquid that may leak into the potential space between the gasket and the cassette membrane. In an embodiment, the texturing may be accomplished by masking the portions of the gasket mold that do not form the portions of the gasket corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Figure 32:
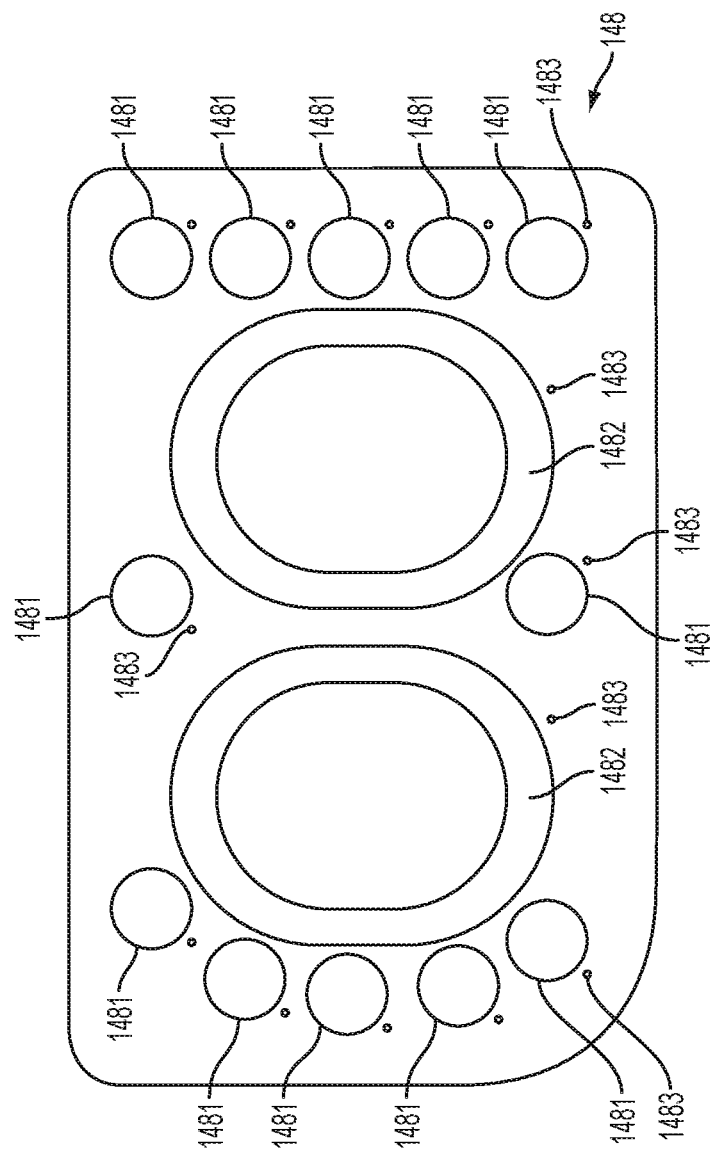
FIG. 32 is a front view of a control surface of the cycler for interaction with a cassette in the FIG. 31 embodiment.

FIG. 32 shows a plan view of the control gasket 148 of the cycler 14 that interacts with the pump chamber side of the cassette 24 (e.g., shown in FIG. 6) to cause fluid pumping and flow path control in the cassette 24. When at rest, the control gasket 148, which may include a sheet of silicone rubber, may be generally flat. Valve control regions 1481 may (or may not) be defined in the control gasket 148, e.g., by a scoring, groove, rib or other feature in or on the sheet surface, and be arranged to be movable or elastically deformable/stretchable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet or gasket 148 at the pump control regions 1482 need not necessarily be stretched or otherwise resiliently deformed during pumping operation.

Typically, the control gasket 148 is constructed from a single material, so that it can be readily formed from a mold. The flat portions of the gasket 148 help to compress and seal the cassette membrane 15 against the border or perimeter walls of the cassette, sealing liquid flow paths within the cassette 24 when it is pressed against the control surface/gasket 148 and its supporting mating block 170. Similarly, as the cassette 24 is pressed against the control surface/gasket 148, the fluid control ports 173A, 173C can be sealed from each other, so that the control chambers 171A, and 2746 can be individually and independently pressurized with positive or negative pneumatic pressure.

Alternatively, the movable portions of the control gasket 148, such as the pump control regions 1482 and valve control regions 1481 may comprise a material with different thickness, elasticity and/or durometer values than the flat portions of the gasket 148. The different materials can be fused together in a molding or overmolding operation, or can be solvent-bonded together, or can be attached using an adhesive. The pump control regions 1482 and valve control regions 1482 of the gasket 148 preferably are constructed of elastomeric material of a thickness and elasticity to permit their adequate movement in response to positive or negative actuation pressure, in order to move the associated pump and valve portions of the cassette membrane 15 a desired amount.

Each of the regions 1481 and 1482 may have an associated vacuum or evacuation port 1483 that may be used to remove all or substantially all of any air or other fluid that may be present between the membrane 15 of cassette 24, and the control gasket 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control gasket 148 will not be pressed into contact with a wall or other relatively rigid feature of the cassette 24. For example, in accordance with one aspect of the disclosure, one or both of the pump chambers of the cassette 24 may include a vacuum vent clearance region formed adjacent the pump chamber. In this illustrative embodiment as shown in FIGS. 3 and 6, the base member 18 may include vacuum vent port clearance or extension features 182 (e.g., recessed areas that are fluidly connected to the pump chambers) adjacent and outside the oval-shaped depressions forming the pump chambers 181 to allow the vacuum vent port 1483 for the pump control region 1482 to remove any air or fluid from between membrane 15 and control gasket 148 without obstruction. The extension feature may also be located within the perimeter of pump chamber 181. However, locating vent port feature 182 outside the perimeter of pump chamber 181 may preserve more of the pumping chamber volume for pumping liquids, e.g., allows for the full footprint of pump chamber 181 to be used for pumping. Preferably, extension feature 182 is located in a vertically lower position in relation to pump chamber 181, so that any liquid that leaks between membrane 15 and control gasket 148 is drawn out through vacuum port 1483 at the earliest opportunity. Similarly, vacuum ports 1483 associated with valves 1481 are preferably located in a vertically inferior position with respect to valves 1481.

Figure 33:
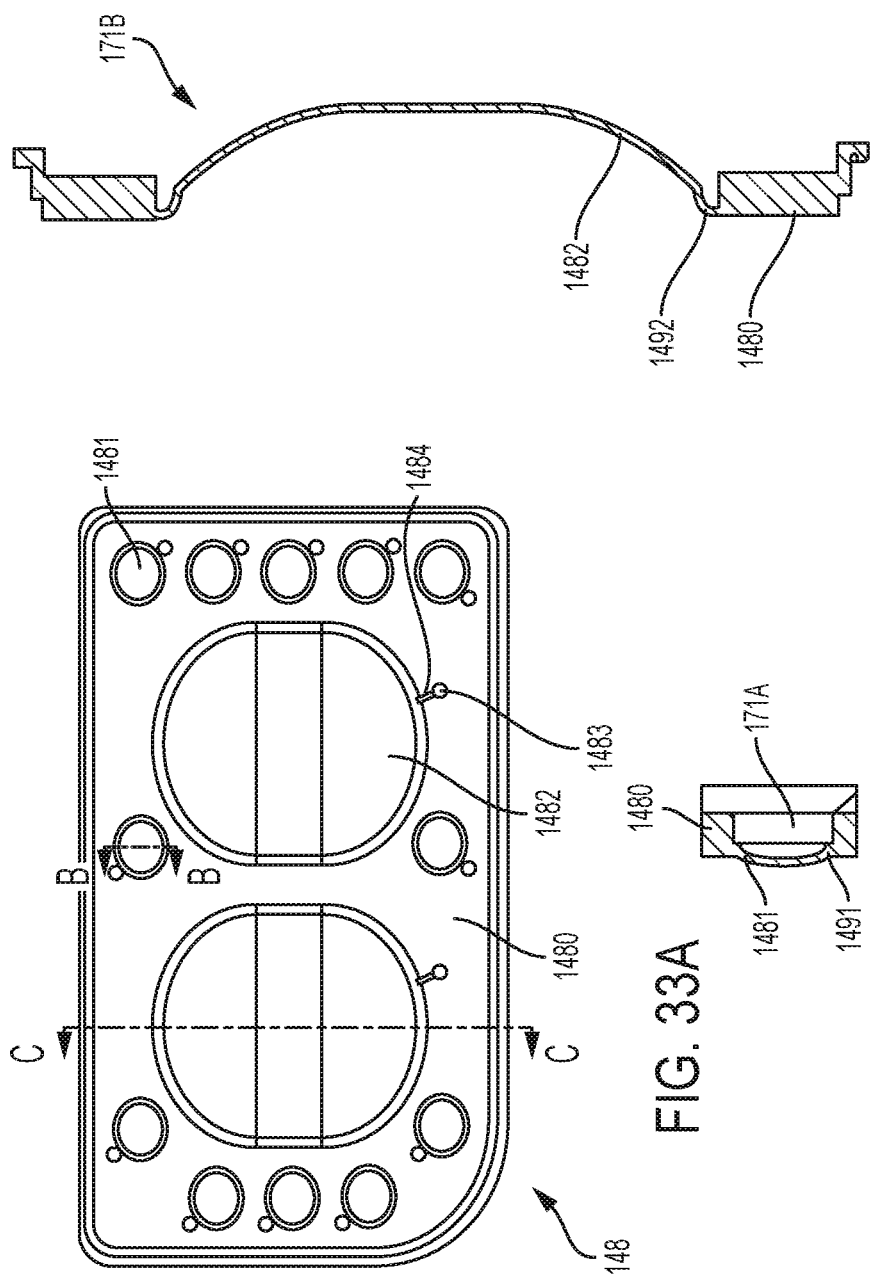
FIG. 33A is a front view of an embodiment of a control surface of the cycler.
FIGS. 33B-C depict selected cross-sectional views of FIG. 33A.

FIG. 33A-C shows that control gasket 148 may optionally be constructed or molded to have a rounded transition between the base element 1480 of control gasket 148 and the actuation portions of its valve and pump control regions 1481, 1482. These junctions or channels 1491 and 1492 may be molded with a small radius to transition from base element 1480 to valve control region 1481 and pump control region 1482, respectively. A rounded or smooth transition helps to prevent premature fatigue and fracture of the material comprising control gasket 148, and may improve its longevity. In an optional embodiment, radial channels 1484 lead from vacuum ports 1483 to the pump control regions 1482 and valve control regions 1481, and may need to be lengthened somewhat to accommodate the transition feature. Junctions or channels 1491 and 1492 function as vacuum channels, transmitting and distributing the vacuum being applied through the pressure delivery block to the potential spaces between the pump control regions 1482 and valve control regions 1481 and the corresponding pump and valve portions of the cassette membrane 15. These vacuum channels optionally may also be used to transmit positive pressure to the potential spaces between gasket control regions and the corresponding cassette membrane regions in order to aid in separating the cassette from the pressure delivery block when desired. The example vacuum channels 1491 and 1492 run along the periphery or perimeter of the pump control regions 1482 or valve control regions 1481 of the gasket 148, and help allow a more uniform application of vacuum.

Although not required, these vacuum channels 1491 and 1492 may optionally extend along the circumference of the periphery of the pump and valve control regions of gasket 148, as shown, for example, in FIG. 133A-C. For either a pump control region 1482 or a valve control region 1481 of the gasket 148, the channel 1484 corresponding to a particular control region may be radially oriented to connect a nearby gasket vacuum port 1483 to channel 1491 or 1492 that extends along a perimeter of its associated gasket control region. Although the vacuum channel 1491, 1492 need not completely encircle its associated pump or valve control region to ensure uniform application of vacuum to the entire surface of the control region, a circumferential arrangement also serves the purpose of providing a flexible mechanical transition between the base element 1480 of gasket 148 and the body of the gasket control region 1481 or 1482.

Figure 34:
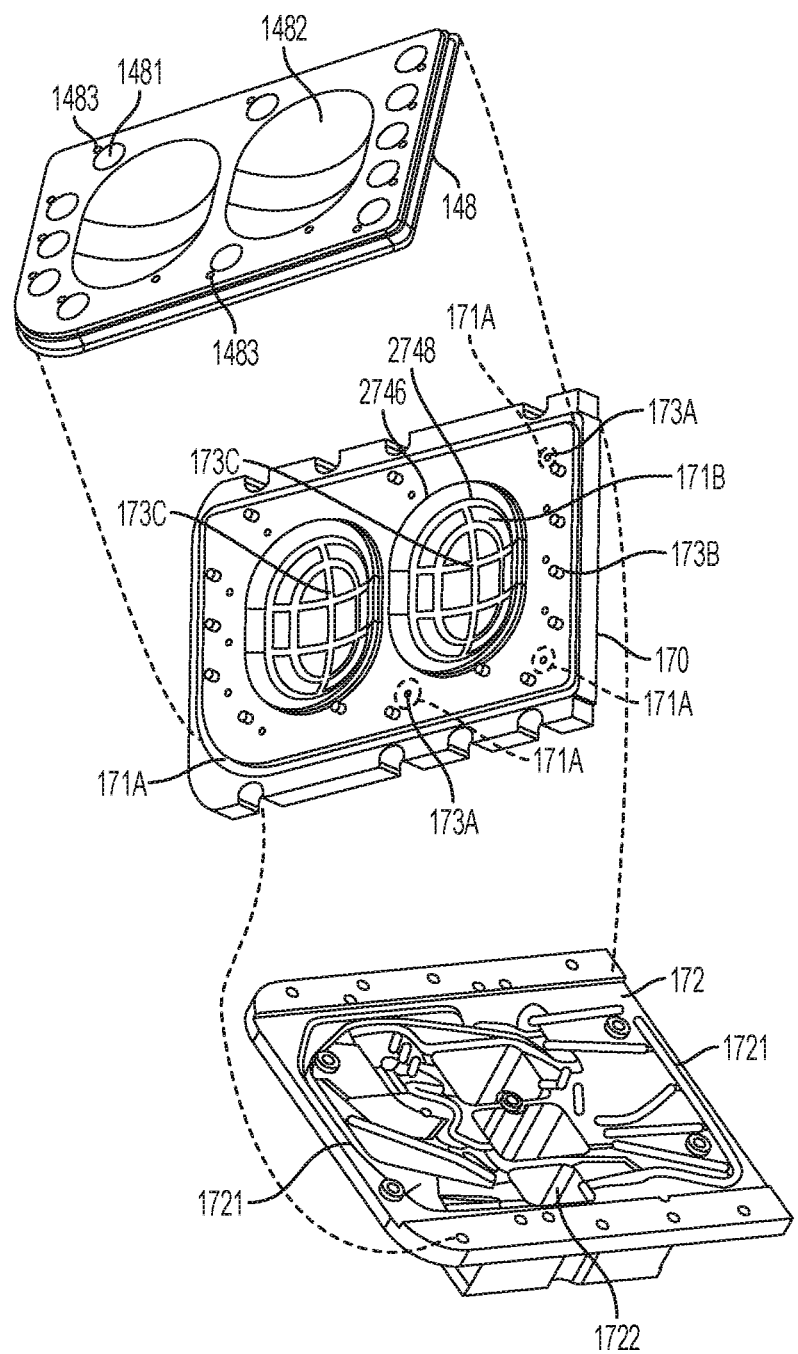
FIG. 34 is an exploded view of an assembly for the interface surface of FIG. 32, with the mating pressure delivery block and pressure distribution module.
Figure 35:
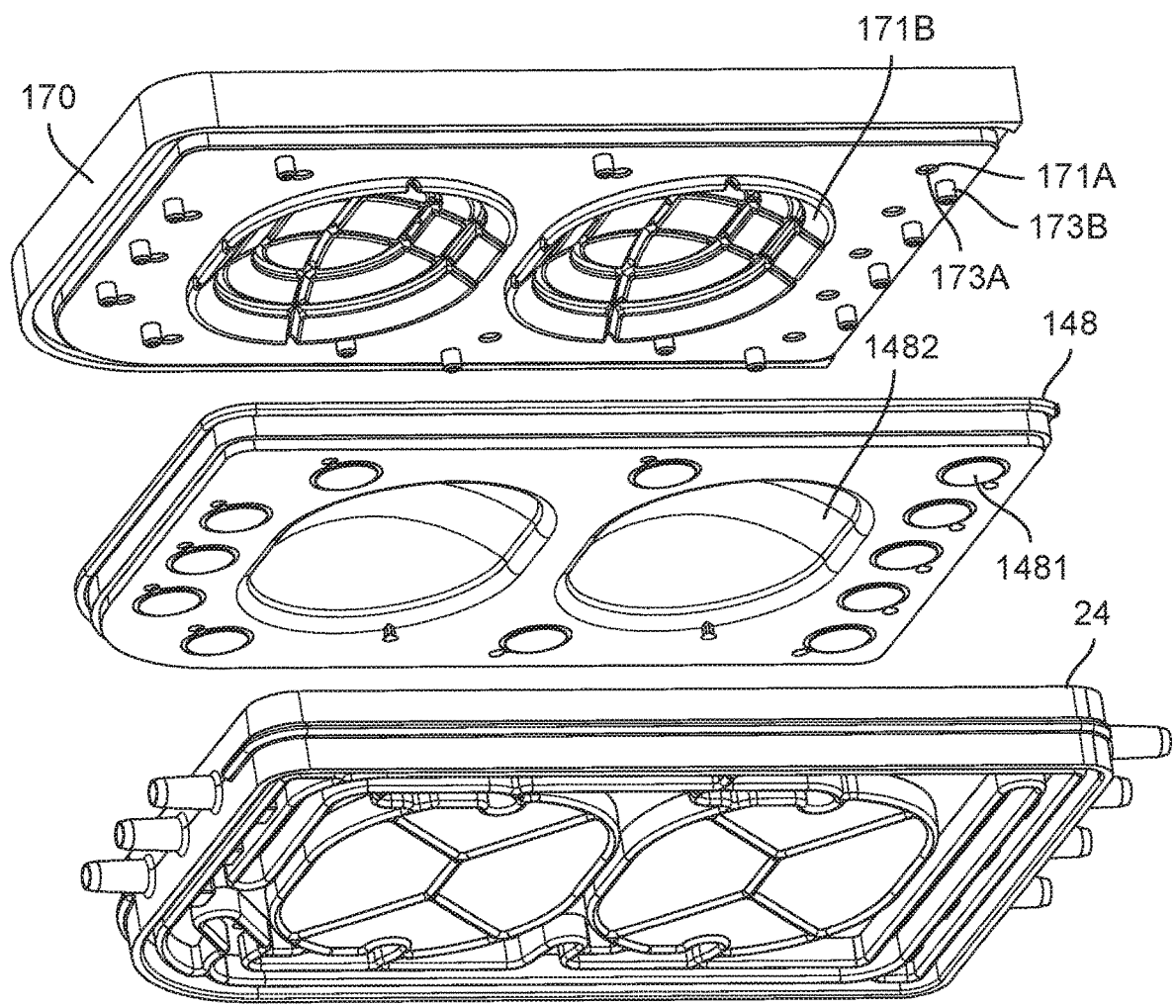
FIG. 35 shows an exploded view of a control gasket interposed between the pressure delivery block of the base unit and the pump cassette.

The control regions 1481 and 1482 may be moved or elastically deformed by controlling a pneumatic pressure and/or volume on a side of the control gasket 148 opposite the cassette 24, e.g., on a back side of the elastomeric sheet that forms the control gasket 148. For example, as shown in FIGS. 34-35, the control gasket 148 may be backed by a mating or pressure delivery block 170 that includes control chambers or depressions 171A located in association with each control region 1481, and control chambers or depressions 171B, located in association with each control region 1482, and that are isolated from each other (or at least can be controlled independently of each other if desired). The control chambers or depressions 171A may define a volume. The surface of mating or pressure delivery block 170 forms a mating interface with cassette 24 when cassette 24 is pressed into operative association with control gasket 148 backed by mating block 170 (see, e.g., FIGS. 34, 35). The control chambers or depressions of mating block 170 are thus coupled to complementary valve or pumping chambers of cassette 24, sandwiching the control regions 1481 and 1482 of control gasket 148 between mating block 170 and the associated regions of cassette membrane 15 (such as shaped portion 151) adjacent to cassette 24. Positively or negatively pressurized air or other control fluid may be moved into or out of the control chambers or depressions 171A, 171B of mating block 170 for the regions 1481, 1482, thereby moving the control regions 1481, 1482 as desired to open/close valve ports of the cassette 24 and/or effect pumping action at the pump chambers 181. In one illustrative embodiment shown in FIGS. 34-35, the control chambers 171A may be arranged as cylindrically-shaped regions or recesses backing each of the valve control regions 1481 of gasket 148. In one configuration of the valve control region 1481 of the gasket 148 (see, e.g. FIG. 33A-C), the surface of the valve control region 1481 is slightly elevated above the overall surface of the gasket 148, biasing the elastically deformable control region toward a corresponding valve seat of the cassette 24. Thus, positive pneumatic pressure applied against the valve control region 1481 is biased toward sealing the cassette 24 membrane 15 against a valve seat. On the other hand, at least a portion of the negative pressure applied to the valve control region 1481 to lift the adjacent cassette membrane 15 off the valve seat may be expended to overcome the biased valve control region 1481 of the control gasket 148. It is also apparent that when the gasket 148 is placed against the underlying mating block 170, a space 1478 under the dome of the control region 1481 combines with the control chamber 171A to become the total control volume that is pressurized positively or negatively to move the control region 1481 toward or away from a valve seat of the cassette 24. The amount of total control volume that needs to be pressurized will vary based on the shape and configuration of the valve control region 1481 of the gasket (e.g., convex vs. concave toward the cassette 24).

Figure 38:
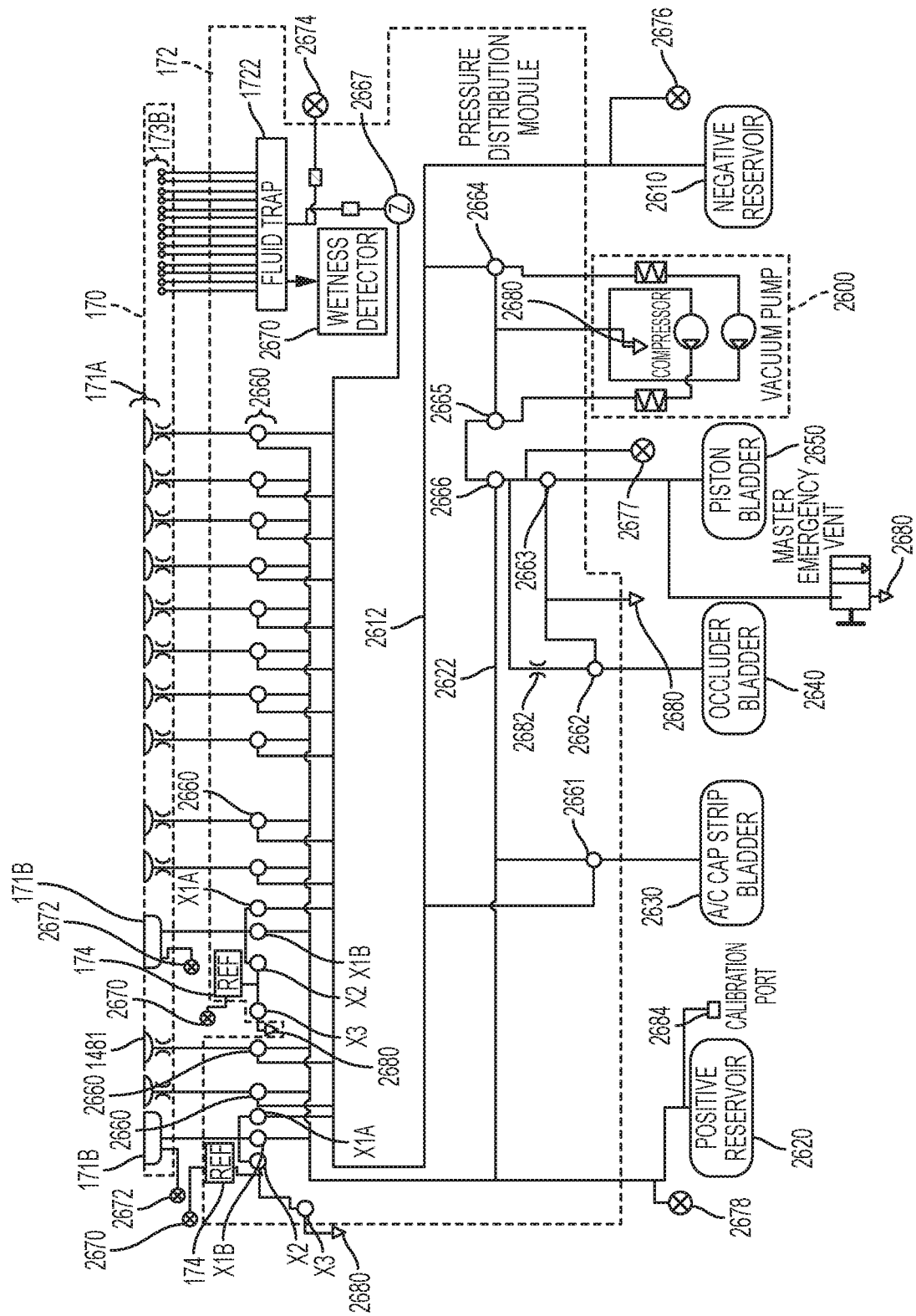
FIG. 38 shows a schematic of the pneumatic system that controls fluid flow through the cycler.

The control chambers or depressions 171B may comprise ellipsoid, ovoid or hemi-spheroid voids or depressions backing the pump control regions 1482. Fluid control ports 173A may be provided for each control chamber 171A so that the cycler 14 can control the volume of fluid and/or the pressure of fluid in each of the valve control chambers 1481. Fluid control ports 173C may be provided for each control chamber 171B so that the cycler 14 can control the volume of fluid and/or the pressure of fluid in each of the volume control chambers 1482. For example, as shown in FIG. 34, the mating block 170 may be mated with a manifold 172 that includes various ports, channels, openings, voids and/or other features that communicate with the control chambers 171A, B and allow suitable pneumatic pressure/vacuum to be applied to the control chambers 171A, B. Control of the pneumatic pressure/vacuum may be performed in any suitable way, such as through the use of controllable valves, pumps, pressure sensors, accumulators, and so on. An example pneumatic schematic with such components is shown in FIG. 38 and further described later in the specification. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

Figure 36:
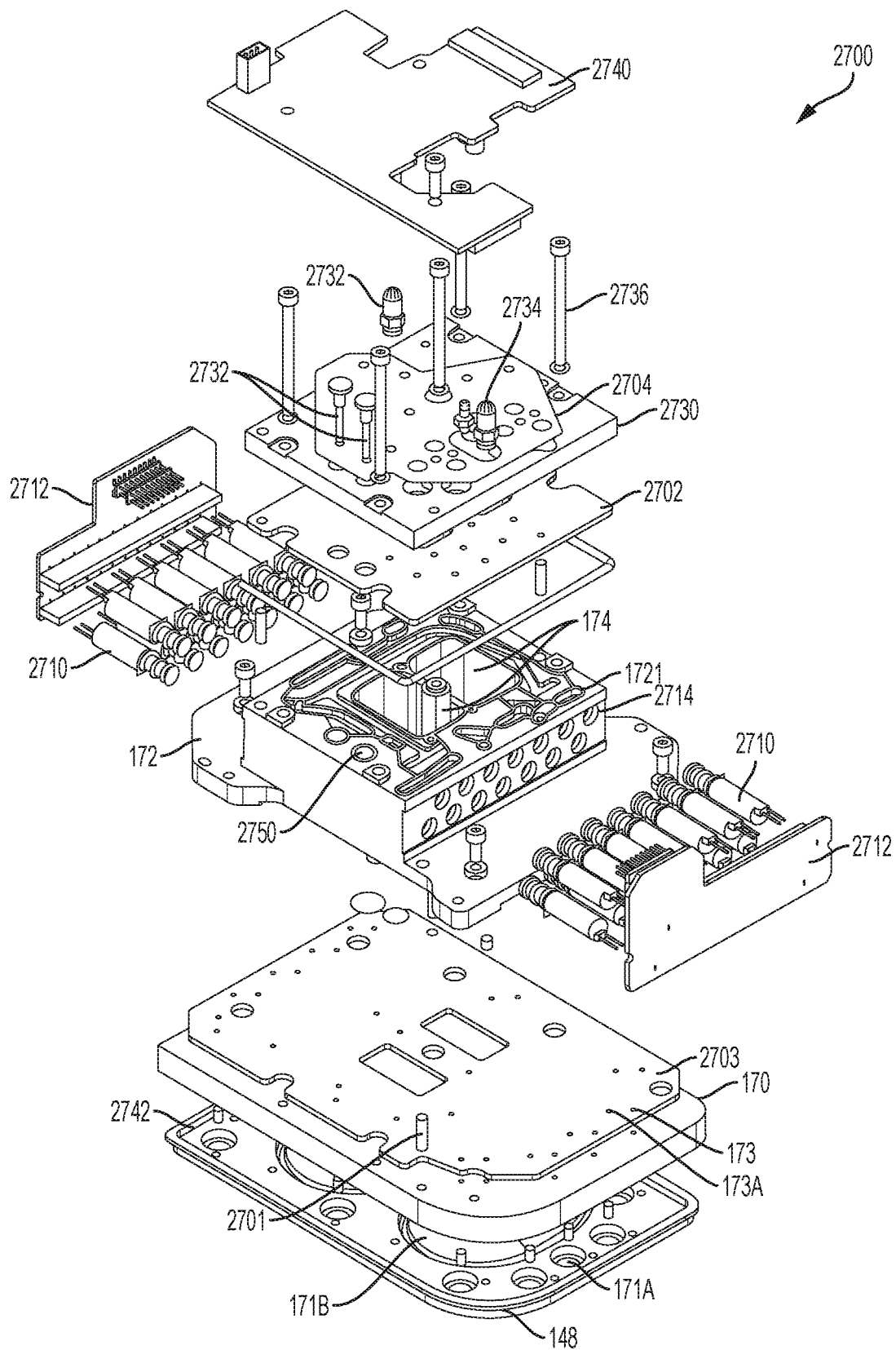
FIG. 36 is an exploded view of the integrated manifold.
Figure 37:
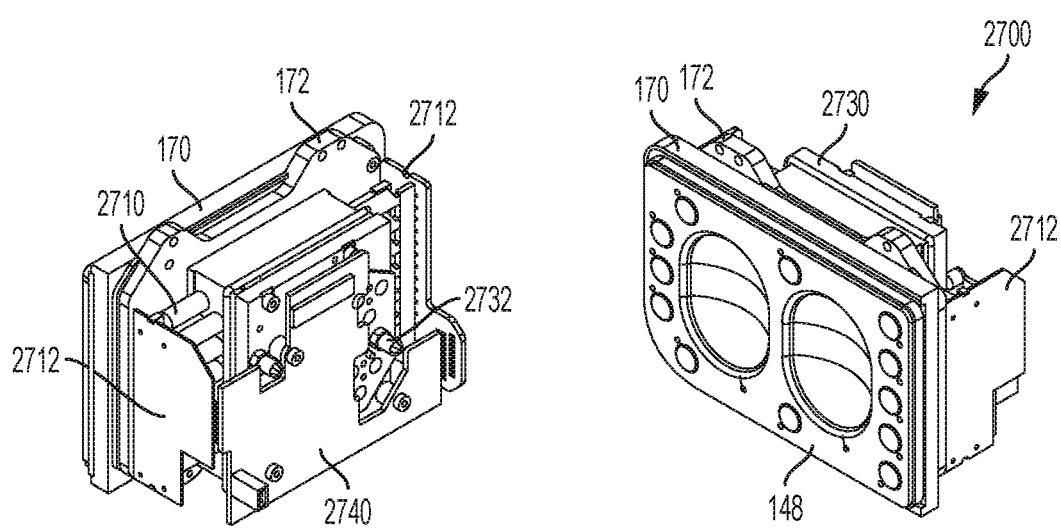
FIG. 37 shows two isometric views of the integrated manifold.

FIG. 36 shows an exploded view of an integrated pressure distribution module or assembly 2700 for use in a fluid flow control apparatus for operating a pumping cassette, and suitable for use as pressure distribution manifold 172 and mating block 170 of cycler 14. FIG. 37 shows an assembled view of integrated module 2700. This example integrated module 2700 includes a pneumatic manifold or block 172, ports 2714 for supply pressures, pneumatic control valves 2710, pressure sensors 2740, a pressure delivery or mating block 170 and a control surface or actuator 148 that includes regions comprising flexible membranes for actuating pumps 171B and valves 171A on a pumping cassette 24. The integrated module 2700 may also include reference chambers 174 within the pneumatic manifold 172 for a pressure/volume measurement process for determining the volume of fluid present in a pumping chamber of a pumping cassette based on the ideal gas laws. The integrated module 2700 may also comprise a vacuum port 173B in the pressure delivery block 170 (see, e.g., FIG. 34 or FIG. 35) and a set of pathways or channels from interfaces between the actuator or gasket 148 and flexible pump and valve membranes 15 of a pumping cassette 24 to a fluid trap 1722 and liquid detection system 2670 in the manifold 172 (see, e.g., the pressure distribution schematic illustrated in FIG. 38). In some embodiments, the pneumatic manifold 172 may be formed as a single block. In other embodiments, the pneumatic manifold 172 may be formed from two or more manifold blocks mated together with gaskets positioned between the manifold blocks. The integrated module 2700 occupies a relatively small space in a fluid flow control apparatus, and eliminates the use of tubes or flexible conduits connecting the manifold ports with corresponding ports of a pressure delivery module or block mated to a pumping cassette 24. Among other possible advantages, the integrated module 2700 reduces the size and assembly cost of the pneumatic actuation assembly of a peritoneal dialysis cycler 14, which may result in a smaller and less expensive cycler 14. Additionally, the short distances between pressure or vacuum distribution ports on the pressure distribution manifold block and corresponding pressure or vacuum delivery ports 173A, 173B, 173C on a mating pressure delivery block 170, together with the rigidity of the conduits connecting the ports, may improve the responsiveness of an attached pumping cassette and the accuracy of cassette pump volume measurement processes. When used in a peritoneal dialysis cycler 14, in an embodiment, an integrated module 2700 comprising a metallic pressure distribution manifold mated directly to a metallic pressure delivery block may also reduce any temperature differences between the control volume 171B and the reference chamber 174 of the cycler 14, which may improve the accuracy of the pump volume measurement process.

An exploded view of an example integrated module 2700 is presented in FIG. 36. The actuator surface or control gasket 148, mounted on a mating block or pressure delivery block 170 includes flexible regions arranged to move back and forth to pump fluid and/or open and close valves by pushing or pulling on a membrane 15 of a pump cassette 24. With respect to cycler 14, the control gasket 148 is actuated by the positive and negative pneumatic pressure supplied to the control volumes 171A, 171B behind the control regions 1481, 1482. The control gasket 148 attaches to the pressure delivery block or mating block 170 by fitting tightly on a raised surface 2744 on the front surface of the mating block 170 with a lip 2742. The mating block 170 may include one or more surface depressions 2746 to align with and support the oval curved shape of one or more corresponding pump control surfaces 1482, forming a pump control chamber. A similar arrangement, with or without a surface depression, may be included in forming a valve control region 171A to align with a corresponding control surface 1481 for controlling one or more valves of a pumping cassette 24. The mating block 170 may further include grooves 2748 on the surface of depression 2746 of mating block 170 behind the pump control surface 1482 to facilitate the flow of control fluid or gas from the port 173C to the entire back surface the pump control surface 1482. Alternatively, rather than having grooves 2748, the depression 2746 may be formed with a roughened surface or a tangentially porous surface.

In one embodiment, the inner wall of the control chambers 171B can include raised elements (somewhat analogous to the spacer elements 50 of the pump chamber 181), for example, as shown in FIG. 34 associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171B, and prevent premature blocking of any control port by the control gasket 148. A pre-formed control gasket 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171B, causing the control region 1482 to prematurely close off one or more ports of the control chamber before the chamber is fully evacuated. Having features on the inner surface of the control chamber 171B that prevent contact between the control region 1482 and the control ports may help to assure that the control region 1482 can make uniform contact with the control chamber inner wall during a fill stroke.

The mating block 170 connects the pressure distribution manifold 172 to the control gasket 148, and delivers pressure or vacuum to various control regions on control gasket 148. The mating block 170 may also be referred to as a pressure delivery block in that it provides pneumatic conduits to supply pressure and vacuum to the valve control regions 1481 and the pump control regions 1482, vacuum to the vacuum ports 1483 and connections from the pump control volumes 171B to the pressure sensors. The ports 173A connect the valve control volumes 171A to the pressure distribution manifold 172. The ports 173C connect the pump control volume 171B to the pressure distribution manifold 172. The vacuum ports 1483 are connected to the pressure distribution manifold 172 via ports 173B. In one embodiment, the ports 173B extend above the surface of the pressure delivery block 170 to pass through the control gasket 148 to provide vacuum at port 1483 without pulling the control surface 148 onto the port 173B and blocking flow.

The pressure delivery block 170 is attached to the front face of the pressure distribution manifold 172. The ports 173A, 173B, 173C line up with pneumatic circuits on the pressure distribution manifold 172 that connect to valve ports 2714. In one example, the pressure delivery block 170 is mated to the pressure distribution manifold 172 with a front flat gasket 2703 clamped between them. The block 170 and manifold 172 are held together mechanically, which in an embodiment is through the use of bolts 2736 or other types of fasteners. In another example, rather than a flat gasket 2703, compliant elements are placed in or molded in either the pressure delivery block 170 or the pressure distribution manifold 172. Alternatively, the pressure delivery block 170 may be bonded to the pressure distribution manifold 172 by an adhesive, double sided tape, friction welding, laser welding, or other bonding method. The block 170 and manifold 172 may be formed of metal or plastic and the bonding methods will vary depending on the material.

Referring now also to FIG. 38, the pressure distribution manifold 172 contains ports for the pneumatic valves 2710, reference chambers 174, a fluid trap 1722 and pneumatic circuitry or of the integrated module 2700 connections provides pneumatic connections between the pressure reservoirs, valves, and contains ports 2714 that receive multiple cartridge valves 2710. The cartridge valves 2710 include but are not limited to the binary valves 2660 controlling flow to valve control volumes 171A, the binary valves X1A, X1B, X2, X3 controlling flow to pump control volumes 171B, and the binary valves 2661-2667 controlling flow to the bladders 2630, 2640, 2650 and pressure reservoirs 2610, 2620. The cartridge valves 2710 are pressed into the valve ports 2714 and electrically connected to the hardware interface 310 via circuit board 2712.

The pneumatic circuitry in the pressure distribution manifold 172 may be formed with a combination of grooves or slots 1721 on the front and back faces and approximately perpendicular holes that connect the grooves 1721 on one face to valve ports 2714, the fluid trap 1722 and to grooves and ports on the opposite face. Some grooves 1721 may connect directly to the reference chambers 174. A single perpendicular hole may connect a groove 1721 to multiple valve ports 174 that are closely spaced and staggered. Sealed pneumatic conduits are formed when the grooves 1721 are isolated from one another by, in one example, the front flat gasket 2703 as shown in FIG. 36.

The presence of liquid in the fluid trap 1722 may be detected by a pair of conductivity probes 2732 (FIG. 36). The conductivity probes 2732 slide through a back gasket 2704, a back plate 2730 and holes 2750 before entering the fluid trap 1722 in the pressure distribution manifold 172.

The back plate 2730 seals the reference volumes 174, the grooves 1721 on the back face of the pressure distribution manifold 172 and provides ports for the pressure sensors 2740 and ports for pressure and vacuum lines 2734 and vents to the atmosphere 2732. In one example, the pressure sensors may be IC chips soldered to a single board 2740 and pressed as a group against the back gasket 2704 on the back plate 2730. In one example, bolts 2736 clamp the back plate 2730, pressure distribution manifold 172 and pressure delivery block 170 together with gaskets 2703, 2702 between them. In another example, the back plate 2730 may be bonded to the pressure delivery manifold 172 as described above.

FIG. 38 presents an example schematic of the pneumatic pressure circuit in the integrated manifold 2700 and pneumatic elements outside the manifold. The pump 2600 produces vacuum and pressure. The pump 2600 is connected via three way valves 2664 and 2665 to a vent 2680 and the negative or vacuum reservoir 2610 and the positive reservoir 2620. Pressures in the positive and negative reservoirs 2620, 2610 are measured respectively by pressure sensors 2678, 2676. The hardware interface 310 controls the speed of the pump 2600 and the position of 3-way valves 2664, 2665, 2666 to control the pressure in each reservoir. The autoconnect stripper element bladder 2630 is connected via three way valve 2661 to either the positive pressure line 2622 or the negative or vacuum line 2612. The automation computer 300 commands the position of valve 2661 to control the location of the stripper element 1461. The occluder bladder 2640 and piston bladder 2650 are connected via three way valves 2662 and 2663 to either the pressure line 2622 or vent 2680. The automation computer 300 commands valve 2663 to connect the piston bladder 2650 to the pressure line 2622 after the door 141 is closed to securely engage the cassette 24 against the control gasket 148. The occluder bladder 2640 is connected to the pressure line 2622 via valve 2662 and restriction 2682. The occluder bladder 2640 is connected to the vent 2680 via valve 2662. The orifice 2682 advantageously slows the filling of the occluder bladder 2640 that retracts the occluder 147 in order to maintain the pressure in the pressure line 2622. The high pressure in the pressure line 2622 keeps the various valve control surfaces 171A and the piston bladder 2650 actuated against the cassette 24, which prevents flow to or from the patient as the occluder 147 opens. Conversely the connection from the occluder bladder 2640 to the vent 2680 is unrestricted, so that occluder 147 can quickly close.

The valve control surfaces 1481 are controlled by the pressure in the valve control volume 171A, which in turn is controlled by the position of the three way valves 2660. The valves 2660 can be controlled individually via commands from the automation computer 300 passed to the hardware interface 310. The valves controlling the pumping pressures in the pump control volumes 171B are controlled with two way valves X1A, X1B. The valves X1A, X1B in one example may be controlled by the hardware interface 310 to achieve a pressure commanded by the automation computer 300. The pressure in each pump control chamber 171B is measured by sensors 2672. The pressure in the reference chambers 174 is measured by sensors 2670. The two way valves X2, X3 respectively connect the reference chamber 174 to the pump control chamber 171B and the vent 2680.

The fluid trap 1722 may be connected to the vacuum line 2612 during operation. The fluid trap 1722 is connected by several lines to the ports 173B in the pressure delivery block 170. The pressure in the fluid trap 1722 is monitored by a pressure sensor 2674 that is mounted on the back plate 2730.

The vacuum ports 1483 may be employed to separate the membrane 15 from the control gasket 148 at the end of therapy before or during the opening the door. The vacuum provided by the negative pressure source to the vacuum ports 1483 sealingly engages the membrane 15 to the control gasket 148 during therapy. In some instances a substantial amount of force may be needed to separate the control surface 148 from the cassette membrane 15, preventing the door 141 from freely rotating into the open position, even when the application of vacuum is discontinued. Thus, in an embodiment, the pressure distribution module 2700 is configured to provide a valved channel between the positive pressure source and the vacuum ports 1483. Supplying positive pressure at the vacuum ports 1483 may aid in separating the membrane 15 from the control gasket 148, thereby allowing the cassette 24 to separate more easily from the control gasket 148 and allow the door 141 to open freely. The pneumatic valves in the cycler 14 may be controlled by the automation computer 300 to provide a positive pressure to the vacuum ports 1483. The manifold 172 may include a separately valved channel dedicated for this purpose, or alternatively it may employ the existing channel configurations and valves, operated in a particular sequence.

In one example, the vacuum ports 1483 may be supplied with positive pressure by temporarily connecting the vacuum ports 1483 to the positive pressure reservoir 2620. The vacuum ports 1483 are normally connected to the vacuum reservoir 2610 via a common fluid collection chamber or fluid trap 1722 in the manifold 172 during therapy. In one example, the controller or automation computer may open valve X1B between the positive pressure reservoir and the volume control chamber 171B and the valve X1A between the negative pressure reservoir and the same volume control chamber 171B simultaneously, which will pressurize the air in the fluid trap 1722 and the vacuum ports 1483. The pressurized air will flow through the vacuum ports 1483 and between the membrane 15 and the control gasket 148, breaking any vacuum bond between the membrane 15 and control surface 148. However, in the illustrated manifold, the stripper element 1491 of the cap stripper 149 may extend while the positive pressure is supplied to common fluid collection chamber 1722 fluid, because the stripper bladder 2630 is connected to a the vacuum supply line 2612. In this example, in a subsequent step, the fluid trap 1722 may be valved off from the now-pressurized vacuum line and the two valves X1A, X1B connecting the positive and vacuum reservoirs to the volume control chamber 171B may be closed. The vacuum pump 2600 is then operated to reduce the pressure in the vacuum reservoir 2610 and the vacuum supply line 2612, which in turn allows the stripper element 1491 to be withdrawn. The door 141 may then be opened after detaching the cassette 24 from the control gasket 148 and retracting the stripper element 1491.

In accordance with an aspect of the disclosure, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control gasket 148. For example, vacuum ports 1483 may align with and be sealingly associated with complementary vacuum ports 173B in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of control gasket 148. By applying vacuum to the fluid collection chamber 1722, fluid may be drawn from each of the vacuum ports 173B and 1483, thus removing fluid from any space between the membrane 15 and the control gasket 148 at the various control regions. However, if there is liquid present at one or more of the regions, the associated vacuum port 1483 may draw the liquid into the vacuum ports 173B and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be placed at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In the example schematic shown in FIG. 38, a calibration port 2684 is depicted. The calibration port 2684 may be used to calibrate the various pressure sensors 2670, 2672, 2674, 2676, 2677, 2678 in the pneumatic system. For example, a pressure reference may be connected to the pneumatic circuit of the cycler via the calibration port 2684. With the pressure reference connected, the valves of the pneumatic system may be actuated so as to connect all of the pressure sensors 2670, 2672, 2674, 2676, 2677, 2678 to the same fluid volume. A known pressure may then be established in the pneumatic system using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly. In some embodiments, selected pressure sensors of the pressure sensors 2672, 2674, 2676, 2677, 2678 may be connected and brought to the pressure of the reference for calibration in groups or individually.

Any fluid handling device (i.e. base unit) that is configured to actuate diaphragm-based pumps and valves on a removable cassette can take advantage of its pneumatic (or hydraulic) cassette interface to receive a calibrating reference pressure via a specialized calibrating cassette (or 'cassette fixture'). A calibrating cassette can have the same overall dimensions as a standard fluid pumping cassette, so that it can provide a sealing interface with the cassette interface or control surface of the base unit. One or more of the pump or valve regions can be allowed to communicate with a corresponding region of the interface to which it mates, so that a reference pneumatic or hydraulic pressure can be introduced through the calibrating cassette and into the pneumatic or hydraulic flow paths of the base unit (e.g. via a pneumatic or hydraulic manifold).

For example, in a pneumatically operated peritoneal dialysis cycler 14, the pneumatic circuitry of the cycler 14 may be accessed directly through the cassette interface of the cycler 14. This may for example, be accomplished using a modified cassette or cassette fixture which allows the control surface 148 to create a seal against the cassette fixture. Additionally, the cassette fixture may be constructed to include at least one access port in fluid communication with a vacuum port 173B of the cassette interface. In the absence of a vacuum port (e.g. in embodiments having slits or perforations in the control surface) the access port may instead be placed in communication with the vacuum vent feature of the cassette interface or control surface.

The cassette fixture (or calibrating cassette) may be constructed to have a direct flow path from an external cassette port to the access port facing the device interface, the external cassette port then being available for connection to a pressure reference. As described above, all or some of the pressure sensors 2670, 2672, 2674, 2676, 2677, 2678 may be placed into fluid communication with a common volume, through the appropriate actuation of pneumatic control valves in the pressure distribution manifold. A known pressure may be established in that volume using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly.

In some embodiments of a pressure distribution manifold, it may not be possible for all of the pressure sensors 2670, 2672, 2674, 2676, 2677, 2678 to be connected to a common volume at one time. In that case, the flow paths to the individual pressure sensors 2670, 2672, 2674, 2676, 2677, 2678 may need to be opened in a sequential manner to ensure calibration of all sensors. Additionally, it should be noted that once calibrated, one or more of the pressure sensors 2670, 2672, 2674, 2676, 2677, 2678 may be used to calibrate other pressure sensors 2670, 2672, 2674, 2676, 2677, 2678 in a pressure distribution manifold of a base unit or cycler 14. The previously calibrated pressure sensor or sensors may be placed into a common volume with the uncalibrated pressure sensor (e.g. via suitable valve actuations). The pressure of the common volume may be known via the calibrated pressure sensor(s). The uncalibrated pressure sensor's reading may be compared to the known pressure of the common volume and then calibrated accordingly.

Figure 39:
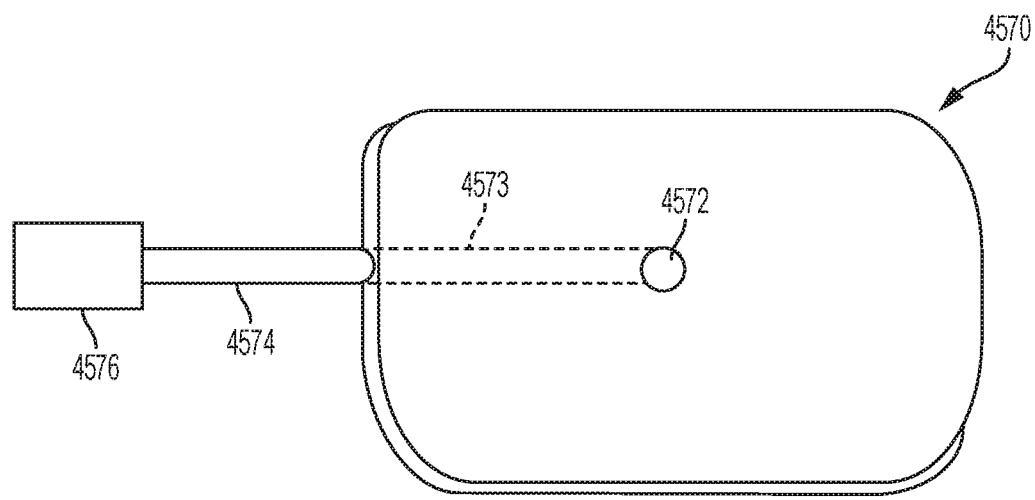
FIG. 39 is a front side view of an embodiment of a cassette fixture.

FIG. 39 depicts a schematized view of an embodiment of a cassette fixture 4570. As shown, the cassette fixture 4570 has the same outline as a standard pump cassette 24 described earlier. The cassette fixture 4570 includes an access port 4572 associated with a specific valve or pump region of a standard cassette to align with its corresponding region on the cassette interface (control surface 148) of the base unit. The cassette fixture 4570 otherwise can have a flat smooth interface surface to allow the control surface to seal against it when it is mated to the base unit or cycler. Preferably, the cassette fixture 4570 is formed from a metal or other hard, stiff material. A resistance to flexing or deformation under pressure may help to increase reliability and consistency over multiple calibrations of multiple cyclers. As shown, the cassette fixture 4570 includes an access port 4572 which is recessed into the face of the cassette fixture 4570. The access port 4572 communicates with a fluid path 4573 extending to tubing 4574 leading away from the cassette fixture 4570. A cassette port or fitting may be included on the side of the cassette for connection via tubing to a reference pressure source 4576 in the example embodiment.

Figure 40:
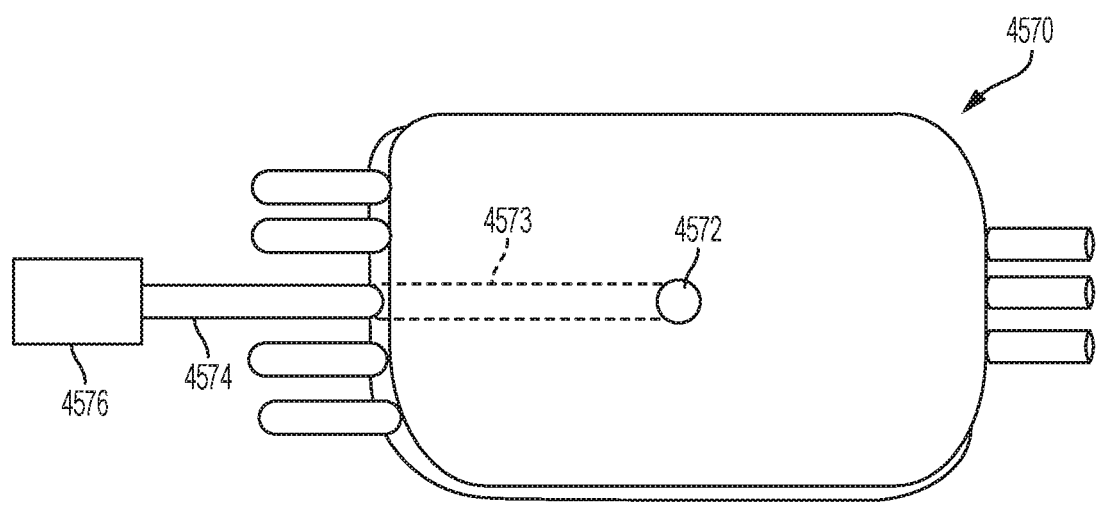
FIG. 40 shows another example of a cassette fixture which is made from a modified cassette such as the cassette shown in FIG. 3.
Figure 41:
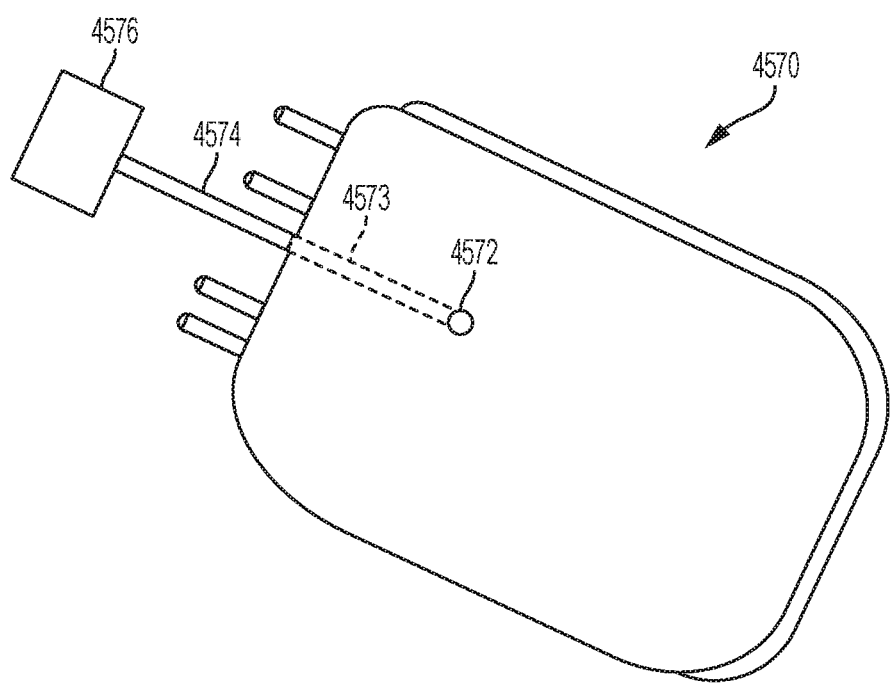
FIG. 41 shows another example of a cassette fixture which is made from a modified cassette.

FIGS. 40 and 41 depict other representations of a cassette fixture 4570 adapted from a modified cassette such as the cassette 24 shown in FIG. 3. In such examples, the cassette fixture 4570 may be made by removing or not including the sheeting or membrane 15 from the control side of the cassette which faces a control surface or cassette interface 148 (see, for example, FIG. 33A-C) of a cycler when installed in the cycler. Referring to FIG. 3, for example, the membrane 15 may not be included on the cassette 24. Thus, the pneumatic circuit of the cycler may be accessed directly through the cassette 24. Alternatively, the membrane or sheeting may be interrupted (e.g. removed, perforated, slit, or the like) on only a portion of the cassette 24 to create the cassette fixture 4570. For example, the membrane 15 may be modified in this manner in the area over which an access port 4572 of the cassette fixture 4570 is located.

Additionally, tubing 4574 may be attached to one or more of the external connection sites of a standard cassette to create the necessary fluid communication path of a cassette fixture 4570. The external connection sites can include any tubing attachment sites on the standard cassette, or may comprise more robust fittings for repeated use in calibration procedures. Referring to FIG. 3, external connection sites may include the cassette spikes 160 and/or the ports 150, 152 and 154. The cassette 24 may then be modified so that all other external connection sites may be blocked, plugged or otherwise sealed.

As above, the tubing 4574 leads from a fluid flow path 4573 fluidically connected to an access port 4572 in the cassette fixture 4570 to provide a connection path to a pressure reference 4576. The access port 4572 may be a pre-existing opening or valve port in the cassette body. Additionally, the fluid path 4573 may be any pre-existing pathway or combination of pathways in the cassette body which allow fluid communication from the access port 4572 to the tubing 4574 or an associated fitting on the side of the cassette. For example, a fluid path 4573 may include one or more valve port, valve well, pump chamber, and/or channel in the cassette 24 body or any combination thereof.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control gasket 148, and other pneumatically-operated components.

In one illustrative embodiment, the pressure in the pump control chambers 171B may be controlled by a binary valve, e.g., which opens to expose the control chamber 171 to a suitable pressure/vacuum and closes to cut off the pressure/vacuum source. The binary valve may be controlled using a saw tooth-shaped control signal which may be modulated to control pressure in the pump control chamber 171B. For example, during a pump delivery stroke (i.e., in which positive pressure is introduced into the pump control chamber 171B to move the membrane 15/control gasket 148 and force liquid out of the pump chamber 181), the binary valve may be driven by the saw tooth signal so as to open and close at a relatively rapid rate to establish a suitable pressure in the control chamber 171B (e.g., a pressure between about 70-90 mmHg). If the pressure in the control chamber 171B rises above about 90 mmHg, the saw tooth signal may be adjusted to close the binary valve for a more extended period. If the pressure drops below about 70 mmHg in the control chamber 171B, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171B. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171B for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171B may detect this fluctuation, which generally has a higher amplitude when the membrane 15/pump control region 1482 are not in contact with the inner wall of the pump chamber 181 or the wall of the pump control chamber 171B. However, once the membrane 15/pump control region 1482 contacts the inner wall of the pump chamber 181 or the wall of the pump control chamber 171B (i.e., the "end of stroke"), the pressure fluctuation is generally damped or otherwise changes in a way that is detectable by the pressure sensor in the pump control chamber 171B. This change in pressure fluctuation can be used to identify the end of stroke, and the pump and other components of the cassette 24 and/or cycler 14 may be controlled accordingly.

Figure 42:
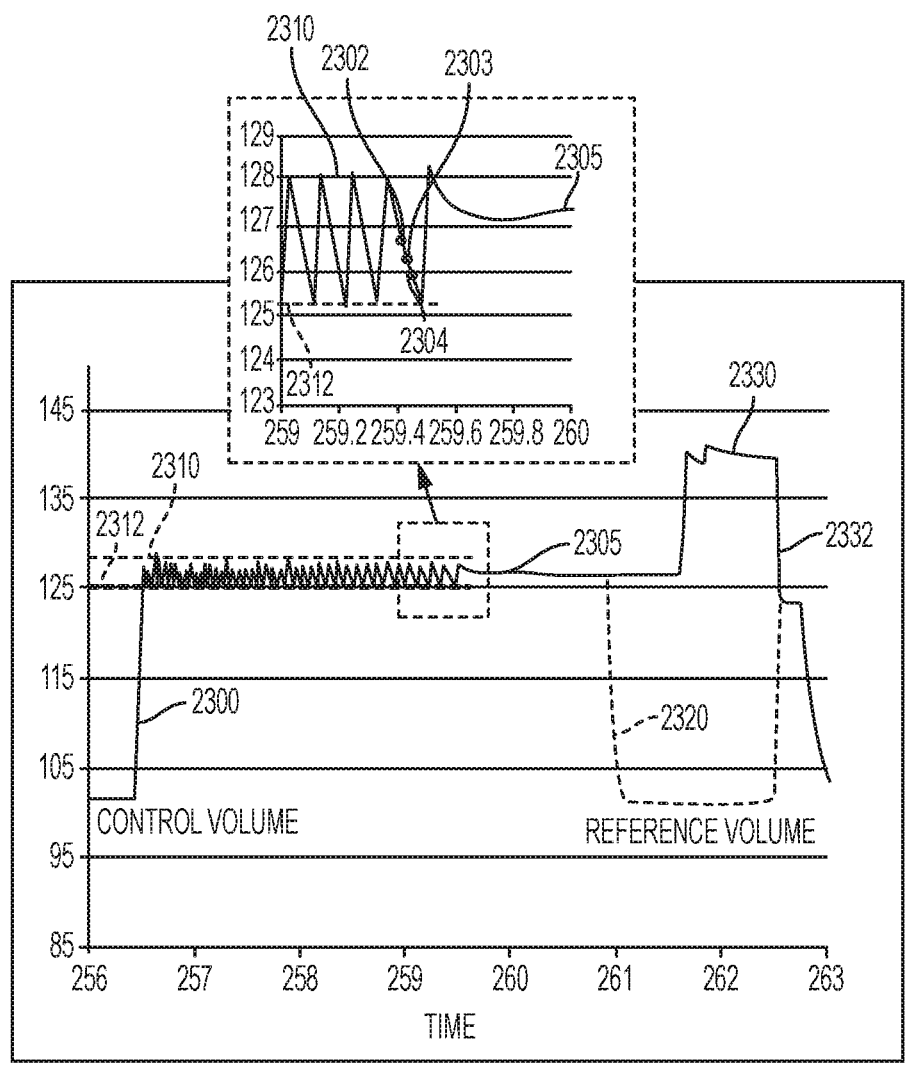
FIG. 42 shows a pressure tracing from a control or actuation chamber of a pumping cassette during a liquid delivery stroke.

In one embodiment, the pneumatic pressure applied to the control chamber 171B is actively controlled by a processor receiving a signal from a pressure transducer 2672 (FIG. 38) connected to the control chamber 171B and a fast acting binary valve X1A, X1B between a pressure reservoir 2620, 2610 and the control chamber 171B. The processor may control the pressure with a variety of control algorithms including closed loop proportional or proportional-integral feedback control that varies the valve duty cycle to achieve the desired pressure in the control volume 171B. In one embodiment, the processor controls the pressure in the control chamber with an on-off controller often called a bang-bang controller. The on-off controller monitors the pressure in the control volume 171B during a deliver stroke and open the binary valve X1B (connecting the control volume 171B to the positive reservoir 2620) when the pressure is less than a lower first limit and closes the binary valve X1B when the pressure is above a higher second limit. During a fill stroke, the on-off controller opens the binary valve X1A (connecting the control volume 171B to the negative reservoir 2610) when the pressure is greater than a third limit and closes the binary valve X1A when the pressure is less than a fourth limit, where the fourth limit is lower than the third limit and both the third and fourth limits are less than the first limit. A plot of the pump control chamber pressure over time during a deliver stroke and the associated pressure measurement is shown in FIG. 42. The control chamber pressure oscillates between a lower first limit and a higher second limit as the membrane 15 moves across the control chamber 171B. The pressure stops oscillating between the limits when the membrane 15 stops moving. The membrane 15 typically stops moving when it contacts either the spacers 50 of the cassette or when the control gasket 148 moving along with it contacts the control chamber surface 171B. The membrane 15 may also stop moving if the outlet fluid line is occluded.

The automation computer (AC) 300 detects the end of stroke by evaluating the pressure signals. There are many possible algorithms to detect the end of pressure oscillation that indicate the end-of-stroke (EOS). The algorithms and methods to detect EOS in the section labeled "Detailed Description of the system and Method of Measuring Change Fluid Flow Rate" in U.S. Pat. No. 6,520,747 and the section describing the filtering to detect end of stroke in U.S. Pat. No. 8,292,594 are herein incorporated by reference.

One example of an algorithm to detect EOS, the AC 300 evaluates the time between the pressure crossing the first and second limits during a deliver stroke or third and fourth limits during a fill stroke. The on-off controller opens and closes the valves X1A, X1B in response to the pressure oscillating between the two limits as the control chamber volume changes during the fill or deliver stroke. When the membrane 15 stops moving at the end-of-stroke, the pressure changes will significantly diminish so that the pressure no longer exceeds one or both limits. The AC 300 may detect EOS by measuring the time between the pressure exceeding alternating limits. If the time since the pressure crossed the last limit exceeds a predefined threshold, then the AC 300 may declare an EOS. The algorithm may further include an initial period during which the AC 300 does not measure the time between limit crossings.

In another example algorithm, the AC 300 evaluates the derivative of the pressure signal with respect to time. The AC 300 may declare an EOS, if the derivative remains below a minimum threshold for a minimum length of time. In a further example, the minimum threshold is the average of the absolute value of the average pressure derivative during the stroke. The algorithm calculates the slope (derivative with respect to time) of a curve fit to a set of data points, where the data points are taken from a moving window. The absolute value of each slope is then averaged over the stroke to calculate the absolute value of the average pressure derivative. In another example of an EOS algorithm, the AC 300 may not include the pressure data until after an initial delay. The AC 300 ignores the initial pressure data to avoid false EOS detections due to irregular pressure traces that occasionally occur during the early part of the stroke. In another example, the AC 300 declares an EOS only after the second derivative of the pressure in the later part of the stroke has remained below a threshold for a minimum time and a wait period of time has past.

The criteria to declare an EOS may be optimized for different pumping conditions. The optimized EOS detection conditions include the second pressure derivative threshold, the minimum time to remain below the second derivative threshold, the duration of the initial delay and a length of the wait period. These EOS detection criteria may be optimized differently, for example, the fill stroke from the bags 20, 22, the deliver stroke to the patient, the fill stroke from the patient, and the deliver stroke to the bags 20, 22. Alternatively each EOS detection criteria may be a function of the pumping pressure in the control chamber 171B.

Pump Volume Delivery Measurement

In another aspect of the disclosure, the cycler 14 may determine a volume of fluid delivered in various lines of the system 10 without the use of a flowmeter, weight scale or other direct measurement of fluid volume or weight. For example, in one embodiment, a volume of fluid moved by a pump, such as a pump in the cassette 24, may be determined based on pressure measurements of a gas used to drive the pump. In one embodiment, a volume determination can be made by isolating two chambers from each other, measuring the respective pressures in the isolated chambers, allowing the pressures in the chambers to partially or substantially equalize (by fluidly connecting the two chambers) and measuring the pressures. Using the measured pressures, the known volume of one of the chambers, and an assumption that the equalization occurs in an adiabatic way, the volume of the other chamber (e.g., a pump chamber) can be calculated. In one embodiment, the pressures measured after the chambers are fluidly connected may be substantially unequal to each other, i.e., the pressures in the chambers may not have yet completely equalized. However, these substantially unequal pressures may be used to determine a volume of the pump control chamber, as explained below.

Figure 43:
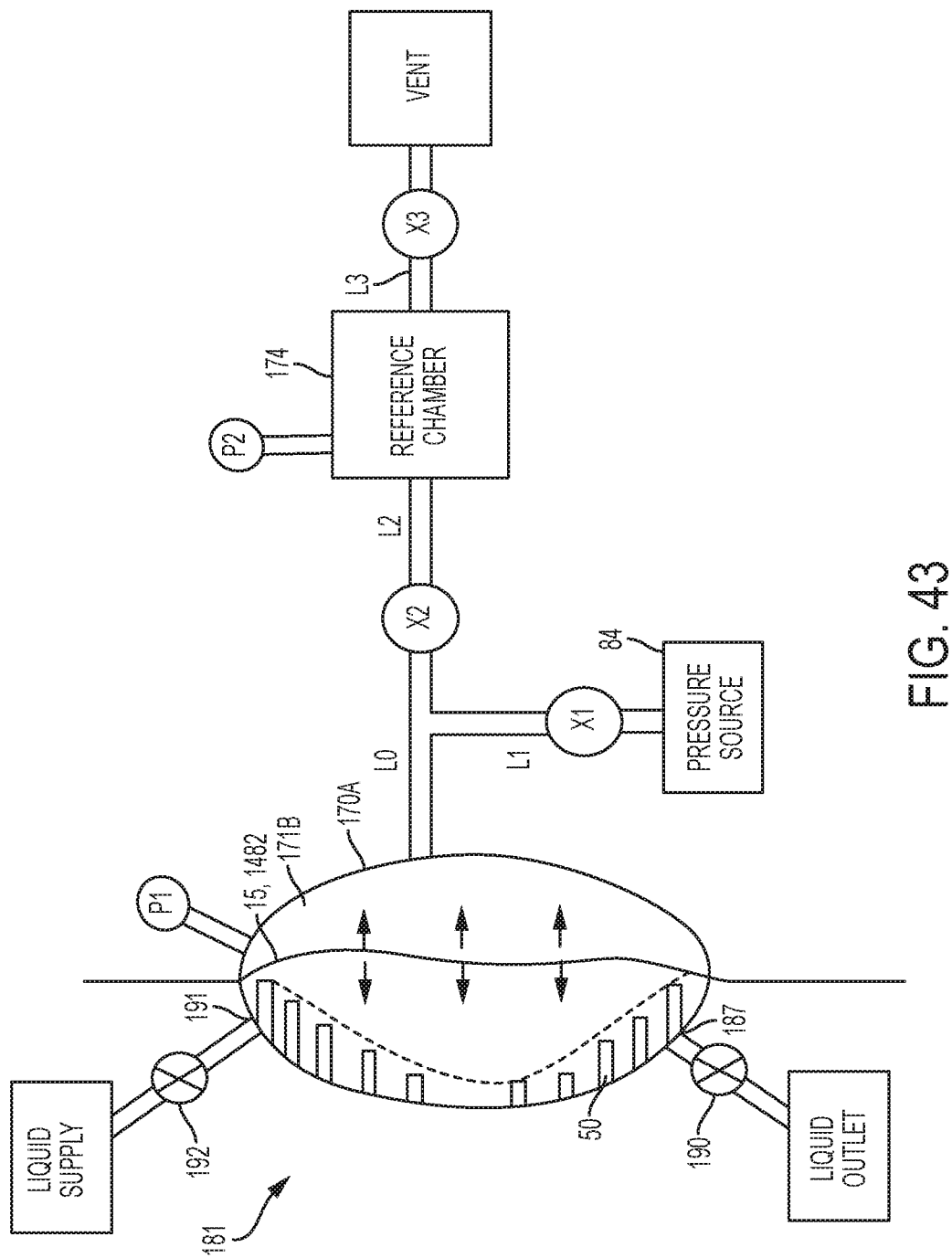
FIG. 43 is a schematic view of a pump chamber of a cassette and associated control components and inflow/outflow paths in an illustrative embodiment.

For example, FIG. 43 shows a schematic view of a pump chamber 181 of the cassette 24 and associated control components and inflow/outflow paths. In this illustrative example, a liquid supply, which may include the heater bag 22, heater bag line 26 and a flow path through the cassette 24, is shown providing a liquid input at the upper opening 191 of the pump chamber. The liquid outlet is shown in this example as receiving liquid from the lower opening 187 of the pump chamber 181, and may include a flow path of the cassette 24 and the patient line 34, for example. The liquid supply may include a valve, e.g., including the valve port 192, that can be opened and closed to permit/impede flow to or from the pump chamber 181. Similarly, the liquid outlet may include a valve, e.g., including the valve port 190, that can be opened and closed to permit/impede flow to or from the pump chamber 181. The liquid supply could include any suitable arrangement, such as one or more solution containers, the patient line, one or more flow paths in the cassette 24 or other liquid source, and the liquid outlet could likewise include any suitable arrangement, such as the drain line, the heater bag and heater bag line, one or more flow paths in the cassette 24 or other liquid outlet. Generally speaking, the pump chamber 181 (i.e., on the left side of the membrane 15 in FIG. 43) will be filled with an incompressible liquid, such as water or dialysate, during operation. However, air or other gas may be present in the pump chamber 181 in some circumstances, such as during initial operation, priming, or other situations as discussed below. Also, it should be understood that although aspects of the disclosure relating to volume and/or pressure detection for a pump are described with reference to the pump arrangement of the cassette 24, aspects of the disclosure may be used with any suitable pump or fluid movement system.

FIG. 43 also shows schematically to the right of the membrane 15 and the control surface 1482 (which are adjacent each other) a control chamber 171B, which may be formed as a void or other space in the mating block 170A associated with the pump control region 1482 of the control surface 148 (see, e.g. FIGS. 33A-C) for the pump chamber 181, as discussed above. It is in the control chamber 171B that suitable air pressure is introduced to cause the membrane 15/control region 1482 to move and effect pumping of liquid in the pump chamber 181. The control chamber 171B may communicate with a line L0 that branches to another line L1 and a first valve X1 that communicates with a pressure source 84 (e.g., a source of air pressure or vacuum). The pressure source 84 may include a piston pump in which the piston is moved in a chamber to control a pressure delivered to the control chamber 171B, or may include a different type of pressure pump and/or tank(s) to deliver suitable gas pressure to move the membrane 15/control region 1482 and perform pumping action. The line L0 also leads to a second valve X2 that communicates with another line L2 and a reference chamber 174 (e.g., a space suitably configured for performing the measurements described below). The reference chamber 174 also communicates with a line L3. Line L3 includes a valve X3 that leads to a vent or other reference pressure (e.g., a source of atmospheric pressure or other reference pressure). Each of the valves X1, X2 and X3 may be independently controlled. Pressure sensors P1, P2 may be arranged, e.g., one sensor P1 at the control chamber 171B and another sensor P2 at the reference chamber 174, to measure pressure associated with the control chamber 171B and the reference chamber 174. These pressure sensors P1, P2 may be positioned and may operate to detect pressure in any suitable way. The pressure sensors P1, P2 may communicate with the control system 16 for the cycler 14 or other suitable processor for determining a volume delivered by the pump or other features.

As mentioned above, the valves and other components of the pump system shown in FIG. 43 can be controlled so as to measure pressures in the pump chamber 181, the liquid supply and/or liquid outlet, and/or to measure a volume of fluid delivered from the pump chamber 181 to the liquid supply or liquid outlet. Regarding volume measurement, one technique used to determine a volume of fluid delivered from the pump chamber 181 is to compare the relative pressures at the control chamber 171B to that of the reference chamber 174 in two different pump states. By comparing the relative pressures, a change in volume at the control chamber 171B can be determined, which corresponds to a change in volume in the pump chamber 181 and reflects a volume delivered from/received into the pump chamber 181. For example, after the pressure is reduced in the control chamber 171B during a pump chamber fill cycle (e.g., by applying negative pressure from the pressure source through open valve X1) so as to displace the membrane 15 and draw the pump control region 1482 into contact with at least a portion of the control chamber 171B wall (or to another suitable position for the membrane 15/region 1482), valve X1 may be closed to isolate the control chamber 171B from the pressure source, and valve X2 may be closed, thereby isolating the reference chamber 174 from the control chamber 171B. Valve X3 may be opened to vent the reference chamber 174 to ambient pressure, then closed to isolate the reference chamber 174. With valve X1 closed and the pressures in the control chamber 171B and reference chamber 174 measured, valve X2 is then opened to allow the pressure in the control chamber 171B and the reference chamber 174 to start to equalize. The initial pressures of the reference chamber 174 and the control chamber 171B, together with the known volume of the reference chamber 171B and pressures measured after equalization has been initiated (but not yet necessarily completed) can be used to determine a volume for the control chamber 171B. This process may be repeated at the end of the pump delivery cycle when the sheet 15/control region 1482 are pushed against the spacer elements 50 of the pump chamber 181. By comparing the control chamber 171B volume at the end of the fill stroke to the volume at the end of the delivery stroke, a volume of liquid delivered from the pump chamber 181 can be determined.

Conceptually, the pressure equalization process (e.g., at opening of the valve X2) is viewed as happening in an adiabatic way, i.e., without heat transfer occurring between air in the control and reference chambers 171B, 174 and its environment. The conceptual notion is that there is an imaginary piston located initially at the valve X2 when the valve X2 is closed, and that the imaginary piston moves in the line L0 or L2 when the valve X2 is opened to equalize the pressure in the control and reference chambers 171B, 174. Since (a) the pressure equalization process happens relatively quickly, (b) the air in the control chamber 171B and the reference chamber 174 has approximately the same concentrations of elements, and (c) the temperatures are similar, the assumption that the pressure equalization happens in an adiabatic way may introduce only small error into the volume measurements. Also, in one embodiment, the pressures taken after equalization has been initiated may be measured before substantial equalization has occurred—further reducing the time between measuring the initial pressures and the final pressures used to determine the pump chamber 181 volume. Error can be further reduced, for example, by using low thermal conductivity materials for the membrane 15/control surface 1482, the cassette 24, the control chamber 171B, the lines L0, L1, L2, L3, the reference chamber 174, etc., so as to reduce heat transfer.

Given the assumption that an adiabatic system exists between the state when the valve X2 is closed until after the valve X2 is opened and the pressures equalize, the following applies:

$$PV^\gamma = \text{Constant} \quad (1)$$

where P is pressure, V is volume and $\gamma$ is equal to a constant (e.g., about 1.4 where the gas is diatomic, such as air). Thus, the following equation can be written to relate the pressures and volumes in the control chamber and the reference chamber before and after the opening of valve X2 and pressure equalization occurs:

$$PrVr^\gamma + PdVd^\gamma = \text{Constant} = PfVf^\gamma \quad (2)$$

where Pr is the pressure in the reference chamber and lines L2 and L3 prior to the valve X2 opening, Vr is the volume of the reference chamber and lines L2 and L3 prior to the valve X2 opening, Pd is the pressure in the control chamber and the lines L0 and L1 prior to the valve X2 opening, Vd is the volume of the control chamber and the lines L0 and L1 prior to the valve X2 opening, Pf is the equalized pressure in the reference chamber and the control chamber after opening of the valve X2, and Vf is the volume of the entire system including the control chamber, the reference chamber and the lines L0, L1, L2, and L3, i.e., Vf=Vd+Vr. Since Pr, Vr, Pd, Pf and $\gamma$ are known, and Vf=Vr+Vd, this equation can be used to solve for Vd. Although reference is made herein to use of a "measured pressure" in determining volume values, etc., it should be understood that such a measured pressure value need not necessarily be any particular form, such as in psi units. Instead, a "measured pressure" or "determined pressure" may include any value that is representative of a pressure, such as a voltage level, a resistance value, a multi-bit digital number, etc. For example, a pressure transducer used to measure pressure in the control chamber may output an analog voltage level, resistance or other indication that is representative of the pressure in the control chamber. The raw output from the transducer may be used as a measured pressure, and/or some modified form of the output, such as a digital number generated using an analog output from the transducer, a psi or other value that is generated based on the transducer output, and so on. The same is true of other values, such as a determined volume, which need not necessarily be in a particular form such as cubic centimeters. Instead, a determined volume may include any value that is representative of the volume, e.g., could be used to generate an actual volume in, say, cubic centimeters.

In an embodiment of a fluid management system ("FMS") technique to determine a volume delivered by the pump chamber 181, it is assumed that pressure equalization upon opening of the valve X2 occurs in an adiabatic system. Thus, Equation 3 below gives the relationship of the volume of the reference chamber system before and after pressure equalization:

$$Vrf = Vri(Pf/Patm)^{-(1/\gamma)} \quad (3)$$

where Vrf is the final (post-equalization) volume of the reference chamber system including the volume of the reference chamber 174, the volume of the lines L2 and L3 and the volume adjustment resulting from movement of the "piston", which may move to the left or right of the valve X2 after opening, Vri is the initial (pre-equalization) volume of the reference chamber 174 and the lines L2 and L3 with the "piston" located at the valve X2, Pf is the final equalized pressure after the valve X2 is opened, and Patm is the initial pressure of the reference chamber 174 before valve X2 opening (in this example, atmospheric pressure). Similarly, Equation 4 (below) gives the relationship of the volume of the control chamber system before and after pressure equalization:

$$Vdf = Vdi(Pf/Pdi)^{-(1/\gamma)} \quad (4)$$

where Vdf is the final volume of the control chamber system including the volume of the control chamber 171B, the volume of the lines L0 and L1, and the volume adjustment resulting from movement of the "piston", which may move to the left or right of the valve X2 after opening, Vdi is the initial volume of the control chamber 171B and the lines L0 and L1 with the "piston" located at the valve X2, Pf is the final pressure after the valve X2 is opened, and Pdi is the initial pressure of the control chamber 171B before valve X2 opening.

The volumes of the reference chamber system and the control chamber system will change by the same absolute amount after the valve X2 is opened and the pressure equalizes, but will differ in sign (e.g., because the change in volume is caused by movement of the "piston" left or right when the valve X2 opens), as shown in Equation 5:

$$\Delta Vr = (-1)\Delta Vd \quad (5)$$

Note that this change in volume for the reference chamber 174 and the control chamber 171B is due only to movement of the imaginary piston. The reference chamber 174 and control chamber 171B will not actually change in volume during the equalization process under normal conditions.

Also, using the relationship from Equation 3, the change in volume of the reference chamber system is given by:

$$\Delta Vr = Vrf - Vri = Vri(-1 + (Pf/Patm)^{-(1/\gamma)}) \quad (6)$$

Similarly, using Equation 4, the change in volume of the control chamber system is given by:

$$\Delta Vd = Vdf - Vdi = Vdi(-1 + (Pf/Pdi)^{-(1/\gamma)}) \quad (7)$$

Because Vri is known, and Pf and Patm are measured or known, ΔVr can be calculated, which according to Equation 5 is assumed to be equal to (−)ΔVd. Therefore, Vdi (the volume of the control chamber system before pressure equalization with the reference chamber 174) can be calculated using Equation 7. In this embodiment, Vdi represents the volume of the control chamber 171B plus lines L0 and L1, of which L0 and L1 are fixed and known quantities. Subtracting L0 and L1 from Vdi yields the volume of the control chamber 171B alone. By using Equation 7 above, for example, both before (Vdi1) and after (Vdi2) a pump operation (e.g., at the end of a fill stroke and at the end of a discharge stroke), the change in volume of the control chamber 171B can be determined, thus providing a measurement of the volume of fluid delivered by (or taken in by) the pump chamber 181. For example, if Vdi1 is the volume of the control chamber 171B at the end of a fill stroke, and Vdi2 is the volume of the control chamber 171B at the end of the subsequent delivery stroke, the volume of fluid delivered by the pump chamber 181 may be estimated by subtracting Vdi1 from Vdi2. Since this measurement is made based on pressure, the volume determination can be made for nearly any position of the membrane 15/pump control region 1482 in the pump chamber 181, whether for a full or partial pump stroke. However, measurement made at the ends of fill and delivery strokes can be accomplished with little or no impact on pump operation and/or flow rate.

One aspect of the disclosure involves a technique for identifying pressure measurement values that are to be used in determining a volume for the control chamber 171B and/or other purposes. For example, although pressure sensors P1, P2 may be used to detect a pressure in the control chamber 171B and a pressure in the reference chamber 174, the sensed pressure values may vary with opening/closing of valves, introduction of pressure to the control chamber 171B, venting of the reference chamber 174 to atmospheric pressure or other reference pressure, etc. Also, since in one embodiment, an adiabatic system is assumed to exist from a time before pressure equalization between the control chamber 171B and the reference chamber 174 until after equalization, identifying appropriate pressure values that were measured as close together in time may help to reduce error. This may be true for example because a shorter time elapsed between pressure measurements may reduce the amount of heat that is exchanged in the system. Thus, the measured pressure values may need to be chosen carefully to help ensure appropriate pressures are used for determining a volume delivered by the pump chamber 181, etc.

As mentioned, L3 of FIG. 43 may have a valve X3 which leads to a vent. In some embodiments, this vent may communicate with the atmosphere or, in other embodiments, another reference pressure. In some embodiments, this vent may be connected via a valve to the control chamber 171B such that the control chamber 171B may be vented (see, e.g., FIG. 38). In prior devices the vent has been used to bring a control chamber 171B from a negative pressure after a fill stroke to ambient pressure before positive pressurization of the control chamber 171B. This brings the control chamber 171B to a higher starting pressure before connection to the pressure source 84 and consequently minimizes the depletion of pressure in a positive pressure source or reservoir 84. As a result, a pump supplying a positive pressure reservoir 84 would be required to run less frequently.

On the other hand, it has since been determined that venting a control chamber 171B which is already at a positive pressure to a lower pressure before subsequently positively repressurizing the chamber for an FMS measurement may be advantageous in some scenarios. Though this new step requires additional work (e.g. pump runtime) to keep the pressure source 84 at its pressure set point, it may be done to help mitigate any possible undesirable effects from back pressure (e.g. due to an occluded line leading to or from the associated pumping chamber, or due to a partial occlusion). Additionally, this may help to increase the overall accuracy of volume measurement and fluid accounting. One possible reason for this is that a pump chamber outlet valve 190—in this case a pneumatically operated membrane valve—may not close as efficiently when the control chamber 171B remains positively pressurized.

In some embodiments, a control system 16 of a cycler 14 may vent the control chamber 171B before taking a measurement to determine fluid volume delivered or filled. Additionally, in some embodiments, the control system 16 of a cycler 14 may vent a first control chamber 171B before performing a pumping operation with a second control chamber included in the installed cassette 24.

In the example embodiment shown in FIG. 43, this venting or back pressure relief may be accomplished by opening valves X2 and X3 and closing valve X1. Thus, the control chamber 171B may be placed into communication with the vent via the reference chamber 174. In other embodiments, of course, a control chamber 171B may be placed into more direct communication with a vent. For example, an additional valve associated with a fluid path in direct communication with the vent may be included. Any other suitable configuration may also be used.

In some embodiments, the control chamber 171B may be vented by placing the control chamber 171B into fluid communication with the vent for a suitable or predetermined period of time. In other embodiments, to control venting of a control chamber 171B, the control system 16 of the cycler 14 may use data from a pressure sensor associated with one or both of the control chambers 171B or reference chamber 174 (or in a location fluidly connectable to the control chamber 171B, such as, for example, a pressure distribution module). In such embodiments, data from the pressure sensor(s) may be used to determine whether or not the control chamber 171B has been sufficiently vented. Once a determination is made that the control chamber 171B has been sufficiently vented, the control system 16 of the cycler 14 may close the appropriate valve to isolate the control chamber 171B from the vent. In order for the control system 16 to determine that the control chamber 171B has been sufficiently vented, the control chamber 171B pressure need not necessarily fully equalize with that of the vent.

In some embodiments, in order to relieve back pressure in a control chamber 171B, it may instead be subjected to a negative pressure source for an appropriate or predetermined period of time. In such embodiments, the control chamber 171B may be placed into communication with a pressure source 84. In the example embodiment shown in FIG. 43, this may be accomplished by opening valve X1 and closing at least valve X3. In the case of a positively pressurized control chamber 171B, the pressure source to which the control chamber 171B is connected may be a negative pressure source. In some embodiments, the control system 16 of the cycler 14 may only open a valve to the negative pressure source for a brief period of time. The brief period of time may be of a duration sufficient to bring the pressure in the control chamber 171B to within a pre-determined range of a predetermined value (in an example, this may be approximately atmospheric pressure), before it is allowed to equalize with the pressure source. In other embodiments, the valve X1 may be modulated to produce the same effect. If it is a vari-valve, its orifice opening may be modulated by the controller; whereas if it is a binary valve, the controller may modulate the rate and magnitude of pressure delivery across the valve using, for example, pulse-width-modulation.

Figure 44:
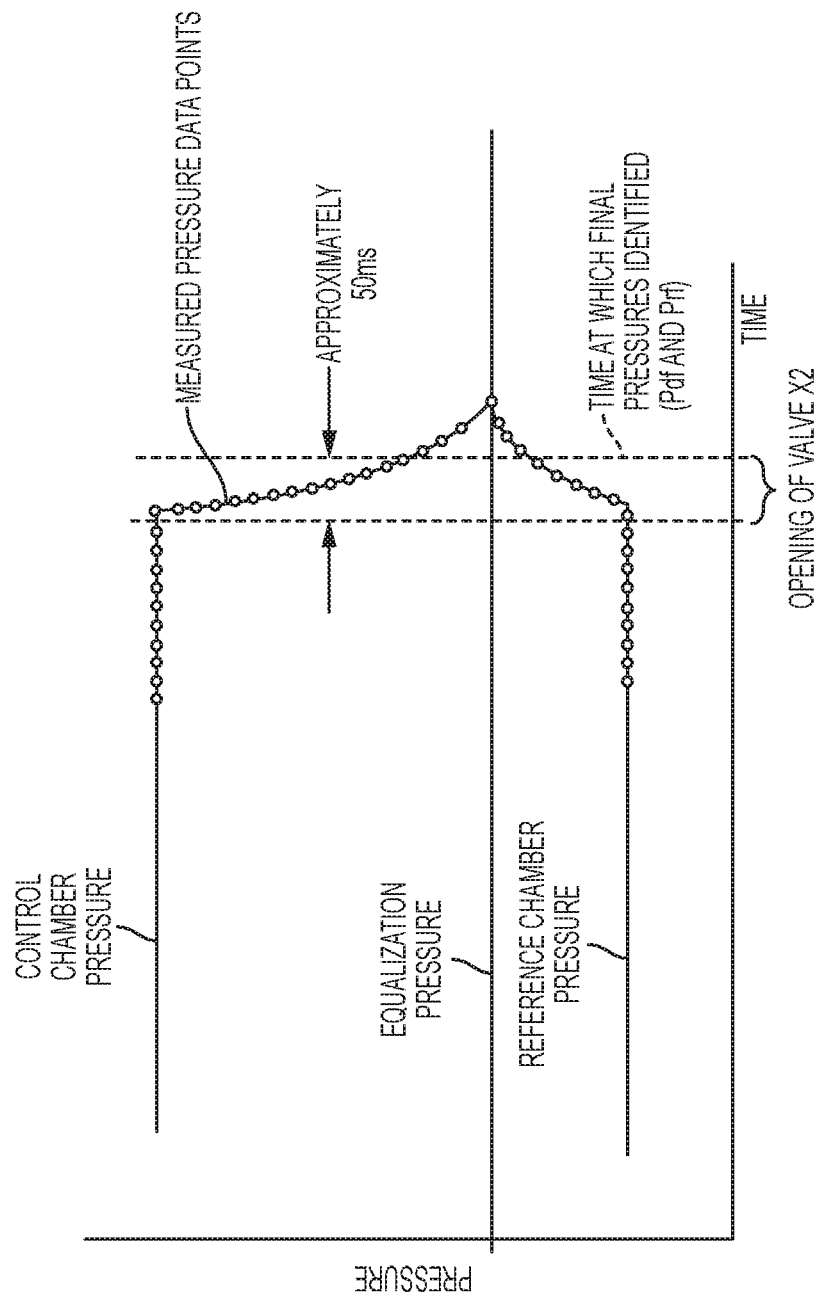
FIG. 44 is a plot of illustrative pressure values for the control chamber and the reference chamber from a point in time before opening of the valve X2 until some time after the valve X2 is opened for the embodiment of FIG. 43.

For purposes of explanation, FIG. 44 shows a plot of illustrative pressure values for the control chamber 171B and the reference chamber 174 from a point in time before opening of the valve X2 until some time after the valve X2 is opened to allow the pressure in the chambers 171B, 174 to equalize. In this illustrative embodiment, the pressure in the control chamber 171B is higher than the pressure in the reference chamber 174 before equalization, but it should be understood that the control chamber 171B pressure may be lower than the reference chamber 174 pressure before equalization in some arrangements, such as during and/or at the end of a fill stroke. Also, the plot in FIG. 44 shows a horizontal line marking the equalization pressure, but it should be understood that this line is shown for clarity and illustrative purposes only. The equalization pressure in general will not be known prior to opening of the valve X2. In this embodiment, the pressure sensors P1, P2 sense pressure at a rate of about 2000 Hz for both the control chamber 171B and the reference chamber 174, although other suitable sampling rates could be used. Before opening of the valve X2, the pressures in the control chamber 171B and the reference chamber 174 are approximately constant, there being no air or other fluid being introduced into the chambers 171B, 174. Thus, the valves X1 and X3 will generally be closed at a time before opening of the valve X2. Also, valves leading into the pump chamber 181, such as the valve ports 190 and 192, may be closed to prevent influence of pressure variations in the pump chamber 181, the liquid supply or liquid outlet.

At first, the measured pressure data is processed to identify the initial pressures for the control chamber 171B and reference chambers 174, i.e., Pd and Pr. In one illustrative embodiment, the initial pressures are identified based on analysis of a 10-point sliding window used on the measured pressure data. This analysis involves generating a best fit line for the data in each window (or set), e.g., using a least squares technique, and determining a slope for the best fit line. For example, each time a new pressure is measured for the control chamber 171B or the reference chamber 174, a least squares fit line may be determined for a data set including the latest measurement and the 9 prior pressure measurements. This process may be repeated for several sets of pressure data, and a determination may be made as to when the slope of the least squares fit lines first becomes negative (or otherwise non-zero) and continues to grow more negative for subsequent data sets (or otherwise deviates from a zero slope). The point at which the least squares fit lines begin to have a suitable, and increasing, non-zero slope may be used to identify the initial pressure of the chambers 171B, 174, i.e., at a time before the valve X2 is opened.

In one embodiment, the initial pressure value for the reference chamber 174 and the control chamber 171B may be determined to be in the last of 5 consecutive data sets, where the slope of the best fit line for the data sets increases from the first data set to the fifth data set, and the slope of the best fit line for the first data set first becomes non-zero (i.e., the slope of best fit lines for data sets preceding the first data set is zero or otherwise not sufficiently non-zero). For example, the pressure sensor may take samples every ½ millisecond (or other sampling rate) starting at a time before the valve X2 opens. Every time a pressure measurement is made, the cycler 14 may take the most recent measurement together with the prior 9 measurements, and generate a best fit line to the 10 data points in the set. Upon taking the next pressure measurement (e.g., ½ millisecond later), the cycler 14 may take the measurement together with the 9 prior measurements, and again generate a best fit line to the 10 points in the set. This process may be repeated, and the cycler 14 may determine when the slope of the best fit line for a set of 10 data points first turns non-zero (or otherwise suitably sloped) and, for example, that the slope of the best fit line for 5 subsequent sets of 10 data points increases with each later data set. To identify the specific pressure measurement to use, one technique is to select the third measurement in the $5^{th}$ data set (i.e., the $5^{th}$ data set with which it was found that the best fit line has been consistently increasing in slope and the $1^{st}$ measurement is the pressure measurement that was taken earliest in time) as the measurement to be used as the initial pressure for the control chamber 171B or the reference chamber 174, i.e., Pd or Pr. This selection was chosen using empirical methods, e.g., plotting the pressure measurement values and then selecting which point best represents the time when the pressure began the equalization process. Of course, other techniques could be used to select the appropriate initial pressure.

In one illustrative embodiment, a check may be made that the times at which the selected Pd and Pr measurements occurred were within a desired time threshold, e.g., within 1-2 milliseconds of each other. For example, if the technique described above is used to analyze the control chamber 171B pressure and the reference chamber 174 pressure and identify a pressure measurement (and thus a point in time) just before pressure equalization began, the times at which the pressures were measured should be relatively close to each other. Otherwise, there may have been an error or other fault condition that invalidates one or both of the pressure measurements. By confirming that the time at which Pd and Pr occurred are suitably close together, the cycler 14 may confirm that the initial pressures were properly identified.

To identify when the pressures in the control chamber 171B and the reference chamber 174 have equalized such that measured pressures for the chamber can be used to reliably determine pump chamber 181 volume, the cycler 14 may analyze data sets including a series of data points from pressure measurements for both the control chamber 171B and the reference chamber 174, determine a best fit line for each of the data sets (e.g., using a least squares method), and identify when the slopes of the best fit lines for a data set for the control chamber 171B and a data set for the reference chamber 174 are first suitably similar to each other, e.g., the slopes are both close to zero or have values that are within a threshold of each other. When the slopes of the best fit lines are similar or close to zero, the pressure may be determined to be equalized. The first pressure measurement value for either data set may be used as the final equalized pressure, i.e., Pf. In one illustrative embodiment, it was found that pressure equalization occurred generally within about 200-400 milliseconds after valve X2 is opened, with the bulk of equalization occurring within about 50 milliseconds. Accordingly, the pressure in the control and reference chambers 171B, 174 may be sampled approximately 400-800 times or more during the entire equalization process from a time before the valve X2 is opened until a time when equalization has been achieved.

In some cases, it may be desirable to increase the accuracy of the control chamber 171B volume measurement using an alternate FMS technique. Substantial differences in temperature between the liquid being pumped, the control chamber 171B gas, and the reference chamber 174 gas may introduce significant errors in calculations based on the assumption that pressure equalization occurs adiabatically. Waiting to make pressure measurements until full equalization of pressure between the control chamber 171B and the reference chamber 174 may allow an excessive amount of heat transfer to occur. In one aspect of the disclosure, pressure values for the control chamber 171B and reference chamber 174 that are substantially unequal to each other, i.e., that are measured before complete equalization has occurred, may be used to determine pump chamber 181 volume.

In one embodiment, heat transfer may be minimized, and adiabatic calculation error reduced, by measuring the chamber pressures throughout the equalization period from the opening of valve X2 through full pressure equalization, and selecting a sampling point during the equalization period for the adiabatic calculations. In one embodiment of an APD system, measured chamber pressures that are taken prior to complete pressure equalization between the control chamber 171B and the reference chamber 174 can be used to determine pump chamber 181 volume. In one embodiment, these pressure values may be measured about 50 ms after the chambers are first fluidly connected and equalization is initiated. As mentioned above, in one embodiment, complete equalization may occur about 200-400 ms after the valve X2 is opened. Thus, the measured pressures may be taken at a point in time after the valve X2 is opened (or equalization is initiated) that is about 10% to 50% or less of the total equalization time period. Said another way, the measured pressures may be taken at a point in time at which 50-70% of pressure equalization has occurred. That is, the reference 174 and control chamber 171B pressures have changed by about 50-70% of the difference between the initial chamber pressure and the final equalized pressure. Using a computer-enabled controller, a substantial number of pressure measurements in the control and reference chambers 171B, 174 can be made, stored and analyzed during the equalization period (for example, 40-100 individual pressure measurements). Among the time points sampled during the first 50 ms of the equalization period, there is a theoretically optimized sampling point for conducting the adiabatic calculations (e.g., see FIG. 44 in which the optimized sampling point occurs at about 50 ms after opening of the valve X2). The optimized sampling point may occur at a time early enough after valve X2 opening to minimize thermal transfer between the gas volumes of the two chambers, but not so early as to introduce significant errors in pressure measurements due to the properties of the pressure sensors and delays in valve actuation. However, as can be seen in FIG. 44, the pressures for the control chamber 171B and reference chambers 174 may be substantially unequal to each other at this point, and thus equalization may not be complete. Note that in some cases, it may be technically difficult to take reliable pressure measurements immediately after the opening of valve X2, for example, because of the inherent inaccuracies of the pressure sensors, the time required for valve X2 to fully open, and the rapid initial change in the pressure of either the control chamber 171B or the reference chamber 174 immediately after the opening of valve X2.

During pressure equalization, when the final pressure for the control chamber 171B and reference chambers 174 are not the same, Equation 2 becomes:

$$PriVri^{\gamma}+PdiVdi^{\gamma}=\text{Constant}=PrfVrf^{\gamma}+PdfVdf^{\gamma} \quad (8)$$

where: Pri=pressure in the reference chamber 171B prior to opening valve X2, Pdi=pressure in the control chamber 171B prior to opening valve X2, Prf=final reference chamber 174 pressure, Pdf=final control chamber 171B pressure.

An optimization algorithm can be used to select a point in time during the pressure equalization period at which the difference between the absolute values of $\Delta Vd$ and $\Delta Vr$ is minimized (or below a desired threshold) over the equalization period. In an adiabatic process, this difference should ideally be zero, as indicated by Equation 5. In FIG. 44 the point in time at which the difference between the absolute values of $\Delta Vd$ and $\Delta Vr$ is minimized occurs at the 50 ms line, marked "time at which final pressures identified." First, pressure data can be collected from the control and reference chambers 171B, 174 at multiple points j=1 through n between the opening of valve X2 and final pressure equalization. Since Vri, the fixed volume of the reference chamber system before pressure equalization, is known, a subsequent value for Vrj (reference chamber system volume at sampling point j after valve X2 has opened) can be calculated using Equation 3 at each sampling point Prj along the equalization curve. For each such value of Vrj, a value for $\Delta Vd$ can be calculated using Equations 5 and 7, each value of Vrj thus yielding Vdij, a putative value for Vdi, the volume of the control chamber system prior to pressure equalization. Using each value of Vrj and its corresponding value of Vdij, and using Equations 3 and 4, the difference in the absolute values of $\Delta Vd$ and $\Delta Vr$ can be calculated at each pressure measurement point along the equalization curve. The sum of these differences squared provides a measure of the error in the calculated value of Vdi during pressure equalization for each value of Vrj and its corresponding Vdij. Denoting the reference chamber 174 pressure that yields the least sum of the squared differences of $|\Delta Vd|$ and $|\Delta Vr|$ as Prf, and its associated reference chamber 174 volume as Vrf, the data points Prf and Pdf corresponding to Vrf can then be used to calculate an optimized estimate of Vdi, the initial volume of the control chamber system.

One method for determining where on the equalization curve to capture an optimized value for Pdf and Prf is as follows:

1) Acquire a series of pressure data sets from the control and reference chambers 171B, 174 starting just before the opening of valve X2 and ending with Pr and Pd becoming close to equal. If Pri is the first reference chamber 174 pressure captured, then the subsequent sampling points in FIG. 44 will be referred to as Prj=Pr1, Pr2, . . . Prn.
2) Using Equation 6, for each Prj after Pri, calculate the corresponding $\Delta$Vrj where j represents the jth pressure data point after Pri.

$$\Delta Vrj=Vrj-Vri=Vri(-1+(Prj/Pri)^{-(1/\gamma)})$$

3) For each such $\Delta$Vrj calculate the corresponding Vdij using Equation 7. For example:
$\Delta Vr1=Vri*(-1+(Pr1/Pri)^{-(1/\gamma)})$
$\Delta Vd1=-\Delta Vr1$
Therefore,
$Vdi1=\Delta Vd1/(-1+(Pd1/Pdi)^{-(1/\gamma)})$
$Vdin=\Delta Vdn/(-1+(Pdn/Pdi)^{-(1/\gamma)})$ Having calculated a set of n control chamber system initial volumes (Vdi1 to Vdin) based on the set of reference chamber 174 pressure data points Pr1 to Prn during pressure equalization, it is now possible to select the point in time (f) that yields an optimized measure of the control chamber system initial volume (Vdi) over the entire pressure equalization period.

4) Using Equation 7, for each Vdi1 through Vdin, calculate all $\Delta Vdj,k$ using control chamber 171B pressure measurements Pd for time points k=1 to n.
For the Vdi corresponding to Pr1:
$\Delta Vd1,1 = Vdi1*(-1+(Pd1/Pdi)^{-(1/\gamma)})$
$\Delta Vd1,2 = Vdi1*(-1+(Pd2/Pdi)^{-(1/\gamma)})$
$\Delta Vd1,n = Vdi1*(-1+(Pdn/Pdi)^{-(1/\gamma)})$
For the Vdi corresponding to Prn:
$\Delta Vdn,1 = Vdin*(-1+(Pd1/Pdi)^{-(1/\gamma)})$
$\Delta Vdn,2 = Vdin*(-1+(Pd2/Pdi)^{-(1/\gamma)})$
$\Delta Vdn,n = Vdin*(-1+(Pdn/Pdi)^{-(1/\gamma)})$ 5) Take the sum-square error between the absolute values of the $\Delta Vr$'s and $\Delta Vdj,k$'s $$S_1 = \sum_{k=1}^{n}(|\Delta V_{d1,k}| - |\Delta V_{rk}|)^2$$

S1 represents the sum-square error of $|\Delta Vd|$ minus $|\Delta Vr|$ over all data points during the equalization period when using the first data point Pr1 to determine Vdi, the control chamber system initial volume, from Vr1 and $\Delta Vr$.

$$S_2 = \sum_{k=1}^{n}(|\Delta V_{d2,k}| - |\Delta V_{rk}|)^2$$

S2 represents the sum-square error of $|\Delta Vr|$ minus $|\Delta Vd|$ over all data points during the equalization period when using the second data point Pr2 to determine Vdi, the control chamber system initial volume, from Vr2 and $\Delta Vr$.

$$S_n = \sum_{k=1}^{n}(|\Delta V_{dn,k}| - |\Delta V_{rk}|)^2$$

6) The Pr data point between Pr1 and Prn that generates the minimum sum-square error S from step 5 (or a value that is below a desired threshold) then becomes the chosen Prf, from which Pdf and an optimized estimate of Vdi, the control chamber 171B initial volume, can then be determined. In this example, Pdf occurs at, or about, the same time as Prf.

7) The above procedure can be applied any time that an estimate of the control chamber 171B volume is desired, but can preferably be applied at the end of each fill stroke and each delivery stroke. The difference between the optimized Vdi at the end of a fill stroke and the optimized Vdi at the end of a corresponding delivery stroke can be used to estimate the volume of liquid delivered by the pump chamber 181.

Air Detection

Another aspect of the disclosure involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber 181 may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present disclosure and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are drawn against the wall of the control chamber 171B, the valve X2 may be closed, and the reference chamber 174 vented to atmospheric pressure, e.g., by opening the valve X3. Thereafter, the valves X1 and X3 may be closed, fixing the imaginary "piston" at the valve X2. The valve X2 may then be opened, allowing the pressure in the control chamber 171B and the reference chamber 174 to equalize, as was described above when performing pressure measurements to determine a volume for the control chamber 171B.

If there is no air bubble in the pump chamber 181, the change in volume of the reference chamber 174, i.e., due to the movement of the imaginary "piston," determined using the known initial volume of the reference chamber system and the initial pressure in the reference chamber 174, will be equal to the change in volume of the control chamber 171B determined using the known initial volume of the control chamber system and the initial pressure in the control chamber 171B. The initial volume of the control chamber 171B may be known in conditions where the membrane 15/control region 1482 are against the wall of the control chamber 171B or the spacer elements 50 of the pump chamber 181. However, if air is present in the pump chamber 181, the change in volume of the control chamber 171B will actually be distributed between the control chamber 171B volume and the air bubble(s) in the pump chamber 181. As a result, the calculated change in volume for the control chamber 171B using the known initial volume of the control chamber system will not be equal to the calculated change in volume for the reference chamber 174, thus signaling the presence of air in the pump chamber 181.

If there is air in the pump chamber 181, the initial volume of the control chamber system Vdi is actually equal to the sum of the volume of the control chamber and lines L0 and L1 (referred to as Vdfix) plus the initial volume of the air bubble in the pump chamber 181, (referred to as Vbi), as shown in Equation 9:

$$Vdi = Vbi + Vdfix \quad (9)$$

With the membrane 15/control region 1482 pressed against the wall of the control chamber 171B at the end of a fill stroke, the volume of any air space in the control chamber 171B, e.g., due to the presence of grooves or other features in the control chamber 171B wall, and the volume of the lines L0 and L1—together Vdfix—can be known quite accurately. Similarly, with the membrane 15/control region 1482 pressed against the spacer elements 50 of the pump chamber 181, the volume of the control chamber 171B and the lines L0 and L1 can be known accurately. After a fill stroke, the volume of the control chamber system is tested using a positive control chamber pre-charge. Any discrepancy between this tested volume and the tested volume at the end of the fill stroke may indicate a volume of air present in the pump chamber 181. Substituting from Equation 9 into Equation 7, the change in volume of the control chamber 171B ΔVd is given by:

$$\Delta Vd = (Vbi + Vdfix)(-1 + (Pdf/Pdi)^{-(1/\gamma)}) \quad (10)$$

Since ΔVr can be calculated from Equation 6, and we know from Equation 5 that ΔVr=(−1) ΔVd, Equation 10 can be re-written as:

$$(-1)\Delta Vr = (Vbi + Vdfix)(-1 + (Pdf/Pdi)^{-(1/\gamma)}) \quad (11)$$

and again as:

$$Vbi = (-1)\Delta Vr/(-1 + (Pdf/Pdi)^{-(1/\gamma)}) - Vdfix \quad (12)$$

Accordingly, the cycler 14 can determine whether there is air in the pump chamber 181, and the approximate volume of the bubble using Equation 12. This calculation of the air bubble volume may be performed if it is found, for example, that the absolute values of ΔVr (as determined from Equation 6) and ΔVd (as determined from Equation 7 using Vdi=Vdfix) are not equal to each other. That is, Vdi should be equal to Vdfix if there is no air present in the pump chamber 181, and thus the absolute value for ΔVd given by Equation 7 using Vdfix in place of Vdi will be equal to ΔVr.

After a fill stroke has been completed, and if air is detected according to the methods described above, it may be difficult to determine whether the air is located on the pump chamber 181 side or the control side of the membrane 15. Air bubbles could be present in the liquid being pumped, or there could be residual air on the control (pneumatic) side of the pump membrane 15 because of a condition (such as, for example, an occlusion) during pumping that caused an incomplete pump stroke, and incomplete filling of the pump chamber 181. At this point, an adiabatic FMS measurement using a negative pump chamber pre-charge can be done. If this FMS volume matches the FMS volume with the positive precharge, then the membrane 15 is free to move in both directions, which implies that the pump chamber 181 is only partially filled (possibly, for example, due to an occlusion). If the value of the negative pump chamber pre-charge FMS volume equals the nominal control chamber 171B air volume when the membrane 15/region 1482 is against the inner wall of the control chamber 171B, then it is possible to conclude that there is an air bubble in the liquid on the pump chamber 181 side of the flexible membrane 15.

Polytropic FMS for Pump Volume Delivery Measurement

In another aspect of the disclosure, the cycler 14 in, for example, FIG. 1A may determine a volume of fluid delivered in various lines of the system 10 without the use of a flowmeter, weight scale or other direct measurement of fluid volume or weight. For example, in one embodiment, a volume of fluid moved by a diaphragm pump, such as a pneumatically driven diaphragm pump including a cassette 24, may be determined based on pressure measurements of a gas used to drive the pump.

In one embodiment, the volume determination is accomplished with a process herein referred to as the two-chamber Fluid Measurement System (2-chamber FMS) process. The volume of fluid pumped by the diaphragm pump may be calculated from the change in the volume of the pneumatic chamber on one side of the diaphragm. The volume of the pneumatic chamber may be measured at the end of each fill and deliver stroke, so that the difference in volume between sequential measurements is the volume of fluid moved by the pump.

The volume of the pneumatic chamber or first chamber is measured with the 2-chamber FMS process that comprises closing the liquid valves into and out of the diaphragm pump, isolating the first chamber from a second chamber of a known volume (reference chamber), pre-charging the first chamber to a first pressure, while pre-charging the second chamber to a second pressure, then fluidically connecting the two chambers, and recording at least the initial and final pressures in each chamber as the pressures equalize. The volume of first chamber may be calculated from at least the initial and final pressures and the known volume of the second chamber.

Figure 45:
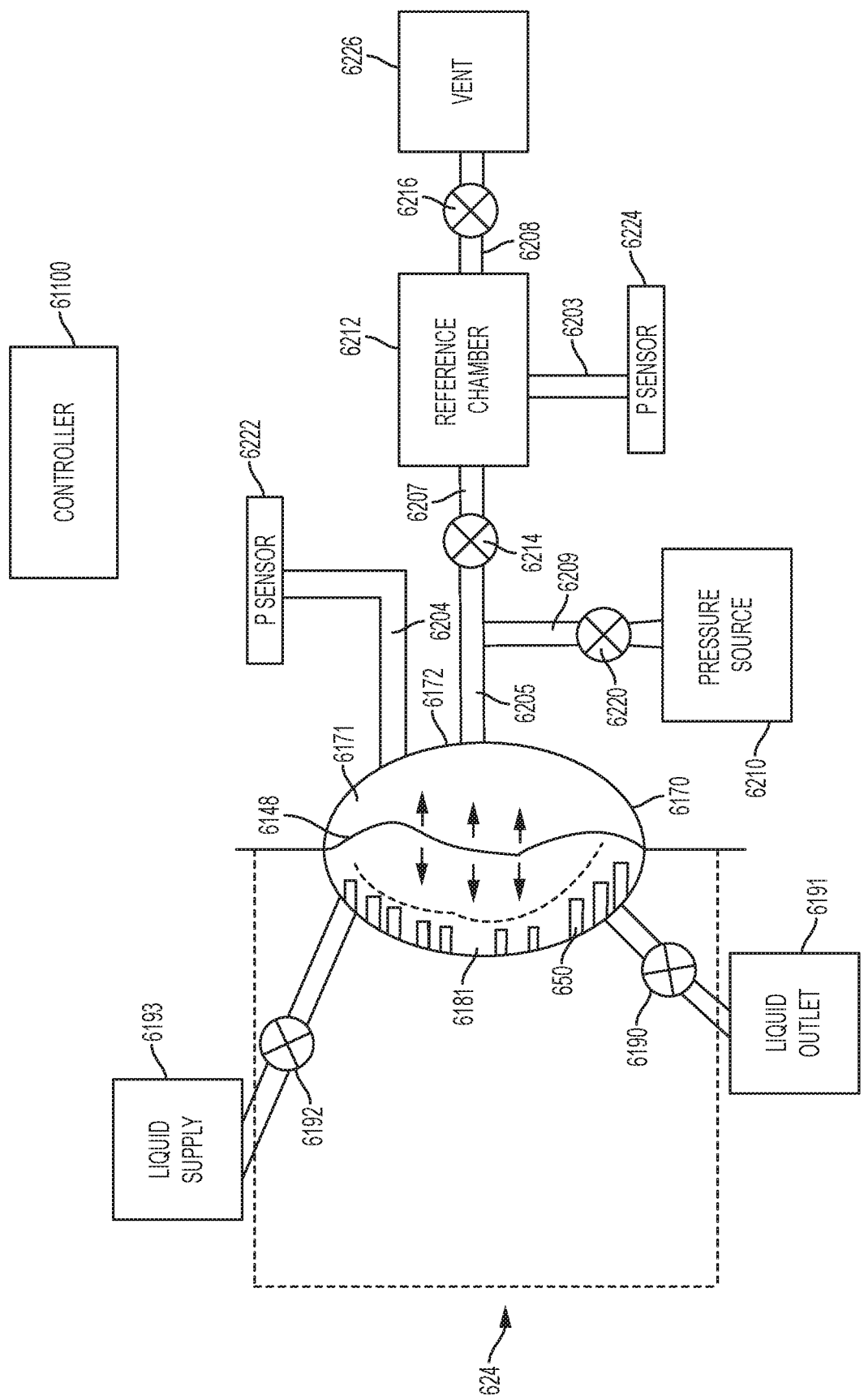
FIG. 45 is a schematic view of a control chamber of a cassette and associated control components including pressure sensors and inflow/outflow paths in an illustrative embodiment.

If the first chamber is precharged to a pressure above the pressure in the second chamber then the 2-chamber FMS process is referred to as positive FMS or +FMS. If the first chamber is precharged to a pressure less than the pressure in the second chamber, then the 2-chamber FMS process is referred to as negative or −FMS. Referring now to FIG. 45, the first chamber is the control chamber 6171 and the second chamber is the reference chamber 6212.

The form of the algorithm to calculate the first chamber volume may depend on the heat transfer characteristics of the first and second chamber and the fluid lines that connect the two chambers. The amount of heat transfer between the structure and the gases during equalization affects the pressures in both the first and second chamber during and after equalization. During equalization, the gas in the chamber with the higher pressure expands toward the other chamber. This expanding gas will cool to a lower temperature and consequently a lower pressure. The cooling of the expanding gas and the loss in pressure may be moderated or reduced by heat transfer from the warmer structure. At the same time, the gas in the chamber initially at a lower pressure is compressed during equalization. The temperature of this compressing gas will rise along with the pressure. The heating of the compressing gas and the rise in pressure may be moderated or reduced by heat transfer from the cooler structure.

The relative importance of heat transfer between the structure (chamber walls, solid material within the chambers) and the gas is a function of the average hydraulic diameter of the chamber, the thermal diffusivity of the gas and the duration of the equalization process. In one example, the two volumes are filled with heat absorbing material such as foam or other matrix that provide enough surface area and thermal mass that the gas temperatures are constant in each chamber during pressure equalization, so that the expansion and compression processes can be modeled as isothermal. In another example, the two chambers are sized and shaped to provide negligible heat transfer, so the expansion and compression processes can be modeled as adiabatic. In another example, the shape and size of the control chamber 6171 changes from measurement to measurement. In measurements after a fill stroke when the control chamber 6171 is small and all the gas is relatively near the chamber wall 6170 or the diaphragm 6148, the heat transfer between the gas and the structure is significant. In measurements after a deliver stroke, the control chamber 6171 is large and open, so that much of the gas is relatively isolated from the chamber walls 6170 or diaphragm 6148 and heat transfer to the gas is negligible. In measurements after a partial stroke the heat transfer between the structure and the gas is significant, but not sufficient to assure constant temperature. In all these measurements, the expansion and compression processes can be modeled as polytropic and the relative importance of heat transfer can be varied from one measurement to the next. A polytropic model can accurately model the equalization process for all geometries and capture the effects of different levels of heat transfer in the first and the second chambers. A more detailed model of the equalization process will more accurately determine the volume of the first chamber from the knowledge of the pressures and the volume of the second chamber.

This section describes an algorithm to calculate the volume of the first chamber 6171 for a polytropic 2-chamber FMS process. The first sub-section describes the two volume FMS or 2-chamber FMS process for an exemplary arrangement of volumes, pressure sources, valves and pressure sensors. The next sub-section conceptually describes the polytropic FMS algorithm for data from a +FMS process and then presents the exact equations to calculate the first volume from the pressure data. The next sub-section presents the concept and equations of the polytropic FMS algorithm for data from a −FMS process. The last sub-section presents the process to calculate the volume of the first chamber 6171 using either set of equations.

The model being described can be applied to any system or apparatus that uses a pneumatically actuated diaphragm pump. The components of the system include a diaphragm pump having at least one pump chamber inlet or outlet with a valved connection to either a fluid source or fluid destination; a pneumatic control chamber separated from the pump chamber by a diaphragm that provides positive or negative pressure to the pump chamber for fluid delivery or filling; the pneumatic control chamber has a valved connection to a reference chamber of known volume and to a positive or negative pressure source; a controller controls the valves of the system and monitors pneumatic pressure in the control chamber and reference chamber. An example of the system is illustrated schematically in FIG. 45, although the specific arrangement of inlets, outlets and fluid and pneumatic conduits and valves can vary. The following description will use a peritoneal dialysis cycler and pump cassette as an example, but the disclosure is by no means limited to this particular application.

Hardware for 2-Chamber FMS Process

Referring now to FIG. 45, a schematic presentation of elements of the cycler and the cassette 624 involved in the 2-chamber FMS process is depicted. The cassette 624 includes two liquid valves 6190, 6192 that are fluidically connected to a liquid supply 6193 and liquid outlet 6191. The cassette 624 includes a diaphragm pump with a variable liquid volume pump chamber 6181 separated by a flexible membrane 6148 from the control chamber 6171. The control chamber 6171 volume is defined by the membrane 6148 and the chamber wall 6170. The control chamber 6171 is the first chamber of unknown volume described above.

A control line 6205 also leads to a connection valve 6214 that communicates with a reference line 6207 and a reference chamber 6212 (e.g., a space suitably configured for performing the measurements described below). The reference chamber 6212 is the second chamber with a known volume described above. The reference chamber 6212 also communicates with an exit line 6208 having a second valve 6216 that leads to a vent 6226 to atmospheric pressure. In another example the vent 6226 may be a reservoir controlled to a desired pressure by one or more pneumatic pumps, a pressure sensor and controller. Each of the valves 6220, 6214 and 6216 may be independently controlled by the controller 61100.

The pressure source 6210 is selectively connected to the control chamber 6171 via lines 6209 and 6205. The pressure source 6210 may include one or more separate reservoirs which are held at specified and different pressures by one or more pneumatic pumps. Each pneumatic pump may be controlled by the controller 61100 to maintain the specified pressure in each reservoir as measured by pressure sensors. A first valve 6220 may control the fluid connection between the pressure source 6210 and the control chamber 6171. The controller 61100 may selectively connect one of the reservoirs in the pressure source 6210 to line 6209 to control the pressure in the control chamber as measured by pressure sensor 6222. In some examples, the controller 61100 may be part of a larger control system in the APD cycler 14.

The control chamber 6171 is connected to the control pressure sensor 6222 via line 6204. A reference pressure sensor 6224 may be connected to the reference chamber 6212 via line 6203. The pressure sensors 6222, 6224 may be an electromechanical pressure sensor that measures the absolute pressure such as the MPXH6250A by Freescale Semiconductors of Japan. The control pressure sensor 6222 and the reference pressure sensor 6224 are connected to the controller 61100, which records the control and reference pressures for subsequent volume calculations. Alternatively, the pressure sensors 6222, 6224 may be relative pressure sensors that measure the pressure in the control and reference chambers relative to the ambient pressure and the controller 61100 may include an absolute pressure sensor to measure the ambient pressure. The controller 61100 may combine the relative pressure signals from sensors 6222, 6224 and the absolute ambient pressure sensor to calculate the absolute pressures in the control chamber 6171 and reference chamber 6212 respectively.

The valves and other components of the FMS hardware shown in FIG. 45 can be controlled by the controller 61100 to execute the 2-chamber FMS process and measure the resulting pressures in control chamber 6171 and in the reference chamber 6212, then calculate the volume of the control chamber 6171. The controller 61100 may be a single micro-processor or multiple processors. In one example, the pressure signals are received by an A-D board and buffered before being passed to the 61100 controller. In another example, a field-programable-gate-array (FPGA) may handle all the I/O between the controller 61100 and the valves and sensors. In another example, the FPGA may filter, store and/or process the pressure data to calculate volume of the control chamber.

2-Chamber FMS Process in APD Cycler

Figure 46:
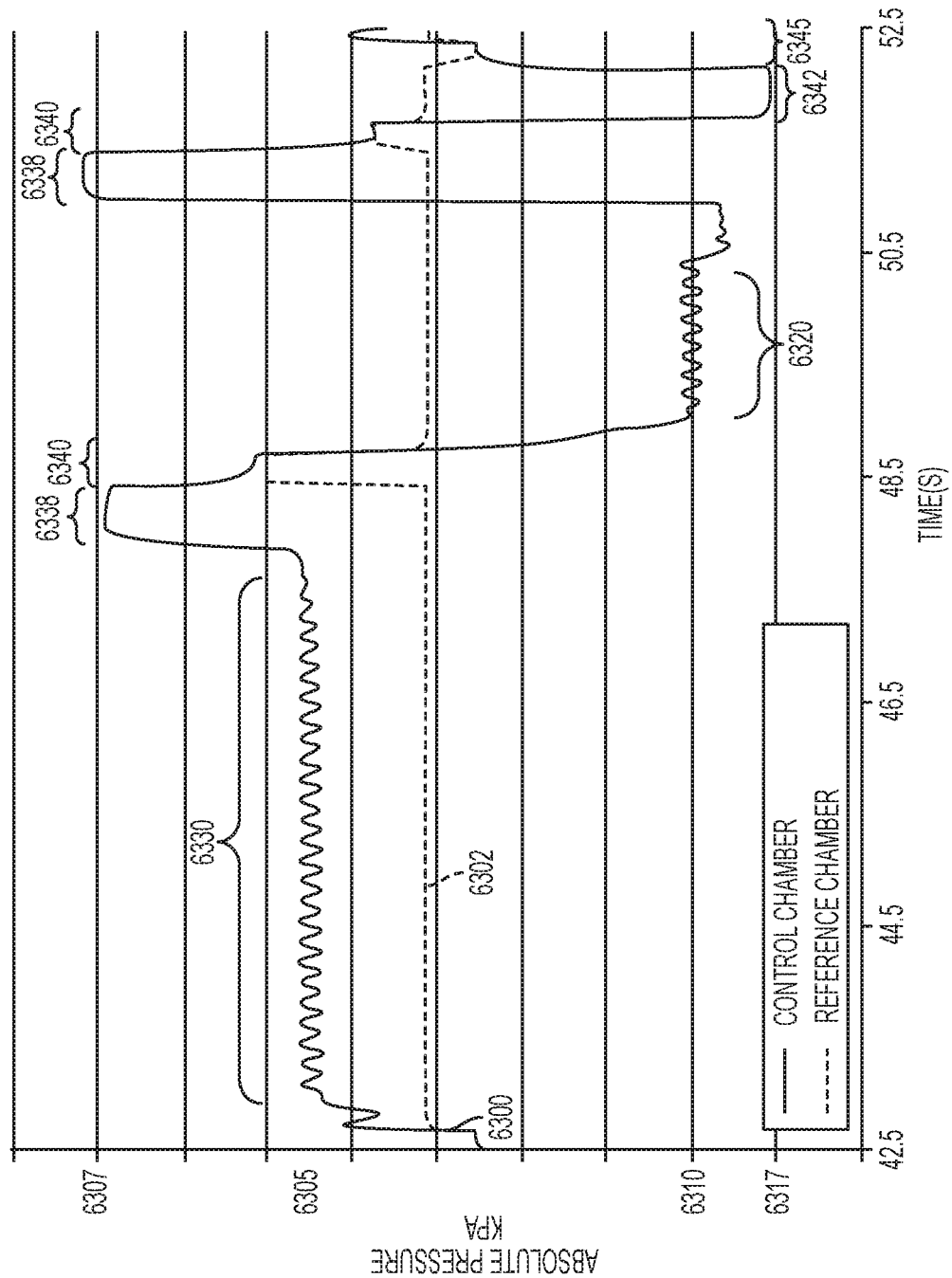
FIG. 46 is a pressure versus time plot for the reference chamber and the control chamber during a pumping and FMS process.

Referring now also to FIG. 46, an exemplary pumping and measurement process is shown in a plot of control chamber pressure 6300 and reference chamber pressure 6302 verses time. As described above, after closing the inlet valve 6192 and opening the outlet valve 6190, the chamber pressure is controlled to a positive value 6305 that pushes fluid out of the pump chamber 6181 during the deliver stroke 6330. At the end of the deliver stroke 6330, the outlet fluid valve is closed and a +FMS process may occur to measure the volume of the control chamber 6171. The FMS process, as described elsewhere, may consist of bringing the control chamber pressure 6330 to a precharging pressure 6307 and allowing a period of pressure stabilization 6338, followed by an equalization process 6340. In other examples, the control chamber pressure 6330 may be returned to near atmospheric pressure before being increased to the precharge pressure 6307. At the end of equalization process 6340, the reference chamber pressure 6302 and possibly the control chamber pressure 6300 can be returned to near atmospheric values.

The fill stroke 6320 occurs after opening the inlet valve 6192 and brings the control chamber pressure 6300 to a negative pressure 6310, while the reference chamber remains near atmospheric, or at a measured and constant pressure. The negative pressure pulls fluid into the pump chamber 6181. At the end of the fill stroke 6320, the inlet valve 6192 is closed and a +FMS process may occur to determine the volume of the control chamber 6171. In some embodiments, a −FMS process may occur after the +FMS process. The −FMS process may include precharging the control chamber to negative pressure 6317, allowing pressure stabilization 6342 and finally an equalization process 6345. The control chamber volume determined from −FMS process may be compared to the control chamber volume determined from the +FMS process to determine whether there is a volume of air or gas in the pump chamber 6181. For example, if the pump chamber includes an air trap having spacers 50 such as ribs or standoffs on the pump chamber rigid wall, air can accumulate among the standoffs. The diaphragm at its full excursion can be prevented from compressing it by the standoffs, and the air may not be detected by a +FMS process alone. In one example, a −FMS process occurs after the deliver stroke 6330.

Figure 47:
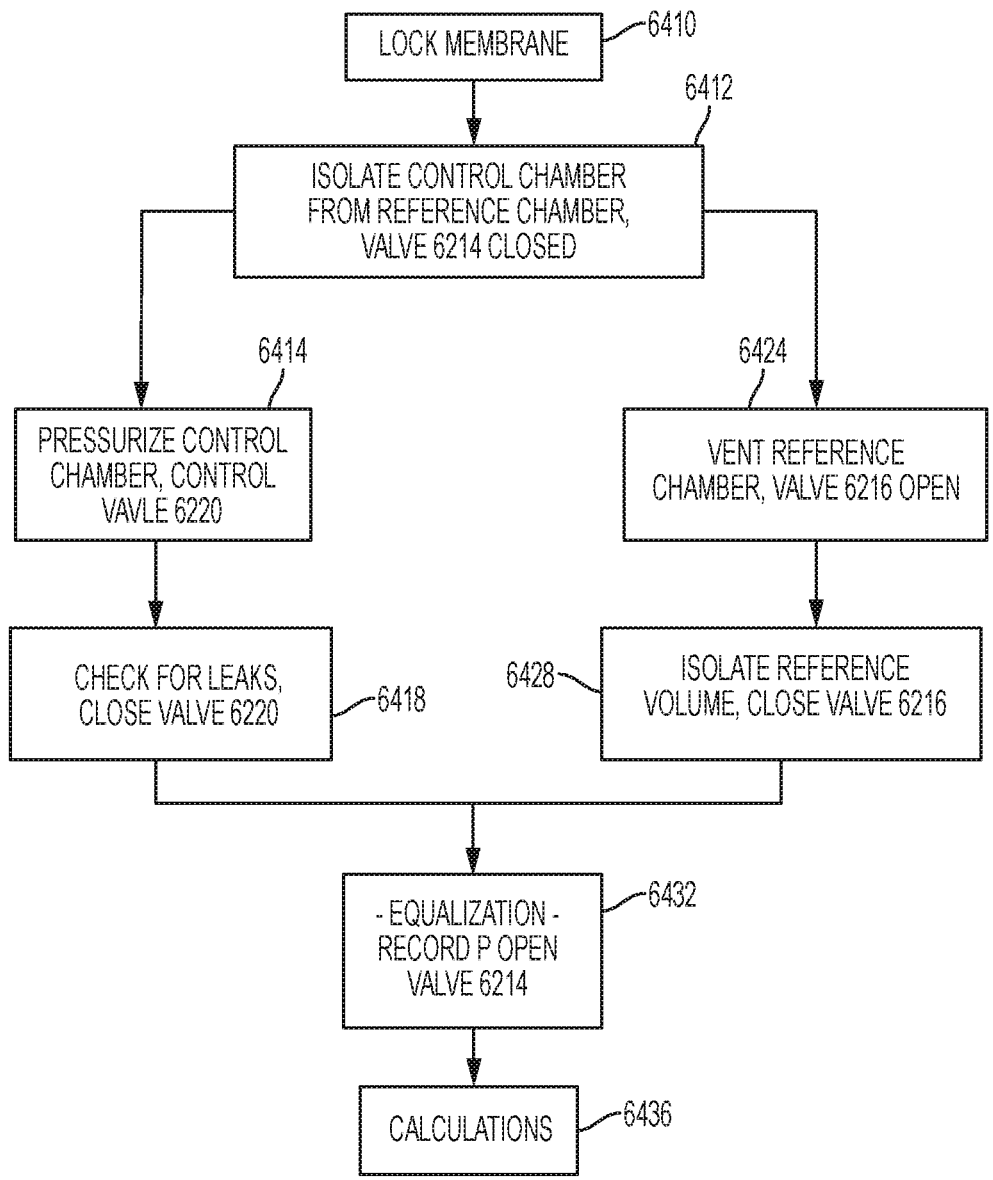
FIG. 47 is a flow chart of pneumatic steps of an FMS process.
Figure 48A:
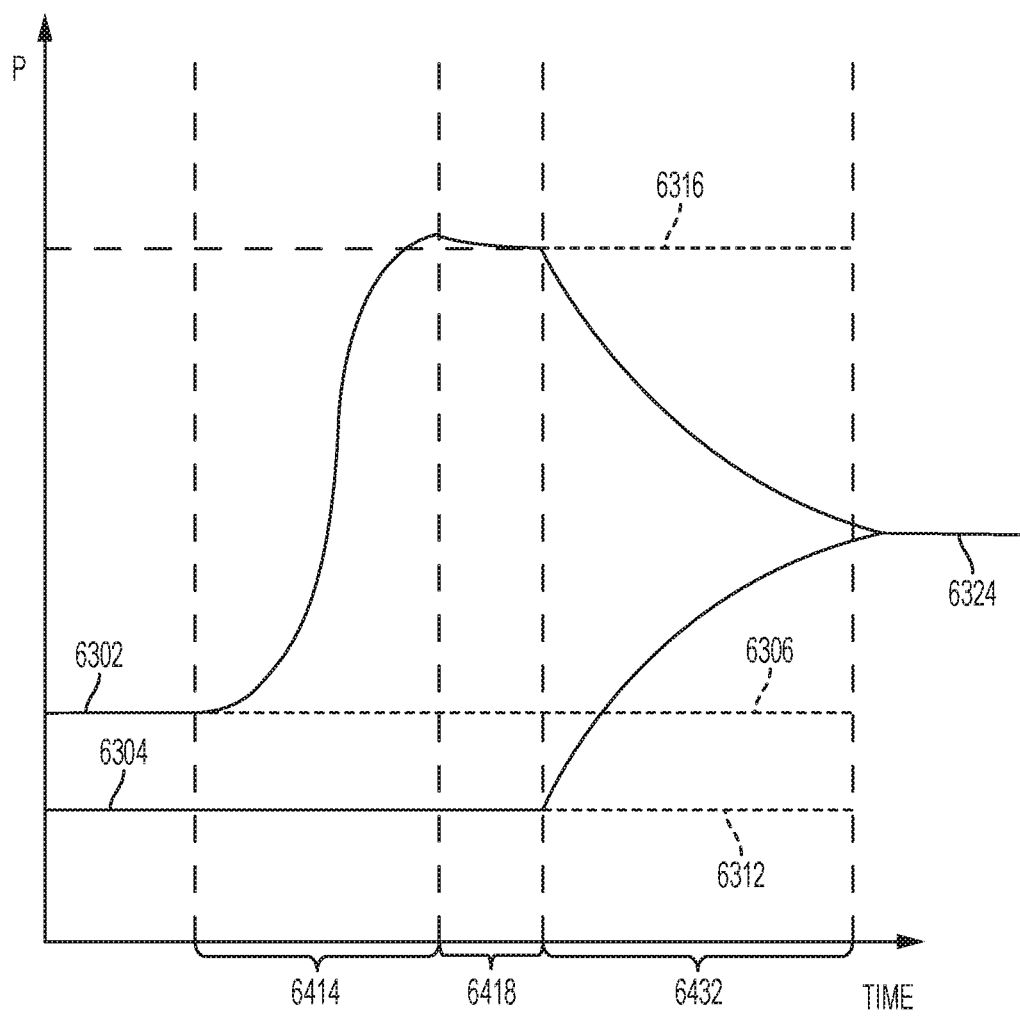
FIG. 48A is a plot of the pumping chamber and reference chamber pressures during the +FMS process.
Figure 48B:
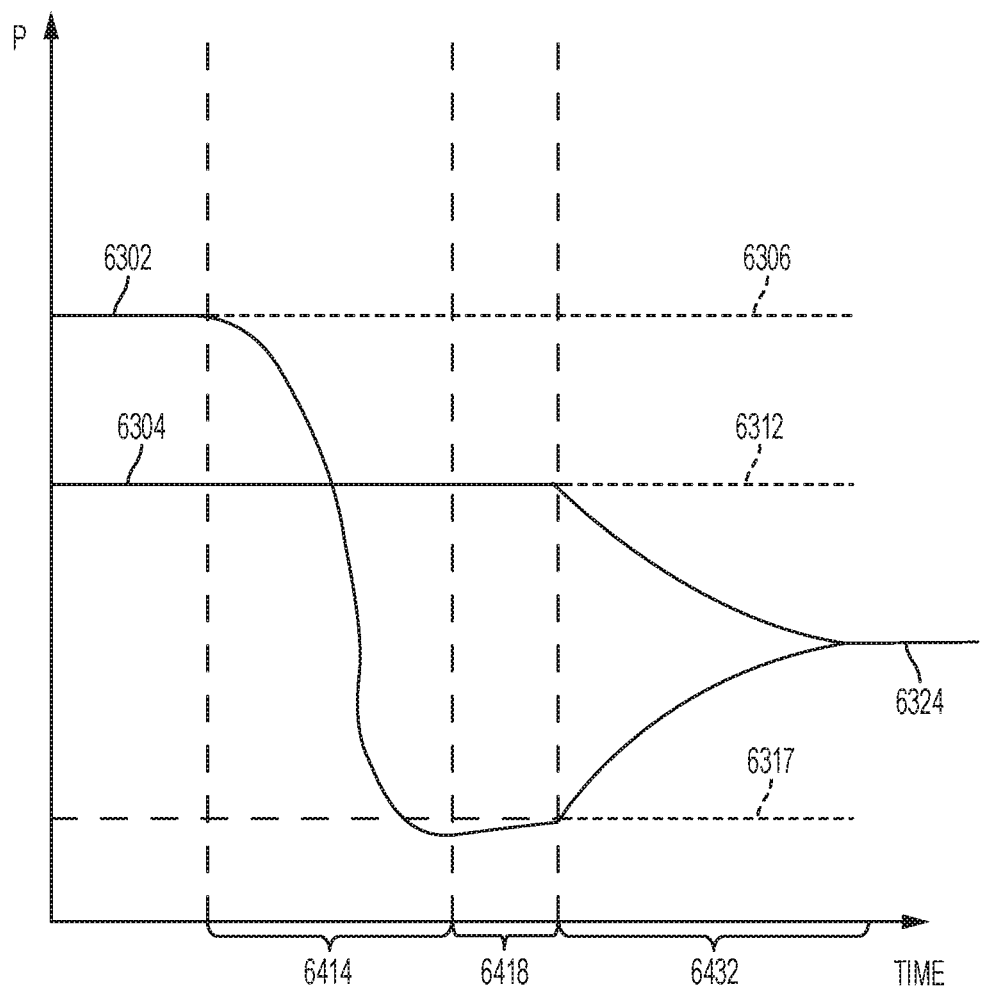
FIG. 48B is a plot of the pumping chamber and reference chamber pressures during the −FMS process.

The +FMS and −FMS processes are described in more detail by referring to the flow chart in FIG. 47, elements in FIG. 46, and the pressure vs. time plots of FIGS. 48A, 48B. The 2-chamber FMS process begins with step 6410 where the position of the membrane 6148 is fixed. The position of the membrane 6148 may be fixed by closing both hydraulic valves 6190, 6192. In some examples, the position of membrane 6148 will vary as the control chamber pressure changes, if gas bubbles are present in the liquid. However, the volume of incompressible liquid between the hydraulic valves 6190, 6192 is fixed. The 2-chamber FMS process will generally measure the volume of air or gas on both sides of the membrane 6148, so any bubbles in the pump chamber 6181 on the liquid side of the membrane 6148 are included in the measured volume of the control chamber 6171.

In step 6412, the control chamber 6171 is fluidically isolated from the reference chamber 6212 by closing connection valve 6214. Then the reference chamber 6212 and control chamber 6171 are fluidically isolated from each other in step 6412. In an embodiment, the reference chamber 6212 is connected to the vent 6226 in step 6424 by opening the second valve 6216. The controller 61100 holds the second valve 6216 open, until reference pressure sensor 6224 indicates that the reference pressure has reached ambient pressure. Alternatively, the controller 61100 may control the second valve 6216 to achieve a desired initial reference pressure in the reference chamber 6212 as measured by the reference pressure sensor 6224. Alternatively, the connection valve 6214 may be closed and the second valve 6216 is open before the FMS process begins. In step 6428, once the desired pressure in the reference chamber 6212 is achieved, the second valve 6216 is closed, which fluidically isolates the reference chamber 6212. The reference chamber steps 6424 and 6428 may be programmed to occur concurrently with the control chamber steps 6414 and 6418.

In step 6414, the control chamber 6171 is pressurized to a desired pressure by connecting the control chamber 6171 to the pressure source 6210 by opening the first valve 6220. The controller 61100 monitors the pressure in the control chamber 6171 with pressure sensor 6222 and controls the first valve 6220 to achieve a desired precharge pressure. The desired precharge pressure may be significantly above the initial reference pressure of the reference chamber 6212 or significantly below the initial reference pressure. In one example, the control chamber 6171 is precharged to approximately 40 kPa above the reference pressure for a +FMS process. In another example, the control chamber 6171 is precharged to approximately 40 kPa below the reference pressure for a −FMS process. In other embodiments, the precharge pressures may be any pressure within the range of 10% to 180% of the initial reference pressure.

The controller 61100 closes the first valve 6220 in step 6418 and monitors the pressure in the control chamber 6171 with pressure sensor 6222. The pressure in the control chamber 6171 may move toward ambient pressure during step 6418 due to gas thermally equalizing with the control chamber wall 6170 and membrane 6148. A large change in pressure during step 6418 may indicate a pneumatic or liquid leak that would invalidate a measurement. The 2-chamber FMS process may be aborted or the calculated volume of the control chamber 6171 may be discarded if the rate of pressure change exceeds a pre-determined allowable rate. The rate of pressure change may be examined after a delay from the pressurization step 6414 to allow the gas in the control chamber 6171 to approach thermal equilibrium with the boundaries 6172, 6148 of the control chamber 6171. In one example, the maximum allowed rate of pressure change during step 6418 is 12 kPA/sec. The 2-chamber FMS process may be aborted and restarted if the rate of pressure change exceeds this predetermined value. In another embodiment, the maximum allowable rate of pressure change is a function of—and will vary based on—the calculated control chamber volume. In one example, the maximum allowed pressure change is 3 kPA/sec for a 25 ml volume and 25 kPA/sec for 2 ml volume. In one example, the FMS process may be carried to completion regardless of the leak rate resulting in a calculated volume of the control chamber 6171. The calculated volume may be discarded and the FMS process restarted if the measured rate of pressure change exceeds the allowable limit for the calculated control chamber volume.

The control chamber 6171 and the reference chamber 6212 are fluidically connected in step 6432, when the controller 61100 opens the connection valve 6214 between the two chambers. The controller 61100 monitors the pressures in each chamber with the pressure sensors 6222, 6224 as the pressure in the control chamber 6171 and reference chamber 6212 equalize. The controller 61100 may record the initial pressure pair and at least one pressure pair at the end of equalization in step 6432. A pressure pair refers to a signal from the control pressure sensor 6222 and a signal from the reference pressure sensor 6224 recorded at approximately the same time. Step 6432 extends from a period of time just before the connection valve 6214 is open to a point in time, when the pressure in the control chamber 6171 and reference chamber 6212 are nearly equal.

The 2-chamber FMS process is completed in step 6436, where the recorded pairs of pressures are used to calculate the volume of the control chamber 6171. The calculation of the control chamber 6171 volume is described in detail below.

The +FMS process is sketched as pressure vs. time plot in FIG. 48A. Reference numbers corresponding to those of the steps in FIG. 47 are included to indicate where those steps are depicted in FIG. 48A. The pressure of the control chamber 6171 is plotted as line 6302. The pressure of the reference chamber is plotted as line 6304. The pressure vs. time plot begins after steps 6410, 6412, 6424, 6428 of FIG. 47 have been completed. At this point the pressure in the reference chamber 6212 is at the desired reference pressure 6312. The pressure in the control chamber 6171 begins at an arbitrary pressure 6306 and during step 6414 increases to the precharge pressure 6316. The arbitrary pressure 6306 may be the pressure of the control chamber 6171 at the conclusion of a previous pumping operation. In another embodiment, the arbitrary pressure 6306 may atmospheric pressure. The control chamber pressure 6302 may drop during step 6418. In step 6432, the control chamber pressure 6302 and reference chamber pressure 6304 equalize toward an equilibrium pressure 6324.

The −FMS process is sketched as pressure vs. time plot in FIG. 48B. The pressure of the control chamber 6171 (FIG. 45) is plotted as line 6302. The pressure of the reference chamber 6312 (FIG. 45) is plotted as line 6304. The horizontal time axis is divided in periods that correspond to the process steps identified with the same reference numbers in FIG. 47. The pressure vs. time plot begins when the pressure in the reference chamber 6212 (line 6302) is at the desired reference pressure 6312 and the pressure in the control chamber 6171 (line 6304) is at an arbitrary pressure. During step 6414, the control chamber pressure 6302 decreases to the negative precharge pressure 6317. The control chamber pressure 6302 may rise during step 6418 as the gas cooled by the sudden expansion of step 6414 is heated by the control chamber walls 6172, 6148. In step 6432, the control chamber pressure 6302 and reference chamber pressure 6304 equalize toward an equilibrium pressure 6324.

Polytropic +FMS Algorithm

Referring again to FIG. 45, the equalization process involves the fluid volumes of three distinct structures: control chamber 6171, reference chamber 6212 and the manifold passages 6204, 6205, 6207, 6209 connecting the two chambers 6171, 6212. In one example, each structure has significantly different hydraulic diameters and thus different levels of heat transfer between the structure and the gas. In this example, the reference chamber 6212 has an approximately cubic shape with a hydraulic diameter of approximately 3.3 cm. Heat transfer during the approximately 30 microsecond equalization process is negligibly small and the gas in the reference chamber 6212 volume is likely to be compressed adiabatically, and can be modeled as such. In contrast, in an exemplary construction, the manifold passages 6204, 6205, 6207, 6209, have an approximately 0.2 cm hydraulic diameter, which is about 15 times smaller than the hydraulic diameter of the reference chamber 6212 volume. Heat transfer in the manifold passages 6204, 6205, 6207, 6209 is high and the gas passing through these passages 6204, 6205, 6207, 6209 is more likely to compress or expand isothermally at approximately the temperature of the manifold walls. The hydraulic diameter of the control chamber 6171 in this example has a minimum of value of approximately 0.1 cm when the pumping chamber 6181 is full of liquid at the end of a fill stroke and the control chamber 6171 is at a minimum volume. The hydraulic diameter of the control chamber 6171 in this example has a maximum value of approximately 2.8 cm when the pumping chamber 6181 has delivered the liquid and the control chamber 6171 is at a maximum volume. The expansion of gas in the control chamber 6171 can be more appropriately modeled with a polytropic coefficient that varies with the size of the control chamber 6171. When the control chamber 6171 volume is at a minimum and the expansion process will be nearly isothermal, the polytropic coefficient can be set to approximately 1. When the control chamber 6171 is at a maximum and the expansion process is near adiabatic, the polytropic coefficient may be set to approximately the ratio of specific heats (cp/cv), which equals 1.4 for air. For 2-chamber FMS measurements at partial strokes, the expansion process will occur with significant heat transfer, but not enough to be isothermal. The polytropic coefficient may be set to a value between 1 and 1.4 for measurements at partial strokes. Since the volume of the control chamber 6171 is the unknown quantity of this analysis, the polytropic coefficient for the control chamber 6171 may be based on an estimate of control chamber 6171 volume.

Figure 49A:
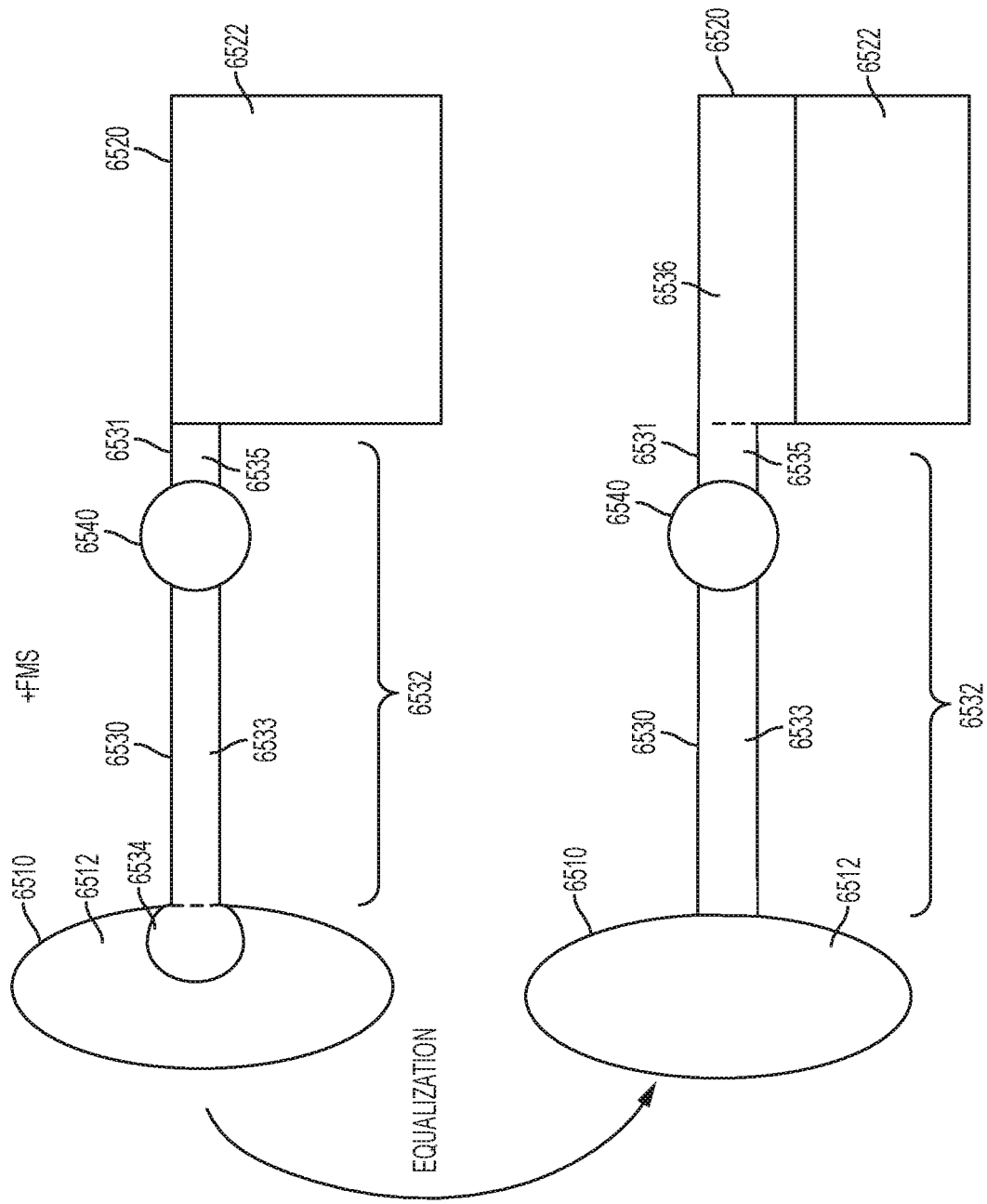
FIG. 49A is an illustration of a polytropic conceptual model of the +FMS process involving three separate closed mass systems.

Referring now to FIG. 49A, the gas in the structures of the control chamber 6510, the reference chamber 6520 and the manifold lines 6530, 6531 can be modeled as three gas masses, 6512, 6532, 6522 that do not mix, but expand, contract, and move through the structures 6510, 6520, 6530, 6531. Conceptually, for modeling purposes, these masses 6512, 6532, 6522 are each a closed-system that may move, change size and exchange energy with the structures, but mass may not enter nor exit the closed-system. The closed-system model is a well understood concept in thermodynamics and fluid dynamics. These masses may also be referred to as a control chamber system 6512, reference chamber system 6522 and a manifold or interconnecting line system 6532.

The volume of the control chamber 6510 can be calculated from the measured control chamber 6510 and reference chamber 6520 pressures based on thermodynamic models of the three masses 6512, 6532, 6522. The control chamber mass or gas 6512 is the gas that occupies the control chamber 6510 at the end of the equalization process. The reference chamber gas 6522 is the gas that occupies the reference chamber 6520 at the beginning of the equalization process. The manifold gas 6532 fills the balance of the structure between the control chamber gas 6512 and the reference chamber gas 6522, including a connecting conduit between the control and reference chambers.

The volume and temperature of the three closed-systems, 6512, 6532, 6522 may then be calculated from initial conditions, pressure pairs, heat transfer assumptions and the constraint of a fixed total volume for the three closed-systems. The pressure equalization can be modeled with a different polytropic coefficient for each volume 6510, 6520, 6530, 6531 to capture the relative importance of heat transfer in each. The constant mass, ideal gas and polytropic process equations for the three systems, 6512, 6532, 6522 can be combined and arranged to calculate the volume of the control chamber 6510. The following paragraphs describe the derivation of one or more sets of equations that allow calculation of the control chamber 6510 volume based on pressures measured during the pressure equalization step of the FMS process (see, 6432 of FIGS. 47 and 48A).

Description of Closed Systems for +FMS

The upper image in FIG. 49A presents the position of the three closed-systems 6512, 6532, 6522 at the start of pressure equalization in the +FMS process. The lower image presents the positions of the three closed systems 6512, 6532, 6522 at the end of the pressure equalization. During the equalization process, the locations of the closed systems 6512, 6532, 6522 are between the two extremes presented in FIG. 49A. By way of an example, neither the control chamber system 6512 nor the reference chamber system 6522 fill their respective structures. The following paragraphs present the closed systems 6512, 6532, 6522 in more detail.

The control chamber gas system 6512 is the gas that fills the control chamber 6510 after pressure equalization. Before pressure equalization, the control chamber gas system 6512 is compressed to the precharge pressure that is higher than the final equalization pressure and therefore does not occupy the entire control chamber 6510. The control chamber gas system 6512 may be modeled as expanding in a polytropic process during pressure equalization of the +FMS process, where the pressure and the volume are related by:

$$p_f V_{cc}^{nCC} = \text{constant}$$

where $p_f$ is the equalized pressure, $V_{CC}$ is the volume of the control chamber 6510, and nCC is the polytropic coefficient for the control chamber 6510.

The reference gas system 6522 is the gas that occupies the entire reference volume 6520 before equalization. The reference gas system 6522 is compressed during equalization as the higher pressure gas in the control chamber 6510 expands and pushed the manifold gas system 6532 into the reference chamber 6520. In one example shown in FIG. 36, the reference chambers (depicted as 174 in FIG. 36) are sufficiently open or devoid of interior features/elements that compression or expansion processes during pressure equalization may be modeled as adiabatic. In this case, the polytropic coefficient (n) may be set equal to approximately the specific heat ratio of the gas present in the chamber. The pressure and the volume of the reference chamber gas 6522 are related by:

$$p_{RO} V_{Ref}^{nR} = \text{constant}$$

where $p_{RO}$ is the initial reference pressure, $V_{Ref}$ is the volume of the reference chamber, and nR is the specific heat ratio for the gas in the reference chamber (nR=1.4 air). In another example, where the chamber 6520 is at least partially filled with a heat absorbing material such as open cell foam, wire mesh, particles, etc. that provides for a near-isothermal expansion, the polytropic coefficient for the reference chamber (nR) may have a value of approximately 1.0.

In the +FMS process, the conduit or manifold gas system 6532 occupies all of the volume of the interconnecting volume 6530, 6531 and a fraction 6534 of the control chamber 6510 before equalization. After equalization, the conduit gas system 6532 occupies the interconnecting volume 6530, 6531 and part of the reference volume 6520. The portion of the conduit gas system 6532 that exists in interconnecting volume 6530 on the control chamber side of the valve 6540 is herein labeled as 6533. The portion of the conduit gas system 6532 that exits in the interconnecting volume 6531 on the reference chamber side of the valve 6540 is referred to as 6535. The portion of the conduit gas system 6532 that exist in the control chamber 6510 pre-equalization is herein labeled as 6534. The portion of the conduit gas system 6532 that exists in the reference chamber 6520 after equalization is referred to as 6536.

In one example the interconnecting volumes 6530 and 6531 may be narrow passages that provide high heat transfer and assure the conduit gas system 6532 in volumes 6530 and 6531 is near the temperature of the solid boundaries or walls of the passages. The temperature of the structure surrounding the interconnecting volumes 6530, 6531 or manifold passages is herein referred to as the wall temperature ($T_w$). In another example, the temperature of the conduit gas system 6532 in volumes 6530, 6531 is in part a function of the wall temperature. The portion of the conduit or manifold gas system in the control chamber 6534 may be modeled with the same temperature as control chamber gas system 6512. The control chamber portion of the conduit gas system 6534 experiences the same expansion as the control chamber gas system 6512 and may be conceived of as having the same temperature as the control chamber gas system 6512. The portion of the lines or manifold gas system in the reference chamber 6536 may be modeled with a temperature that is in part a function of the wall temperature. In another example, the reference chamber portion of the conduit gas system 6536 may be modeled as not interacting thermally with the boundaries of the reference chamber 6520, so that the temperature of the conduit gas system portion 6536 is a function of the wall temperature and the reference chamber 6520 pressures.

The equations in this section use the following nomenclature:

variables
γ: specific heat ratio
n: polytropic coefficient
p: pressure
V: volume
T: temperature
superscripts:
n: polytropic coefficient
nCC: polytropic coefficient for the control chamber
nR: polytropic coefficient for the reference chamber
subscripts:
c: control chamber system
CC: physical control chamber
f: value at end of equalization
i: $i^{th}$ value
IC: physical interconnecting volume or manifold passages
IC_R: physical interconnecting volume on the reference chamber side of valve
IC_CC: physical interconnecting volume on the control chamber side of valve
l: lines or interconnecting/manifold system
0: value at start of equalization
pmp: pump
r: reference system
Ref: physical reference chamber
w: wall of interconnecting volume The equations for the control chamber 6510 may be derived from the conceptual model of the three separate mass systems in FIG. 49A and the understanding that the total volume of the control chamber mass 6510, reference chamber mass 6520 and interconnecting volumes mass 6530, 6531 is fixed. This relationship can be expressed as the sum of the volume changes of each closed system 6512, 6522, 6532 being zero for each $i^{th}$ set of values from the start to the end of pressure equalization:

0=change in volume of+change in volume
   of+change in volume of control chamber mass
   interconnecting mass reference chamber mass $$0 = \Delta V_{ci} + \Delta V_{ri} + \Delta V_{li} \tag{13}$$

where the $i^{th}$ value of $\Delta V_{ci}$, $\Delta V_{ri}$, $\Delta V_{li}$ represents these values at the same point in time. Equations can be developed for the volume change of the control chamber gas system ($\Delta V_{ci}$), the reference gas system ($\Delta V_{ri}$), and the conduit gas system ($\Delta V_{li}$) based on the pressure/volume relationship of a polytropic process and the ideal gas law. The equation for the $i^{th}$ volume change of the control chamber gas system 6512 is equal to the $i^{th}$ volume of the control chamber mass 6512 less the volume of the control chamber mass 6512 at the start of equalization. The volume of the control chamber mass 6512 at time i is calculated from the volume of the control chamber 6510 times the ratio of the final control chamber 6510 pressure over the control chamber 6510 pressure at time i, raised to one over the polytropic coefficient for the control chamber 6510:

current change in volume of control chamber mass = (14)

current volume of control chamber mass − initial volume of control chamber mass $$\Delta V_{ci} = V_{CC}\left(\frac{P_{CCf}}{P_{CCi}}\right)^{1/nCC} - V_{CC}\left(\frac{P_{CCf}}{P_{CC0}}\right)^{1/nCC}$$

The equation for the reference gas system volume change ($\Delta V_r$) is derived from the pressure/volume relationship for a polytropic process. The equation for the $i^{th}$ volume change of the reference chamber gas system 6522 is equal to the $i^{th}$ volume of the reference chamber mass 6522 less the volume of the reference chamber mass 6522 at the start of equalization. The volume of the reference chamber mass 6522 at time i is calculated from the structural volume of the reference chamber 6520 times the ratio of the initial reference chamber 6520 pressure over the reference chamber 6520 pressure at time i, raised to one over the polytropic coefficient for the reference chamber 6520:

current change in volume of reference chamber mass = (15)

current volume of reference chamber mass − initial volume of reference chamber mass $$\Delta V_{ri} = V_{Ref}\left(\frac{P_{Ref0}}{P_{Refi}}\right)^{1/nR} - V_{Ref}$$

The equation for the volume change of the interconnecting gas system 6532 ($\Delta V_1$) is derived from the constant mass gas of the system ($V*\rho$=constant). The equation for the $i^{th}$ volume change of the conduit gas system 6532 is equal the current volume of the system less the original volume of the interconnecting gas system 6532. The current volume of the interconnecting or line gas system 6532 is the initial volume times the ratio of initial over current density of the system. The initial volume of the interconnecting gas system 6532 is the sum of the volumes 6534, 6533 and 6535 pictured in the upper image FIG. 49A:

current change in volume of interconnecting mass = (16)

current volume of interconnecting mass + initial volume of interconnecting mass $$\Delta V_{Ii} = (\Delta V_{cf} + V_{IC})\frac{\rho_{I0}}{\rho_{Ii}} - (\Delta V_{cf} + V_{IC}).$$

The density terms $\rho_{I0}$, $\rho_{Ii}$ are the average density of the gases in the conduit gas system at the start of equalization and at some point, i, during equalization. The conduit gas system 6532 includes gases as different temperatures and pressures. The conduit gas system 6532 includes gas in the volume in the control chamber 6510 in a volume labeled 6534, gas in manifold passages on the control chamber side of the valve 6540 labeled 6533, gas in manifold passages on the reference chamber side of the valve 6540 labeled 6535, and gas in the reference chamber labeled 6536.

These four equations may be combined develop an expression for the volume ($V_{CC}$) of the control chamber 6510 as a function of the measured pressure pairs at the start of pressure equalization ($P_{CC\,0}$, $P_{Ref\,0}$), at any point during the equalization ($P_{CC\,i}$, $P_{Ref\,i}$), the control chamber pressure at approximately the end of equalization ($P_{CCf}$) and the fixed volumes of the reference chamber ($V_{Ref}$) and interconnecting volume ($V_{IC}$):

$$V_{CC} = \frac{V_{Ref}\left[\left(\frac{P_{Ref0}}{P_{Refi}}\right)^{1/nR} - 1\right] + V_{IC}\left(\frac{\rho_{I0}}{\rho_{Ii}} - 1\right)}{\left[1 - \left(\frac{P_{CCf}}{P_{CCi}}\right)^{1/nCC}\right] + \left[\left(\frac{P_{CCf}}{P_{CC0}}\right)^{1/nCC} - 1\right]\left(\frac{\rho_{I0}}{\rho_{Ii}}\right)} \quad (17)$$

where the densities of the manifold or line system 6532 ($\rho_{I0}$, $\rho_{Ii}$) are evaluated with the initial pressure pairs ($P_{CC\,0}$, $P_{Ref\,0}$) and any pressure pair ($P_{CC\,i}$, $P_{Ref\,i}$) during equalization along with the associated temperatures as described below.

The densities of the conduit gas system ($\rho_{I0}$, $\rho_{Ii}$) in equations (16) may be calculated from the volume-weighted average density for each physical volume (i.e. control chamber 6510, reference chamber 6520, and interconnecting volumes 6530, 6531):

$$\rho_{Ii} = \frac{\rho_{CCi}(\Delta V_{cf} - \Delta V_{ci}) + \rho_{IC\_CC}V_{IC\_CC} + \rho_{IC\_R}V_{IC\_R} - \rho_{ri}\Delta V_{ri}}{(\Delta V_{cf} - \Delta V_{ci} + V_{IC\_CC} + V_{IC\_R} + \Delta V_{ri})} \quad (18)$$

$$\rho_{CCi} = \frac{P_{CCi}}{RT_{CCi}} = \text{density of gas in control chamber}$$

$$\rho_{IC\_CCi} = \frac{P_{CCi}}{RT_{IC\_CC}} =$$

density of gas in manifold line on control chamber side of valve $$\rho_{IC\_Ri} = \frac{P_{Refi}}{RT_{IC\_CC}} =$$

density of gas in manifold line on reference chamber side of valve $$\rho_{ri} = \frac{P_{Refi}}{RT_{lr}} = \text{density of gas in reference chamber}$$

where R is the universal gas constant for air, the temperatures, $T_{IC\_CC}$, $T_{IC\_R}$, $T_{lr}$, may be functions in part of the temperature of the interconnecting volume walls. In another example, the temperatures, $T_{IC\_CC}$, $T_{IC\_R}$, $T_{lr}$, may be functions in part of the temperature of the interconnecting volume walls and the gas temperature of the control chamber ($T_{CCi}$) In another example, the temperatures, $T_{IC\_CC}$, $T_{IC\_R}$, $T_{lr}$, may be the interconnecting wall temperature ($T_W$). In another example, the temperatures may be control chamber temperature ($T_{CCi}$) The value of $\Delta V_{ri}$, is calculated from equation (14). The value of $\Delta V_{cf} - \Delta V_{ci}$ is the volume of 6534 and is calculated as $$\Delta V_{cf} - \Delta V_{ci} = V_{CC\,Est}\left[1 - \left(\frac{P_{CCf}}{P_{CCi}}\right)^{1/nCC}\right] \quad (19)$$

The density of the conduit gas system 6532 before pressure equalization may be calculated from an equation similar to (18) that is the volume-weighted average density for each physical volume (i.e. control chamber 6510 and interconnecting volumes 6530, 6531):

$$\rho_{I0} = \frac{\frac{P_{CCi}(\Delta V_{cf})}{T_{CC0}} + \frac{P_{CC}V_{IC\_CC}}{T_W} + \frac{P_{Ref}V_{IC\_R}}{T_W}}{R(\Delta V_{cf} + V_{IC\_CC} + V_{IC\_R})} \quad (20)$$

The change in the control chamber gas system volume ($\Delta V_{cf}$) used in equation (18) is calculated from the physical volume of the control chamber 6510 times the quantity one minus the ratio of the final control chamber pressure over the initial control chamber pressure raised to one over the polytropic coefficient for the control chamber:

$$\Delta V_{cf} = V_{CC\,Est}\left[1 - \left(\frac{P_{CC\,f}}{P_{CC\,i}}\right)^{1/nCC}\right]. \tag{21}$$

An estimate of the control chamber 6510 volume can be derived by assuming constant temperature for the conduit gas system 6532, so that the density ratio ($\rho_{i0}/\rho_{if}$) is equal to the pressure ratio ($P_{i0}/P_{if}$) To further simplify the estimate, the polytropic coefficient is replaced by the specific heat ratio ($\gamma$). In this simpler equation, the control chamber 6510 volume is a function of the measured pressure pairs at the start of pressure equalization ($P_{CC\,0}$, $P_{Ref\,0}$) and at the end of equalization ($P_{CC\,f}$, $P_{Ref\,f}$) and the fixed volumes of the reference chamber ($V_{Ref}$) and interconnecting volume ($V_{IC}$):

$$V_{CC\,Est} = \frac{V_{Ref}\left[\left(\frac{P_{Ref\,0}}{P_{Ref\,f}}\right)^{\frac{1}{\gamma}} - 1\right] + V_{IC}\left(\frac{P_{CC\,0}}{P_{CC\,f}} - 1\right)}{\left[\left(\frac{P_{CC\,f}}{P_{CC\,0}}\right)^{\frac{1}{\gamma}} - 1\right]\left(\frac{P_{CC\,0}}{P_{CC\,f}}\right)} \tag{22}$$

The gas in the three closed systems 6512, 6522, 6532 may be modeled as an ideal gas, so the temperature can be determined from the initial conditions and the new pressure or volume:

$$T_i = T_0\left(\frac{p_0}{p_i}\right)^{(n-1)/n} \text{ or } T_i = T_0\left(\frac{V_0}{V_i}\right)^{n-1} \tag{23}$$

The initial temperature of the gas in the control chamber ($T_{CC\,0}$) may be calculated from the temperature of the interconnecting volume walls, the precharge pressure 6316 (FIG. 48A) and the pressures in the control chamber 6510 just before precharge 6306. The compression of gas in the control volume to the precharge pressure can be modeled as a polytropic process and using the ideal gas law in equation (23). The control chamber 6510 pressure before precharging 6306 is referred herein as the pumping pressure (Ppmp):

$$T_{CC\,0} = T_W\left(\frac{P_{pmp}}{P_{CC\,0}}\right)^{\frac{1}{nCC}-1}. \tag{24}$$

The temperature of the gas in the control chamber 6510 at the $i^{th}$ step ($T_{CC\,i}$) during expansion may be calculated from the initial control chamber 6510 temperature, the precharge pressure 6316 (FIG. 48A) and the $i^{th}$ control chamber 6510 pressure ($P_{CC\,i}$) using equation (23):

$$T_{CC\,i} = T_{CC\,0}\left(\frac{P_{CC\,0}}{P_{CC\,i}}\right)^{\frac{1}{nCC}-1} \tag{25}$$

The value of the polytropic coefficient for the control chamber gas system (nCC) used in equations 14, 17, 19, 21, 25 may vary with the volume of the control chamber 6510 and range from approximately 1 for small volumes to approximately the specific heat ratio for large volumes. The specific heat ratio for air and other systems of predominantly diatomic molecules is 1.4. In one example the value of nCC (for +FMS) can be expressed as a function of the estimated control chamber volume (eqn 22):

$$nCC = 1.4\text{-}3.419 \times 10^{-5}(23.56 - V_{CC\,Est})^{3.074} \tag{26}$$

A method to determine a relationship between the volume of the control chamber ($V_{CC}$) and its polytropic coefficient (nCC) is described in a following section.

Polytropic −FMS Algorithm

A −FMS algorithm similar to the +FMS algorithm, described above, can be developed to calculate the volume of the control chamber 6171 in FIG. 45 from the control chamber 6171 and reference chamber 6212 pressures for a −FMS process. In the −FMS process the first chamber (e.g. 6171) is precharged to a pressure below the known second chamber (e.g. 6212).

Figure 49B:
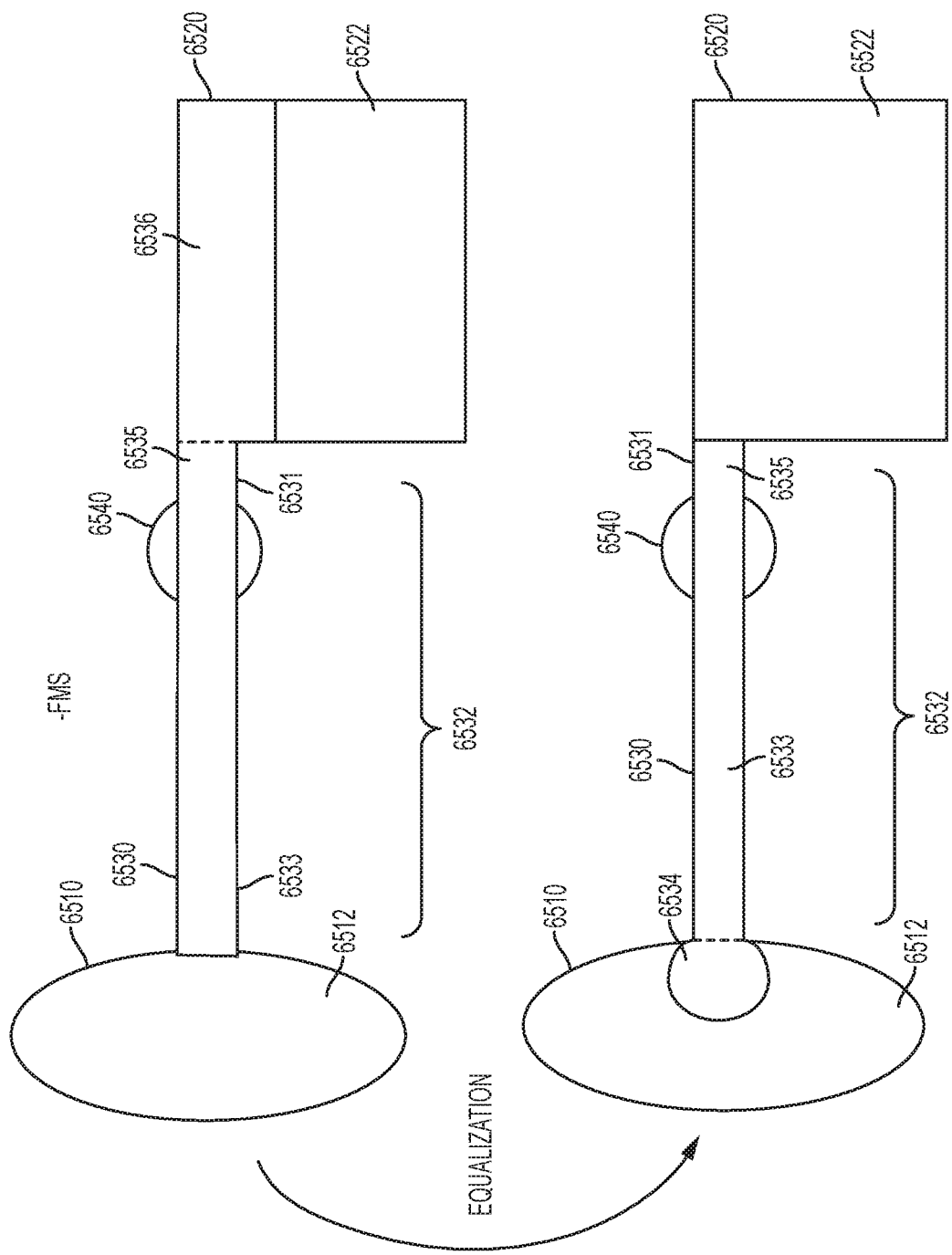
FIG. 49B is a plot of the polytropic expansion constant for +FMS verses control chamber volume.

Referring now to FIG. 49B, the gas in the structures of the control chamber 6510, the reference chamber 6520 and the manifold lines 6530, 6531 can be modeled as three gas masses, 6512, 6532, 6522 that do not mix, but expand, contract, and move through the structures 6510, 6520, 6530, 6531. The volume of the control chamber 6510 can be calculated from the measured control chamber 6510 and reference chamber 6520 pressures based on thermodynamic models of the three masses 6512, 6522, 6532. In the −FMS algorithm, the control chamber mass 6512 is the gas that occupies the control chamber 6510 at the start of the equalization process. The reference chamber mass 6522 is the gas that occupies the reference chamber 6520 at the end of the equalization process. The manifold gas 6532 fills the balance of the structure between the control chamber gas 6512 and the reference chamber gas 6522.

The volume and temperature of the three conceptual closed-systems, 6512, 6532, 6522 may then be calculated from initial conditions, pressure pairs, heat transfer assumptions and the constraint of a fixed total volume for the 3 closed-systems 6512, 6532, 6522. The pressure equalization can be modeled with a different polytropic coefficient for each volume 6510, 6520, 6530, 6531 to capture the relative importance of heat transfer in each. The constant mass, ideal gas and polytropic process equations for the three systems, 6512, 6522, 6532 can be combined and arranged to calculate the volume of the control chamber 6510. The following paragraphs describe the derivation of one or more sets of equations that allow calculation of the control chamber 6510 volume based on pressures measured during the pressure equalization step of the −FMS process.

Description of Closed Systems for −FMS

The upper image in FIG. 49B presents the positions of the three closed-systems 6512, 6522, 6532 at the start of pressure equalization in the −FMS process. The lower image presents the positions of the three closed systems 6512, 6522, 6532 at the end of the pressure equalization. During the equalization process, the locations of the closed systems 6512, 6522, 6532 are between the two extremes presented in FIG. 49B. By way of an example, neither the control chamber system 6512 nor the reference chamber system 6522 fill their respective structures 6510, 6520. The following paragraphs present the closed systems in more detail.

The control chamber gas system 6512 in the −FMS algorithm is the gas that fills the control chamber 6510 before equalization. The control chamber gas system 6512 is compressed during pressure equalization as the initially higher pressure reference chamber gas system 6522 expands and pushes the manifold gas system 6532 into the control chamber 6510. The control chamber gas system 6512 may be modeled with a polytropic compression during pressure equalization of the −FMS process, where the pressure and the volume are related by:

$$p_0 V_{CC}^{nCC} = \text{constant}$$

where $p_0$ is the initial pressure in the control chamber 6510, $V_{CC}$ is the volume of the control chamber 6510, and nCC is the polytropic coefficient for the control chamber 6510.

The reference gas system 6522 in the −FMS algorithm is the gas that occupies the entire reference volume 6520 after equalization. The reference gas system 6522 expands during equalization as the higher pressure gas in the reference chamber 6520 pushes the manifold gas system 6532 out of the reference chamber 6520 and toward the control chamber 6510. In one example shown in FIG. 36, the reference chambers (labeled 174 in FIG. 36) are sufficiently open or devoid of interior features/elements that compression or expansion processes during pressure equalization may be modeled as adiabatic, so the polytropic coefficient (nR) may be set equal to approximately the specific heat ratio of the gas present in the chamber. The pressure and the volume of the reference chamber gas 6522 are related by:

$$P_{R0} V_{Ref}^{nR} = \text{constant}$$

where $p_{R0}$ is the initial reference chamber 6520 pressure, $V_{Ref}$ is the volume of the reference chamber 6520, and nR is the specific heat ratio for the reference chamber (nR=1.4 air). In another example, where the reference chamber 6520 is filled with a heat absorbing material such as open cell foam, wire mesh, particles, etc that provides for a near-isothermal expansion, the polytropic coefficient for the reference chamber (nR) may have a value of approximately 1.0.

In the −FMS process, the conduit or manifold gas system 6532 occupies all of the volume of the interconnecting volume 6530, 6531 and a fraction 6536 of the reference chamber 6520 before equalization. After equalization, the conduit gas system 6532 occupies the interconnecting volume 6530, 6531 and a fraction 6534 of the control chamber 6510. The portion of the conduit gas system 6532 that exists in interconnecting volume 6530 on the control chamber side of the valve 6540 is herein labeled as 6533. The portion of the conduit gas system 6532 that exits in the interconnecting volume 6531 on the reference chamber side of the valve 6540 is referred to as 6535. The portion of the conduit gas system 6532 that exists in the control chamber 6510 is herein labeled as 6534. The portion of the conduit gas system 6532 that exists in the reference chamber 6520 is referred to as 6536.

In one example the interconnecting volumes 6530 and 6531 may be narrow passages that provide high heat transfer that assure the conduit gas system 6532 in volumes 6530 and 6531 is near the temperature of the solid boundaries or walls of the passages. The temperature of the structure surrounding the interconnecting volumes 6530, 6531 or manifold passages is herein referred to as the wall temperature ($T_W$). In another example, the temperature of the conduit gas system 6532 in volumes 6530, 6531 is in part a function of the wall temperature. The portion of the conduit gas system in the control chamber 6534 may be modeled with the same temperature as control chamber gas system 6512. The control chamber portion of the conduit gas system 6534 experiences the same expansion as the control chamber gas system 6512 and may be conceived of as having the same temperature as the control chamber gas system 6512. The portion of the lines or manifold gas system in the reference chamber 6536 may be modeled with a temperature that is in part a function of the wall temperature. In another example, the reference chamber portion of the conduit gas system 6536 may be modeled as not interacting thermally with the boundaries of the reference chamber 6520, so that the temperature of the conduit gas system portion in the reference chamber 6536 is a function of the wall temperature and the reference chamber 6520 pressures.

The equations in this section use the following nomenclature:

variables
γ: specific heat ratio
n: polytropic coefficient
p: pressure
V: volume
T: temperature
superscripts:
n: polytropic coefficient
nCC: polytropic coefficient for the control chamber
nR: polytropic coefficient for the reference chamber
subscripts:
c: control chamber system
CC: physical control chamber
f: value at end of equalization
i: $i^{th}$ value
  IC: physical interconnecting volume or manifold passages
  IC_R: physical interconnecting volume on the reference chamber side of valve
  IC_CC: physical interconnecting volume on the control chamber side of valve
l: lines or manifold/interconnecting system
0: value at start of equalization
pmp: pump
r: reference system
Ref: physical reference chamber
w: wall temperature of interconnecting volume The equations for the control chamber 6510 may derived from the conceptual model of the three separate mass systems in FIG. 49B and the understanding that the total volume of the control chamber mass 6512, reference chamber mass 6522 and interconnecting volumes mass 6532 is fixed. This relationship can be expressed as the sum of the volume changes of each closed system 6512, 6522, 6532 being zero for each $i^{th}$ set of values from the start to the end of pressure equalization:

0=change in volume of+change in volume
    of+change in volume of control chamber mass
    interconnecting mass reference chamber mass $$0 = \Delta V_{ci} + \Delta V_{ri} + \Delta V_{li} \quad (13)$$

where the $i^{th}$ value of $\Delta V_{ci}$, $\Delta V_{ri}$, $\Delta V_{li}$ represents these values at the same point in time. Equations can be developed for the volume change of the control chamber gas system ($\Delta N_{ci}$), the reference gas system ($\Delta V_{ri}$), and the conduit gas system ($\Delta V_{li}$) based on the pressure/volume relationship of a polytropic process and the ideal gas law. The equation for the $i^{th}$ volume change of the control chamber gas system 6512 is equal to the $i^{th}$ volume of the control chamber mass 6512 less the volume of the control chamber mass 6512 at the start of equalization. The volume of the control chamber mass 6512 at time i is calculated from the volume of the control chamber 6510 times the ratio of the final control chamber 6510 pressure over the control chamber 6510 pressure at time i, raised to one over the polytropic coefficient for the control chamber 6510:

current change in volume of control chamber mass = (27)

current volume of control chamber mass + initial volume of control chamber mass $$\Delta V_{ci} = V_{CC} \left(\frac{P_{CC0}}{P_{CCi}}\right)^{1/nCC} - V_{CC}$$

The equation for the reference gas system volume change ($\Delta V_r$) is derived from the pressure/volume relationship for a polytropic process. The equation for the $i^{th}$ volume change of the reference chamber gas system 6522 is equal to the $i^{th}$ volume of the reference chamber mass 6522 less the volume of the reference chamber mass 6522 at the start of equalization. The volume of the reference chamber mass 6522 at time i is calculated from the structural volume of the reference chamber 6520 times the ratio of the initial reference chamber 6520 pressure over the reference chamber 6520 pressure at time i, raised to one over the polytropic coefficient for the reference chamber 6520:

current change in volume of reference chamber mass = (28)

current volume of reference chamber mass + initial volume of reference chamber mass $$\Delta V_{ri} = V_{Ref}\left(\frac{P_{Reff}}{P_{Refi}}\right)^{1/nR} - V_{Ref}\left(\frac{P_{Reff}}{P_{Ref0}}\right)^{1/nR}$$

The equation for the volume change of the interconnecting gas system 6532 ($\Delta V_I$) is derived from the constant mass gas of the system ($V^*\rho$=constant). The equation for the $i^{th}$ volume change of the conduit or manifold gas system 6532 is equal to the current volume of the system 6532 less the original volume of the system 6532. The current volume of the interconnection or manifold gas system 6532 is the initial volume times the ratio of initial over current density of the system 6532. The initial volume of the interconnecting gas system 6532 is the sum of the volumes 6534, 6533 and 6535 pictured in FIG. 49B:

current change in volume of interconnecting mass = (29)

current volume of interconnecting mass + initial volume of interconnecting mass $$\Delta V_{Ii} = (\Delta V_{Rf} + V_{IC})\frac{\rho_{I0}}{\rho_{Ii}} - (\Delta V_{Rf} + V_{IC}).$$

The density terms $\rho_{I0}$, $\rho^{Ii}$ are the average density of the gases in the conduit gas system 6532 at the start of equalization and at some point, i, during equalization. The conduit gas system 6532 includes gases as different temperatures and pressures. The conduit gas system 6532 includes gas in the volume of the control chamber 6510 in a volume labeled 6534, gas in manifold passages on the control chamber side of the valve 6540 labeled 6533, gas in manifold passages on the reference chamber side of the valve 6540 labeled 6535, and gas in the reference chamber labeled 6536.

These four equations may be combined develop an expression for the volume ($V_{CC}$) of the control chamber 6510 as a function of the measured pressure pairs at the start of pressure equalization ($P_{CC\_0}$, $P_{Ref\_0}$), at any point during the equalization ($P_{CC\_i}$, $P_{Ref\_i}$), the reference chamber 6520 pressure at approximately the end of equalization ($P_{Reff}$) and the fixed volumes of the reference chamber ($V_{Ref}$) and interconnecting volume ($V_{IC}$):

$$V_{CC} = \frac{V_{Ref}\left[\left(\frac{P_{Reff}}{P_{Refi}}\right)^{1/nR} - \left(\frac{P_{Reff}}{P_{Ref0}}\right)^{1/nR}\right] + (\Delta V_{Rf} + V_{IC})\left(\frac{\rho_{I0}}{\rho_{Ii}} - 1\right)}{\left[1 - \left(\frac{P_{CC0}}{P_{CCi}}\right)^{1/nCC}\right]} \quad (30)$$

where the densities of the line system 6532 ($\rho_{I0}$, $P_{Ii}$) are evaluated with the initial pressure pairs ($P_{CC\_0}$, $P_{Ref\_0}$) and any pressure pair ($P_{CCi}$, $P_{Ref\_i}$) during equalization along with the associated temperatures as described below.

The densities of the conduit gas system ($\rho_{I0}$, $\rho_{Ii}$) in equations (29) may be calculated from the volume-weighted average density for each physical volume (i.e. control chamber 6510, reference chamber 6520, and interconnecting volumes 6530, 6531):

$$\rho_{Ii} = \frac{-\rho_{CCi}(\Delta V_{cf}) + \rho_{IC_{CC}}V_{IC_{CC}} + \rho_{IC_R}V_{IC_R} + \rho_{ri}\Delta V_{ri}}{(\Delta V_{cf} + V_{IC\_CC} + V_{IC\_R} + \Delta V_{ri})} \quad (31)$$

$$\rho_{CCi} = \frac{P_{CCi}}{R\,T_{CCi}} = \text{density of gas in control chamber}$$

$$\rho_{IC\_CCi} = \frac{P_{CCi}}{R\,T_{IC\_CC}} =$$

density of gas in manifold line on control chamber side of valve $$\rho_{IC\_Ri} = \frac{P_{Refi}}{R\,T_{IC\_CC}} = \text{density of gas in}$$

manifold line on reference chamber side of valve $$\rho_{ri} = \frac{P_{Refi}}{R\,T_{Ir}} = \text{density of gas in reference chamber}$$

where R is the universal gas constant for air, the temperatures, $T_{IC\_CC}$, $T_{IC\_R}$, $T_{Ic}$, may be functions in part of the temperature of the interconnecting volume walls. In another example, the temperatures, $T_{IC\_CC}$, $T_{IC\_R}$, $T_{Icr}$, may be functions in part of the temperature of the interconnecting volume walls and the gas temperature of the reference chamber ($T_{Ref\_i}$). In another example, the temperatures, $T_{IC\_CC}$, $T_{IC\_R}$, $T_{Ic}$, may be the interconnecting wall temperature ($T_W$). In another example, the temperatures may be reference chamber temperature ($T_{Ref\_i}$).

The value of $\Delta V_{cf}$ for equation (31) is calculated from equation (27), where the final control chamber pressure ($P_{CCf}$) is used for $P_{CCi}$ and $V_{CC\,Est}$ is used for $V_{CC}$. The value of $\Delta V_{ri}$ for equation (31) is calculated from equation (28).

The density of the conduit gas system 6532 before pressure equalization may be calculated from an equation similar to equation (31) that is the volume-weighted average density for each physical volume (i.e. control chamber 6510 and interconnecting volumes 6530, 6531):

$$\rho_{I0} = \frac{\frac{P_{ref0}(\Delta V_{rf})}{T_W} + \frac{P_{CC}V_{IC\_CC}}{T_W} + \frac{P_{Ref}V_{IC\_R}}{T_W}}{R(\Delta V_{rf} + V_{IC\_CC} + V_{IC\_R})} \quad (32)$$

An estimate of the control chamber 6510 volume can be derived by assuming constant temperature for the conduit or manifold gas system 6532, so that the density ratio ($\rho_{l0}/\rho_{lf}$) is equal to the pressure ratio ($P_{l0}/P_{lf}$). To further simplify the estimate, the polytropic coefficient is replaced by the specific heat ratio ($\gamma$). In this simpler equation, the volume of the control chamber ($V_{CC}$) in the −FMS process can be expressed as a function of three pressures (i.e. the measured pressure pair at the start of pressure equalization ($P_{CC\ 0}$, $P_{Ref\ 0}$), and a single equalization pressure ($P_f$)), as well as the fixed volumes of the reference chamber ($V_{Ref}$) and interconnecting volume ($V_{IC}$), and the polytropic coefficients for the reference chamber (nR) and control chamber (nCC):

$$V_{CC\ Est} = \frac{V_{Ref}\left[1-\left(\frac{P_f}{P_{Ref\ 0}}\right)^{1/\gamma}\right] + (\Delta V_{Rf} + V_{IC})\left(\frac{P_{CC\ 0}}{P_f}-1\right)}{\left[1-\left(\frac{P_{CC\ 0}}{P_f}\right)^{1/\gamma}\right]}. \quad (33)$$

The gas in the three closed systems 6512, 6522, 6532 may be modeled as an ideal gas, so the temperature can be determined from the initial conditions and the new pressure or volume:

$$T_i = T_0\left(\frac{p_0}{p_i}\right)^{(n-1)/n} \text{ or } T_i = T_0\left(\frac{V_0}{V_i}\right)^{n-1} \quad (23)$$

The initial temperature of the gas in the control chamber ($T_{CC\ 0}$) may be calculated from the temperature of the interconnecting volume walls, the precharge pressure 6316 (FIG. 48B) and the pressures in the control chamber 6510 just before precharge 6306 (see FIG. 48B) modeling it as polytropic process and using the ideal gas law in equation (23). The control chamber pressure before precharging 6306 is referred herein as the pumping pressure (Ppmp):

$$T_{CC\ 0} = T_W\left(\frac{P_{pmp}}{P_{CC\ 0}}\right)^{\frac{1}{nCC}-1} \quad (24)$$

The value of the polytropic coefficient for the control chamber gas system (nCC) may vary with the volume of the control chamber 6510 and range from approximately 1 for small volumes to approximately the specific heat ratio for large volumes. The specific heat ratio for air and other systems of predominantly diatomic molecules is 1.4. In one example the value of nCC for −FMS can be expressed as a function of the estimated control chamber volume (equation 21):

$$nCC = 1.507 - 1.5512 \times 10^{-5}(23.56 - V_{CC\ Est})^{3.4255} \quad (34)$$

A method to determine a relationship between the volume of the control chamber ($V_{CC}$) and its polytropic coefficient (nCC) is described in a following section.

Determining the Polytropic Coefficient $n_{CC}$

The value of polytropic coefficient $n_{CC}$ may be determined experimentally or analytically. The polytropic coefficient compares the potential temperature change of the gas due to heat transfer with the structure to temperature change caused by pressure changes. The value of the polytropic coefficient may vary with the pressure changes, the rate of pressure changes and the shape and size of the gas volume.

Figure 50A:
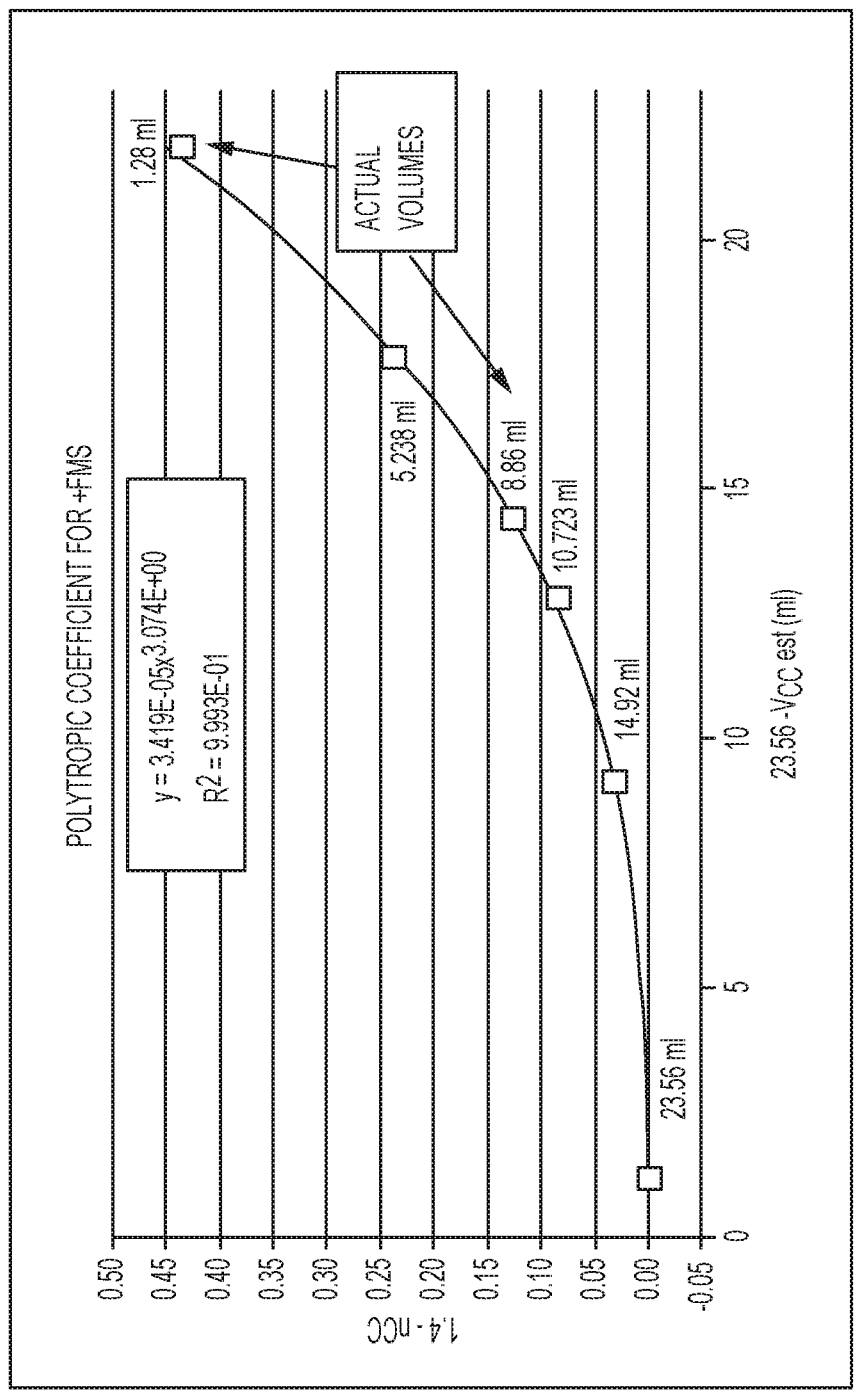
FIG. 50A is an illustration of the polytropic conceptual model of the −FMS process involving three separate closed mass systems.

In one embodiment, the polytropic coefficient $n_{CC}$ is determined experimentally by creating control chamber 6171 (FIG. 45) with a known volume and executing the +FMS process or the −FMS process and recording the control chamber and reference chamber pressures during equalization. The polytropic +FMS algorithm including equations (17), (18), (20) is applied to the set of pressure measurements and the known control chamber volume ($V_{CC}$) in order to solve for the value of the polytropic coefficient for the control chamber ($n_{CC}$). This process to determine the polytropic coefficient was repeated for several different volumes ranging 1.28 ml, which is the typical of the control chamber 6171 after a fill stroke to 23.56 ml which is typical of the control chamber 6171 after a deliver stroke. These volumes, of course, differ depending on the cassette and system used. The FMS process may be repeated several times for each volume to improve the accuracy of the determination of $n_{CC}$. One example of this experimental determination $n_{CC}$ for +FMS process is shown in FIG. 50A, where the value of $n_{CC}$ is plotted versed the estimated volume of the control chamber ($V_{CC\ Est}$) as calculated by equation (22) for six different volumes. A power equation was fit to the data to produce equation (26) which expresses the polytropic coefficient in terms of the estimated volume control chamber. The plot in FIG. 50A plots the value, 1.4-$n_{CC}$, vs. 23.56-$V_{CC\ Est}$ in order to better fit the data with simple equation.

Figure 50B:
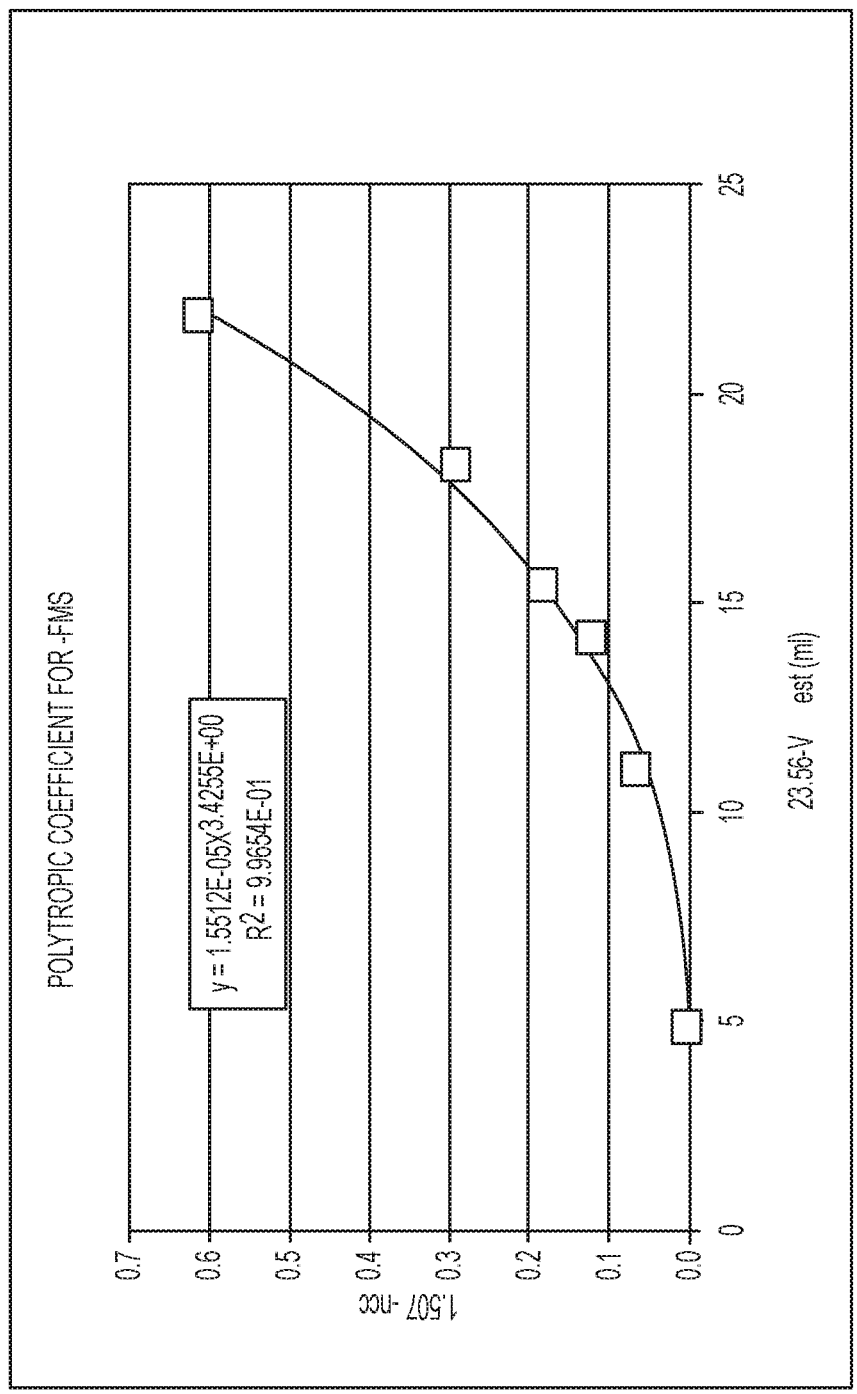
FIG. 50B is a plot of the polytropic expansion constant for −FMS verses control chamber volume.

In a similar fashion, the polytropic coefficient ($n_{CC}$) for −FMS may be determined by applying the −FMS process to a known control chamber volume and recording the control chamber and reference chamber pressures during equalization. The polytropic −FMS algorithm comprising equations (30), (31), (32) is applied to the set of pressure measurements and the known control chamber volume ($V_{CC}$) in order to solve for the value of the polytropic coefficient for the control chamber ($n_{CC}$). This process to determine the polytropic coefficient was repeated for several different volumes. An example of the resulting values for $n_{CC}$ for the −FMS process is shown in FIG. 50B, where the value of $n_{CC}$ is plotted versed the estimated volume of the control chamber ($V_{CC\ Est}$) as calculated by equation (33) for six different volumes. A power equation was fit to the data to produce equation (34) which expresses the polytropic coefficient ($n_{CC}$) in terms of the estimated volume control chamber ($V_{CC\ Est}$). The plot in FIG. 50B plots the value, 1.507-$n_{CC}$, vs. 23.56-$V_{CC\ Est}$ in order to better fit the data with simple equation.

In one embodiment, the fixed known control chamber volume is created by attaching a machined volume to the front of the mounting plate 170 (FIG. 34), so that the machined volume is sealed to the mounting plate 170 and covers the ports 173C connecting the control chamber to pressure source and pressure sensor.

Polytropic FMS Calculation Procedure for $V_{CC}$

Figure 51:
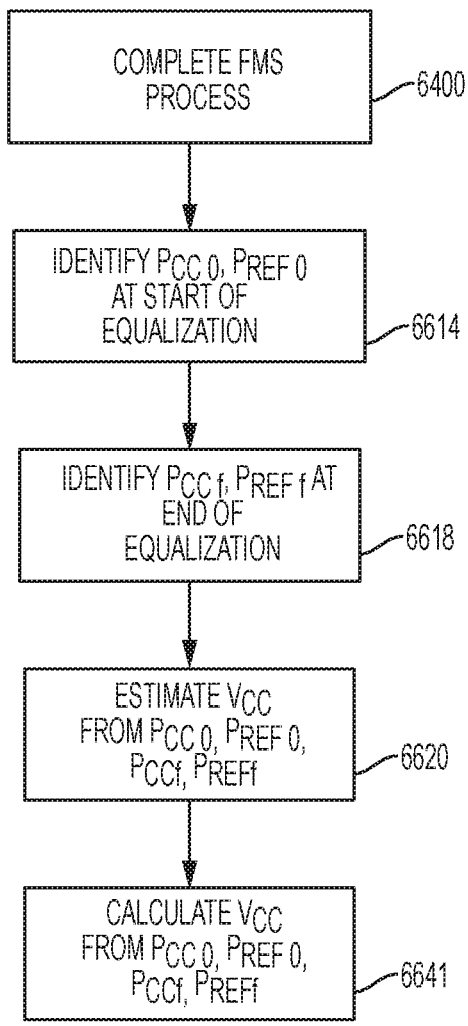
FIG. 51 is a flow chart of basic AIA FMS calculation steps.
Figure 52:
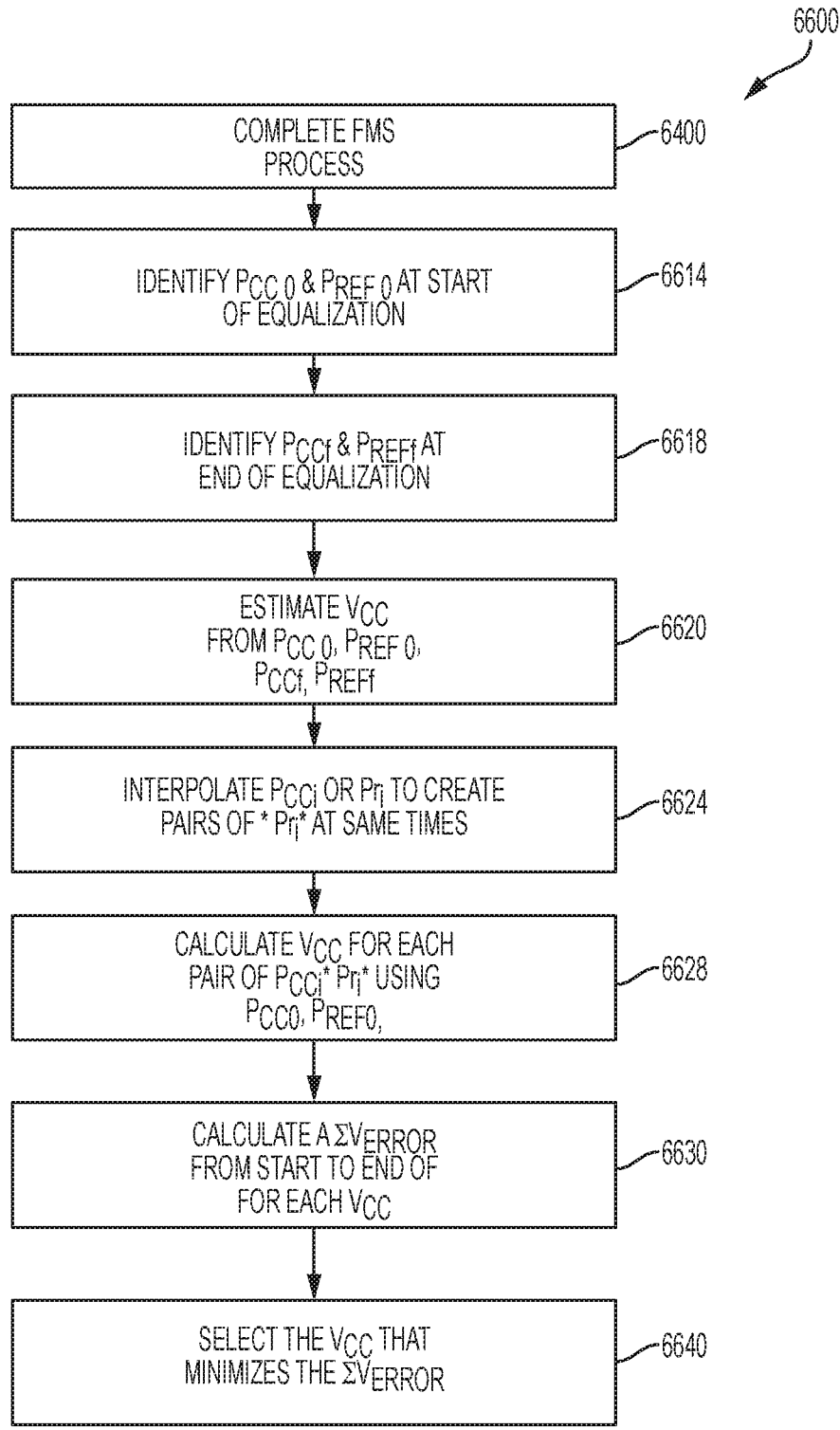
FIG. 52 is a more detailed flow chart of AIA FMS calculation steps.

Referring now to FIGS. 51 and 52, flowcharts to calculate the volume of the control chamber from the pressure data recorded during a 2-chamber FMS process and the polytropic FMS algorithm are presented. The flowchart in FIG. 39 presents a relatively simple process that requires a minimum of pressure data to calculate the volume of the control chamber ($V_{CC}$). The flowchart in FIG. 52 describes a more complex calculation to more accurately calculate the volume of the control chamber ($V_{CC}$) that requires multiple pressure pairs during the equalization process.

The simple polytropic FMS calculation procedure presented in FIG. 51 is executed by a processor or controller and starts with step 6400 that comprises completing either the +FMS or −FMS process described above and storing in memory multiple pressure pairs that were recorded during the equalization process. In step 6614, the controller analyzes the multiple pressure pairs to identify the initial control chamber pressure ($P_{CC\ 0}$) and the initial reference pressure ($P_{Ref0}$) as the control chamber and reference pressures when the equalization process starts. Methods or procedures to identify the start of equalization or the initial pressures are described in a previous section titled Pump Volume Delivery Measurement, where the initial control chamber and reference chamber pressures are referred to as Pd and Pr. In step 6618, the controller analyzes the multiple pressure pairs to identify the final control chamber pressure ($P_{CC\ f}$) and the final reference pressure ($P_{Ref\ f}$) when the control chamber and reference chamber pressures have nearly equalized or are changing at a sufficient low rate. One or more methods to identify when the control chamber and reference chamber pressures have nearly equalized are described in a previous section titled Pump Volume Delivery Measurement.

Alternatively, steps 6614 and 6618 to identify the initial and final pressures for the control chamber and reference chamber may occur during the FMS process 6400. The controller or FPGA processor may identify the initial and final pressures and store only those values. In one example, the initial pressures could be the control chamber and reference pressures, when the connection valve opens and the final pressures could be the control chamber and reference pressures when the second valve opens to vent the reference and control chambers after equalization.

In step 6620, the volume of the control chamber is estimated from the initial and final pressures using either equation (22) for a +FMS process or equation (34) for a −FMS process. In step 6641, for a +FMS process, the resulting estimate of the control chamber volume ($V_{CC\ Est}$) is then used in equations (26) to calculate the polytropic coefficient for the control chamber ($n_{CC}$). This polytropic value ($n_{CC}$) and the estimated volume ($V_{CC\ Est}$) along with initial and final pressure pairs are supplied to equations (17), (18), (19) for a +FMS process to calculated the control chamber volume ($V_{CC}$). In step 6641 for a −FMS process, the polytropic coefficient ($n_{CC}$) is calculated with equation 34 and the control chamber volume ($V_{CC}$) is calculated with equations (30), (31), (32).

A processor such as controller 61100 in FIG. 45, may perform steps 6614-6618 (FIG. 51) on the stored pressure pairs. In an alternative embodiment, a processor 61100 may perform steps 6614 and 6618 during the pressure equalization without storing the pressure pair.

A more complex calculation of the control chamber volume ($V_{CC}$) is described in FIG. 52. The initial steps of completing the FMS 6400, identifying the initial control chamber pressure ($P_{CC\ 0}$) and initial reference chamber pressure ($P_{Ref0}$) 6614, identifying the final control chamber pressure ($P_{CC\ f}$) and final reference chamber pressure ($P_{Ref\ f}$) 6618, and estimating the control chamber volume ($V_{CC\ Est}$) 6620 are the same as described above for FIG. 51.

The steps 6624, 6628, 6630 and 6640 are similar to the calculation steps described above in the section titled Pump Volume Delivery Measurement, except that the calculation of the control chamber volume ($V_{CC}$) is based on equations (17), (18), (19) for a +FMS process and equations (30), (31), (32) for a −FMS process. In step 6624, the pressure pairs of the control chamber pressure ($P_{CC\ i}$) and reference chamber pressure ($P_{ri}$) are corrected by interpolations with previous subsequent pressure pairs to calculate pressures pairs ($P_{CCi*}$, $P_{ri*}$) that occurred at exactly the same time. In other embodiments, step 6624 is skipped and subsequent calculations use the uncorrected pressure pair ($P_{CC\ i}$, $P_{ri}$). In step 6628, a control chamber volume ($V_{CC}$) is calculated for each pressure pair. In steps 6630, 6640, the optimization algorithm described in the section titled Pump Volume Delivery Measurement is carried out to identify the optimal final pressure pair ($P_{CC\ f}$, $P_{Ref\ f}$) and the resulting control chamber volume ($V_{CC}$).

In an alternative embodiment, the calculations described FIGS. 51 and 52 may be carried out in a processor that is separate from the controller 61100 in FIG. 45. The calculations may for example be carried out in the FPGA that also handles the input and output signals to and from the actuators, valves and pressure sensors.

Air Detection with the Polytropic FMS Algorithm

Referring now to FIG. 43, another aspect of the disclosure involves the determination of a presence of air in the pump chamber 181, and if present, the volume of air present. Such a determination can be important, e.g., to help ensure that a priming sequence is adequately performed, to remove air from the cassette 24, and/or to help ensure that air is not delivered to the patient. In certain embodiments, for example, when delivering fluid to the patient through the lower opening 187 at the bottom of the pump chamber 181, air or other gas that is trapped in the pump chamber 181 may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present disclosure and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 171B. A +FMS procedure as described in FIG. 47 may be carried out to measure the pressure equalization and calculate the apparent volume of the control chamber 171B (FIG. 34) as described above. However, the +FMS procedure after a fill stroke, provided that the membrane is off the spacers 50, will also measure the volume of any gas or air bubbles on the liquid side of the membrane 15.

The volume of the control chamber when the membrane 15 is against the control chamber wall 171B is generally a known value based on the design and manufacturing process. This minimum control chamber volume is $V_{CC\ Fix}$. The control chamber volume measured during a +FMS procedure at the end of a fill command is $V_{CC+}$. If the measured control chamber volume ($V_{CC+}$) is greater than $V_{CC\ Fix}$, then the control system 16 or controller 61100 may command a −FMS procedure that calculates a control chamber volume ($V_{CC-}$). If the −FMS procedure gives substantially the same control chamber volume as the +FMS, then the controller may recognize that the fill line is occluded. Alternatively if the −FMS procedure produces a smaller control chamber volume, then the controller recognizes the difference as the size of the sum of the air bubbles ($V_{AB}$):

$$V_{AB} = V_{CC+} - V_{CC-} \tag{30}$$

A similar method may be used at the end of the deliver stroke, when the membrane 15 is against the spacers 50. A +FMS procedure will not measure the volume of air in the liquid, but only the volume of air in the control chamber 171B, when the membrane 15 is against the spacers 50.

However, a −FMS procedure will pull the membrane 15 away from the spacers 50 and will measure the volume of air on the dry side (i.e. control chamber 171) and the liquid side (pump chamber 181) of the membrane 15. Therefore for the air volume in the liquid ($V_{AB}$) can also be determined at the end of the deliver stroke:

$$V_{AB} = V_{CC-} - V_{CC+} \tag{31}$$

Air Calibration

A further aspect of this disclosure includes a method to calibrate the −FMS process and +FMS process with direct measurements of the control chamber volume 6171 (FIG. 45) using pressure measurements independent of the pressure measurements associated with an FMS process. This method to calibrate the 2-chamber FMS processes is herein referred to as the Air Cal method. The hardware references in this section will be directed to FIG. 45, but apply equally to the equivalent hardware components other pneumatically actuated diaphragm pumps. The Air Cal method provides a number of benefits including but not limited to: improving the accuracy of the 2-chamber FMS method over the full range of control chamber volumes, as well as allowing the use of nominal volumes for the reference chamber ($V_{Ref}$) 6212 and the volume of the interconnecting volumes ($V_{IC}$) 6204, 6205, 6207, 6209. The method also allows for compensation of differences between the actual and nominal volumes of the reference chamber 6212 and the interconnecting volumes 6204, 6205, 6207, 6209. The method also allows for compensation of differences between the actual and the assumed heat transfer in the different volumes of the 2-chamber FMS hardware including the control chamber 6171, reference chamber 6212, and the interconnecting volumes, 6204, 6205, 6207, 6209.

The Air Cal method combines control chamber 6171 pressure measurements with a measurement of displaced fluid to measure the volume of the control chamber 6171 at several membrane 6148 positions between touching the control chamber wall 6172 and contacting the spacers 650 on the cassette 624. These measurements of the control chamber volume (VCIso) are compared to the FMS calculated values for the control chamber volumes (VFMS i) to calculate a calibration coefficient (CCal i) for each calculated FMS volume (VFMS i). A calibration equation can then be fitted to a plot of the CCal i values versus the VFMS i values. The calibration equation may then be used to improve the accuracy of the control chamber volume calculations. The Air Cal method may be applied to both the +FMS and −FMS processes and may result in separate calibration equations for each.

Air Calibration for +FMS

Figure 53A:
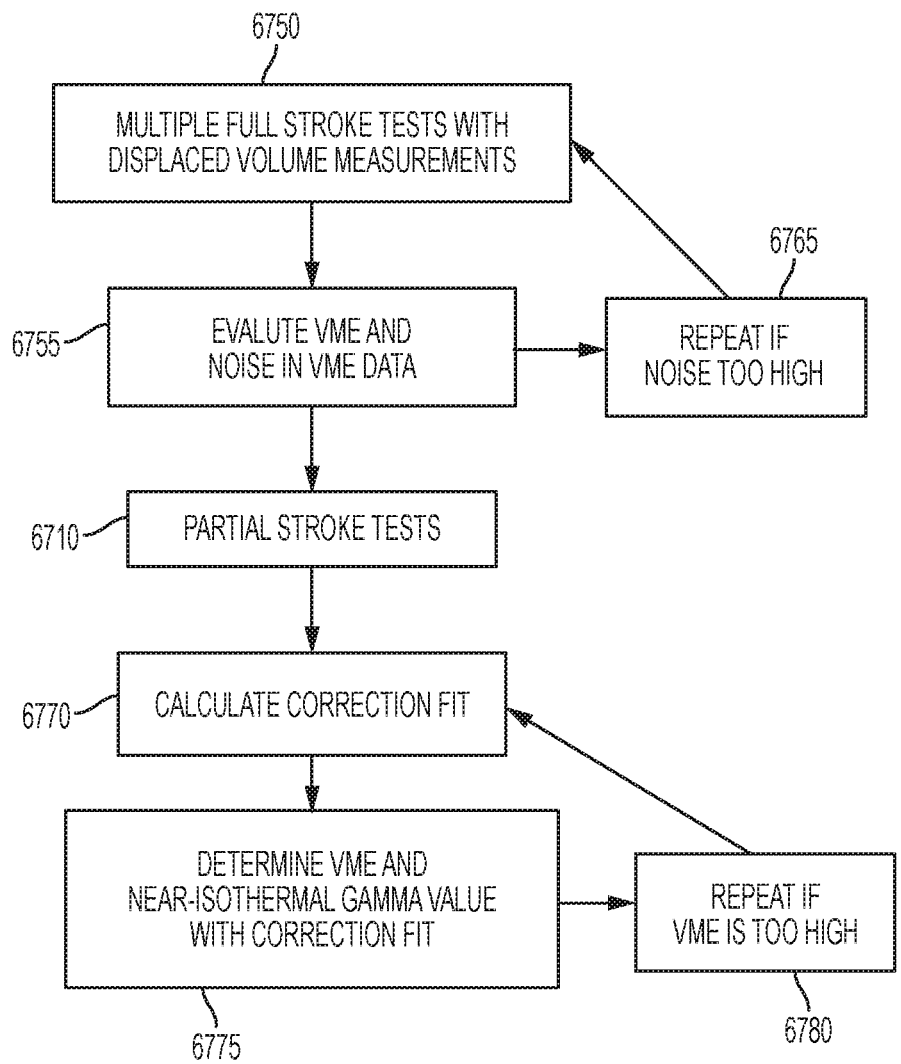
FIG. 53A is a flow chart for an FMS calibration method for a diaphragm pump.
Figure 53B:
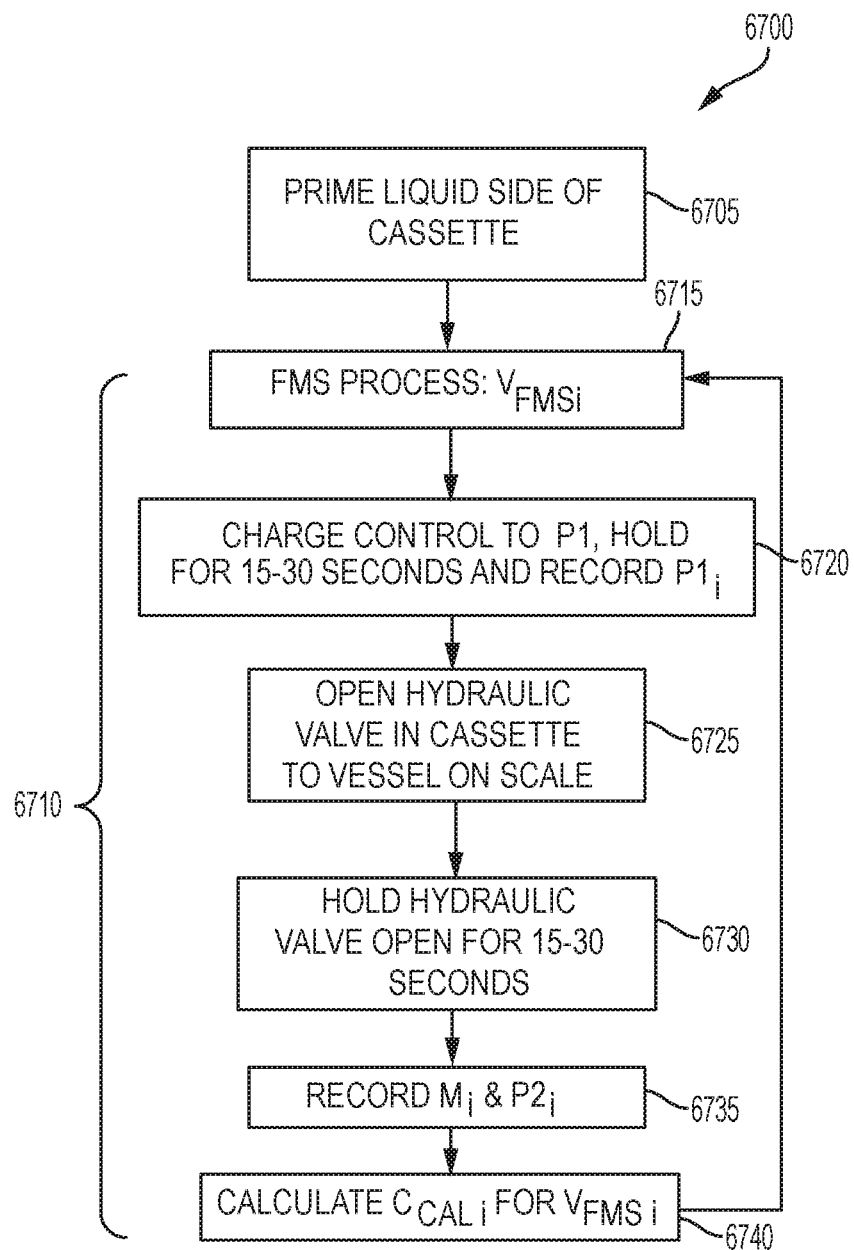
FIG. 53B is a flow chart for calibrating partial stroke volumes for the FMS calibration method.
Figure 55:
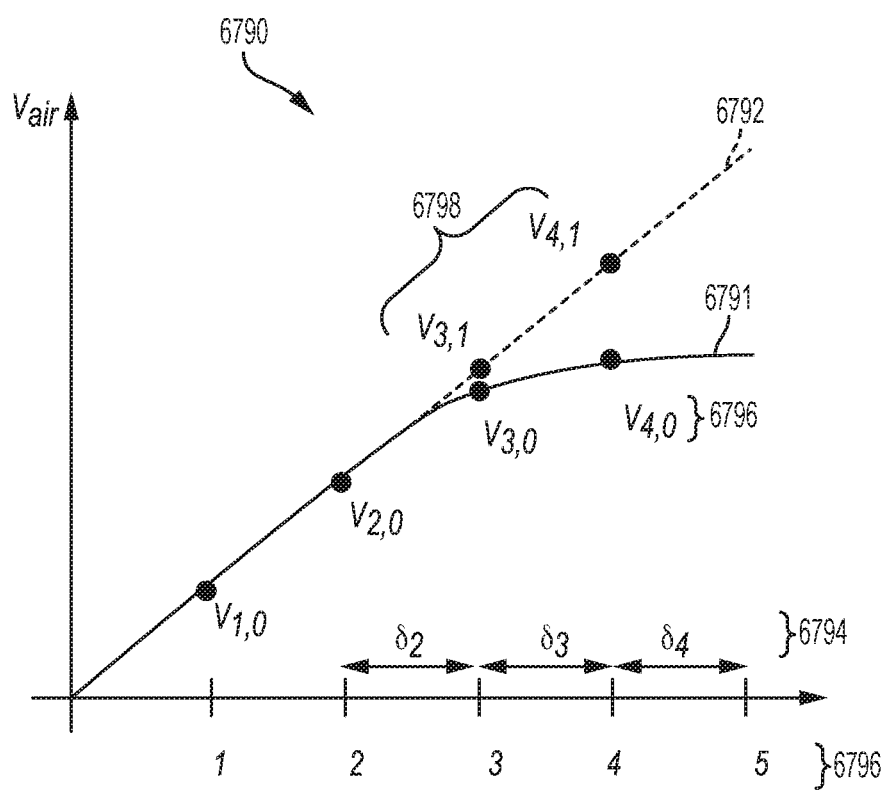
FIG. 55 is a depiction of correction of volume measurements during partial stroke calibration when the pump diaphragm approaches the chamber wall.

The flowchart 6700 in FIG. 53B describes an example of the Air Cal method. The hardware setup for the Air Cal includes a pneumatically driven pump that is primed with liquid and the outlet plumbed to a mass scale or graduated cylinder. The hardware setup also includes 2-chamber FMS hardware such as a control volume or chamber 6171, pressure sensors 6222, 6224, a number of valves 6214, 6220 and a reference volume or chamber 6212. A controller 61100 to command the pneumatic valves 6214, 6220, record the pressures from the pressure sensors 6222, 6224 and perform the 2-chamber FMS procedure and calculations is also included.

One example of the hardware setup is the combination of the cassette 24 and the APD cycler 14 in which it is installed shown in FIG. 31. In this example, the output of the cassette 24 would be plumbed to a mass scale, graduated cylinder, or other fluid measuring apparatus.

Referring back to FIG. 53B and the hardware references in FIG. 45, the first step, 6705, primes the pump or cassette 624 and output lines with liquid. The prime also fills the pump chamber 6181 with fluid.

As indicated by the bracket for cycle 6710, the procedure cycles through steps 6715 through 6740 several times during the Air Cal method. The first step of Air Cal cycle 6710 completes a +FMS process 6715 that produces a provisional measurement of the control chamber volume ($V_{FMSi}$) for i=1. The Air Cal procedure applies equally to other volume measurement techniques which may alternatively be used step 6715. In step 6720, the pressure in the control chamber 6171 is increased to approximately P1 by controlling first valve 6220 and holding the gas for a period of time to allow the gas to come into thermal equilibrium with the chamber walls 6172, and the gasket 6148. In one example, the pressure is held at P1 for 15 to 30 seconds. In another example, the pressure is raised to P1, the pneumatic valve 6220 is closed and the gas in the control chamber 6171 comes to thermal equilibrium with the walls 6172, 6148. The control chamber 6171 is isolated by closing valves 6220 and 6214. The pressure at the end of step 6720 is recorded as $P1_i$.

In step 6725, a hydraulic valve 6190 in cassette 624 is released or opened, which allows the pressure in the control chamber 6171 to push fluid through hydraulic valve 6190 and onto the mass scale. In step 6730 the hydraulic valve 6190 is held open long enough for the gas or air in the control chamber 6171 to reach pressure equilibrium with liquid on the pump side 6181 (which happens quickly) and to come to thermal equilibrium with the control chamber walls 6172, 6148 (which may take several seconds). In one example, the hydraulic valve 6190 is held open for 15 to 30 seconds. In step 6735, the pressure in the control chamber 6171 is recorded as $P2_i$ and the change in the mass scale is recorded at $M_i$. The hydraulic valve 6190 is then closed.

In step 6740, the calibration coefficient (CCal) is calculated from the first and second pressures ($P1_i$, $P2_i$) and the displaced liquid mass ($M_i$):

$$C_{Cal\,i} = \frac{V_{CIso\,i}}{V_{FMS\,i}} \tag{35}$$

where $V_{CIso\,i}$ is the isothermal determined volume of the control chamber at the ith position:

$$V_{CIso\,i} = M_i * \rho \frac{P_{2i}/P_{1i}}{1 - P_{2i}/P_{1i}} \tag{36}$$

where ρ is the density of the liquid in the cassette 624 and where $V_{FMS\,i}$ is calculated per equations (17), (18), (19) for a +FMS process.

Cycle 6710 may be repeated multiple times until the membrane 6148 reaches the far side of the pump volume or chamber 6181 and contacts the spacers 650. In step 6745, an equation for the calibration coefficient as a function of the FMS determined volume CCal(VFMS) is fit to the data. The output of the FMS calculations for the volume of the control chamber 6171 described in the previous sections can now be corrected to obtain a more accurate measure of the control chamber 6171 volume for all possible volumes:

$$V_{CC} = V_{FMS} \cdot C_{cal}(V_{FMS}) \tag{37}$$

Air Calibration for −FMS

A calibration coefficient can also be obtained for the −FMS process by the Air Cal procedure described in FIG. 53B. In the −FMS Air Cal method, the pump chamber 6181 and the fluid line to the scale are primed (step 6705) and the container on the scale is partial filled with liquid. A −FMS process is completed in step 6715 resulting in a −FMS measurement of the control chamber 6171 volume ($V_{FMSi}$) using and equations (30), (31), (32). In step 6720, the control chamber 6171 pressure is charged to a pressure P1 that is well below the ambient pressure. In step 6725, the low pressure in the control chamber 6171 draws fluid into the pump chamber 6181 and out of the container on the mass scale. Steps 6730 through 6745 are the same as described above for the +FMS Air Cal procedure. The resulting equation for the calibration coefficient as a function of the −FMS calculated volume CCal(VFMS) may be applied to −FMS results.

Improved Air Calibration

The accuracy of the $V_{CISO\ i}$ values may be further increased by considering $V_{CISO\ i-1}$ and $V_{CISO\ i+1}$ values. The procedure described in FIG. 53B, determines the control chamber 6171 volumes sequentially, which may cause their values to be related. Thus value of $V_{CISO\ i}$ may be expected to smoothly change from the ith−1 to the $i^{th}$ to the ith+1 position and so on. This dependence on nearby results is especially useful at the maximum and minimum values, which are harder to accurately measure due to the small volume of liquid moved by the pumps. The value of any control chamber volume ($V_{CIso\ i}$) can be expressed by two other independent measurements including the previous control chamber volume ($V_{CIso\ i-1}$) plus the displaced liquid volume, the following control chamber volume ($V_{CIso\ i+1}$) minus the displaced liquid volume:

$$V_{CIso\ i} = V_{CIso\ i-1} + \rho \cdot m_{i-1} = V_{CIso\ i} = V_{CIso\ i+1} - \rho \cdot m_{i+1}$$

Thus the values of $V_{CIso}$ can be improved by averaging them with the adjoining values and the displaced volumes ($\rho \cdot m_{i-1}$):

$$V_{CIso\ i,1} = \tfrac{1}{3}(V_{CIso\ i-1} + \rho \cdot m_{i-1} + V_{CIso\ i} + V_{CIso\ i+1} - \rho \cdot m_{i+1}) \quad (38)$$

The resulting averaged values $V_{CIso\ i,1}$ can be averaged again by feeding $V_{CIso\ i,1}$ into equation (38) on the right side to produce $V_{CIso\ i,2}$. This iterative averaging process can be continued until the values of $V_{CIso\ i}$ stop changing or converge to a value.

The process is a little different for the first and last volume, as there are values on only one side. The equation to average the first $V_{CIso\ 1,1}$ and last $V_{CIso\ N,1}$ volumes are:

$$V_{CIso\ 1,1} = \tfrac{1}{2}(V_{CIso\ 1} + V_{CIso\ 2} - \rho \cdot m_2) \quad (39)$$

$$V_{CIso\ N,1} = \tfrac{1}{2}(V_{CIso\ N} + V_{CIso\ N-1} - \rho \cdot m_{N-1}) \quad (40)$$

Again, the resulting averaged values $V_{CIso\ 1,1}$ and $V_{CIso\ N,1}$ can be fed into the right hand side of equations (39) (40) to calculate $V_{CIso\ 1,2}$ and $V_{CIso\ N,2}$. This iterative averaging process can be continued until the values of $V_{CIso\ 1}$ and $V_{CIso\ N}$ stop changing or converge to a value. In cases, where the initial values of $V_{CIso\ 1}$ and $V_{CIso\ N}$ are questionable or known to be be unreliable, the intial values of $V_{CIso\ 1,2}$ and $V_{CIso\ N,2}$ can be set based on their more reliable neighbor values:

$$V_{CIso\ 1,1} = (V_{CIso\ 2} - \rho \cdot m_2)$$

$$V_{CIso\ N,1} = (V_{CIso\ N-1} - \rho \cdot m_{N-1})$$

Then subsequent averaging for $V_{CIso\ 1,2}$ and $V_{CIso\ N,2}$ can proceed as above.

Substantially Instantaneous or Continuous Flow Rate and Stroke Displacement Estimation In some embodiments, the flow rate to or from a pump chamber of a diaphragm pump, and/or the stroke displacement of a pump chamber (i.e. the extent to which the diaphragm has traversed the pump chamber) may be estimated while a pumping stroke is occurring. This may be accomplished either during a fluid delivery stroke, or a fluid filling stroke of the diaphragm pump. These estimates may be available during the progression of a pump stroke once sufficient data is collected for controller analysis, the controller then being able to act on continuously updated pressure information to calculate a cumulative volume of fluid moved into or out of the pumping chamber. Such real-time information may aid in an early determination of an end of stroke, may reduce the number of partial strokes performed, may permit more accurate delivery of small volumes or increments of fluid, may more efficiently deliver a precise target fluid volume, and may provide for earlier detection of occlusions and other reduced flow conditions, as well aid in priming of a fluid line, etc. This information may also help to increase fluid throughput through a pumping cassette.

Flow rate and stroke displacement or stroke progress estimation during a pump stroke may be accomplished by monitoring pressure decay in a control chamber while a pump stroke is in progress. Data produced from monitoring the rate of pressure decay may be used by a controller to determine fluid flow rate through a pumping chamber. Since pressure decay during a pump stroke is indicative of a change in volume of the control chamber as the pumping chamber fills with or empties of fluid, monitoring this decay over the course of a pump stroke may allow a controller to estimate stroke displacement as it occurs.

In embodiments in which an on/off, binary, or "bang-bang" pressure controller is used, the pressure controller may need to repeatedly actuate a valve to connect and disconnect a control chamber to a pressure reservoir in order to maintain a desired pressure during pumping. For example, as fluid is pumped out of a pumping chamber during a delivery stroke, the volume of the associated control chamber will increase. This will in turn cause a decay in the pressure of the control chamber. The process or algorithm can be used either with the application of negative pressure to fill the pumping chamber or with the application of positive pressure to evacuate fluid from the pumping chamber. The term 'pressure decay' as used herein is meant to refer to a decay in the absolute value of the actual pressure being measured (i.e., a decrease toward ambient pressure in an applied positive pressure, or an increase toward ambient pressure in an applied negative pressure). Once the pressure in the control chamber falls out of an allowed pressure range, the pressure controller may regulate the control chamber pressure by opening a valve to a pressure reservoir. The allowed pressure range may be within a range of a pressure set point. This pressure regulation or maintenance may involve connecting the chamber to a suitable pressure source for a period of time sufficient to bring the control chamber pressure approximately to a desired value and/or back within the allowed range. The pressure will again decay as more fluid is delivered to or from the pumping chamber and re-pressurization will again be needed. This process will continue until the end of the stroke is reached.

The repeated re-pressurization will generate a pressure regulation waveform that appears substantially saw tooth in nature. Referring again back to FIG. 42, an example plot showing a pressure regulation waveform as described above is depicted. As shown, the waveform oscillates between a lower pressure threshold 2312 and an upper pressure threshold 2310. The pressure decays (see data points 2302-2304) as the stroke progresses, fluid moves out of the pumping chamber, and the volume of the control chamber changes. In the example plot in FIG. 42, the control chamber volume is expanding as fluid is pumped out of the pumping chamber of the diaphragm pump to a destination. An end-of-stroke is indicated when the pressure decay levels off 2305, at which point an FMS volume determination can be conducted by fixing the chamber volume (i.e., closing inlet and outlet fluid valves to the pumping chamber), and equalizing 2332 the chamber pressure with the pressure of a known reference volume.

Each pressure decay may be monitored such that the volume of the control chamber can be approximately known during the course of a pump stroke. This information may allow a determination of the amount of pump stroke displacement that has occurred when compared with the initial volume of the chamber. The initial volume of the pumping chamber can be determined, for example, by performing a pre-stroke FMS measurement. This method generally involves determining the volume of a closed chamber by measuring its change in pressure when brought into communication with a reference chamber of known volume and pressure. The determination involves closing fluid inlet an outlet valves of the pumping chamber to ensure a constant volume of the control chamber of the pump, and then connecting the control chamber to a reference chamber. The process may be modeled as isothermal or adiabatic, depending on the heat transfer properties and dynamics of the system. The system may also be modeled as a polytropic process to optimize measurement accuracy. Other methods of determining the initial volume of the control chamber can be used. For example, the controller may be programmed to assume that the initial control chamber volume is substantially the control volume physically measured during manufacture of the chambers of the pumping system. This assumption may be employed, for example, when the controller has computed that a preceding end-of-stroke state was fully reached.

The determination of real-time or continuous volume changes in the control and pumping chambers of a diaphragm pump during a pump stroke is substantially different from previously disclosed pressure-based volume determinations, in that a fluid inlet or outlet valve remains open to allow fluid to continue to flow into or out of the pumping chamber. Additionally a reference chamber of known volume and pressure is unnecessary. To distinguish this process from a control chamber/reference chamber equalization process (a 'two-chamber' FMS), the continuous measurement process here described can more aptly be considered a 'one-chamber' FMS. Although the pumping chamber remains open to an inlet or outlet fluid line, the associated control chamber remains a closed system, which allows for determination of a second volume once an initial volume is known. Pressure data is repeatedly sampled while the control volume is isolated from a gas source or sink (i.e., no change in mass in the control volume). Under these circumstances, controller calculations based on an algorithm using a polytropic process may provide more accurate results. The method is only now feasible, because electronic processors capable of rapid data acquisition and computation are now available. For example, a high speed application specific integrated circuit can be employed, or preferably an FPGA device can now be dedicated to this task, relieving a main system processor from having to share its computing resources and reduce its efficiency. A sufficiently robust FPGA in some embodiments can be reconfigurable or reprogrammable for the blocks of time needed to perform on-the-fly or real time volume measurements during a pump stroke, while maintaining some resources for other tasks. Real time or on-the-fly volume measurements may be accomplished by finding the volume of the control chamber at two points between a closure and an opening of the supply valve used to regulate the control or pumping chamber pressure. The volume difference between the two points in time may allow the controller to estimate a relatively real-time flow rate.

As shown in FIG. 42, a high-speed controller can acquire a series of pressure data points 2302, 2303, 2304, each of which allows the controller to successively compute a chamber volume change associated with each point. Assuming that the controller has determined a starting volume of the control chamber, a change in volume at a subsequent pressure decay point can be computed. An ending volume associated with point 2302, for example, may then be used as a starting volume at point 2303 in order to calculate the ending volume at point 2303, and so on.

Figure 56:
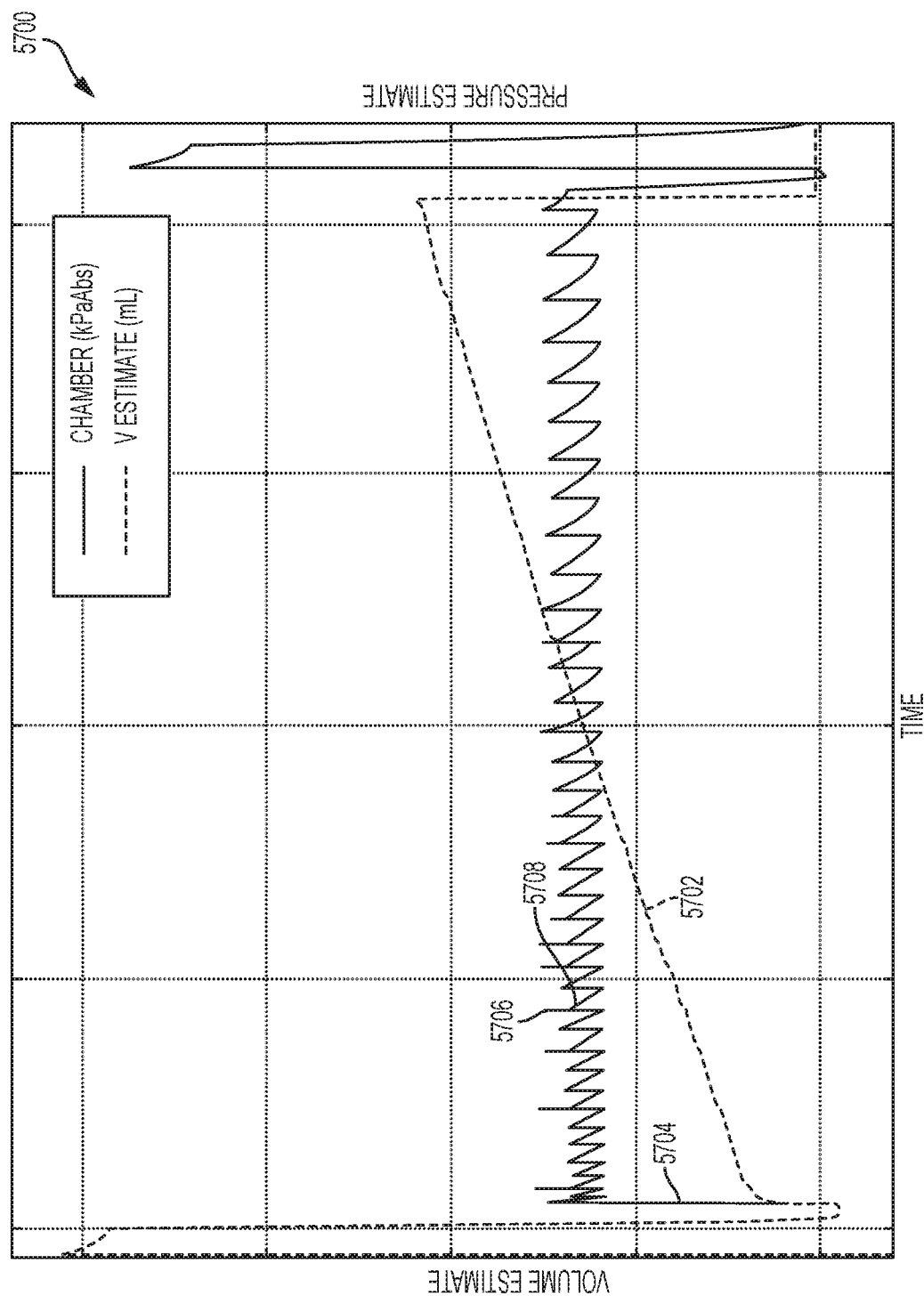
FIG. 56 shows a pressure tracing from a control or actuation chamber of a pumping cassette during a liquid delivery stroke.

FIG. 56 depicts an example graph 5700 with traces representative of pressure in a control chamber and estimated pumped volume from that chamber. The volume estimate trace 5702 is created by sampling pressure data points on each pressure decay 5708 of the pressure trace 5704. As described above, the controller may use the pressure difference between two pressure data points to determine a volume displaced in an associated pumping chamber. The controller may then calculate a cumulative volume of fluid moved in or out of the pumping chamber. As more and more pressure decay 5708 and re-pressurization events 5706 occur, the cumulative volume indicated by the volume estimate trace 5704 increases. Since the processor is capable of rapidly sampling and analyzing the data points, the volume estimate is able to be updated continuously as shown in the example graph 5700. As a result, the volume delivered to or from the pumping chamber can be accurately estimated while the stroke is in progress. This estimate is generated without halting the pumping of fluid and without the use of a reference chamber.

Any number of suitable mathematical methods may be used to model the pressure decay of the control (or pumping) chamber throughout a pump stroke. But it should be understood that a pressure decay curve at one point in the pump stroke may appear quite similar to a pressure decay curve at another point during the pump stroke, yet represent a different amount of volume change in the pumping chamber. Programming a controller to analyze the pressure decay curves during a pump stroke by using a polytropic model may help to resolve these potential differences in volume change.

One-chamber FMS—computing real-time or continuous volume changes in the control or pumping chamber using a polytropic model—may be feasible in systems using either binary or variable orifice valves connecting the pump control chamber to a pressure reservoir (positive or negative pressure). Pressure data can be acquired and analyzed during the time that either type of valve is closed (although this time period is likely much shorter when a vari-valve is used). In either case, the pressure decay during fluid egress (or pressure rise during fluid ingress) can be sampled, the volume change computed, and the process repeated to provide real-time volume change data. In the following description, a polytropic modeling process is applied to a system using binary valves in regulating the pressure in the control or pump chamber. The description applies to other types of valves and pressure regulation protocols.

In general, a one-chamber FMS protocol can be applied to any gas-driven (e.g., air-driven) diaphragm pump having a fluid pumping chamber separated from a control chamber by a flexible diaphragm. During a pump stroke, as fluid either enters or leaves the pumping chamber, the control chamber will be a closed system for at least part of the time as the controller regulates the pressure delivered to the control chamber and diaphragm. A valve connecting the control chamber to a pressure source will close once the pressure in the control chamber reaches or exceeds a high threshold value. The valve will open again (either fully or partially) as the pressure decays from fluid movement into or out of the pumping chamber, creating alternating periods during the pump stroke in which the control chamber is closed to air ingress or egress. During these phases in which the control chamber is isolated, a change in pressure reflects a change in the volume of the control chamber—and therefore the pumping chamber. An initial volume at the beginning of the pressure decay period must be known from a prior measurement, or assumed. A terminal volume can then be calculated from a measured pressure change between the initial and terminal volume. The terminal volume can then be used as the initial volume for the next calculation as the pressure decays further during the control chamber isolation phase. In this way, a controller can rapidly acquire pressure readings during the pressure decay phases of the pump stroke to compute in a nearly continuous manner the change in volume of the pumping chamber, and can thus estimate an instantaneous fluid flow rate into or out of the pump. The relationship between pressure and volume of a gas in a closed system is governed by a standard equation describing the behavior of ideal gases, and it may be best to assume a polytropic process in the calculation, in which a polytropic coefficient can vary between 1 and a value representing the heat capacity ratio of the gas used in the pump (adiabatic coefficient for that gas).

A polytropic process is governed by the equation:

$$PV^n = \text{constant}$$

where P=pressure, V=volume, and the polytropic exponent, "n", is a number between 1 and γ (γ being 1.4, the coefficient describing an adiabatic system for most gases including air). Since the right hand side of the equation is a constant, two consecutive points in time can be compared. To compare two consecutive points in time, the following equation may be employed:

$$P_t V_t^n = P_{t-1} V_{t-1}^n$$

where $P_t$ is the pressure at time t, $V_t$ is the volume at time t, $P_{t-1}$ is the pressure at time t−1, and $V_{t-1}$ is the volume at time t−1.

Rearranging the equation to solve for $V_t$ and simplifying yields the following equations:

$$V_t^n = \frac{P_{t-1} V_{t-1}^n}{P_t}$$

$$V_t = \sqrt[n]{\frac{P_{t-1} V_{t-1}^n}{P_t}}$$

$$V_t = \frac{P_{t-1}^{1/n} \times V_{t-1}^{n/n}}{P_t^{1/n}}$$

$$V_t = V_{t-1}\left(\frac{P_{t-1}}{P_t}\right)^{1/n}$$

As shown in the above equations, the current volume of the chamber, $V_t$, can be determined if the volume at the end of the preceding time interval has been determined. This volume may then be used to determine stroke displacement if desired. Additionally, by tracking the amount of time between $V_t$ and $V_{t-1}$, it is possible to determine a rate of flow over that time span. An average flow rate over a portion of the pump stroke may be determined by averaging multiple flow rate determinations using successively paired pressure data values. Additionally, knowing the starting volume and nominal ending volume of the control chamber may provide an independent determination of the amount of time needed to complete the pump stroke. In an example, a data sample set may be acquired every 10 ms and may include 20 data samples. In such embodiments, the amount of time between $V_t$ and $V_{t-1}$ will be 0.5 ms. The preferred data sampling rate will depend, among other things, on the expected duration of a pump stroke, the rate of pressure decay observed by the controller, the degree of measurement error or noise associated with the pressure signal, and the sampling speed and processing capability of the controller (e.g., whether a dedicated FPGA is being used).

In some embodiments, the controller may compute the volume change at each data point sampled. This has the advantage of minimizing the effects of heat transfer between measurement points. On the other hand, the signal noise during measurement may yield a less accurate computation for the change in actual volume. In another embodiment, the processor may sample a set of pressure data points within a time period in which heat transfer is presumed to be at an acceptable level, and the pressure data set may be filtered or smoothed by the processor before an initial smoothed pressure measurement and a final smoothed pressure measurement is used to compute the final volume at the end of the time period. The effects of signal noise on the accuracy of the measurement can thus be reduced.

There are time periods during a pumping stroke in which pressure data acquisition is either not possible or inadvisable. For example, when the pressure supply valve is open and the pump chamber pressure is spiking, fluid flow into or out of the pumping chamber continues. As a first approximation, it may be assumed that the fluid flow rate during this short period of time remains approximately unchanged from the flow rate measured shortly before the opening of the pressure supply valve. The volume change estimated in this manner may then be added to the volume representing the last measured pressure data point to arrive at the initial volume for the next measured pressure data point. Additionally, there may be prescribed points of time during a stroke at which pressure data points may be ignored. For example, depending on the data sampling rate, pressure information immediately preceding a pressure rise during a pressurization event may be inaccurate. Some aliasing may also be present for data points directly following a pressurization event. In an embodiment, data points collected by the controller within a predetermined period of time before and after a pressurization event may be discarded or ignored to further improve the accuracy of the flow determination process.

In embodiments which use an FPGA for pressure data acquisition and analysis, issues stemming from an inferior sampling rate may present less of a concern. In certain embodiments, an FPGA may also have the resource capacity to control the relevant valves in the pumping system. By controlling the pressure supply valves, the FPGA may be able to schedule the sampling of pressure data more efficiently. Synchronization of events may be improved, and aliasing problems with data sampling may be reduced.

Certain assumptions may also be made at the beginning of a pump stroke. A small amount of fluid movement into or out of the pumping chamber is likely to be present prior to the first pressure decay event. Although inertial forces may limit the initial fluid flow, the controller can be programmed to estimate an initial fluid flow and volume change prior to the first data sampling point during pressure decay. Such an assumption may allow for the estimation of changes in chamber volume while pressure decay information at the beginning of the stroke is not available. The amount of fluid assumed to have been moved at the start of a stroke may depend on the pumping pressure applied to the control and pumping chambers. The controller may be programmed to include a pre-determined volume of fluid movement based on the value of the applied pressure. Alternatively, after number of data points have been sampled to determine an estimated flow rate, the flow rate may be used to extrapolate for the volume moved while the data was unavailable. It may, for example, be assumed that the flow rate over that period of time was substantially equal to the currently estimated flow rate. This assumption that the flow rate is constant may then be used to determine an estimate of the volume moved over the period which data was unavailable.

Figure 57:
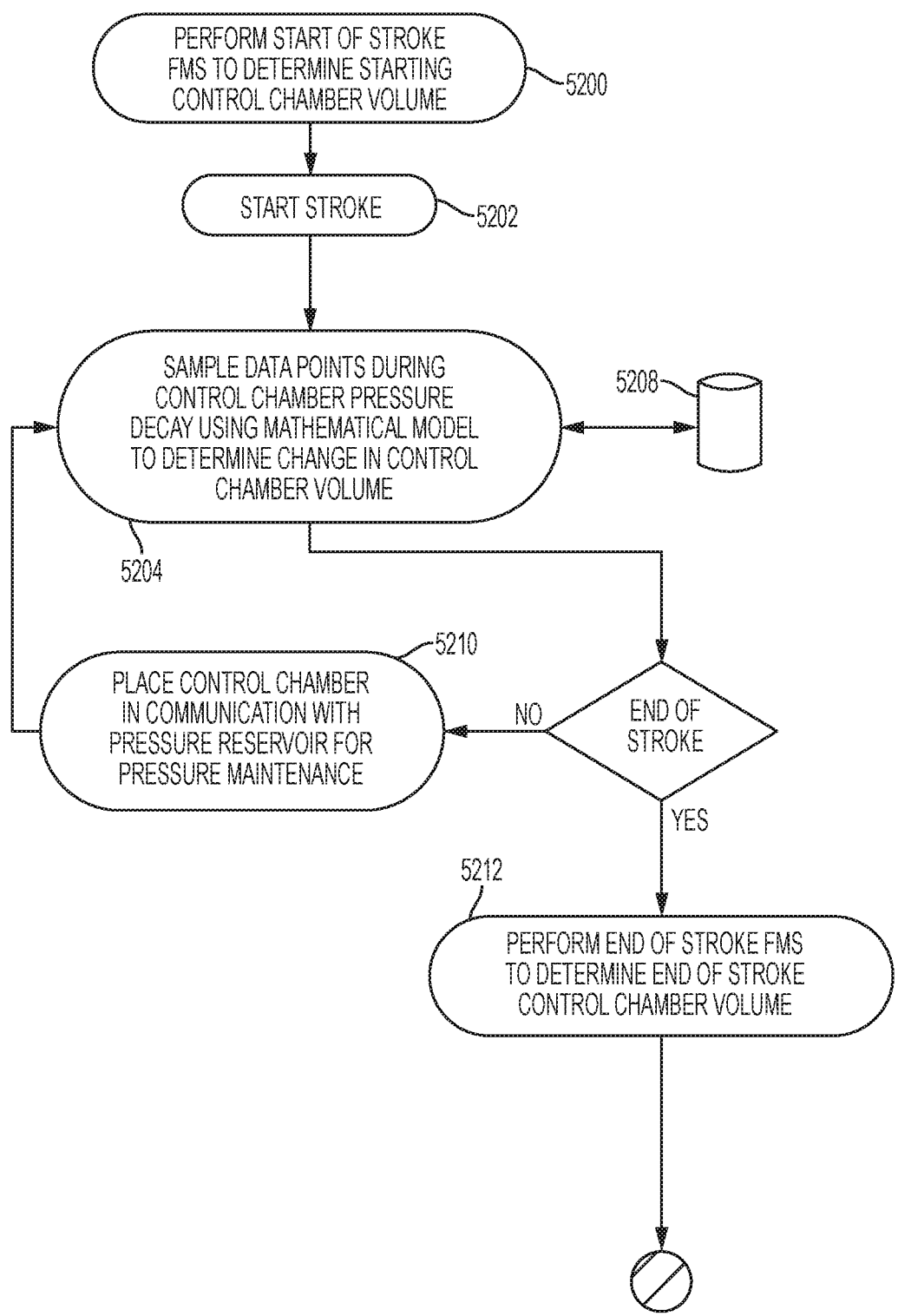
FIG. 57 shows a graph plotting pressure in a control or actuation chamber during a liquid deliver stroke and a cumulative volume estimation plot during the liquid delivery stroke.

FIG. 57 shows a flowchart detailing an example of a number of steps which may be used to estimate control chamber volume changes during a pump stroke. As shown, the flowchart begins in step 5200, where a pre-stroke FMS measurement is made, which in an embodiment includes freezing the volume of the pumping and control chambers, measuring control chamber pressures and equalizing pressures with a reference volume chamber. This measurement may provide a starting control chamber volume measurement. Alternatively, the starting control chamber volume may be assumed by the controller to be a fixed and known quantity if the controller has calculated that the preceding end-of-stroke of the pumping chamber has been fully completed. A pump stroke may then be started in step 5202. In step 5204, the control chamber pressure decay (or the decay of the absolute value of the pressure) may be monitored as the stroke displaces and causes fluid to move into or out of the pumping chamber. In some specific embodiments, multiple data points may be sampled along each decay curve and the mathematical model described above may be used to determine changes in control chamber volume as the pump stroke proceeds. Data points and volume information may be saved in memory 5208.

Assuming the end of stroke is not detected, once the pressure in the control chamber falls outside of a predetermined range (e.g. falls below a predetermined pressure value), step 5210 may be performed. In step 5210, the pressure controller may perform pressure maintenance on the control chamber (i.e. re-pressurize the control chamber) to bring the control chamber pressure back to approximately a preprogrammed desired value (which may, for example, be at or near a high pressure bound of the range). After completing step 5210, step 5204 may be repeated with the collected data again being saved in memory 5208. This may continue until an end of stroke condition is detected. End of stroke detection is described elsewhere.

In the event an end of stroke condition is detected, a post-stroke FMS measurement (determining volume by measuring control gas pressure) may be taken in step 5212. This measurement may be compared to the measurement from step 5200 to check and/or more precisely determine the total volume moved during the stroke. Additionally, this post-stroke FMS measurement may serve as the starting control chamber volume measurement for the next stroke performed by that pump chamber.

Other means of determining that the pump has fully completed its pump stroke may be used. If so, the result of that determination may then be used to initialize the controller to the control chamber's starting volume for the next pump stroke. Methods other than volume determination by pressure measurement may be used to assess the final volume of the control and pumping chambers, whether or not a pump stroke has been fully completed. However the final chamber volume is determined, that value may then be used to initialize the controller as the chamber's starting volume for the next pump stroke.

The polytropic coefficient, "n", of the above described mathematical model may be initialized at a specific value. For example, in some embodiments, the coefficient may be set to 1.4 or $\gamma$ (representing an adiabatic process for air). The initialized value may differ depending on the embodiment, the type of control fluid, or the intended flow rate. For example, embodiments with a relatively fast flow rate may be more appropriately modeled as an adiabatic system while embodiments with a slower flow rate may be more appropriately modeled as an isothermal system.

The coefficient may then be adjusted to a value yielding greater agreement between the computed real-time flow rate and the measured final volume change at end-of-stroke over a plurality of pump strokes. This may be done by using feedback collected over one or more pump strokes using any suitable software algorithm, or using a controller such as a proportional controller or PID controller. Feedback may be in the form of a calculated delivered volume determined by a comparison of the pre-stroke and post-stroke FMS measurement. The final FMS measurement volume and estimated real-time volume change determined using a current value for "n" may be compared. If the volumes differ by more than a predetermined amount the value for "n" may be adjusted. The new coefficient value may then be saved and used as the initial value for the next pump stroke. In an example, the coefficient "n" may be adjusted using data collected over several pump strokes. For example, values for "n" that would have yielded the final (e.g. FMS measured) volume moved for a number of strokes may be averaged together. In the absence of significant changes in ambient conditions (e.g., fluid or environmental temperature changes), an averaging or other numerical filtering procedure may decrease the time needed to produce accurate flow rate and stroke displacement measurements, as it may not be necessary to have the controller perform repeated comparisons of pre-stroke and post-stroke FMS measurements.

Figure 58:
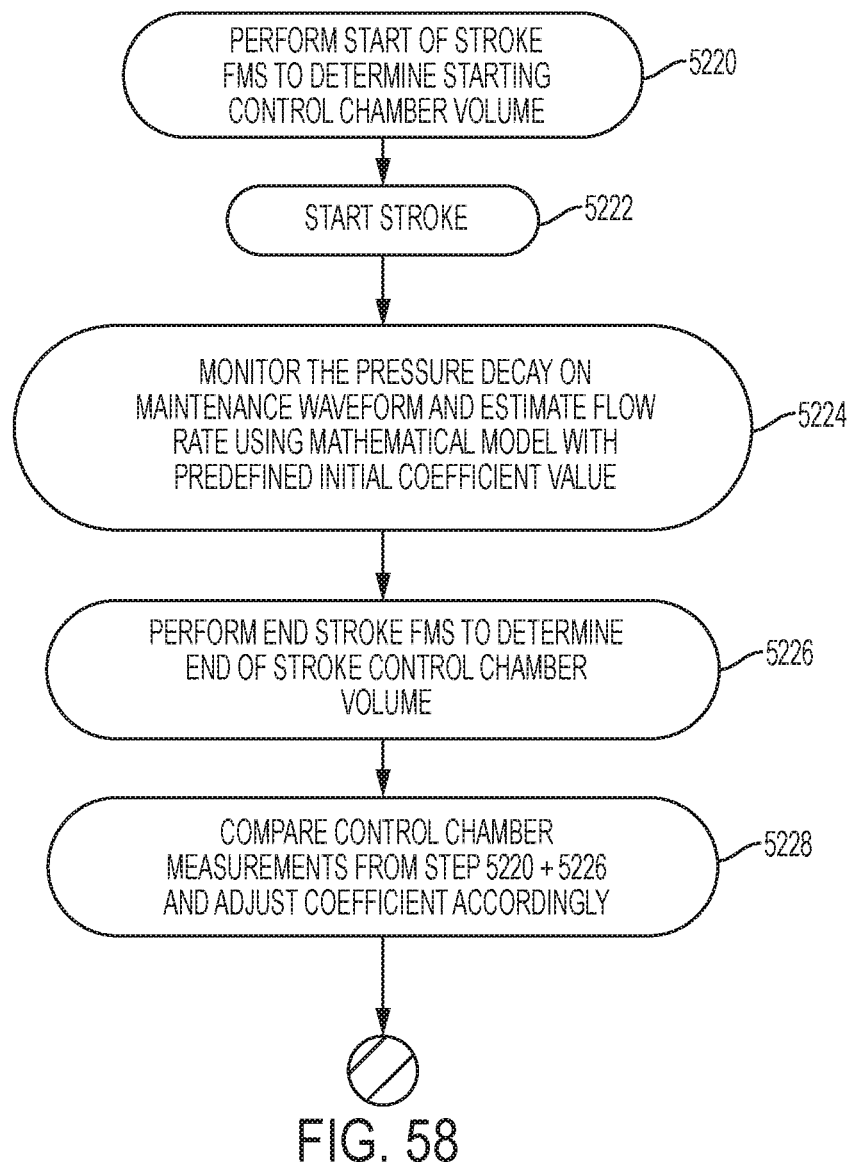
FIG. 58 shows a flowchart outlining a number of steps which may be used to estimate control chamber volume changes over time.

FIG. 58 shows a flowchart outlining an example of a number of steps to adjust the coefficient of the mathematical model as described above. As shown, in step 5220, a pre-stroke FMS measurement may be taken to determine a starting volume for a control chamber. The stroke may then begin in step 5222. In step 5224, the pressure decay on the pressure regulation waveform may be monitored. Volume change of the control chamber may be determined using the example mathematical pressure-volume model with a pre-defined initial exponent coefficient value. Once the stroke has completed, in step 5226, a post-stroke FMS measurement may be made to determine the end of stroke control chamber volume. In step 5228, the volume measurements from step 5220 and 5226 may be compared to determine the total control chamber volume change over the stroke. The coefficient may be adjusted based on this comparison to align the two final values if necessary. For example, the coefficient may be adjusted to the value which would have yielded the volume change found by using the FMS measurements.

As mentioned above, a flow rate estimation as a stroke is progressing may be used for a number of purposes including, but not limited to, detection of occlusions, detection of low flow or no flow conditions, detection of end of stroke, detection of fluid line prime state, etc. The flow rate estimation may be monitored to determine if it is likely that an end of stroke condition is present. For example, if the real-time flow rate drops below a predefined threshold (e.g. 15 mL/min), it may be an indication that a pump stroke has been fully completed (i.e. the maximum volume of fluid has been moved given the physical limitations of the pump). If the flow rate estimate drops below the predefined threshold, an FMS measurement may be performed on the chamber and the volume delivered may be verified. If the FMS measurement determines the end of stroke has been reached, the chamber may move onto the next pumping operation (or pump stroke). If an end of stroke condition has not been reached, the controller may undertake a number of actions, including, for example, attempting to resume the pump stroke. Alternatively, the detection of a reduced flow condition may be indicative of an occlusion of the fluid line, an occlusion alert or alarm may be triggered, or a fluid pushback attempt may be made to determine if an occlusion exists.

In some embodiments, the controller may be programmed with an arming routine (a software trigger) to keep it from declaring an end-of-stroke condition prematurely. This may help to avoid false triggering of an end of stroke determination. For example, a lack of cumulative pressure data at the beginning of a stroke may increase the effect of signal noise in a flow rate determination. In an example, the controller may be programmed with a trigger that is armed only after a pre-determined time period has elapsed after the initiation of the pump stroke. In some embodiments the software trigger may be the attainment of a predetermined flow rate value. Or the trigger may be armed after is the controller estimates that a predetermined volume of fluid has been moved. Requiring that the end of stroke detection trigger be armed before an end of stroke condition is detected may help to reduce the number of partial strokes performed and may help to increase throughput of fluid through a pumping cassette. To help prevent a scenario in which the arming criteria is not reached and the end of stroke is never detected, the trigger may be armed after the stroke has been in progress for a predetermined amount of time. In other embodiments, after a predetermined period of time has elapsed since the beginning of the stroke without the arming criteria being met, and end of stroke may automatically be triggered.

Figure 59:
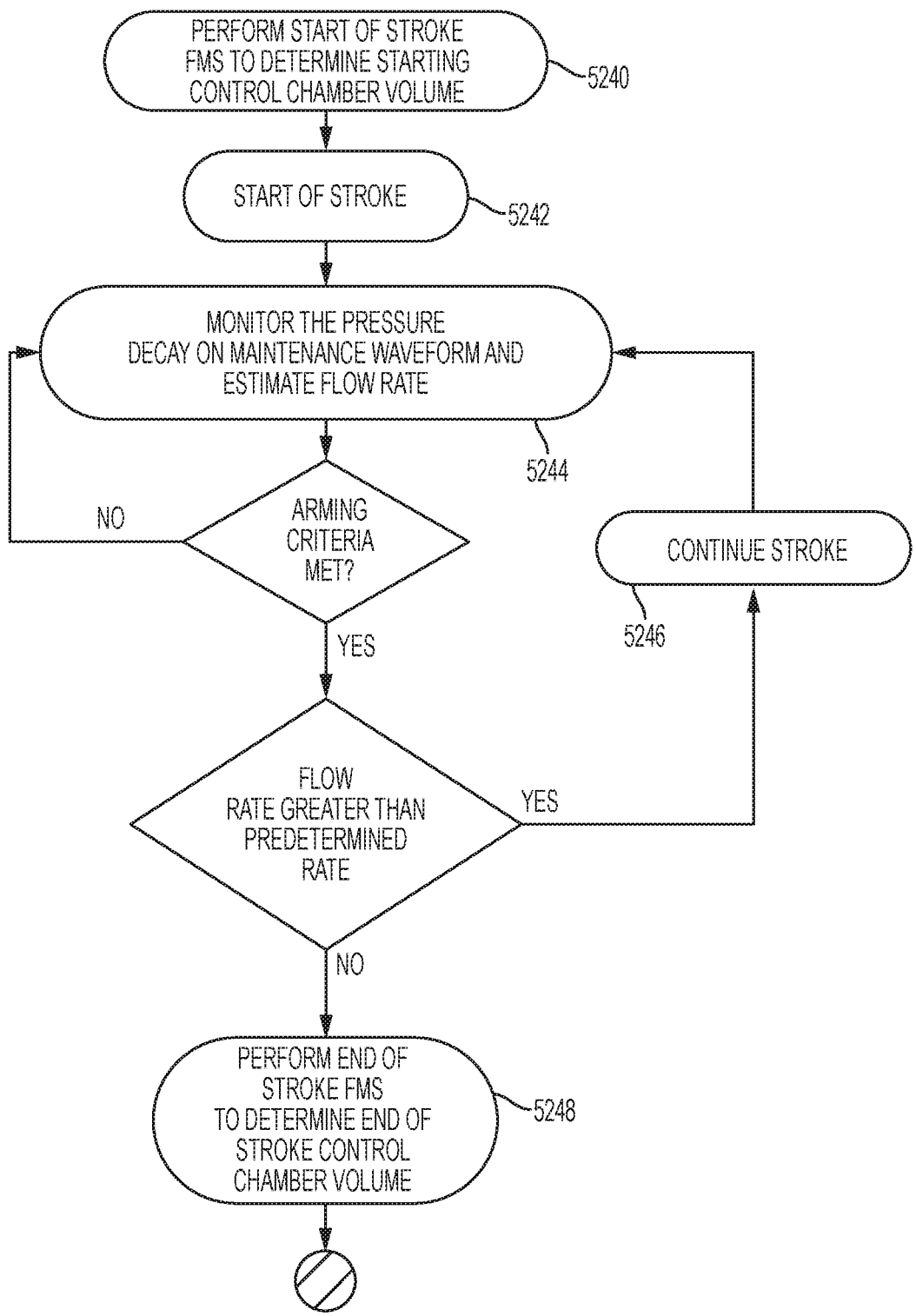
FIG. 59 shows a flowchart outlining a number of steps to adjust an equation used to estimate control chamber volume changes over time during a pump stroke.

FIG. 59 shows a flowchart outlining a number of example steps to detect end of stroke based on a real-time flow rate estimation. As shown, in step 5240, a pre-stroke measurement may be performed to determine the starting volume of a control chamber. The pump stroke is then started in step 5242. As the stroke progresses, in step 5244, the pressure decay on the control chamber pressure regulation or maintenance waveform is monitored. A flow rate is estimated based on the pressure decay. When the end of stroke arming criteria is met, the controller determines whether the flow rate is above a pre-established or predetermined flow rate. If the flow rate is above the predetermined flow rate, the pump stroke continues in step 5246 and flow rate estimation continues in step 5244. In the event that the flow rate drops below the predetermined flow rate, in step 5248, the stroke may be ended and an end of stroke FMS measurement may be made to determine the control chamber volume.

In some embodiments, estimation of control chamber volume change over the progression of the stroke may be used to predict the amount of time necessary to complete the stroke. Since the starting volume as well as the nominal or projected end volume of the stroke is known and flow rate may be determined using control chamber volume change, the controller may use this information to estimate how long the entire stroke should take. Correspondingly, the controller can calculate an estimate of how much time is needed to complete the remaining portion of the stroke. Once the predicted end time of the stroke is reached, the stroke may be stopped and an FMS measurement may be made. In the event that the FMS measurement indicates the stroke was a partial stroke, a number of actions may be taken. In some embodiments, a cycler may attempt to retry the stroke. Alternatively, controller detection of a reduced flow condition may be an indication for an occlusion alert or alarm, or a pushback attempt may be made to determine if an end-of-line occlusion can be relieved.

Figure 60:
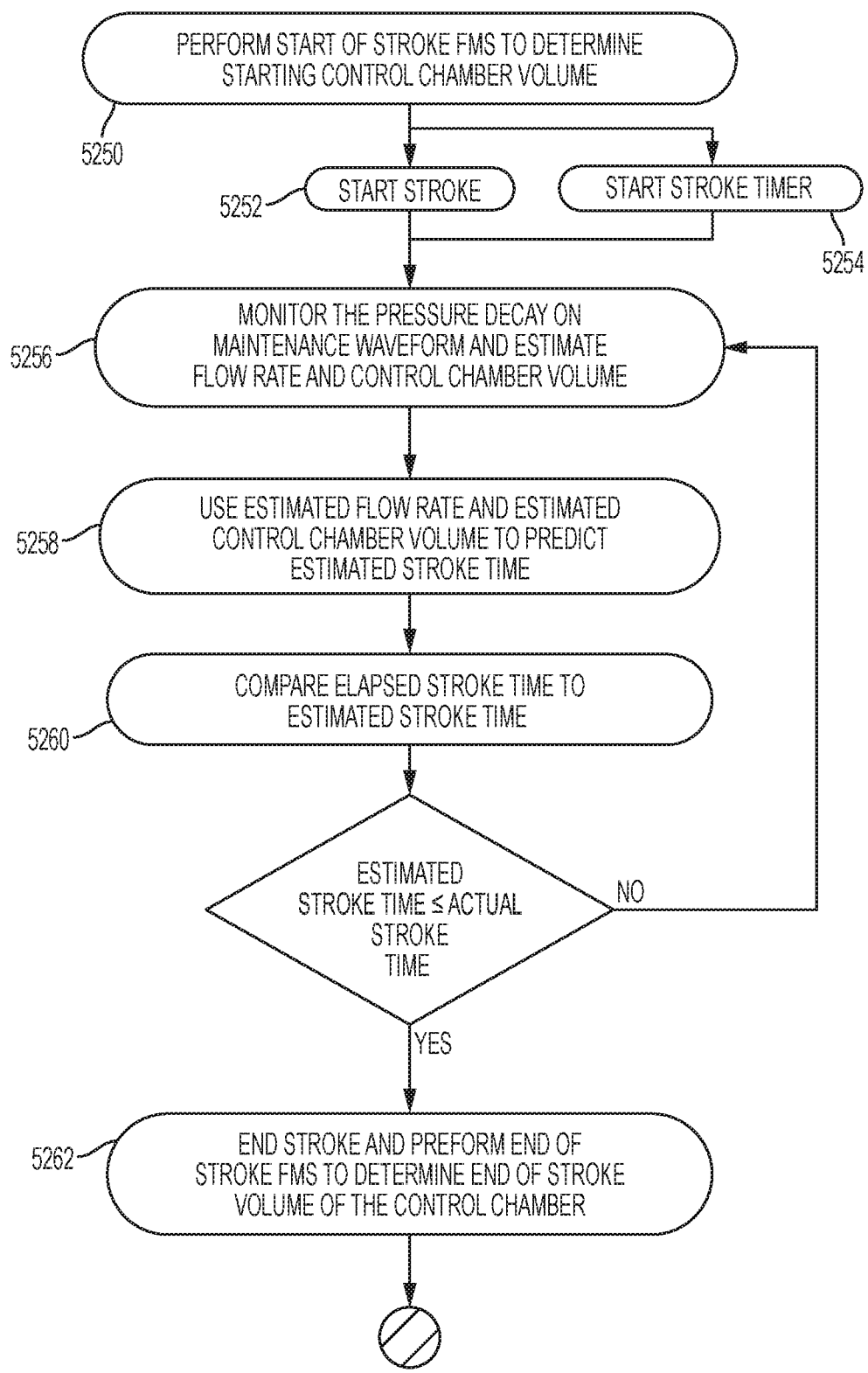
FIG. 60 shows a flowchart outlining a number of steps to detect end of stroke based on flow rate during a stroke.

FIG. 60 shows a flowchart outlining a number of example steps which may be used to determine end of stroke by predicting time necessary to complete a stroke. As shown, in step 5250, a pre-stroke FMS measurement may be taken to determine the starting volume of a control chamber. A stroke is started in step 5252. When the stroke begins, a stroke timer can be started in step 5254. As the stroke progresses, in step 5256, the pressure decay on the pressure regulation or maintenance waveform for the control chamber is monitored. This may be used to estimate the control chamber volume and flow rate. These estimates may then be used in step 5258 to project an estimated stroke time. The estimated stroke time may be calculated by finding the difference between a current chamber volume and the projected end of stroke chamber volume. The estimated flow rate may then be used to find the amount of time required to complete the stroke. The estimated end-of-stroke time may then be compared to the elapsed stroke time in step 5260. If the estimated end-of-stroke time is longer than the elapsed stroke time, steps 5256, 5258, and 5260 may be repeated. If the estimated end-of-stroke time is less or equal to than the actual elapsed stroke time, the controller may declare an end of stroke condition. In step 5262, the stroke is ended and an FMS measurement may be taken to determine the post-stroke volume of the control chamber. In some embodiments, remaining stroke time estimations may be made until a predetermined amount of stroke time remains or a predetermined amount of stroke displacement has occurred. The controller continues the stroke until that time expires and step 5262 can then be performed.

The availability of real-time flow rate estimation offered by the exemplary mathematical model described above may allow for earlier detection of reduced flow conditions as well. Instead of having a controller wait for a stroke to finish, performing a volume measurement and comparing it to a previous measurement, the controller can be programmed to respond to a real-time flow rate that is less than an expected flow rate threshold. The controller can be programmed to stop the pump stroke at that point to perform a more precise volume measurement (e.g., via an FMS measurement) to verify the flow rate estimate. Thus, reduced flow conditions may be detected without the need to complete prolonged pumping strokes caused by the reduced flow. This may save time, reduce patient discomfort, and may help to increase overall fluid throughput of a pumping cassette. It may also allow a therapy to transition more quickly from the end of a drain phase to the fill phase of the next cycle. This increased efficiency may allow for more therapy time to be allocated to dwells. In one example, the controller may be programmed to declare a reduced flow condition when the flow rate estimate is below a threshold of 50 mL/min. In some embodiments, before a reduced flow condition is declared, the flow rate may have to remain below the threshold for a predefined period of time (e.g. 30 seconds).

Optionally, there may be a plurality of reduced flow condition classifications defined by different flow thresholds. For example, in addition to a low flow threshold (e.g. <50 mL/min) the controller may be programmed to recognize a 'no flow' threshold which is set lower than the low flow threshold (e.g. <15 mL/min).

Figure 61:
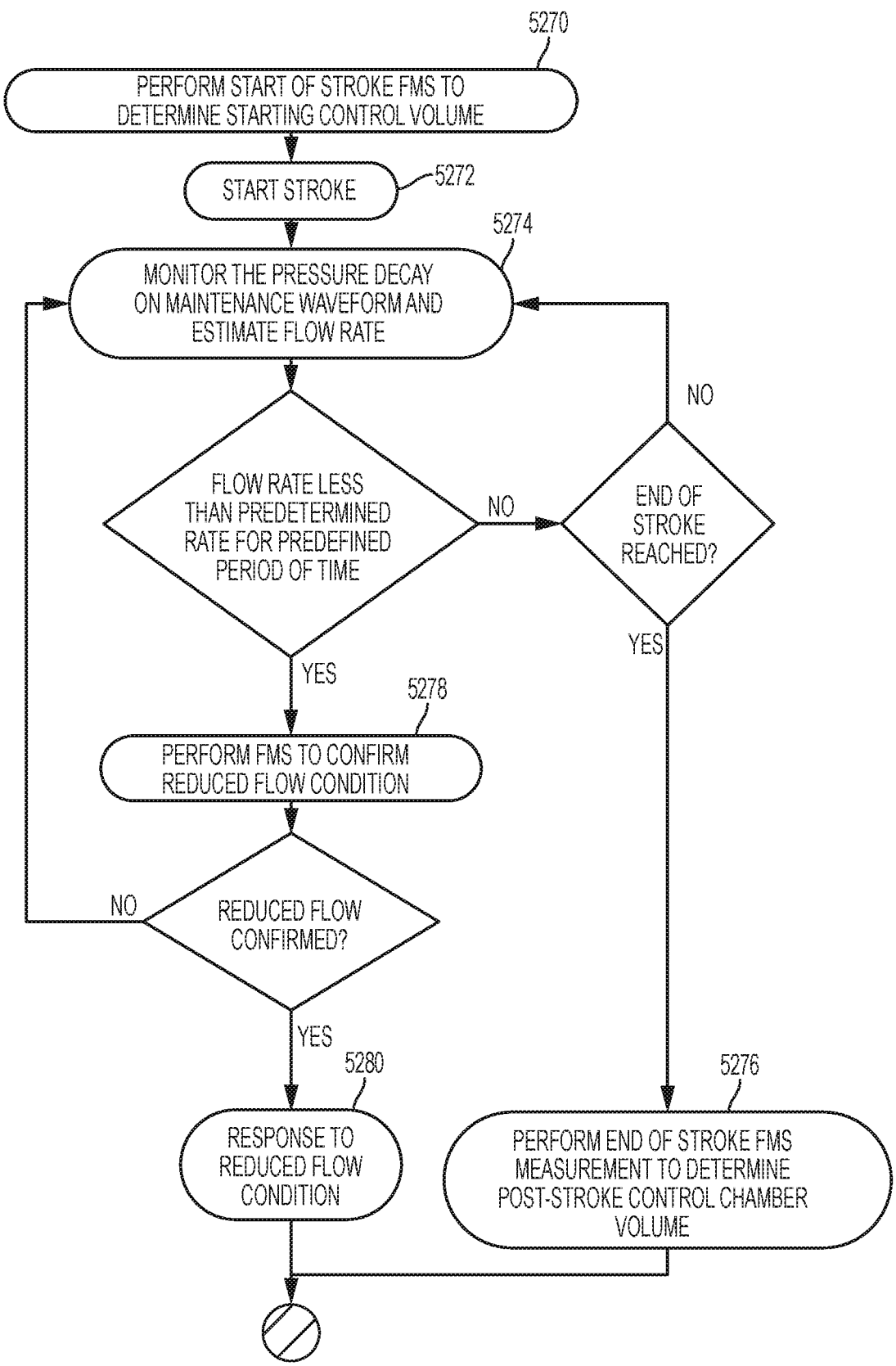
FIG. 61 shows a flowchart outlining a number of steps to determine end of stroke by predicting time necessary to complete a stroke.

FIG. 61 shows a flowchart outlining a number of example steps which may be used to detect a reduced flow condition during a pump stroke. As shown, in step 5270 a pre-stroke FMS measurement may be taken to determine the starting volume of a control chamber. A stroke is then started in step 5272. In step 5274, the pressure decay on the pressure regulation or maintenance waveform may be monitored such that real-time control chamber volume change and flow rate may be estimated. The controller continues with the pump stroke as long as the flow rate is greater than a predetermined flow rate for a predetermined period of time. The controller continues to monitor the pressure decay waveforms as described in step 5274. If the end of stroke is reached, an end of stroke FMS measurement may be made in step 5276 to determine the end of stroke control chamber volume. If is the controller determines that the flow rate is less than the predetermined flow rate for a predetermined period of time, an FMS measurement may be made in step 5278 to confirm that a reduce flow condition exists. If the reduced flow condition is not confirmed, the stroke may continue, and the controller continues to compute flow rate based on the control chamber pressure regulation or maintenance waveform as described above in step 5274.

If the reduced flow condition is confirmed by the FMS measurement in step 5278, in step 5280 a reduced flow or occlusion notification, alert, or alarm may be sent to the user. This may be done via a user interface and may be accompanied by an audible message or tone, vibratory indication, etc. The response generated by the cycler controller may be dependent on the flow rate detected. Before indicating an occlusion is present, a pushback of fluid into the fluid reservoir (or peritoneal cavity, depending on the fluid line) may be triggered. In the event that the pushback attempt is unsuccessful, the controller may issue an occlusion alert.

In some embodiments, in the event a reduced flow condition is detected, a cycler controller may verify whether or not a target volume for a pumping operation (e.g. a drain phase) has been achieved (e.g., a completed peritoneal drain). If the target volume or more has been moved, the controller may declare that the pumping operation has been completed. In some embodiments, a device controller may require a minimum defined time period to have elapsed to ensure that the fluid reservoir (e.g., solution bag, heater bag, or a patient's peritoneum) is substantially empty.

Real-time measurement of fluid flow during a pump stroke can permit the targeting of specific fluid volume deliveries less than a full pump stroke volume, or an integer multiple of a full pump stroke volume. The controller may be programmed to end a stroke when the chamber volume change estimated through pressure measurement indicates that the target volume has been delivered or withdrawn. Upon this occurrence, the controller may initiate an FMS measurement to confirm that the target volume was actually reached. Real-time fluid flow measurement may avoid the need to perform multiple FMS measurements while repeatedly making small displacement partial strokes to avoid over-shooting the target volume. Such a targeting scheme may be particularly desirable in a pediatric application in which the amount of time spent approaching but not overshooting a target volume would otherwise take a relatively large portion of time in a pumping operation.

Figure 62:
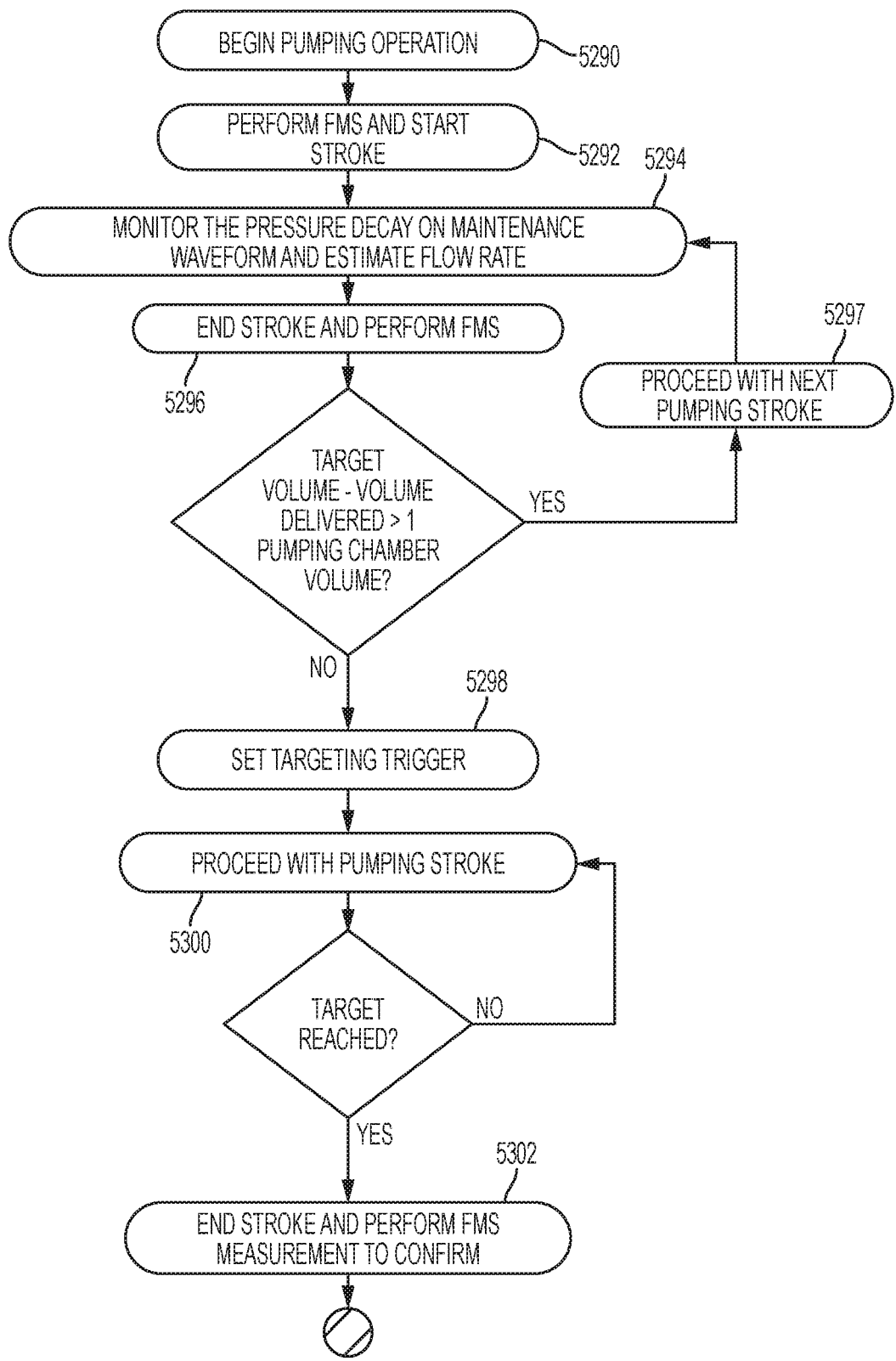
FIG. 62 shows a flowchart outlining a number of steps to detect a reduced flow condition while a pump stroke is in progress.

FIG. 62 shows a flowchart outlining a number of example steps that may be used to determine when a target volume of fluid has been moved. As shown, the steps make use of an estimated volume moved based on measurement of pressure decay during a stroke to end the stroke when the target volume is estimated to have been reached. A pumping operation begins at step 5290. This operation may, for example, be a fill phase for a peritoneal dialysis cycle. When the pumping operation begins, an FMS measurement may be made and a pump stroke is started as shown in step 5292. During the stroke, the pressure decay on the pressure regulation or maintenance waveform may be monitored in step 5294. This allows for an estimation of volume displacement and flow rate as the stroke progresses. The stroke may end and a post-stroke FMS measurement may be conducted in step 5296. A cycler controller tracks the computed cumulative volume to see if the difference between the target volume and the total volume of fluid delivered during the pumping operation is greater than a full pump chamber volume. If so, the controller proceeds to command the next pump stroke in step 5297. Steps 5294, 5296, and 5297 may be repeated until the difference between the target volume and total volume pumped is less than the volume of one full pump chamber. At this point, in step 5298, if the delivery of another full chamber volume would cause the target volume to be exceeded, step 5298 is performed.

In step 5298, a targeting trigger may be set as the difference between the total delivered volume for the pumping operation and the target volume for the pumping operation. The pump stroke may then proceed in step 5300 until the controller calculates through pressure decay measurements that the target volume has been reached. At this point, step 5302 may be performed in which the stroke is ended and an FMS measurement may be made to confirm that the target volume of fluid has been moved.

Computing an estimated flow rate from a pressure decay curve during a pump stroke may also allow the controller to close a valve or valves in a preemptive manner in order to more precisely deliver a pre-determined fluid volume. That is, the valve(s) may be closed before the target volume is delivered to account for a delay between the controller command and the valve's mechanical response. The flow which occurs during the period of time required to physically close the valve(s) may then cause the target volume to be substantially met. Specifically, the controller may estimate the amount of time required to physically to close the valve(s). In some embodiments, this estimation may be a preprogrammed value. For example, for a particular valve arrangement the response delay may be approximately 100 ms. Based on a real time computation of the flow rate, the volume of fluid moved during the valve response delay can be estimated. This amount of fluid may be subtracted from the target volume to yield a valve closure trigger volume. Once the valve closure trigger volume has been met, the cycler controller can command the valves to close.

Volumetric Pumping Volume Calibration

Prior to a cycler 14 being provided to a patient, the volumetric pumping measurements made by the cycler 14 may be calibrated. As an output of the calibration, the cycler 14 may be provided with calibration data which is thereafter used during pumping to adjust volume measurements collected by the cycler 14. This may help to mitigate any error in volumetric calculations which is peculiar to a particular cycler 14. As mentioned elsewhere herein (see, e.g. FIG. 53A-55), a calibration may be accomplished by installing a disposable cassette 24 into the cycler 14 and pumping fluid to or from a mass scale. A calibration coefficient for the cycler 14 may be calculated based on the measured mass transferred and the FMS values calculated by the cycler 14.

Such a calibration, however, may be subject to some variability in its precision depending on manufacturing differences between disposable cassettes 24. Such differences may arise between production lots of cassettes 24. Additionally, it is possible for differences to be present within particular lots. Aspects of the sheeting or membrane 15 on the cassette 24 may potentially contribute an amount of variability. Where a pre-formed region is included on the sheeting 15, some variability may be attributable to the pre-form generation process. Additionally, during the calibration process, the cassette 24 may be in a liquid containing or wetted state. In the event that air remains in the cassette 24, it is possible that this air may impact the calibration.

In some embodiments, one or more volumetric standard cassettes or volumetric calibration cassettes may be used in place of a disposable pumping cassette 24 during calibration. Though described in relation to cyclers 14 detailed herein, such volumetric standard cassettes may similarly be used in other cassette based pumping systems. In general, a volumetric calibration cassette may be of similar dimensions and possess the same general layout as a disposable cassette 24 so as to interface with the cycler 14 and seal against the control gasket 148 as if it were a disposable cassette 24. Thus, with the volumetric standard cassette acting as a disposable cassette analog, the calibration may be performed under similar circumstances as would be present with a typical disposable cassette 24. The cycler 14 may apply pressure to a volumetric standard cassette through the control gasket 148 in the same manner as with a disposable cassette 24. Though the volumetric standard cassette may not pump any fluid or be completely incapable of being used for fluid pumping, it may be used to conduct volume measurements based on gas laws as described above. Since the pump chamber regions of various volumetric standard cassettes may be designed to mimic particular pump chamber fill volumes, the cycler 14 may make measurements of the control chamber 171B (see, e.g. FIG. 43) volume knowing what the outcome of that measurement should be. Thus, by taking a control chamber 171B (see, e.g. FIG. 43) volume measurement with a volumetric calibration cassette, a calibration can be made to adjust for error in the volume measurement data collected by that particular cycler 14. Thus the calibration may be cycler specific and unimpacted by disposable cassette variability, limitations related to resolution of a mass scale, or other factors. Additionally, or alternatively, such a volumetric calibration cassette may be used as part of a process testing procedure during manufacture. For example, the volumetric calibration cassette could be used to establish an ideal baseline for a cycler 14. Disposable cassettes 24 could be tested by a cycler 14 and compared to this baseline. In the event that a disposable cassette 24 deviates from the ideal baseline by more than a predetermined amount, related disposable cassettes 24 (e.g. those from the same lot) could be singled out for further inspection.

These volumetric standard cassettes may be constructed of a robust, rigid, and dimensionally stable material. Various metals such as steel or aluminum, for example, may be used. Plastics such as ABS, polycarbonate, acrylic, Ultem, Peek, and/or PET may be used in certain embodiments. Other materials such as ceramics, glass, etc. are also possible. These volumetric calibration cassettes may be machined, injection molded, constructed via a material additive process (e.g. 3-D printed), or made in any other suitable manner. The volumetric calibration cassettes may emulate pre-primed cassettes whose flow paths are fluid filled. The pump chambers regions of these cassettes may be designed to have a predefined geometry which is selected to be representative of a desired fill volume in an ideal disposable pumping cassette 24. A number of volumetric standard cassettes may be constructed to reflect a variety of selected fill volumes (e.g. substantially full, substantially empty or fully delivered, and any number of fill volumes therebetween). The shape of the pump chamber on a volumetric calibration cassette for any particular volume may be chosen to have an analogous shape to that present in a disposable cassette 24 when its pump chamber 181 contains the same volume. In some embodiments, the shape of the pump chamber on a volumetric standard or calibration cassette may mimic the shape of a pump chamber 181 of an ideal disposable cassette 24 when operated by the cycler 14 to contain the desired volume. The surface area of the pump chamber regions on any volumetric standard cassettes may all be substantially equal even where the volumetric standard cassettes are constructed to be representative of different volumes. This may be desirable as sheeting 15 of a disposable pumping cassette 24 demonstrates minimal stretching over the range of a pumping stroke. Thus the surface area of the pump chamber region 151 of the sheeting 15 should not change substantially regardless of the volume contained in the pumping chamber 181 of the disposable pumping cassette 24. This may help ensure that the control surface 148 displaces or bends in a representative manner during volume measurement of an installed volumetric calibration cassettes. After construction, a verification of the volume of the volumetric calibration cassette may be conducted. This may be done by weight, volume of water displacement, a characterization performed with a vision system, measuring with a 3D CMS, or in any other suitable manner. In some examples, the surface area of the pump chamber region of volumetric calibration cassettes may also be verified.

Referring now primarily to FIGS. 63A-63C a number of views of an example disposable cassette 24 are shown. FIG. 63A depicts a top down view of a disposable cassette 24. The disposable cassette 24 is shown in cross-section (taken at the corresponding cut planes of FIG. 63A) in FIGS. 63B and 63C. As can be seen from FIG. 63B, the disposable cassette 24 includes a number of flow paths which pass through the mid-body 44 of the cassette 24. Additionally, there are a number of walls 46 and valve ports 186 which project away from the mid-body 44 of the cassette 24. A rim 48 is present at the periphery of the disposable pumping cassette 24 and extends to a height greater than the height of the walls 46. The membrane 15 is attached to this rim 48. These features are described in greater detail above.

As best shown in FIG. 63C, the pump chambers 181 of the disposable pumping cassette 24 are shown in a delivered state. In this state, the membrane 15 is against the spacers 50 which leaves some volume of the pump chambers 181 to act as an air trap during operation. The pump chambers 181 and spacers 50 are further described above. The disposable cassette 24 shown includes a number of inlet/outlet ports 150, 152, 154, 155.

Figures 64A, 64B, 64C:
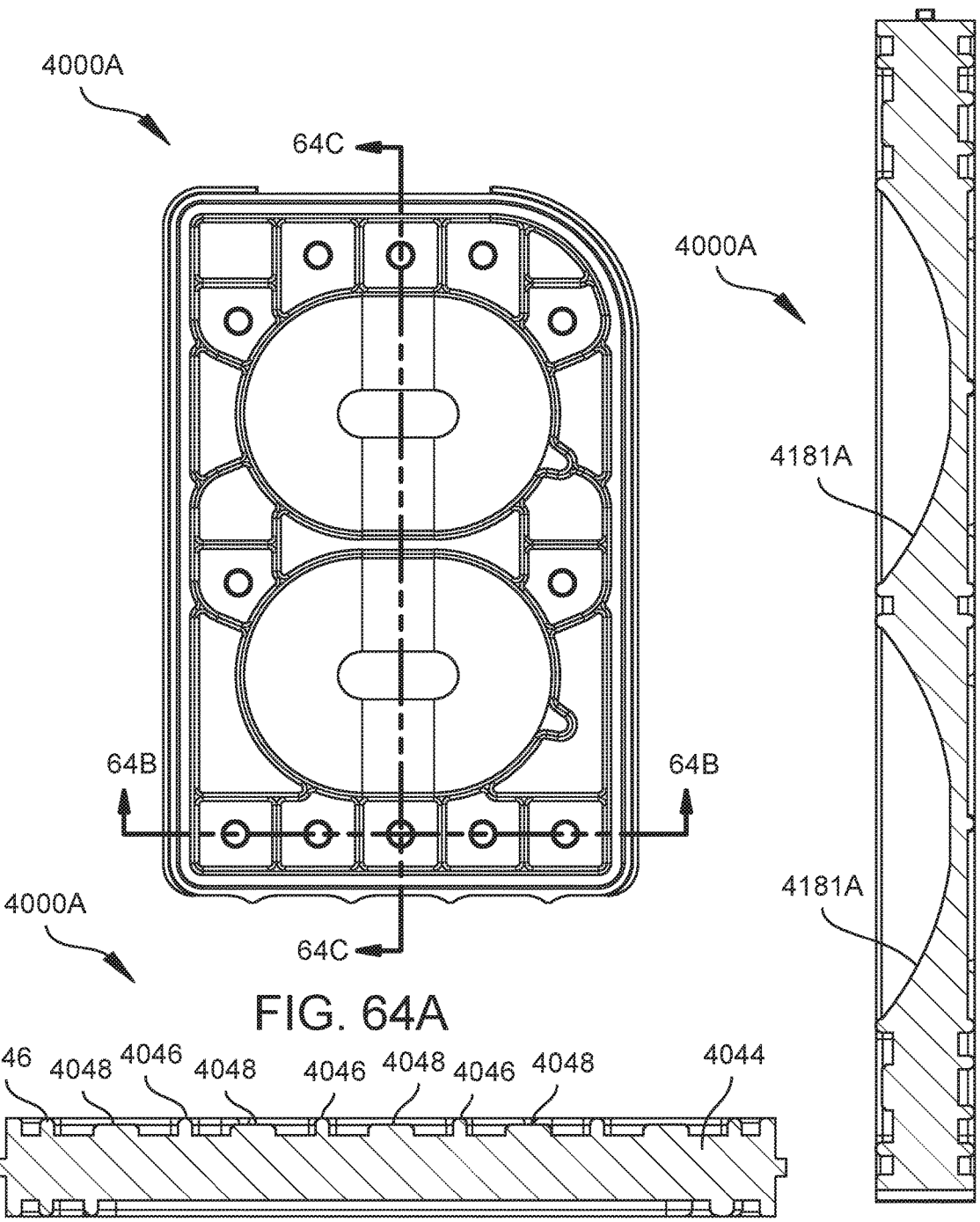
FIG. 64A depicts a top down view of an exemplary volumetric standard cassette.
FIG. 64B depicts a cross-sectional view taken at line 64B-64B of FIG. 64A.
FIG. 64C depicts a cross-sectional view taken at line 64C-64C of FIG. 64A.
Figure 64D:
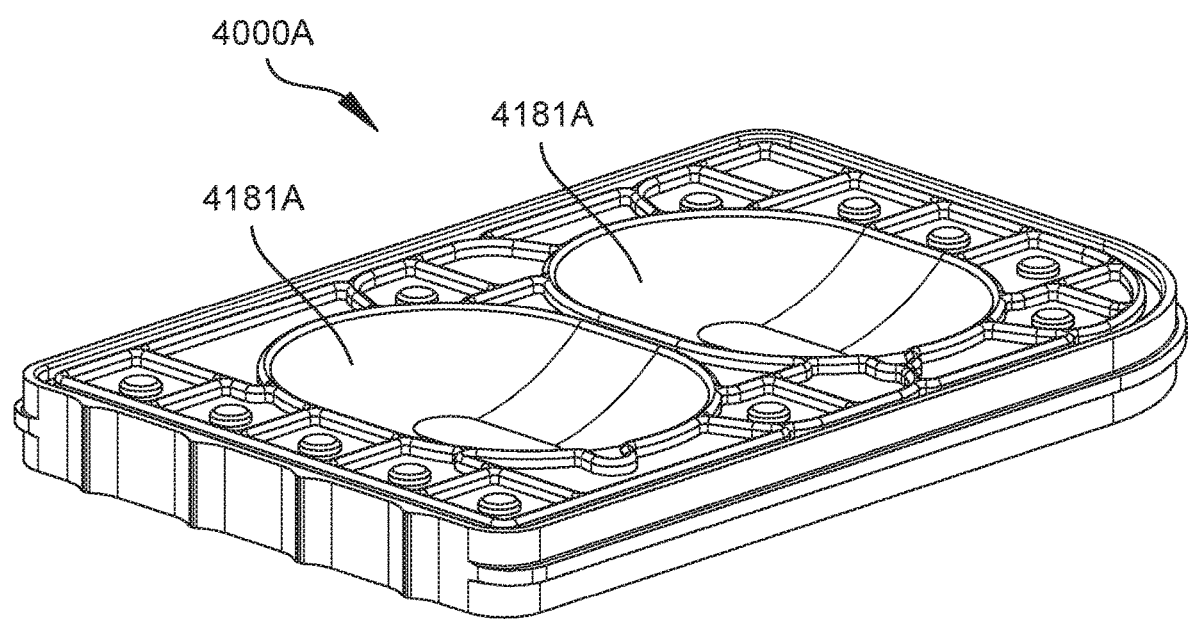
FIG. 64D depicts a perspective view of an example volumetric standard cassette.
Figure 65A:
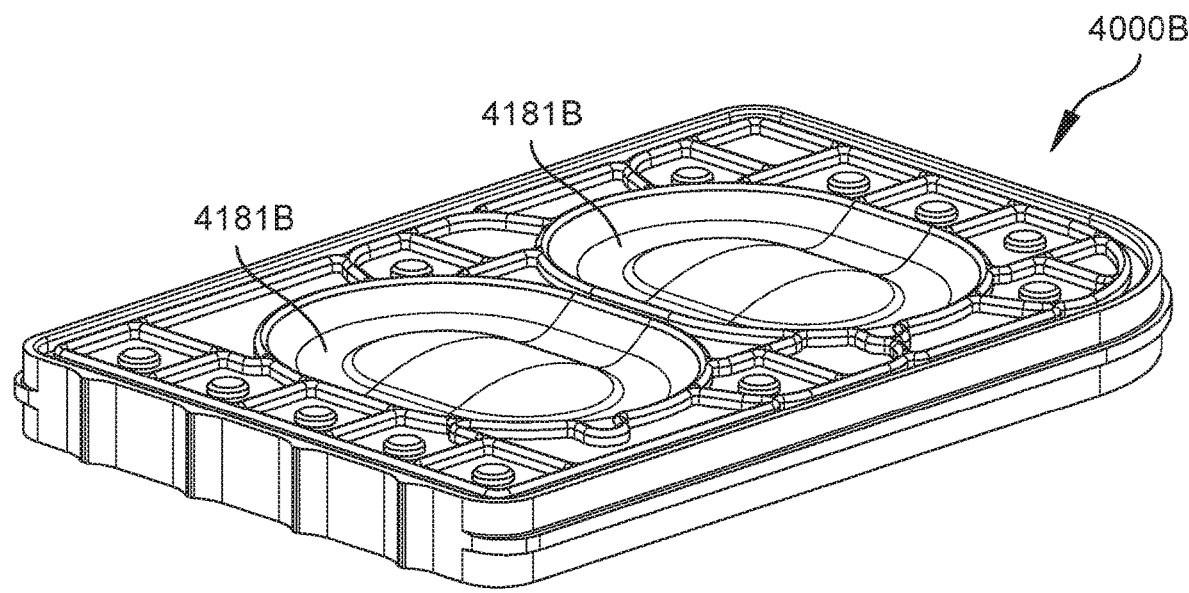
FIG. 65A depicts a perspective view of another example volumetric standard cassette.
Figure 65B:
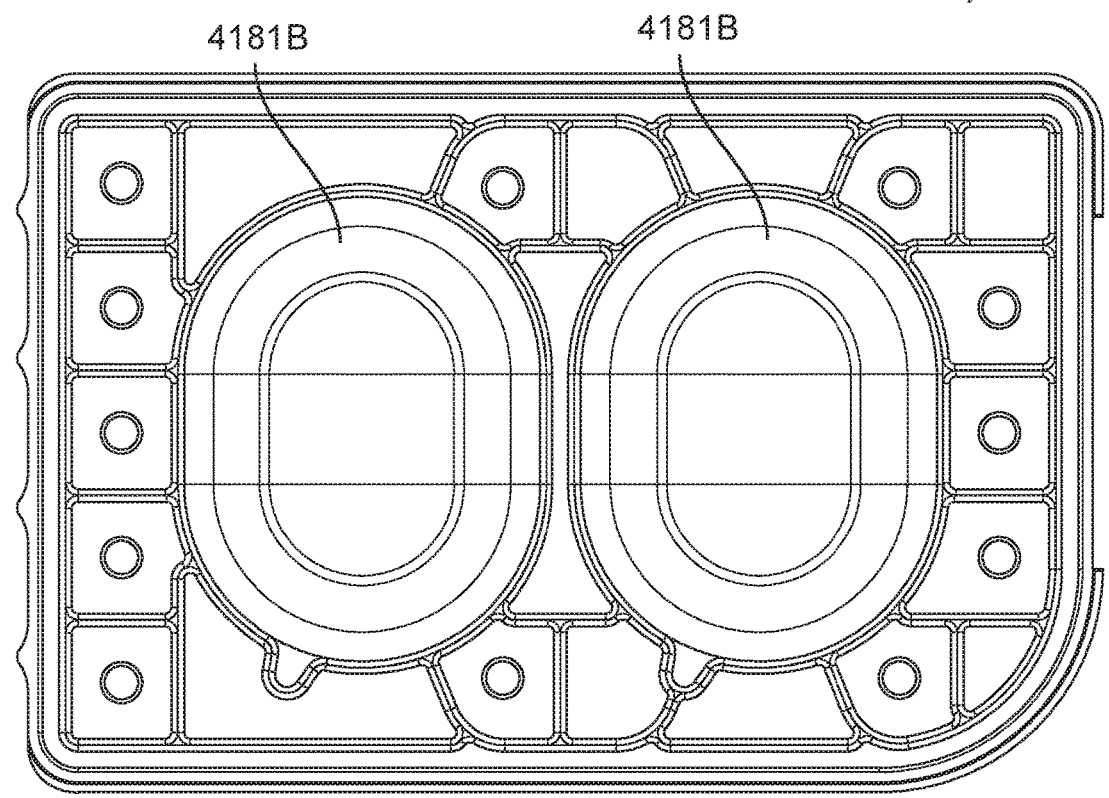
FIG. 65B depicts a top down view of the volumetric standard cassette shown in FIG. 65A.
Figure 66A:
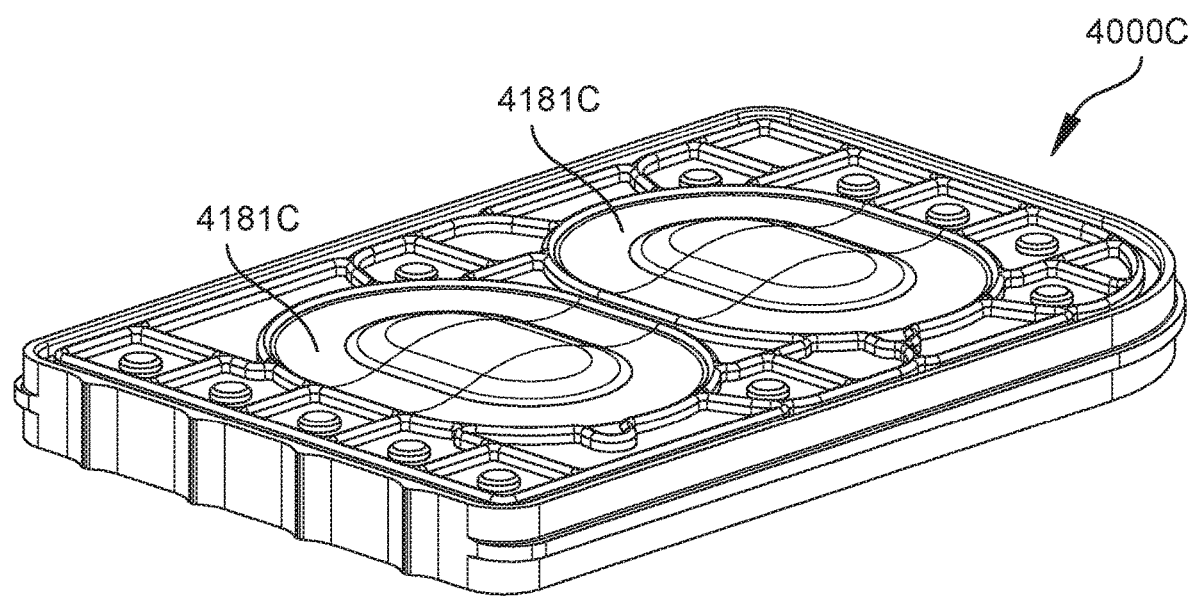
FIG. 66A depicts a perspective view of another example volumetric standard cassette.
Figure 66B:
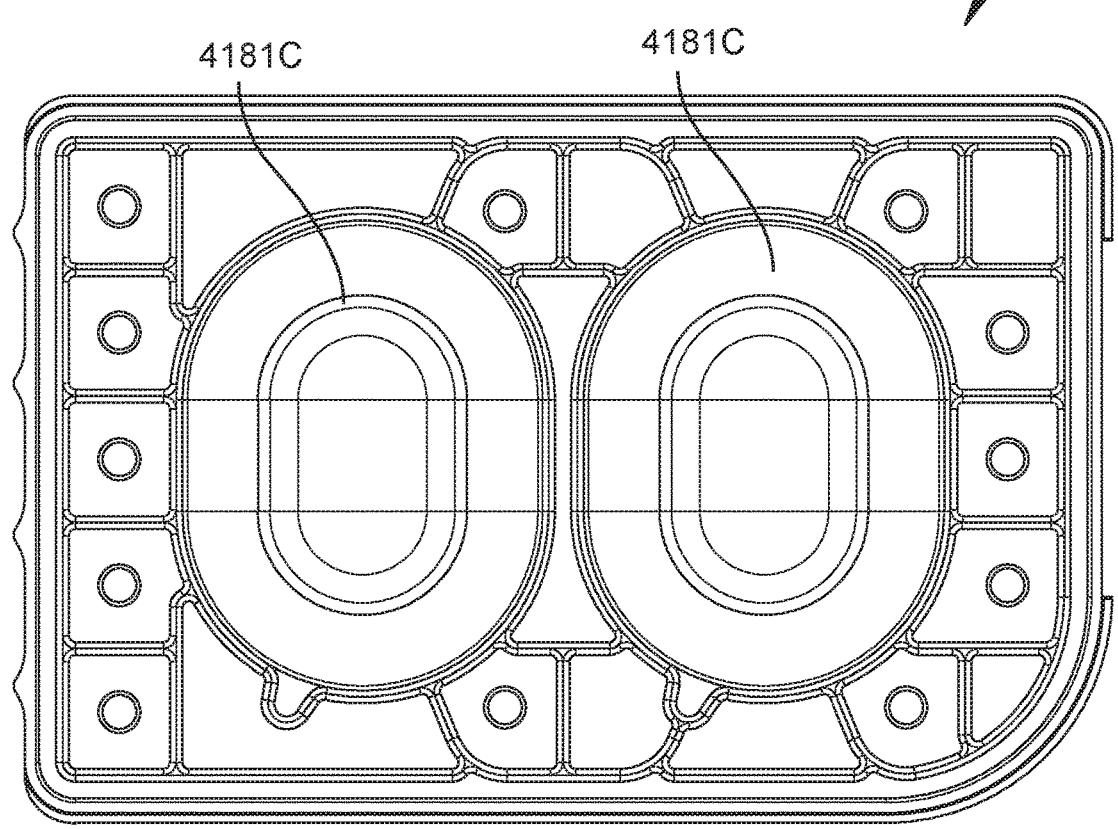
FIG. 66B depicts a top down view of the volumetric standard cassette shown in FIG. 66A.

In contrast, FIGS. 64A-64C depict various views of an example volumetric or standard calibration cassette 4000A. This volumetric calibration cassette 4000A and others described herein may be used to calibrate a cycler 14 for operation with disposable cassettes 24 similar to that shown in FIGS. 63A-63C as well as those shown elsewhere herein (e.g. the disposable cassette 24 with spikes 160 shown in FIG. 6). A top down view of an example volumetric calibration cassette 4000A is shown in FIG. 64A. The volumetric calibration cassette 4000A may have an equivalent or nearly equivalent overall footprint to the disposable cassette 24. No sheeting 15 may be included on volumetric calibration cassettes such as volumetric calibration cassette 4000A. As shown in FIG. 64B (a cross-section taken at line 64B-64B of FIG. 64A), the volumetric calibration cassette 4000A may be devoid of flow paths, orifices, valve ports, pass throughs in the mid-body 4044, etc. Instead, the volumetric calibration cassette 4000A may include a solid mid-body 4044. The mid-body 4044 may be thicker than that of the disposable cassette 24. For example, the mid-body 4044 may be at least twice as thick, or between 2 and 3 times as thick as the mid-body 44 of a disposable cassette 24 (see, e.g., FIG. 63B). The example mid-body 4044 extends over the majority (about ⅔) of the thickness of the volumetric calibration cassette 4000A. The thickness of the midbody 4044 may be between ½ and ¾ the thickness of the thickest portion of the volumetric calibration cassette 4000A in various embodiments.

The example volumetric calibration cassette 4000A (and others described herein) includes walls 4046 at the same locations as those of the disposable cassette 24. These walls may extend away from the mid-body 4044 to the same point as in a disposable cassette 24. In some embodiments, the side of a volumetric standard cassette opposite the pump chambers may be devoid of walls and substantially flat. The walls may act as sealing walls or ribs which press against portions of the control gasket 148 when the volumetric calibration cassette 4000A is installed in a cycler 14. The walls may thus ensure that the control chambers 171 of the cycler 14 are isolated from communication with other regions of the control gasket 148 after a volumetric calibration cassette 4000A is installed within the cycler 14.

The exemplary volumetric calibration cassette 4000A also includes projections 4048. These projections 4048 are disposed at the locations of the valve ports 186 of the disposable cassette 24 and extend to the same height as valve ports 186 on the disposable cassette 24. The projections 4048 are solid and include no orifice. In alternative embodiments, an orifice may be included. Each of the projections may be completely surrounded by walls extending from the mid-body 4044.

In the example, the walls and projections are shorter in height measured from the surface of the midbody 4044 due to the enlarged mid-body 4044. In some embodiments, the walls and/or projections 4048 may extend to a point slightly above the respective end points of the walls or valve ports 186 in a disposable cassette 24. For example, the walls and/or projections may extend an additional distance equivalent to (or nearly the same as, but perhaps slightly greater than) the thickness of the membrane 15 of the disposable cassette 24. This may help to make a volumetric calibration cassette 4000A a closer analog to a disposable cassette 24 when installed in the cycler 14 for a calibration procedure.

The walls may have a height sufficient to prevent the gasket 148 (see, e.g., FIG. 33A-C) from contacting the mid-body 4044 when a volumetric calibration cassette 4000A is installed in the cycler 14.

Additionally, any drafts present on the disposable cassette 24 to facilitate molding may be removed in a volumetric calibration cassette 4000A particularly if the volumetric calibration cassette 4000A is machined. Likewise certain curvatures, such as radii on the walls or rim of the volumetric calibration cassette 4000A, may be removed or made tighter to facilitate ease of machining. In some embodiments, the projections 4048 may be omitted as well. As the example volumetric calibration cassette 4000A does not include sheeting 15 (i.e. is open faced), the rim 48 present on the disposable cassette 24 may be of uniform height with the walls 4046 of the calibration cassette 4000A. Additionally, the inlet/outlet ports 150, 152, 154, 155 may be removed. As best shown in FIG. 64C, instead of spacers 50 (see, e.g., FIG. 63C), the pump chamber regions 4181A of the volumetric calibration cassette 4000A may be solid. Other volumetric calibration cassettes described herein may be of similar construction. Though the volumetric calibration cassettes shown herein are depicted as solid, certain embodiments may be hollow or have hollow regions.

Figure 67A:
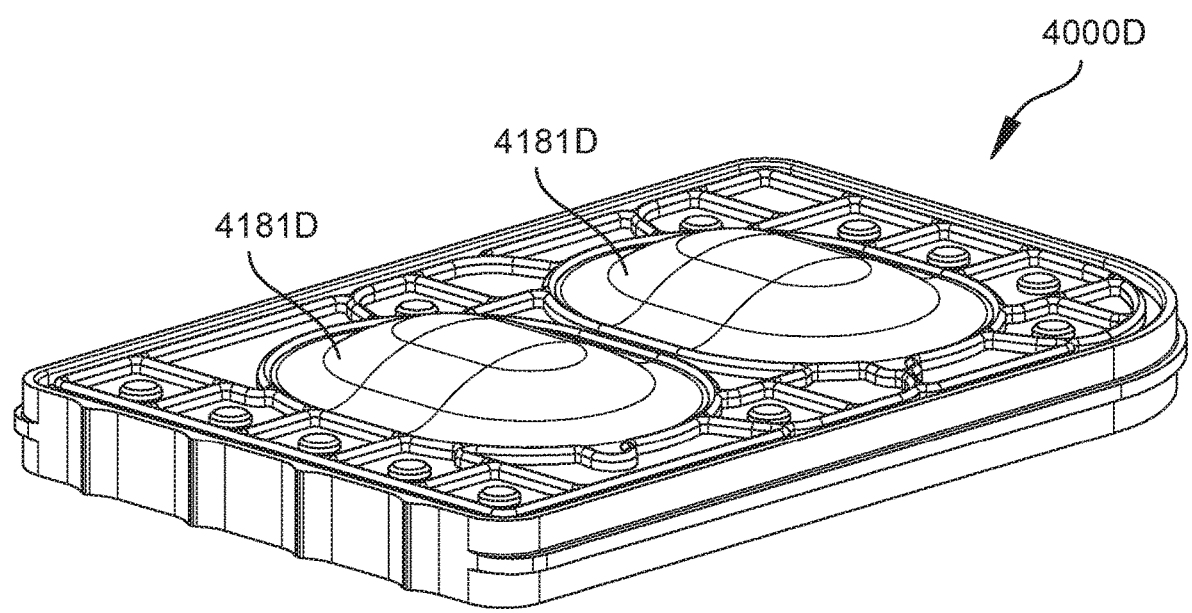
FIG. 67A depicts a perspective view of another example volumetric standard cassette.
Figure 67B:
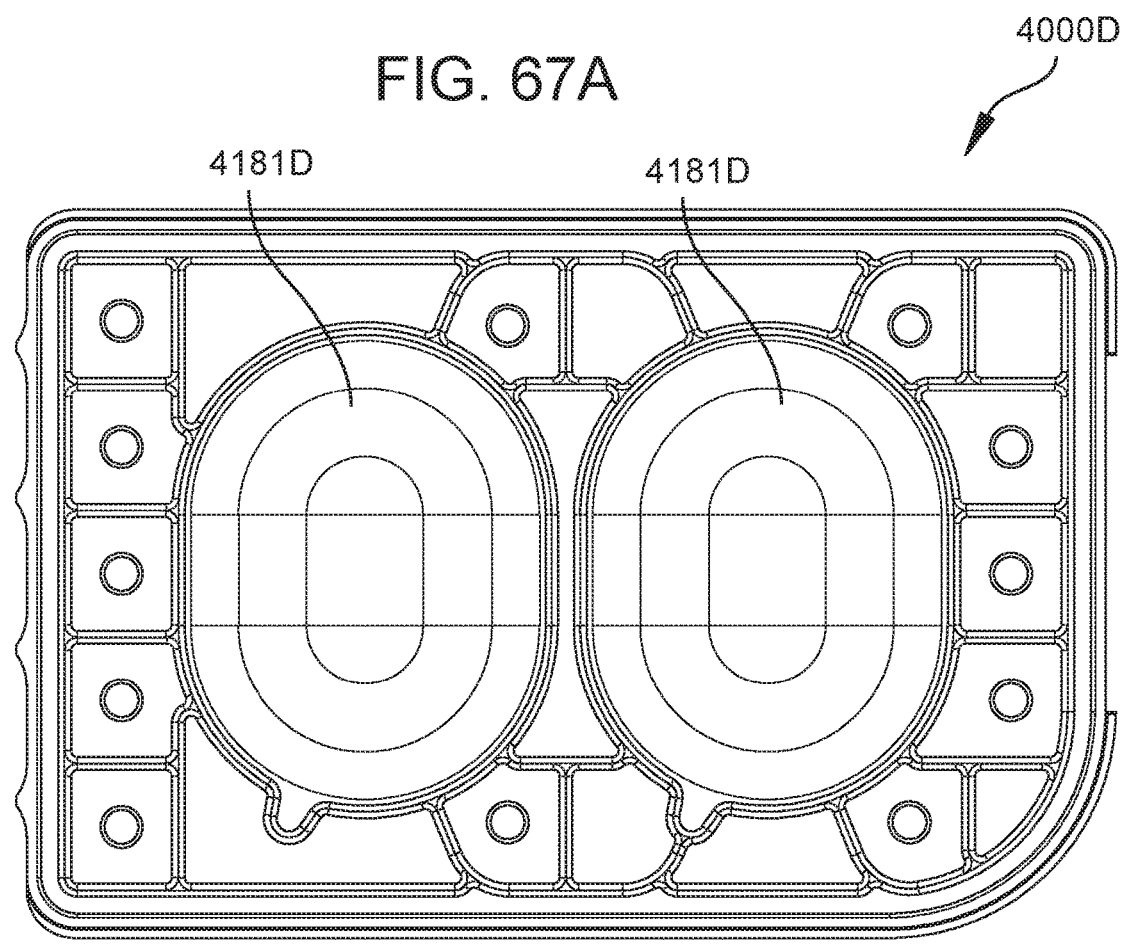
FIG. 67B depicts a top down view of the volumetric standard cassette shown in FIG. 67A.

Referring now also to FIGS. 64D-67B, a number of example volumetric calibration cassettes 4000A-D are depicted. The volumetric calibration cassette 4000A shown in FIGS. 64A-64D is constructed such that its pump chamber regions 4181A are shaped to mimic a fully delivered state in an ideal disposable cassette. FIGS. 65A-65B depict another volumetric calibration cassette 4000B which is structured to have its pump chamber regions 4181B mimic partially filled disposable cassette 24 pump chambers 181. The pump chamber regions 4181B of the example volumetric calibration cassette 4000B in FIG. 65A-65B each have a geometry representative of a 5.625 ml fill volume in an ideal disposable cassette 24. Another volumetric calibration cassette 4000C is depicted in FIGS. 66A-66B. This volumetric calibration cassette 4000C is shaped again to have its pump chamber regions 4181C mimic partially filled disposable cassette 24 pump chambers 181. Each of the pump chamber regions 4181C of the volumetric calibration cassette 4000 in FIGS. 66A-66B has a geometry representative of an 11.250 ml fill volume in an ideal disposable cassette 24. FIGS. 67A-67B depict a further volumetric calibration cassette 4000D example with its pump chamber regions 4181D mimicking partially filled disposable cassette 24 pump chambers 181. Each pump chamber region 4181D has a geometry representative of a 16.875 ml fill volume in an ideal disposable cassette 24.

Figure 68A:
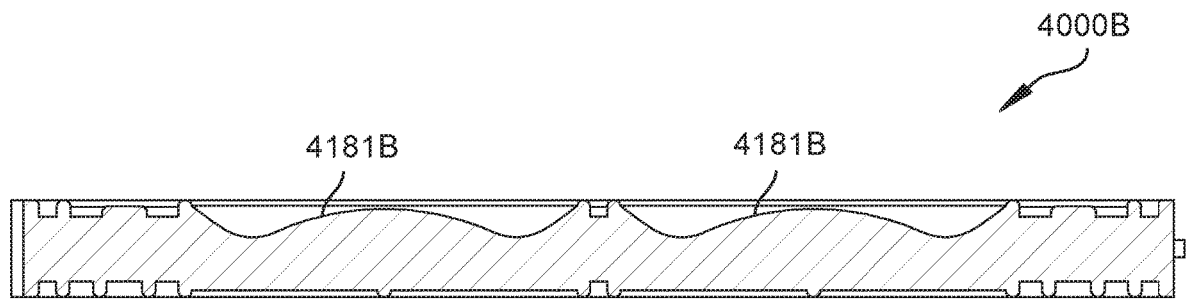
FIG. 68A depicts a cross-sectional view of the example volumetric standard cassette depicted in FIG. 65A.
Figure 68B:
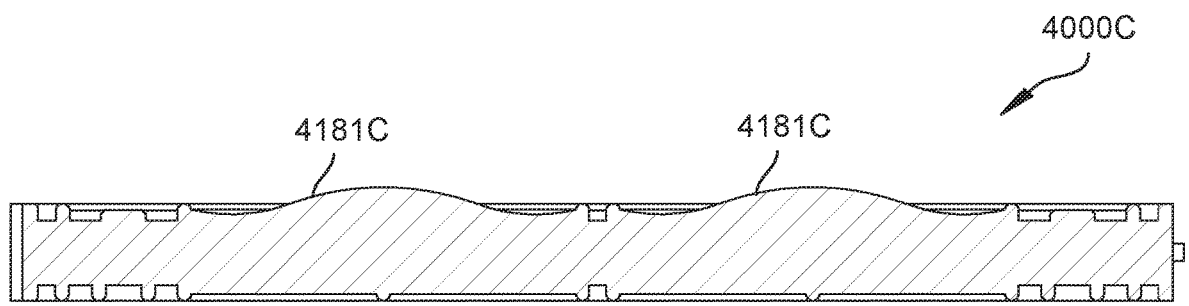
FIG. 68B depicts a cross-sectional view of the example volumetric standard cassette depicted in FIG. 66A.
Figure 68C:
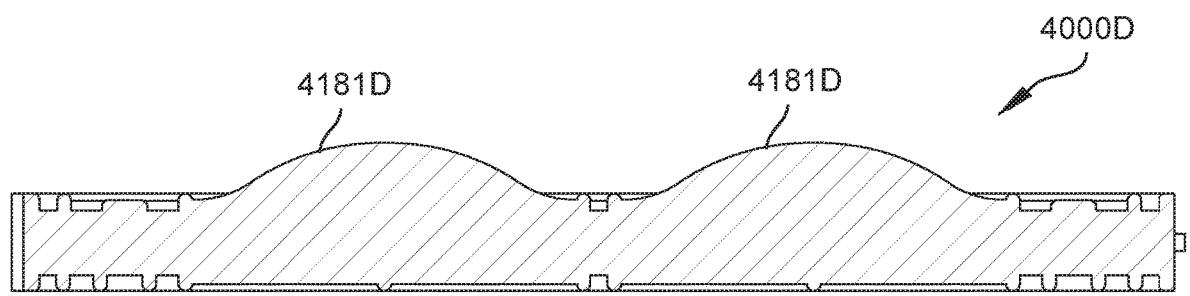
FIG. 68C depicts a cross-sectional view of the example volumetric standard cassette depicted in FIG. 67A.

Cross-sectional views of the volumetric calibration cassettes 4000B-D (all taken at the location of cut plane 64C-64C in FIG. 64A) are shown in FIGS. 68A-68C. As shown, the pump chamber regions 4181B-D of the volumetric calibration cassettes 4000B-D may be contoured to mimic the curvature of a membrane 15 in a disposable cassette 24 as a pump stroke occurs. This may help to ensure that the control gasket 148 is able to seat flushly against the volumetric calibration cassettes 4000B-D when control chamber 171 volume measurements are being taken. In other embodiments, the contours of the pump chamber regions 4181B-D may be constructed with sharper features. That is, curvature may be smaller in radius and the pump chamber regions 4181A-D may have portions which are plateaued, flat, or nearly flat. Preferably, volumetric calibration cassettes 4000B-D should be constructed such that their pump chamber regions 4181B-D are free from any undercut features. Some volumetric calibration cassettes may, however, have portions in their pump chamber regions which are perpendicular to the mid-body 4044 or nearly perpendicular to the mid-body 4044.

Figure 69A:
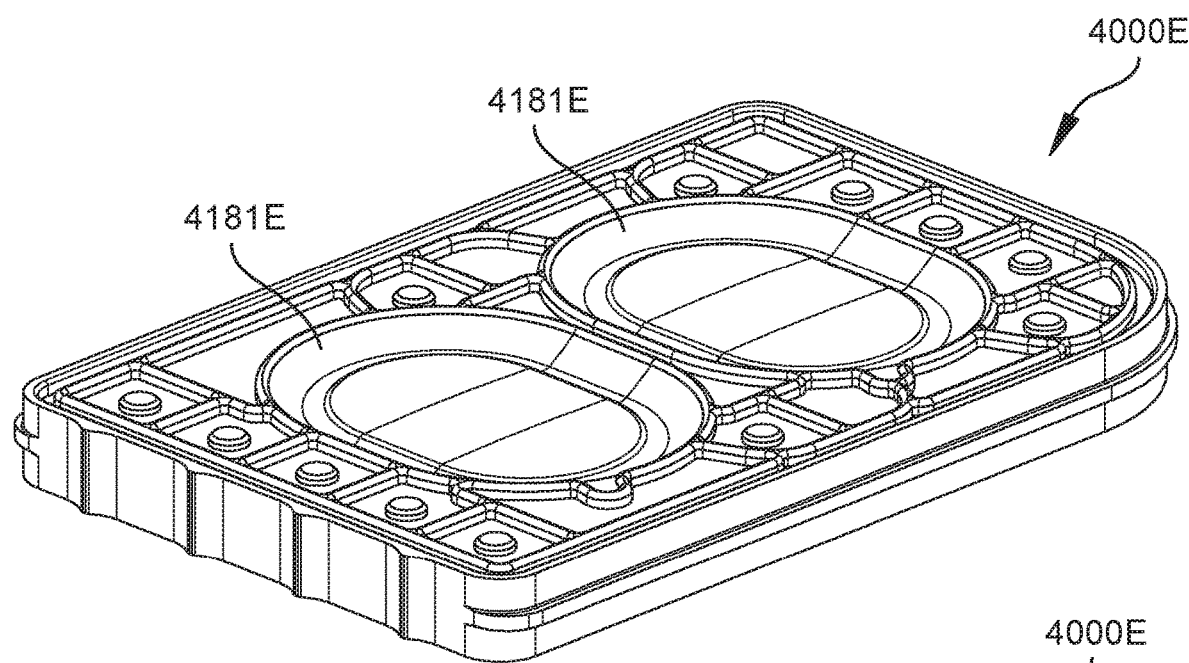
FIG. 69A depicts a perspective view of another example volumetric standard cassette.
Figure 69B:
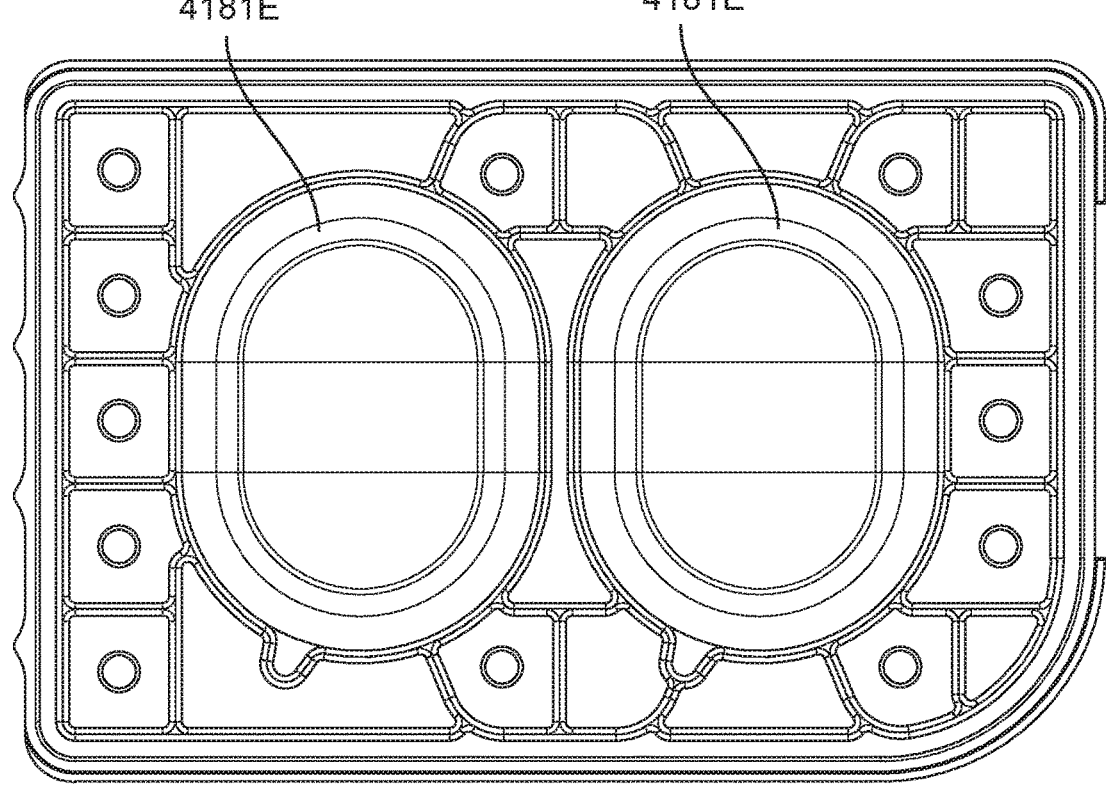
FIG. 69B depicts a top down view of the volumetric standard cassette shown in FIG. 69A.
Figure 70A:
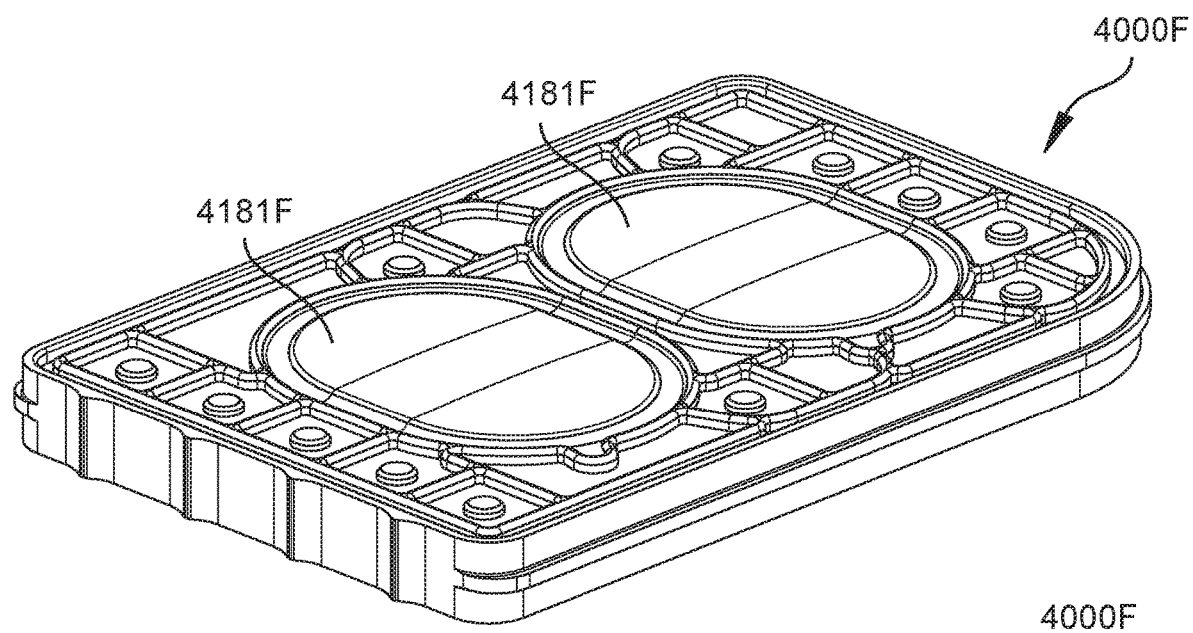
FIG. 70A depicts a perspective view of another example volumetric standard cassette.
Figure 70B:
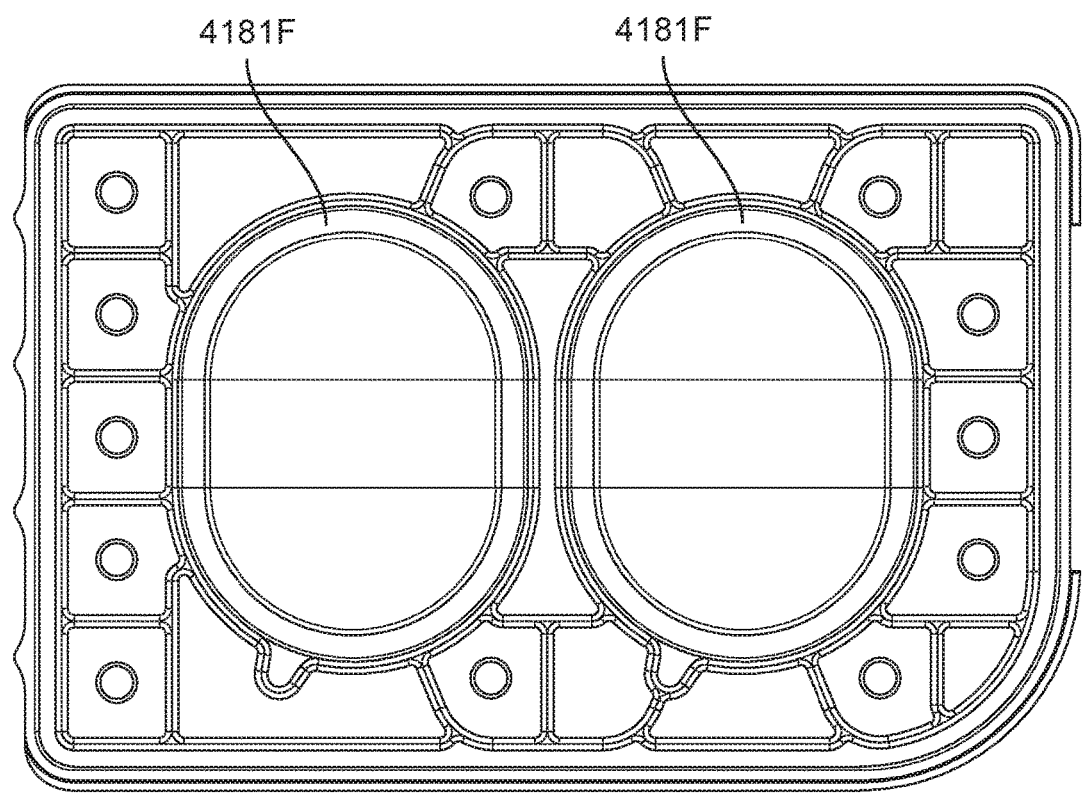
FIG. 70B depicts a top down view of the volumetric standard cassette shown in FIG. 70A.
Figure 71A:
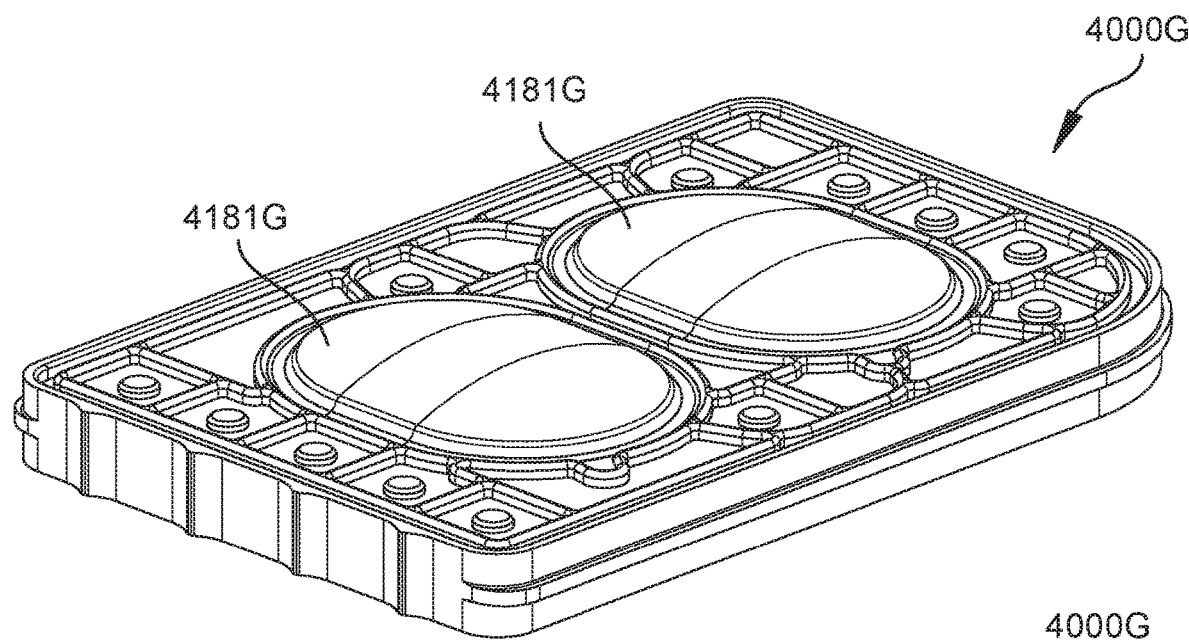
FIG. 71A depicts a perspective view of another example volumetric standard cassette.
Figure 71B:
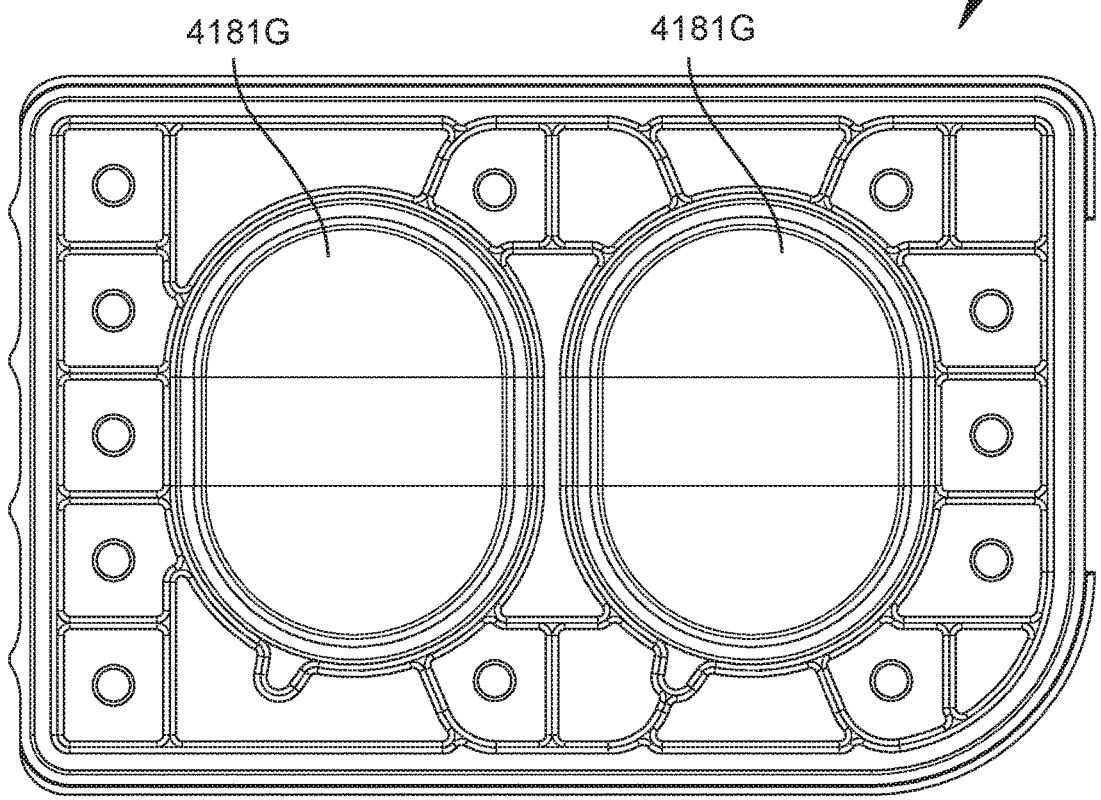
FIG. 71B depicts a top down view of the volumetric standard cassette shown in FIG. 71A.
Figure 72A:
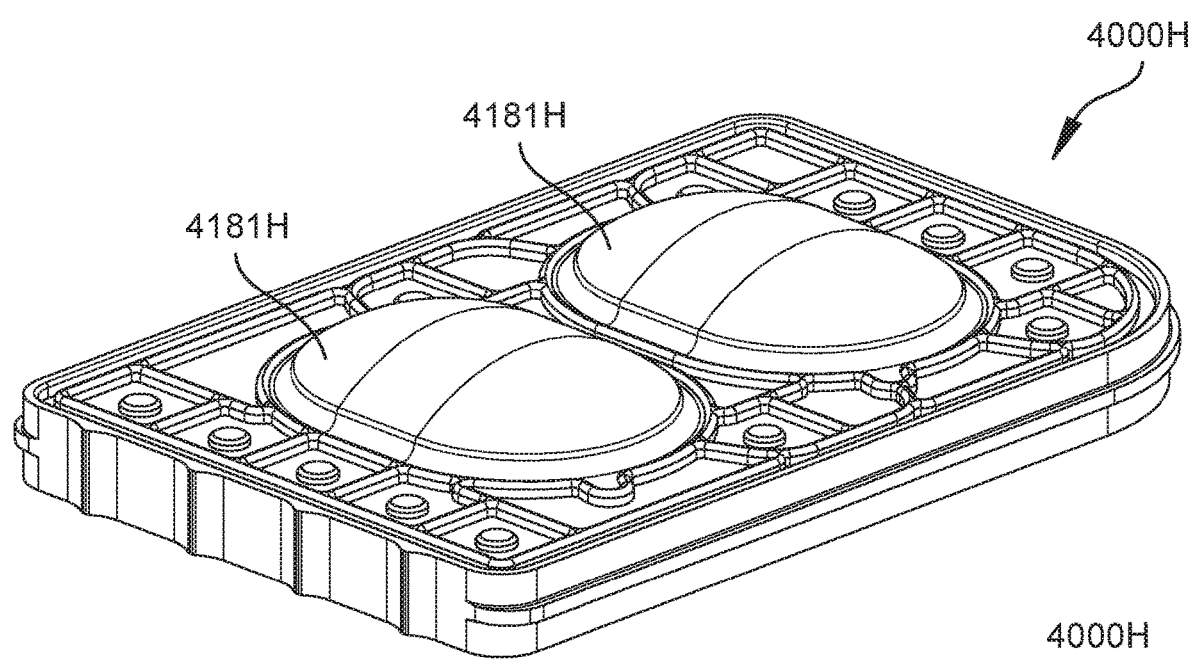
FIG. 72A depicts a perspective view of another example volumetric standard cassette.
Figure 72B:
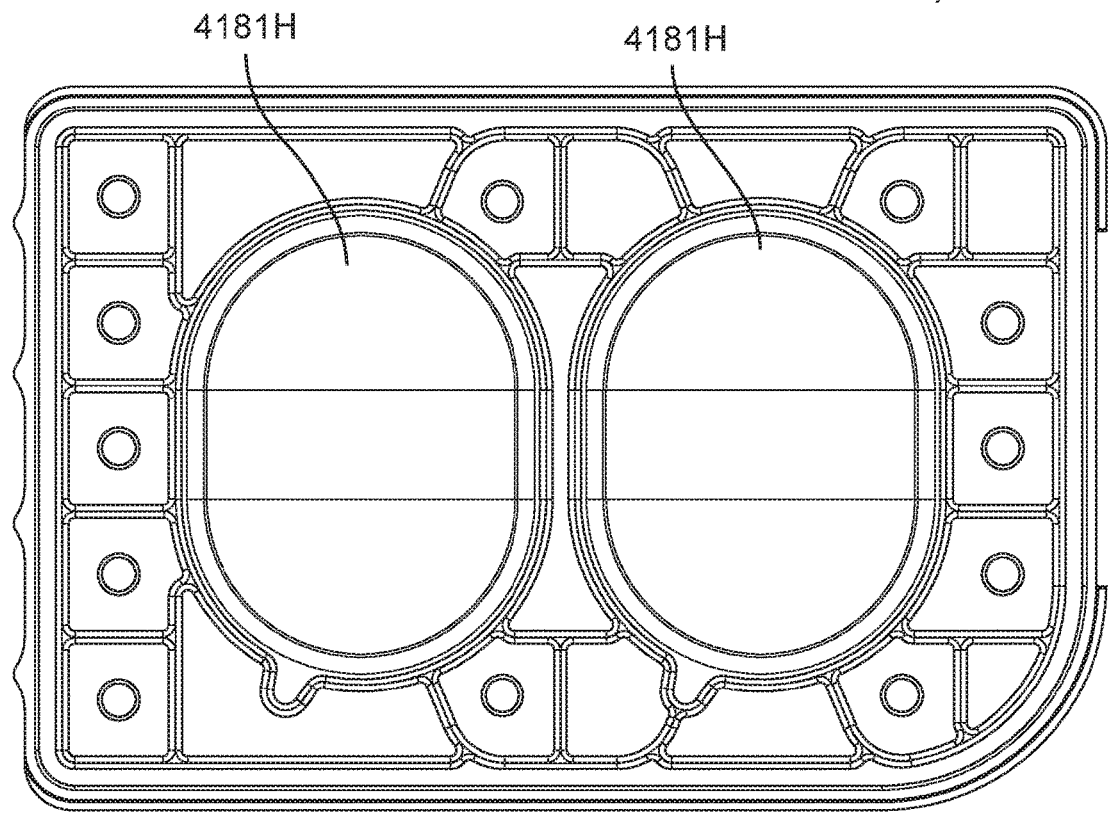
FIG. 72B depicts a top down view of the volumetric standard cassette shown in FIG. 72A.
Figure 73A:
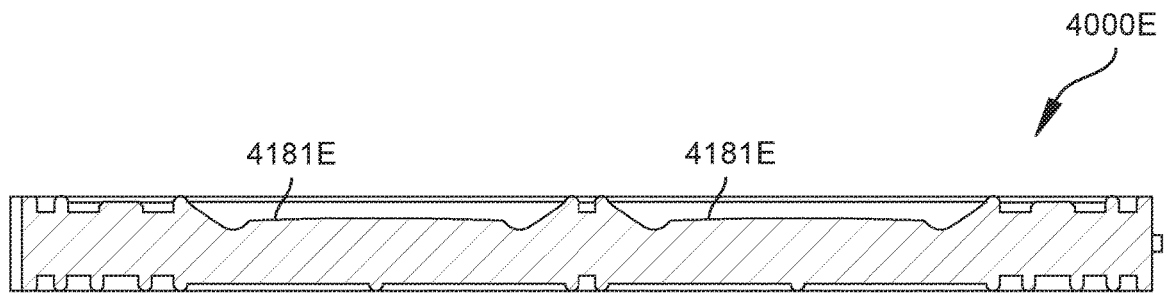
FIG. 73A depicts a cross-sectional view of the example volumetric standard cassette depicted in FIG. 69A.
Figure 73B:
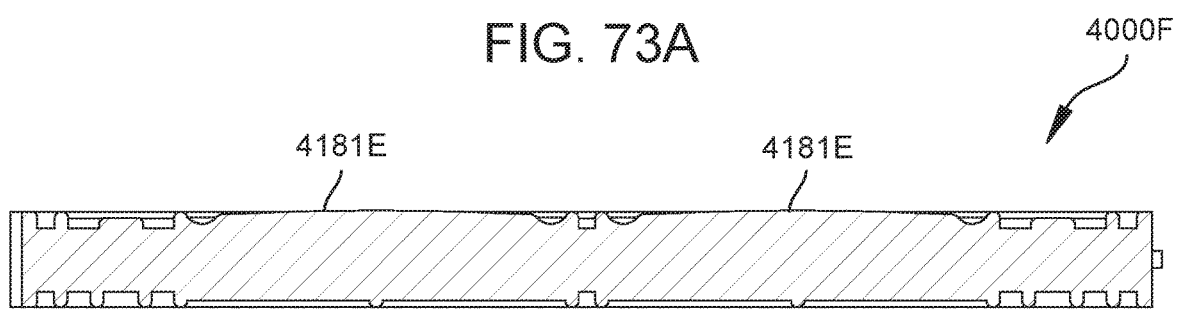
FIG. 73B depicts a cross-sectional view of the example volumetric standard cassette depicted in FIG. 70A.
Figure 73C:
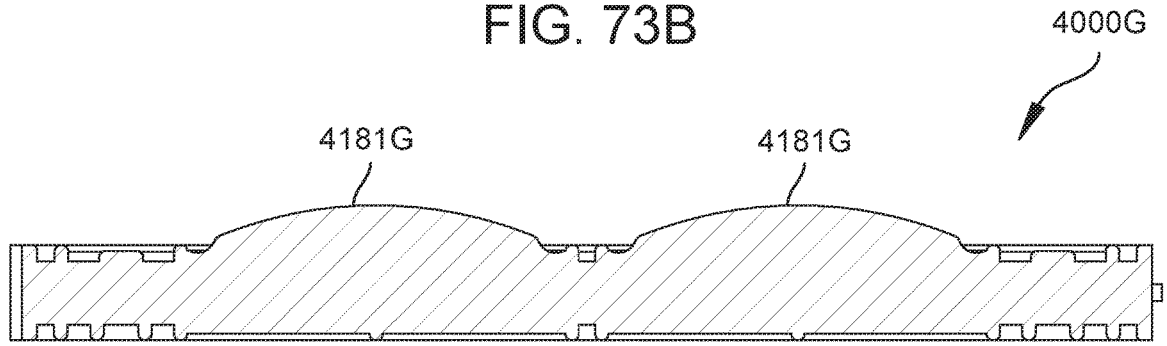
FIG. 73C depicts a cross-sectional view of the example volumetric standard cassette depicted in FIG. 71A.
Figure 73D:
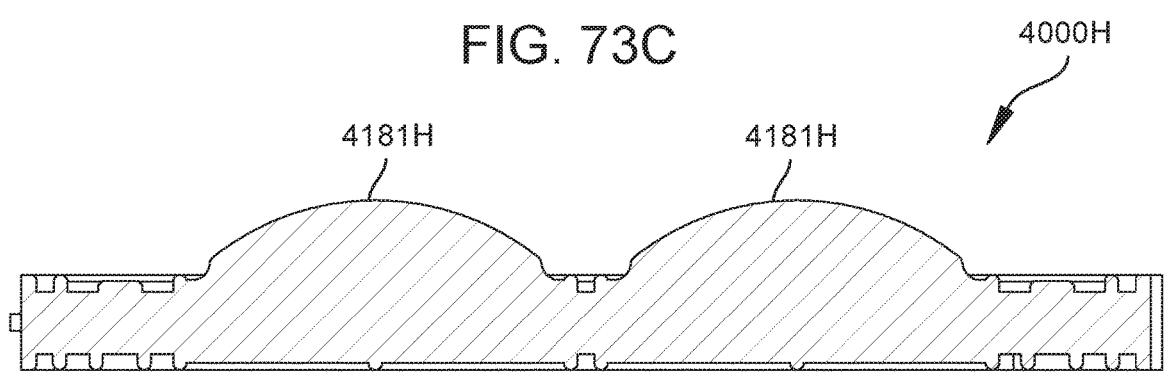
FIG. 73D depicts a cross-sectional view of the example volumetric standard cassette depicted in FIG. 72A.

Referring now also to FIGS. 69A-69B, a number of example volumetric calibration cassettes 4000E-H are depicted. These volumetric calibration cassettes 4000E-H include pump chamber control regions 4181E-H which have sharper features as well as some plateaued regions. FIGS. 69A-69B depict a volumetric calibration cassette 4000E which is structured to have its pump chamber regions 4181E each have a geometry representative of a 5.625 mL fill volume. The volumetric calibration cassette 4000F depicted in FIGS. 70A-70B is constructed such that each of its pump chamber regions 4181F has a geometry representative of an 11.250 mL fill volume. FIGS. 71A-71B depict a further volumetric calibration cassette 4000G example with its pump chamber regions 4181G geometries being representative of a 16.875 mL fill volume. The example volumetric calibration cassette 4000H in FIGS. 72A-72B has pump chamber regions 4181H each shaped so as to be representative of a full pump chamber volume (22.5 ml) in a disposable cassette 24. Cross-sectional views of the volumetric calibration cassettes 4000B-D (all taken at the location of cut plane 64C-64C in FIG. 64A) are shown in FIGS. 73A-73D.

The fidelity of the pump chamber regions 4181A-H to the actual geometry of the sheeting 15 assumed by a disposable set 24 when filled with a given volume may be more important depending on the type of volume measurement being performed. Where a positive FMS and a negative FMS may be performed (described above) closer fidelity may be desirable. In certain examples, the geometry of the sheeting 15 may be determined or approximated by pumping an epoxy or the like (e.g. epoxy with fillers) through a disposable cassette and allowing the epoxy to cure when the pump chamber of the disposable cassette is in a desired fill or delivery state. Preferably the epoxy or other material used may demonstrate predictable or minimal volumetric shrinkage during curing.

Figure 74:
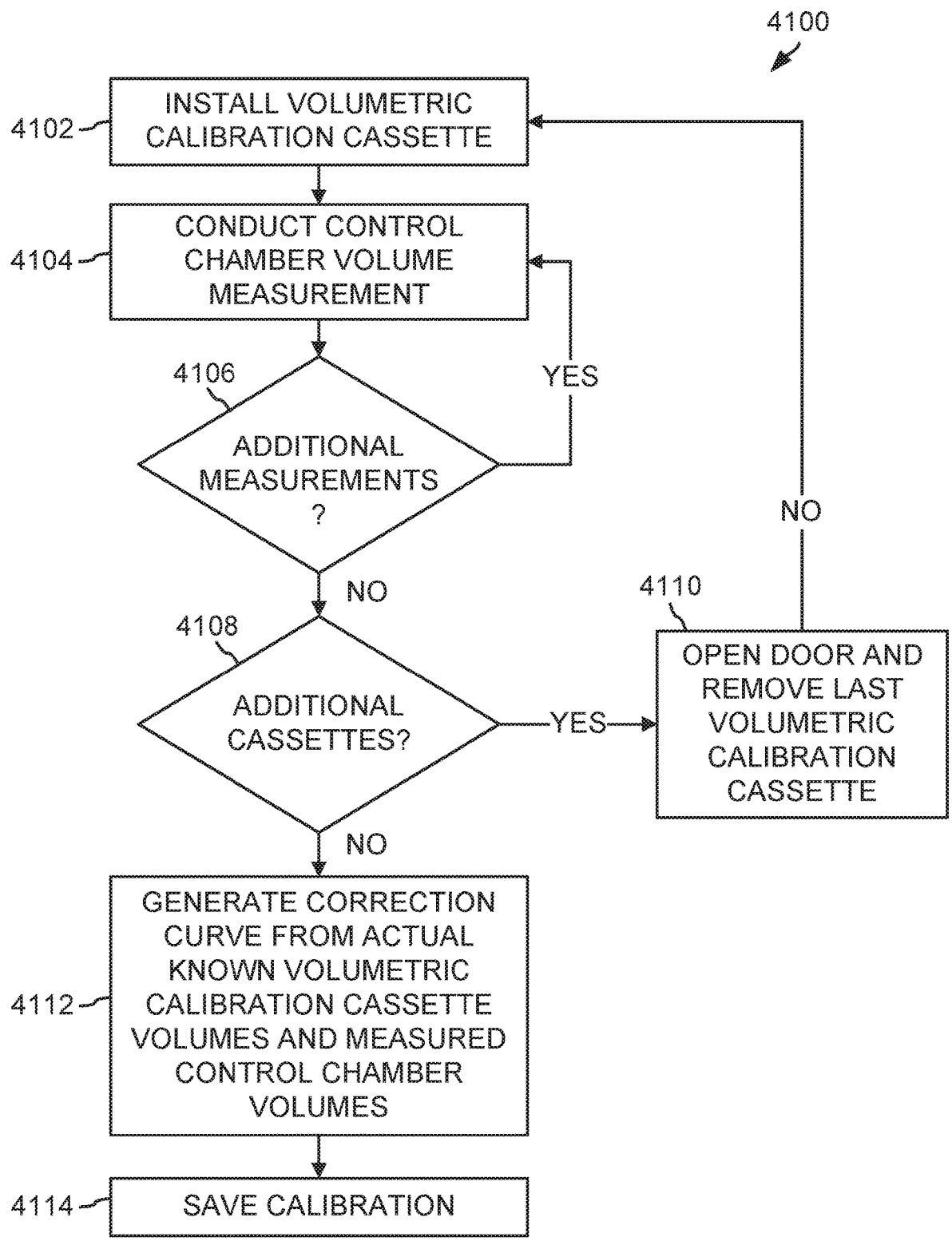
FIG. 74 depicts a flowchart detailing a number of example actions which may be executed to perform a calibration with one or more volumetric calibration cassette(s)

Referring now to FIG. 74, a flowchart 4100 detailing a number of example actions which may be executed to perform a calibration with at least one volumetric calibration cassette is depicted. As shown a volumetric standard or calibration cassette may be installed in a cycler 14 in block 4102. This may include locking of the door 141 and inflation of an air bladder in the door 141 (see, e.g. FIG. 31) behind the mounting location 145 (see, e.g. FIG. 31) to squeeze the volumetric calibration cassette between the mounting location 145 and the control surface 148 (see, e.g. FIG. 31). The volumetric standard cassette may be installed in the same mounting location 145 as a disposable pumping cassette 24 used in conducting a therapy. The mounting location 145 may thus be configured to accept both disposable pumping cassettes 24 and volumetric calibration cassettes. The fluid trap may also be subjected to a negative pressure in block 4102. The cycler 14 may measure the volume of the pump chamber region of the installed volumetric standard cassette in block 4104. The volume measurement of the pump chamber region of the volumetric standard cassette may be indirect via a control chamber volume measurement, for example. To do this, the cycler 14 may conduct an FMS measurement as previously described. If, in block 4106, there are additional measurements to be made using that volumetric calibration cassette, the cycler 14 may return to block 4104. Typically, the cycler 14 may conduct a number of FMS measurements for each control chamber 171. The cycler 14 may conduct a number of FMS measurements as if conducting a volume measurement (e.g. an FMS measurement as described elsewhere herein) after completing or completing part of a fill stroke. The cycler 14 may conduct a number of FMS measurements as if conducting an FMS measurement after completing or completing part of a deliver stroke. Additionally, the cycler 14 may perform a number of measurements using a positive FMS and a number of measurements using a negative FMS. These processes are described in greater detail above. Any measurements taken may be individually taken from each of the control chambers 171 of the cycler 14. Additionally, measurements may be taken for different fill and delivery pumping pressure pairs utilized by the cycler 14. For instance, a cycler 14 may use a relatively low negative pressure followed by a high delivery pressure when pumping fluid from a patient to a drain destination to help increase patient comfort. When pumping from a source solution bag to a heater bag a high fill and delivery pressure may be used to speed fluid transfer. Such pumping pressure pairs are described in greater detail elsewhere herein.

Once all measurements have been taken for a particular volumetric standard or calibration cassette, other volumetric calibration cassettes may be installed so as to more accurately build a correction curve. If, in block 4108, there are additional volumetric calibration cassettes, the door of the cycler 14 may be opened to remove the previous cassette in block 4110. Blocks 4102, 4104, 4106, may repeat until all volumetric calibration cassettes have been used to collect data. Depending on the embodiment, there may be less than ten cassettes (e.g. 4-5) though a greater number may be used (e.g. a dozen, two dozen, or more). In certain examples, volumetric calibration cassettes may be constructed in 1 mL increments from having substantially empty pump chambers to substantially full pump chambers. Alternatively, volumetric calibrations cassettes may be incremented by a percentage of the full pump chamber volume. Starting from empty, an additionally, 5% or 10% of the total fill volume may be added for each volumetric calibration cassette. Typically, the volumetric calibration cassettes used may include at least volumetric calibration cassettes which are representative disposable cassettes with fully delivered and fully filled pump chambers. A number (e.g. 2-3 or more) of volumetric calibration cassettes representative disposable cassettes whose pump chambers are partially filled to different amounts may also be used. In some embodiments, volumetric calibration cassettes having volumes which are outside the pump stroke volume range of a disposable pumping cassette 24 may also be used. For example, a volumetric standard cassette having a pump chamber volume representative of a greater than empty condition may be used. Such a volumetric standard cassette may, for example, be designed to generate a control chamber volume around 110-150% (e.g. 125%) of the expected volume for a volumetric standard cassette representative of an empty disposable cassette 24 pumping chamber 181. Use of such volumetric calibration cassettes may help ensure that the derivative of any correction curve built does not rapidly increase or decrease outside of the bounds of the normal pumping range of disposable pumping cassette 24.

Once, in block 4108, no additional volumetric calibration cassettes are present, one or more correction curve may be generated in block 4112. This correction curve may serve as a cycler specific calibration equation which corrects for volumetric measurement error which may be unique to that cycler. As a set of standardized volumetric calibration cassettes are used, this cycler specific correction curve may correct for volumetric measurement error attributable to the cycler itself. No contribution due to variability of disposable cassettes may be introduced. Where correction curves are generated for positive and negative FMS, two correction curves may be generated in block 4112. Correction curves may also be generated for deliver stroke related measurements and fill stroke related measurements. Correction curves may be generated for each pumping pressure pair used by the cycler. Additionally, any correction curves may be generated for each individual control chamber. The correction curves may be generated based on the relevant measured control chamber volumes taken by the cycler 14 and the known volumes which the pump chamber regions of the volumetric calibration cassettes represent. In some embodiments, if the correction is greater than a certain magnitude, the cycler 14 may be flagged for further inspection. Where multiple readings of a control chamber are taken from each volumetric calibration cassette for a specific set of conditions, these readings may be averaged together or otherwise analyzed to arrive at a single value. These single values may be used to generate the correction curve. A line or curve such as a best fit polynomial may be fitted (e.g. determined with a linear or nonlinear regression analysis such as a least squares regression) through the values included in the data set. In other embodiments, all collected measurements for each specific set of conditions may be fit with a line or curve (e.g. determined with a linear or nonlinear regression analysis such as a least squares regression). In some embodiments, the line or curve may be subjected to various constraints. For instance, a set of limits on the allowable derivative values of the line or curve at certain regions may be enforced. For example, regions of the line or curve directly outside of the collected data points from the volumetric standard cassettes may be subject to such constraint. The derivative values may be required to be within a predefined range. Such a constraint may be applied to regions of the line that are, e.g., 1-5 ml beyond the expected pump chamber 181 volumes of a disposable cassette 24 which the volumetric calibration cassettes have been modeled after. The zero crossing of the line or curve may be subjected to such constraints.

Prior to generating the single value from each set of measurements at each specific set of conditions or prior to generating the line or curve, the collected measurement readings may be analyzed to determine conformance to some predefined criteria. For example, the readings may be checked to ensure that they have an expected distribution such as normal distribution and an error may be generated if nonconformance is detected. In some examples, a standard deviation or other variability measure may be calculated for each set of measurements and compared to an allowable threshold. If in breach of the threshold an error may be triggered. Alternatively, if the data collected is determined to be objectionable, the cycler 14 may prompt a user to reinstall the volumetric standard or calibration cassette such that the data may be recollected. There may be a cap on the number of allowed recollection attempts before an error is triggered. The correction curve, however it is generated, may be stored in a memory of the cycler 14, in block 4114, as an equation or potentially a look up table.

Figure 75:
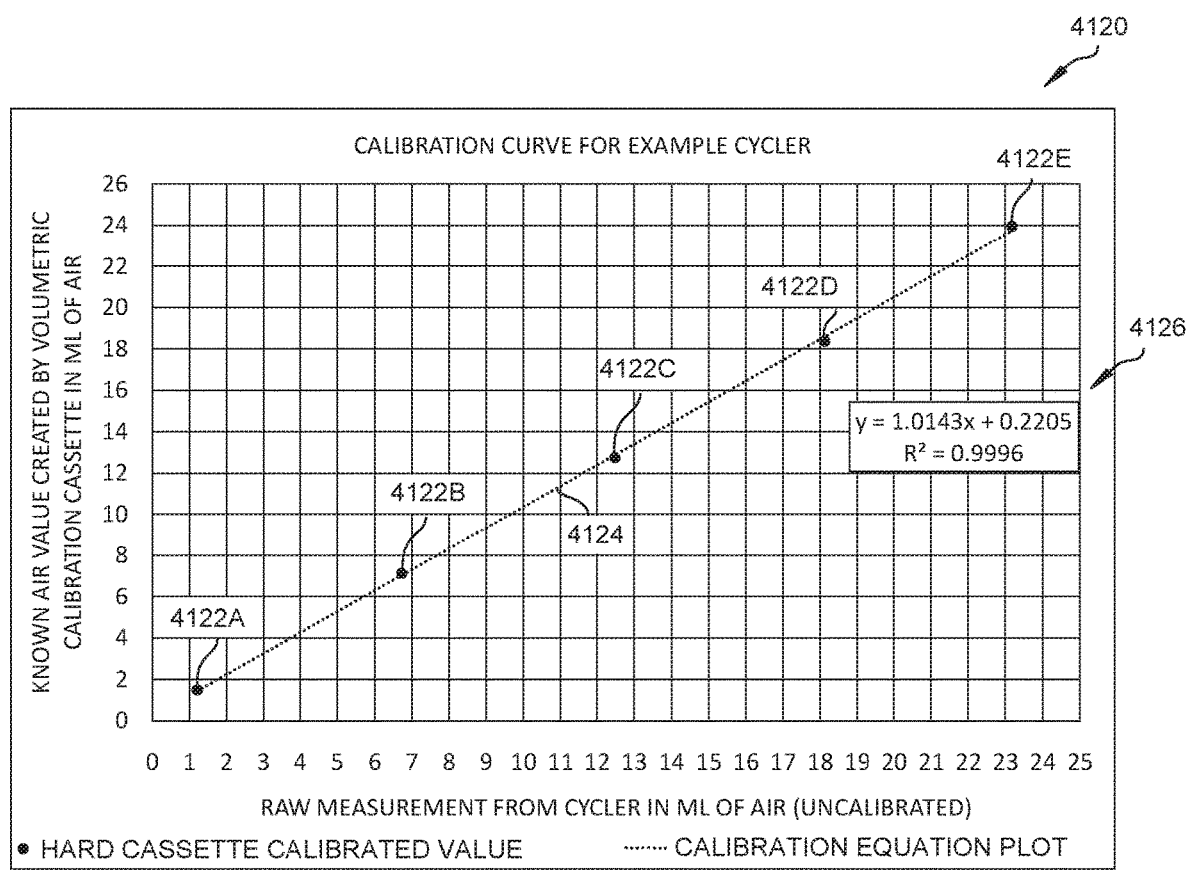
FIG. 75 depicts a graph showing an example calibration curve for a control chamber of a cycler.

Referring now to FIG. 75, a graph 4120 showing an example calibration curve for a control chamber of a cycler 14 is depicted. As shown, a number of points 4122A-E are plotted on the graph 4120. Each point 4122A-E is plotted to show the known air volume which should have been measured in a cycler control chamber by particular volumetric calibration cassette over raw control chamber volume as measured by the cycler for specific volumetric calibration cassettes. As shown, example data from five different exemplary volumetric calibration cassettes is included. Depending on the embodiment, a greater or lesser number of volumetric calibration cassettes may be used and the number of data points on the graph would reflect this. The raw value represented by each point 4122A-E is representative of an average of a number of measurements which would be taken for each particular volumetric calibration cassette. From this illustrational data, a linear regression analysis was performed to arrive at a calibration equation 4126. This equation is plotted as dotted line 4124. When a disposable cassette 24 is in use, a component of the control system of the cycler 16 (e.g. a processor or FPGA) may input raw measurement data into this equation to arrive at a closer determination of control chamber volume. This may increase accuracy of fluid transfer accounting by the control system 16 as the cycler 14 pumps fluid via a disposable cassette 24.

Figure 76:
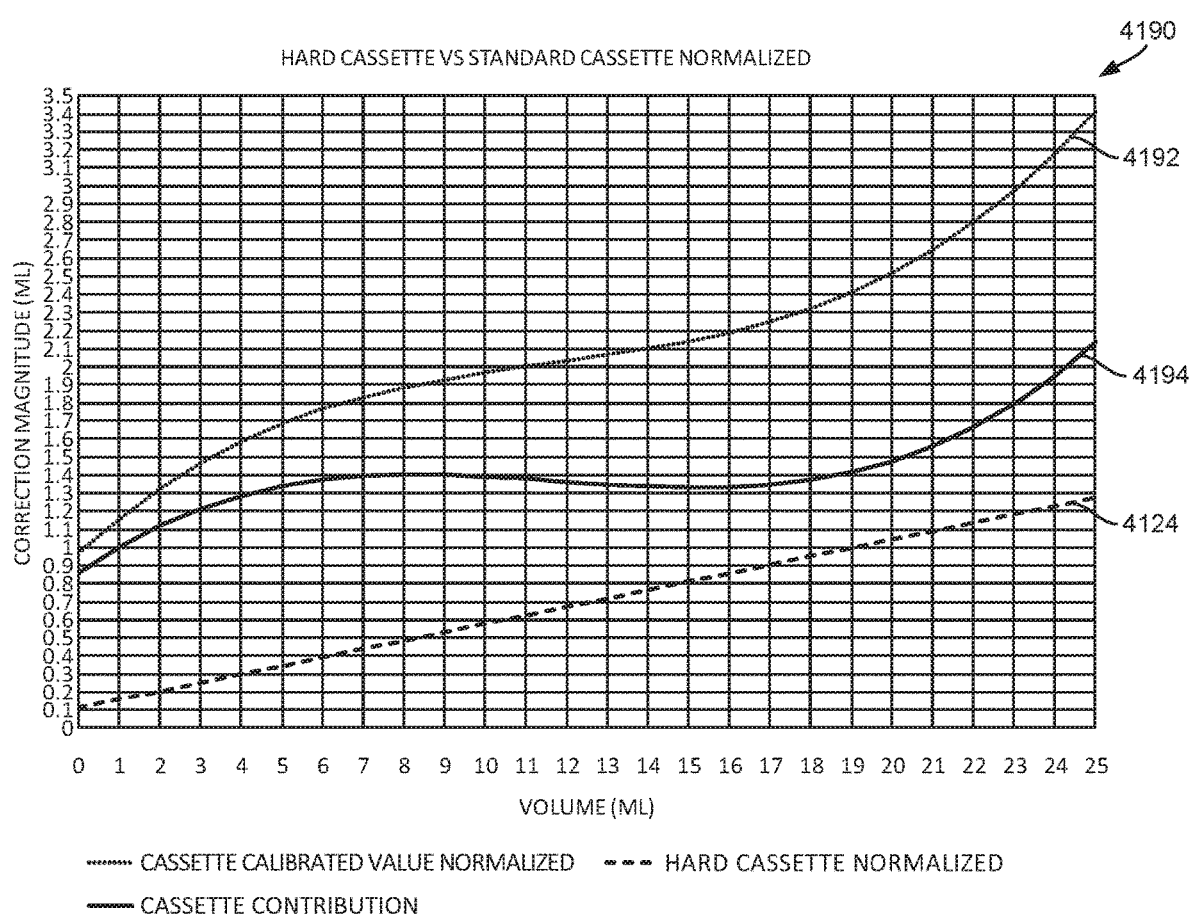
FIG. 76 depicts an illustrative graph showing a number of calibration curves which may be used by a cycler.

Referring now to FIG. 76, in some embodiments, once a cycler 14 has been calibrated, the calibration curves of the cycler 14 may be further modified. The calibration curve may, for example, be adjusted to a refined calibration curve based on data collected from a number of disposable cassettes 24 used in cyclers 14 which have been pre-calibrated with volumetric calibration cassettes. This may allow for aspects of the disposable cassettes 24 such as sheeting 15 to be accounted for in the final refined calibration curve which may help to further increase the precision of volumetric transfer measurements performed by the cycler 14. The refinement may be performed a single time in certain embodiments. Alternatively, the refinement to the calibration curve may be lot specific and may update each therapy when a new disposable cassette 24 is installed in the cycler 14. Thus, in either case, the final calibration curve used by the cycler 14 may be constructed from a cycler 14 specific correction and a disposable cassette 24 related correction.

FIG. 76 depicts an illustrative graph 4190 showing a number of calibration curves 4192, 4194, 4124 which may be used by a cycler 14. Specifically, a cycler 14 specific curve 4124, a disposable correction curve 4194, and a final correction curve 4192 are plotted. The final correction curve 4192 may be determined via the following equation in certain embodiments:

$V_{Final} = V_{cyclercorrected}(V_m) + V_{disposablecorrected}(V_m)$ where $V_{cyclercorrected}$ is the raw measured control chamber volume ($V_m$) corrected for the particular cycler's 14 error contribution and $V_{disposablecorrected}$ is the raw measured control chamber volume corrected for disposable related error contribution. As a result $V_{Final}$ is a refined calibration curve correcting for cycler 14 and disposable pumping cassette 24 related volumetric measurement error. Depending on the embodiment $V_{cyclercorrected}$ may be an equation such as $AV_m^3 + BV_m^2 + CV_m + D$ where $V_m$ is the raw control chamber measurement of the cycler and A, B, C, and D are coefficients determined to generate a best fit based on the calibration data. Again depending on the embodiment, $V_{disposablecorrected}$ may be an equation such as $EV_m^3 + FV_m^2 + GV_m + H$ where $V_m$ is the raw control chamber measurement of the cycler and E, F, G, and H are coefficients determined to generate a best fit based on the calibration data. Though both $V_{cyclercorrected}$ and $V_{disposablecorrected}$ are shown as third order equations above, these may be higher or lower order polynomials in other embodiments. In some embodiments, the polynomial chosen may be that which generates a highest $R^2$ value out of a selection of a linear equation up to, for example, fifth order best fit polynomial.

In other embodiments, the final correction curve may be determined differently. In some embodiments $V_{Final}$ may be equal to a compound function. A first function may be applied to the raw control chamber volume measurement ($V_m$). A second function may then be applied to this result to arrive at a determination for $V_{Final}$. For example, in some embodiments an equation such as:

$$V_{Final} = V_{disposablecorrected}(V_{cyclercorrected}(V_m)) \text{ may be used}$$

In such embodiments, the raw measured volume ($V_m$) may feed into a function which yields the corrected cycler volume measurement ($V_{cyclercorrected}$) similarly to as described above. In turn, $V_{cyclercorrected}$ may then feed into a function that corrects for disposable related error contribution to provide $V_{disposablecorrected}$ which may be equal to the final volume ($V_{Final}$). $V_{disposablecorrected}$ may be an equation such as $EV_{cyclercorrected}^3 + FV_{cyclercorrected}^2 + GV_{cyclercorrected} + H$ where E, F, G, and H again are coefficients determined to generate a best fit. As above, the use of a third order equation is exemplary and higher or lower order polynomials may be used in other embodiments.

Figure 77:
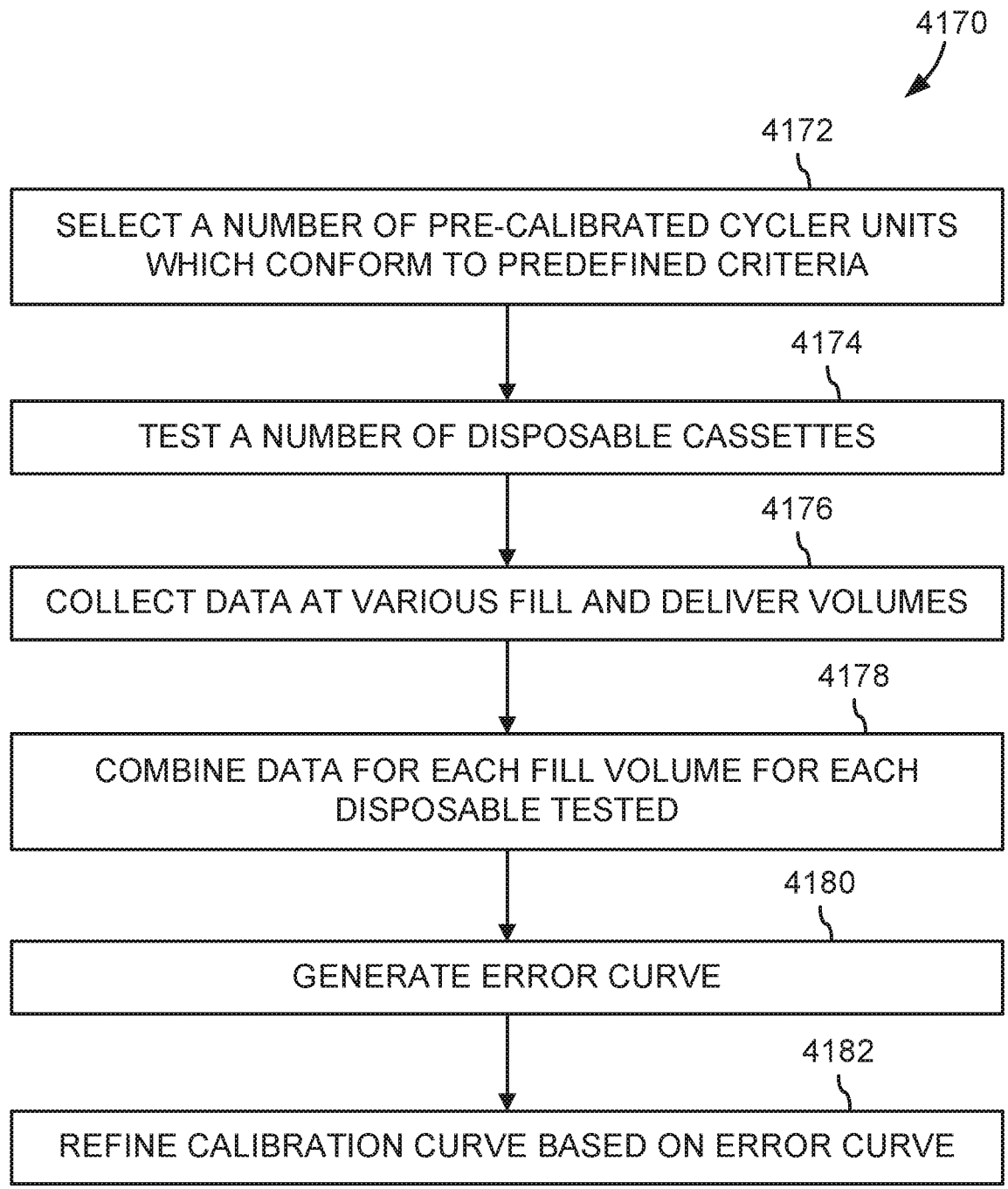
FIG. 77 depicts a flowchart depicting a number of example actions which may be used to refine a calibration curve for a cycler.

Referring now to FIG. 77, a flowchart 4170 depicting a number of example actions which may be used to refine a calibration curve for a cycler 14 are shown. In block 4172, a number of cyclers 14 which have been pre-calibrated with volumetric standard cassettes may be selected. The cyclers 14 selected may be chosen such that they conform to certain predefined criteria. For example, disposable cassettes 24 may be installed in the pre-calibrated cyclers 14 and data may be collected. This data may be screened to identify a group of cycler 14 which are operating with some predefined degree of measurement precision. A predefined variance criteria (such as an allowed standard deviation) may be imposed on the measurements of the cycler 14 for any particular set of test conditions such that all of the cyclers 14 are similar and representative of typical cycler 14 units.

In block 4174, a number of disposable pumping cassettes 24 may be tested using the cyclers 14 and data from the testing may be collected in block 4176. The disposable pumping cassettes 24 tested may be selected from a plurality of different manufacturing lots (e.g. ten or more). Additionally, a number (e.g. dozens) of disposable pumping cassettes 24 may be chosen from each of the lots. These disposable pumping cassettes 24 may be tested by commanding pumping of various volumes of fluid from a reservoir and comparing measurements from the cycler 14 collected during the transfer of these volumes to consequent weight deltas as determined by a scale monitoring the reservoir.

In block 4178, the data may be combined. This may be done in any number of ways. For example, all raw data points may be combined together. These data points may be in pairs including a transfer volume measured by the cycler 14 and a measured volume displaced from the reservoir (e.g. converted from the weight delta on the scale using density). Alternatively, data collected for a particular disposable pumping cassette 24 may be analyzed and the outputs of the analysis for each disposable pumping cassette 24 may be combined. For example, a correction curve for each disposable pumping cassette 24 may be generated from the raw data collected using that disposable pumping cassette 24 and each of these correction curves may be combined.

In block 4180, a correction curve may be generated using the combined data. This correction curve may be used to refine the calibration curve generated using volumetric standard cassettes for each cycler 14 in block 4182. Thus, a refined calibration curve which takes into account error peculiar to a particular cycler 14 and error attributable to aspects common to disposable pumping cassettes 24 may be created.

As mentioned elsewhere herein, a cycler 14 may operate using a number of different calibration curves. For example, the cycler 14 may use one of a set of delivery calibration curves when performing a delivery stroke. The particular delivery curve used may be determined based on the pumping pressures being employed for that delivery stroke. The same may be true of fill strokes. Each of these calibration curves may be modified based on data collected from disposable pumping cassettes 24 in the manner described above to create refined calibration curves.

Figure 78:
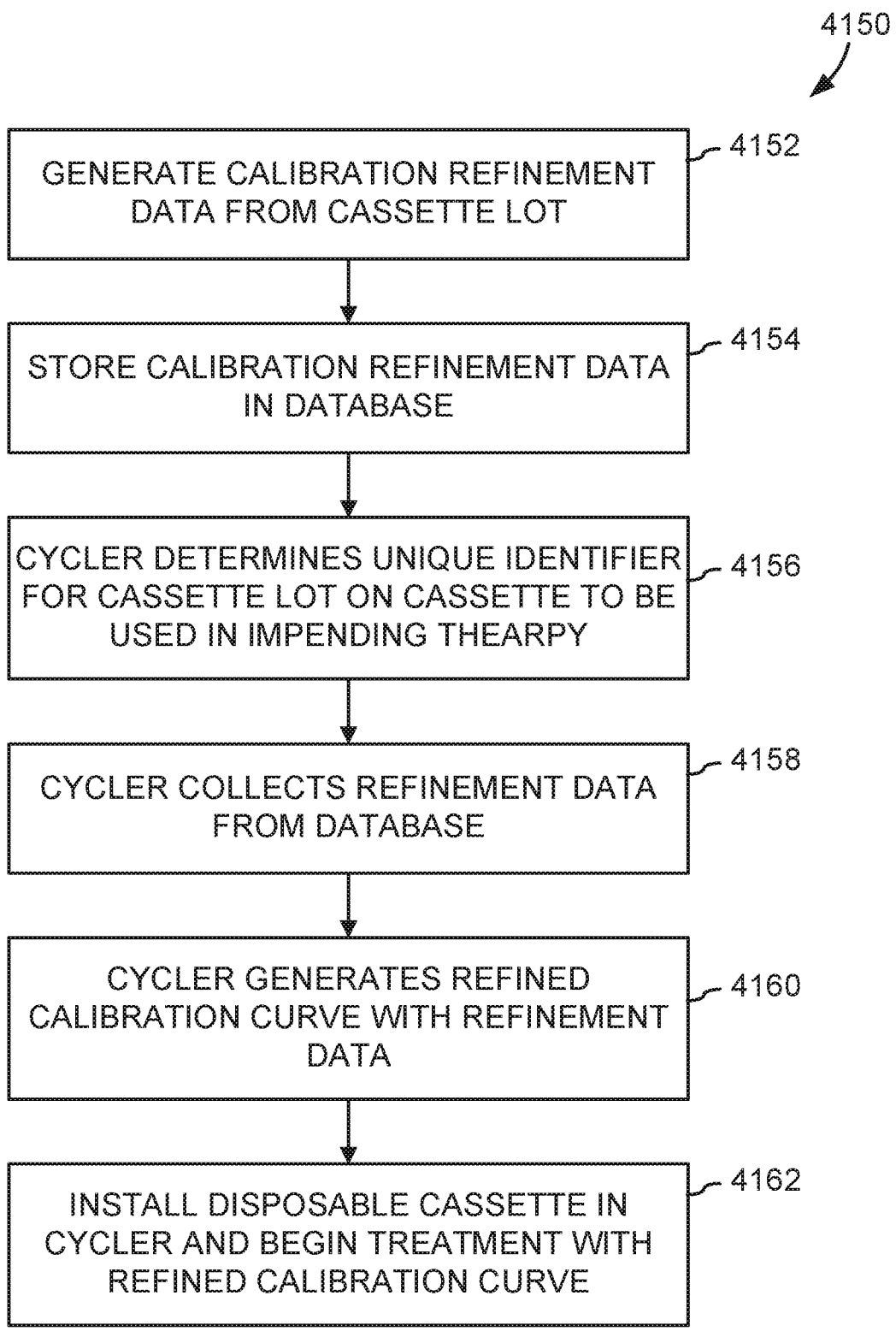
FIG. 78 depicts a flowchart showing a number of example actions which may be used refine a calibration curve of a particular cycler based on information related to a disposable cassette about to be used in an impending therapy.

Referring now to FIG. 78, a flowchart 4150 showing a number of example actions which may be used refine a calibration curve of a particular cycler 14 based on information related to a disposable cassette 24 about to be used in an impending therapy is depicted. As shown, calibration data may be collected for a specific manufacturing lot of disposable pumping cassettes 24 in block 4152. This may be done similarly to as described above in relation to FIG. 77. In block 4154, this data may be stored in a database and associated with a unique identifier for that production lot. In block 4156, a cycler may determine the unique identifier for the manufacturing lot of the cassette about to be used in an impending therapy. In some embodiments, the cycler 14 may generate a prompt for the user to input a lot identifier included on the disposable cassette 24, over pack for the set 12, or some other portion of the set 12. This information may be input to a user interface or touch screen display of the cycler 14. In some embodiments, an identifier (e.g. a coded identifier such as a bar code, data matrix, QR code, RFID, etc.) may be included on the cassette 24, over pack, or a portion of the set 12. The cycler 14 may prompt a user to scan this identifier with a scanning device included as part of the cycler 14 or attached to the cycler 14 as an auxiliary device via a connection port such as a USB port, RS-232 port, etc. In embodiments where the cycler 14 includes an auto-ID assembly, an imager of that assembly may be used to collect data from the identifier. The refinement data associated with the lot identifier may then be collected from the database by the cycler 14 in block 4158. In certain examples, the cycler 14 may be collect this data from a server via a wireless or wired network or internet connection. In block 4160, the cycler may generate a refined calibration curve using the refinement data associated with the disposable cassette 24 lot. This may be done as described elsewhere herein. In block 4162, the disposable cassette 24 may be installed in the cycler 14 and treatment may begin using the refined calibration curve.

Figure 79:
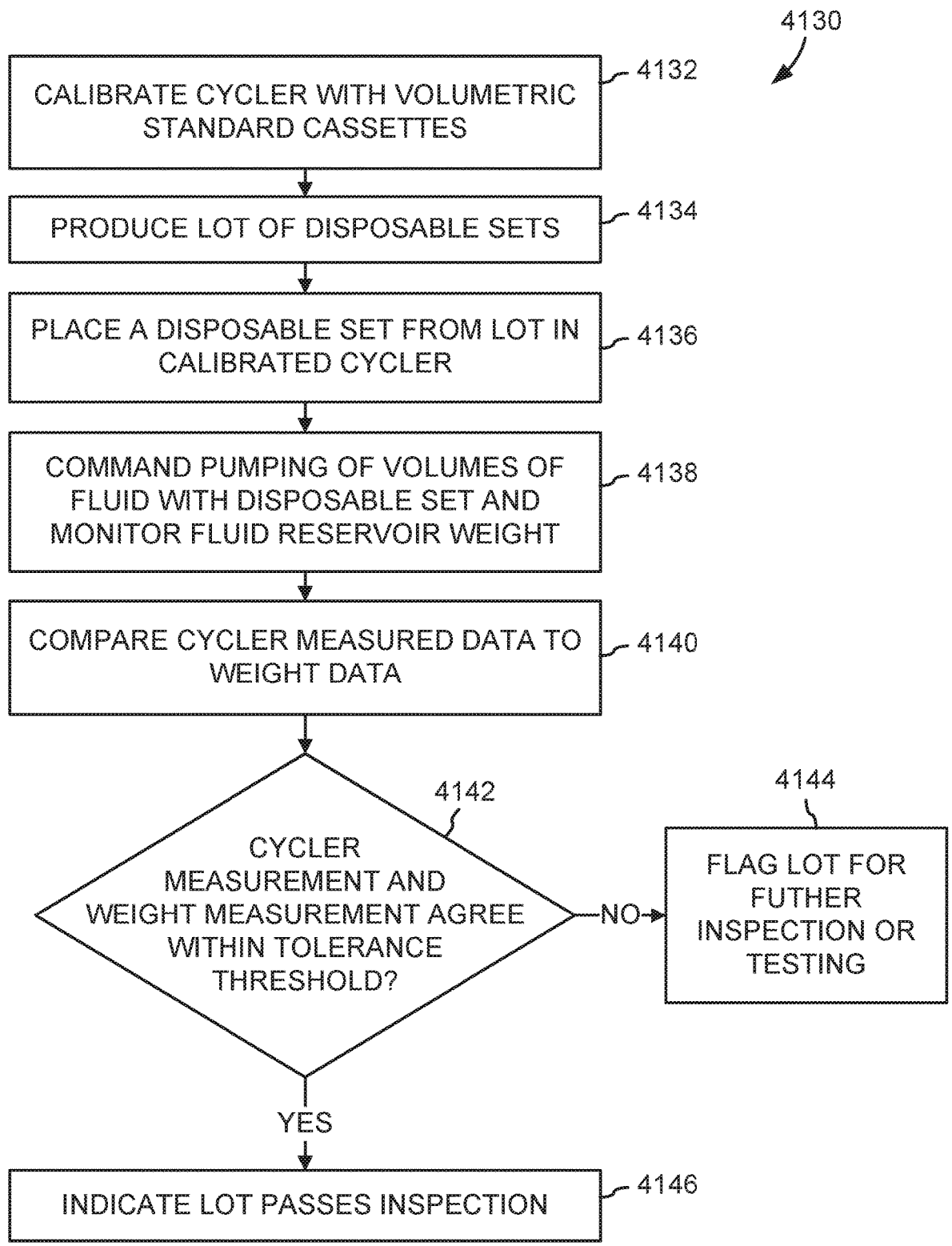
FIG. 79 depicts a flowchart depicting a number of example actions which may be used to test production lots of disposable cassettes during manufacture.

Referring now to FIG. 79, a flowchart 4130 depicting a number of example actions which may be used to test production lots of disposable cassettes during manufacture 24 is depicted. As shown, in block 4132, a cycler 14 may be calibrated with a number of volumetric standard cassettes as described elsewhere herein. Optionally, a refinement to the calibration curve for the cycler 14 may also be applied as described elsewhere herein. A production lot of disposable pumping cassettes 24 may be manufactured in block 4134. A disposable pumping cassette 24 from the production lot may be placed in a calibrated cycler in block 4136. The cycler may command pumping of predetermined measured volumes of fluid via the disposable set and the weight of a fluid reservoir may be monitored in block 4138. Thus a number of measurement pairs may be collected. One member of the pair may be a volume measurement reading for a specific volume transfer performed by the cycler 14. The other may be a weight change measurement of the reservoir which resulted from that volume transfer. A comparison between each of the measurement pairs may be made in block 4140. The weight data may be converted into a volume using the fluid density during the comparison. This comparison may generate a deviation value between the calibrated cycler's 14 measured transfer volume and actual weight determined transfer volume from each data pair. As error attributable to the cycler has been calibrated out, any deviation should be due to variation attributable to the disposable pumping cassette 24. If, in block 4142, pairs of cycler volume measurements and weight data do not agree within a predetermined tolerance range, the production lot may be flagged from further testing or investigation in block 4144. Alternatively, the lot may be rejected. If, in block 4142, the cycler volume measurement and weight data are in agreement, an indication that the lot passes inspection may be generated in block 4146. In some embodiments, a certain number of pairs may need to exceed the tolerance range before the lot is flagged in block 4144.

In some embodiments, multiple disposable pumping cassettes 24 from the production lot may be tested. The deviation data from each of the disposable pumping cassettes 24 may be checked for agreement with predefined tolerance thresholds as just described. Additionally, the data may be checked to ensure it has an expected distribution or level of variance between disposable pumping cassettes 24 and the lot may be flagged if the data does not.

Head Height Detection

In some circumstances, it may be useful to determine the heightwise location of the patient relative to the cassette 24 or other portion of the system 10. For example, dialysis patients in some circumstances can sense a "tugging" or other motion due to fluid flowing into or out of the patient's peritoneal cavity during a fill or drain operation. To reduce this sensation, the cycler 14 may reduce the pressure applied to the patient line 34 (see, e.g., FIG. 1A) during fill and/or drain operations. However, to suitably set the pressure for the patient line 34, the cycler 14 may determine the height of the patient relative to the cycler 14, the heater bag 22 (see, e.g., FIG. 1A), drain or other portion of the system. For example, when performing a fill operation, if the patient's peritoneal cavity is located five feet above the heater bag 22 or the cassette 24, the cycler 14 may need to use a higher pressure in the patient line 34 to deliver dialysate than if the patient's peritoneal cavity is located five feet below the cycler 14. The pressure may be adjusted, for example, by alternately opening and closing a binary pneumatic source valve for variable time intervals to achieve the desired target pump chamber pressure. An average desired target pressure can be maintained, for example, by adjusting the time intervals to keep the valve open when the pump chamber pressure is below the target pressure by a specified amount, and to keep the valve closed when the pump chamber pressure is above the target pressure by a specified amount. Any adjustments to maintain the delivery of a complete stroke volume can be made by adjusting the fill and/or delivery times of the pump chamber. If a variable orifice source valve is used, the target pump chamber pressure can be reached by varying the orifice of the source valve in addition to timing the intervals during which the valve is opened and closed. To adjust for patient position, the cycler 14 may momentarily stop pumping of fluid, leaving the patient line 34 in open fluid communication with one or more pump chambers 181 (see, e.g., FIG. 3) in the cassette 24 (e.g., by opening suitable valve ports in the cassette 24). However, other fluid lines may be closed, such as the upper valve ports 192 (see, e.g., FIG. 6) for the pump chambers 181. In this condition, the pressure in the control chamber for one of the pumps may be measured. As is well known in the art, this pressure correlates with the "head" height of the patient, and can be used by the cycler 14 to control the delivery pressure of fluid to the patient. A similar approach can be used to determine the "head" height of the heater bag 22 (which will generally be known), and/or the solution containers 20, as the head height of these components may have an effect on pressure needed for pumping fluid in a suitable way. An example head height detection and pressure adjustment method is described in U.S. Pat. No. 6,503,062 entitled Method For Regulating Fluid Pump Pressure, to Gray et al, filed Jul. 10, 2000 which is hereby incorporated by reference herein in its entirety.

A head height detection determination can be used in a variety of applications and the head height detections described herein may be generalizable to any cassette based pumping system, but are described herein with relation to a dialysis cycler. Such a determination may be made at a plurality of times, for instance just after cycler priming, before fluid transfer to and from the patient, or when altered (e.g. decreased) flow conditions are detected. Head height detection may also be performed simultaneously with fluid transfer through a separate chamber of a pumping cassette. Head height detection may be performed for multiple locations of interest within the system simultaneously. The layout of fluid buses in the cassette may be arranged to facilitate this. For example, two locations of interest within the system where simultaneous measurement or measurement and simultaneous volume transfer is desired may communicate with different fluid buses. Locations of interest may also have dedicated fluid pathways to facilitate these simultaneous actions. Where used in a cycler which admixes dialysate instead of using dialysate from a pre-mixed bag, head height detection may be of particular usefulness. For example, head height detection may confirm the components of interest are in an expected location. Since air within a pump chamber may be under varying states of compression due to differences in source head height, this may allow a set of assumptions regarding behavior of any air in a pump chamber to be made. This may help to increase mixing and general volume transfer accuracy as volumetric displacements calculated by the cycler may be captured with more robust reliability.

In embodiments which are configured to perform continuous flow rate and stroke displacement estimation (see, e.g. FIGS. 56-62) the pump membrane or sheeting 151 (see, e.g., FIG. 4) of the sheeting/membrane 15 may be precisely positioned to allow for repeatable determination of both positive and negative head heights over a maximized detection range. Use of a cassette 24, having pre-formed pump sheeting 151 which is flaccid or displaced substantially without stretching throughout the stroke may provide further benefit. The pump sheeting 151 target position may be an intermediary location or state between the displacement extremes of the pump sheeting 151 (e.g. a pump chamber 181A, B fully filled and fully delivered pump sheeting 151 position). This may repeatably allow for a single head height determination process to reliably detect the head height of a location of interest.

The maximized detection range may be selected such that the range is most inclusive or entirely inclusive of expected head heights for a location of interest (e.g. patient, heater bag 22, source bag, other source component). In certain examples, the maximized detection range may be a range which allows for the detection of a maximum positive and negative head height of about the same absolute value (e.g. absolute values within several mm of one another). Depending on the location of interest, the pump chamber sheeting 151 position and thus detection range may be adjusted to favor detection of a greater range of either positive or negative head heights.

Figure 80:
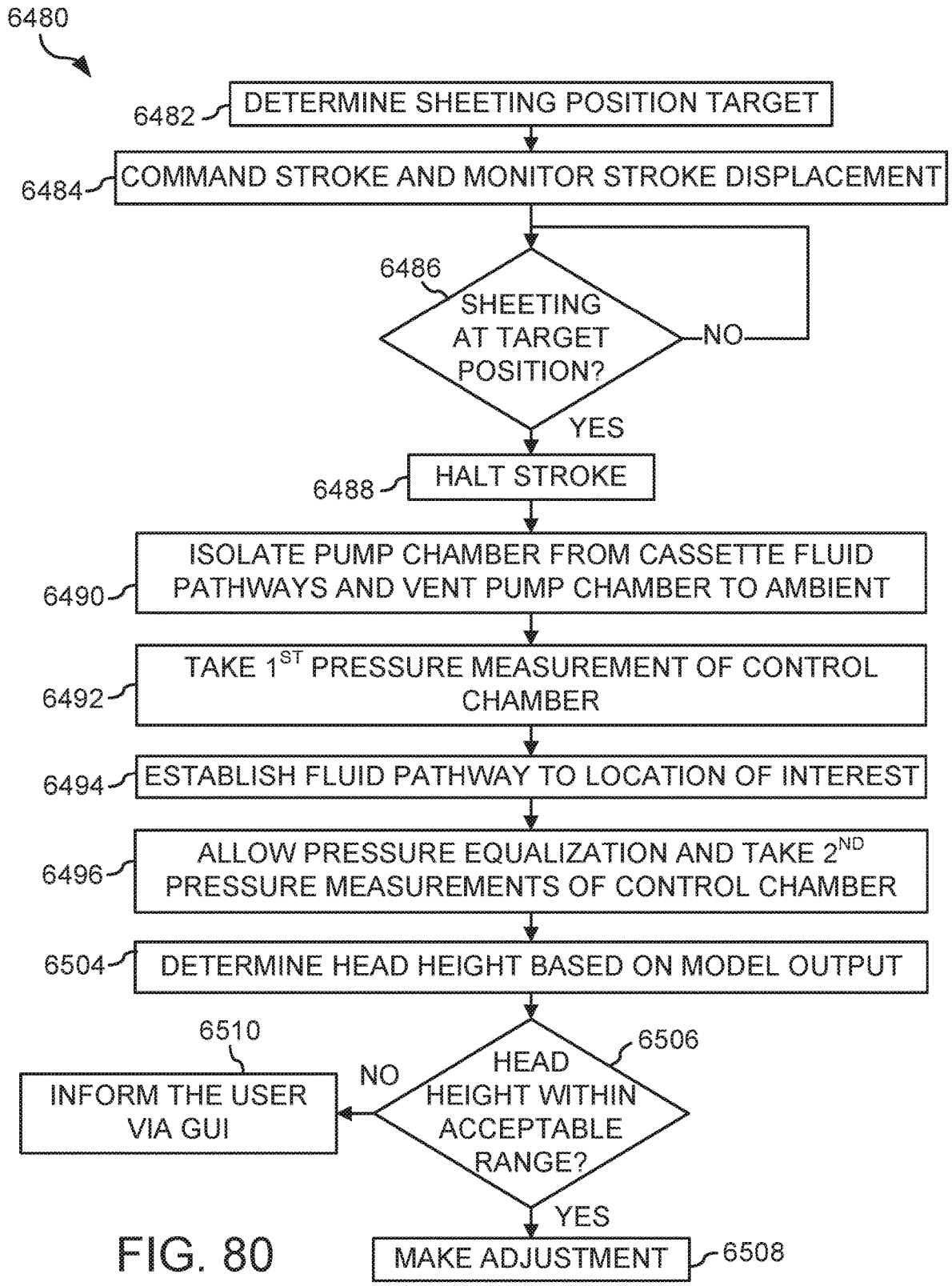
FIG. 80 shows a flowchart detailing a number of example actions which may be executed to detect a head height of a component of interest of the system.

Referring now to the flowchart 6480 depicted in FIG. 80, in block 6482, a controller or control system 16 of the cycler 14 may determine a pump sheeting 151 (see, e.g. FIG. 4) target position. The pump sheeting 151 position target may also be a predetermined position. In some embodiments, a target position may be predetermined for each of a number of locations of interest. The target position used may that associated with the location for which head height is to be determined.

In block 6484, the controller may command the cycler 14 to start a pumping stroke. The pumping stroke may be a fill stroke or delivery stroke depending on the starting position of the pump sheeting 151 with respect to its target position. Stroke displacement, and thus pump sheeting 151 location may also be monitored during the stroke in block 6484. Again, this may be accomplished as described in relation to FIGS. 56-62 for example. If, in block 6486, the controller determines the pump sheeting 151 is at its target position, the stroke may be halted at that point by the controller in block 6488. Optionally, a volume measurement including a pressure equalization of the control chamber 171B volume (whose pressure is known) with a known reference volume at known pressure may be performed to verify the pump sheeting 151 is at the target position.

In block 6490, the pump chamber 181A, B may be isolated by closing inlet/outlet cassette fluid valves 190, 192 (see, e.g., FIG. 6) to/from the pump chamber 181A, B. The control chamber 171A, B through which pressure is applied to the pump chamber sheeting 151 may also be vented in block 6490. The control chamber 171A, B may be vented to a venting reservoir such as the ambient atmosphere. Once the control chamber 171A, B has equalized with the venting reservoir, the control chamber 171A, B may be isolated. A first pressure of the control chamber 171A, B may be may be measured in block 6492.

In block 6494, various fluid valves of the cassette 24 may be opened to establish fluid communication between the pump chamber 181A, B and the location of interest. In block 6496, pressure equalization between the control fluid in the control chamber 171A, B and the fluid in the pump chamber 181A, B may occur. In some embodiments, block 6494 may allow for a predefined time period to elapse over which pressure equalization occurs. Alternatively, at least one pressure sensor in communication with the control chamber 171A, B fluid may be monitored. In the latter case, block 6496 may end once the sensor data indicates pressure of the control chamber 171A, B is relatively stable. For example, block 6496 may end once pressure has not deviated greater than a certain amount or outside of a range for a period of time.

A head height of the location of interest may then be determined in block 6504. Head height may be determined by relating the density, acceleration of the fluid due to gravity, and the pressure at the end of block 6496 to the head height of the component of interest. The head height may be equal to the pressure at the end of block 6496 (density*acceleration due to gravity). In some embodiments, the calculated head height may be checked against an acceptable range to ensure the system 10 is properly set up. If, in block 6506, the head height is within the acceptable range, pumping pressures may be adjusted to compensate for the head height in block 6508 as mentioned above. If, in block 6506, the head height is not within the acceptable range, an alert may be generated by a controller for display on a GUI of the cycler 14 in block 6510.

Referring back to block 6482, in some embodiments, multiple models may be employed to determine the target position based on a desired maximized detection range. If, for example, the time needed for pressure in the control chamber 171A, B and pump chamber 181A, B to equalize is above or below a threshold, different models may be used. If below, a first model may be used; if above, a second model may be used. Additional models and thresholds may be included in some embodiments. The first model may be an isothermal model while the second model may be an adiabatic model. The choice of model may be determined based on flow rates from other portions of the therapy or pre therapy. Alternatively, one of the first or second models may be used initially. The controller may re-perform the head height determination if warranted by the pressure equalization time.

The first model may operate based on the following example equation:

$$P_f = (P_i(V_{con,i}))/V_{con,f}$$

Where $P_f$ is the final pressure of the control chamber 171A, B volume after equalization in block 6496, $P_i$ is the first pressure from block 6492, $V_{con,i}$ is the initial control chamber 171A, B volume when pump sheeting 151 is at the target position, and $V_{con,f}$ is the final control chamber 171A, B volume.

The second model may operate based on the following example equation:

$$P_f = (P_i(V_{con,i}/V_{con,f})^\gamma$$

Where $\gamma$ is a heat capacity ratio (e.g. 1.4).

By assuming that the pump chamber sheeting 151 transits from the target position to an extreme of travel, these models may be employed to determine the target position based on a desired maximized detection range. For any given target pump sheeting 151 position (and therefore $V_{con,i}$) head height sensitivity ranges may be determined. $P_i$ may be known (e.g. set at 101 kPa, or measured by a sensor communicating with ambient). By assuming the pump sheeting 151 will transit to an extreme of travel, a value for $V_{con,f}$ may also be known. From this, pressure changes needed to bottom out the pump sheeting 151 at an extreme of travel, and therefore head height sensitivity can be determined. Thus, it is possible to choose a sheeting target position which has the greatest sensitivity range to different head heights based on observed equalization time.

In the event that a controller determines the head height to be around the edge of a sensitivity range, optionally a second head height detection determination may be made. If the head height is at an edge of the sensitivity range, it can be surmised the pump sheeting 151 had displaced to or near an extreme of travel. In the second head height detection determination, the pump sheeting 151 position target used may be the opposite extreme of travel. This would allow for greater visibility on head heights of the type (e.g. positive or negative) detected in the first head height determination but of greater magnitude.

Figure 81:
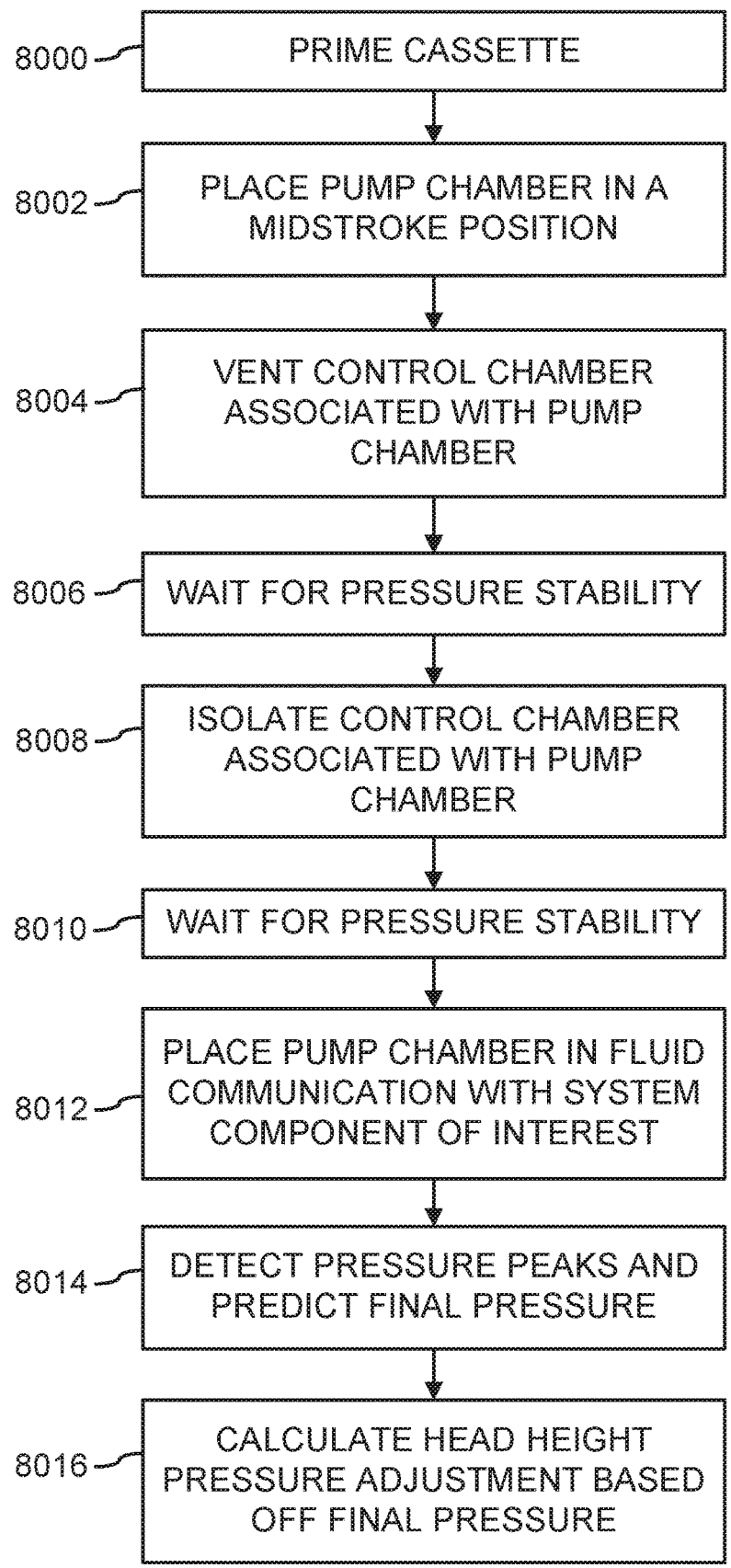
FIG. 81 shows a flowchart detailing a number of example actions which may be executed to adjust a pumping pressure based of a determined head height of a component of interest.

FIG. 81 shows a number of exemplary actions which may be executed to calculate head height pressure in another embodiment of a head height determination. As shown in FIG. 81, in block 8000 the cassette may be primed. In block 8002, a pump chamber may be placed in an initial state where the chamber's sheeting can displace in response to any pressure exerted by the head height of a component of interest. In certain embodiments, the sheeting may be placed in a state where it may displace in response to either positive or negative pressure. Thus, if the pump chamber is placed in fluid communication with a system component of interest at either positive or negative head height with respect to the pump chamber, the establishment of fluid communication between the chamber and the component of interest may displace the sheeting. This state may be referred to an intermediate or mid-stroke state or position. This intermediate position may be determined by the control system as described above or may be preset.

In situations where it is anticipated that the head height of the component of interest will exert a positive pressure on a pump chamber, the pump chamber may be placed in a first biased state in block 8002. The first bias state may be a state which biases the detection range toward detection of positive head heights. For example, the pump chamber may be left in a fully delivered state. Likewise, if it is anticipated that the head height of the component of interest will be negative with respect to a pump chamber, the pump chamber may be placed in a second biased state in block 8002. The second biased state may be a state which biases the detection range toward detection of negative head heights.

In block 8004, the control chamber associated with the pump chamber to be used for measuring head height may be vented. In block 8006, the control system of the cycler may wait for pressure stability within the control chamber to be achieved. In block 8008, the control chamber associated with the pump chamber may be isolated. In block 8010, the control system of the cycler may wait for the pressure to stabilize within the control chamber. In block 8012, the pump chamber may be placed in fluid communication with a system component of interest. In block 8014, control system may detect a number of pressure peaks and predict a final pressure of the control chamber (described in more detail below, e.g., in reference to FIG. 83). In block 8016, the control system may calculate an appropriate head height pressure adjustment based off the final pressure. This adjusted pressure may be used for subsequent fluid transfer to/from the component of interest.

Figure 82:
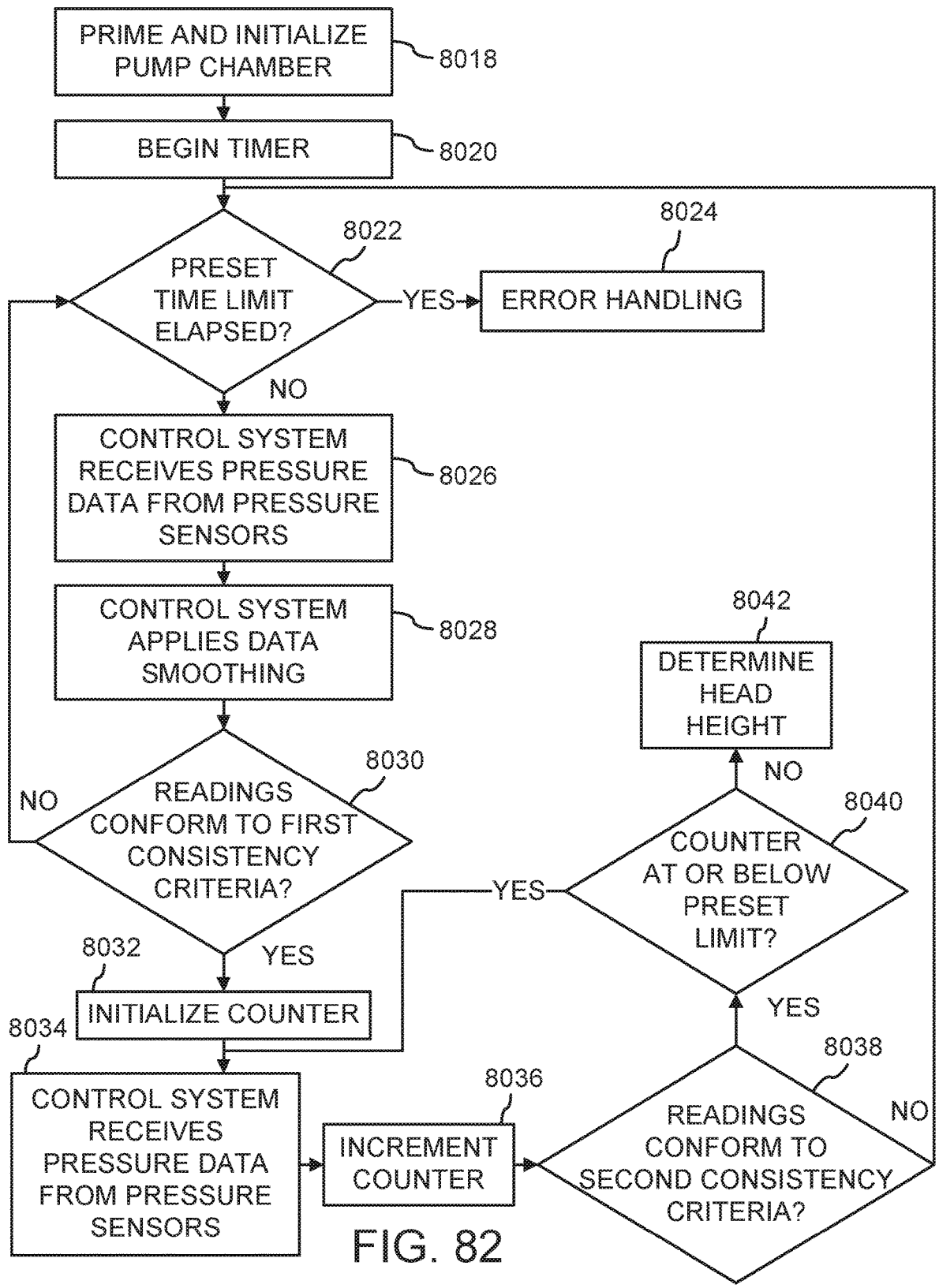
FIG. 82 shows a flowchart detailing a number of example actions which may be executed during a head height detection of a component of interest of the system.

Referring now also to FIG. 82, a consistency check may be used in blocks 8006 and 8010 of FIG. 81 to detect pressure stability in the control chamber associated with the pump chamber to be used for measuring head height of the component of interest. Consistency checks may also be used in the head height determination described in relation to FIG. 80. When at least one pressure consistency criteria is met during the consistency check, the consistency check may be deemed to have passed. During a consistency check, pressure samples may be taken at a set time interval or intervals. In some embodiments, the interval could be set to about 5-30 milliseconds (e.g. ~10 milliseconds). These samples may be numerically processed and analyzed for the presence of a predefined pattern or characteristic. When that predefined pattern or characteristic is detected, a signal may be generated which indicates that stability has been achieved and the head height detection determination may be continued.

To check for consistency, a moving average generated from the sensor data may be employed. For example, the difference (or its absolute value) between two consecutive moving average pressure samples may be calculated. Once the pressure difference is consistently near zero for the first and a number of subsequent moving average pressure samples, a signal may be generated indicating that the pressure stability has been achieved. In some embodiments, a threshold of less than a 0.03 kPa deviation from zero could be used to determine if the pressure difference is sufficiently near zero. The number of pressure samples used in the moving average window could be set to five. If pressure stability is not detected within the time delay period then it may be determined that pressure stability has not been achieved, the end pressure may be noted and the process may repeat. In some embodiments, absence of pressure stability may trigger an error to be generated by the control system or trigger error generation after a retry cap has been exceeded. In some embodiments, the control system may present an alert on a graphical user interface of the cycler asking the user to check the system or stop moving around for a period of time.

FIG. 82 is illustrative of an exemplary consistency check. In block 8018, the cassette may be primed. In block 8020, a timer may begin. The timer may set an amount of time during which it is expected that pressure stability should be achieved. The timer may be between 2-6 seconds (e.g. 3 seconds) in various embodiments. If it is determined, in block 8022, that the timer has elapsed, the control system may execute a predefined error handling protocol in block 8024. For example, the control system may generate an error signal or perform a retry of the consistency check while incrementing a retry counter (this may be limited by a retry cap).

If the preset time limit has not elapsed, the control system may receive pressure data from one or more pressure sensor monitoring the control chamber in block 8026. In block 8028, the control system may apply data smoothing to the pressure data. In some embodiments, a moving average can be used to smooth the data. The moving average may employ a moving window size of 3-10 values (e.g. ~5) though this window size may grow or shrink in a relationship to sampling frequency. Any window size sufficient to filter out excessive noise may be utilized.

In block 8030, the control system may determine whether the data conforms to a first consistency criteria. If the data does not conform to the first consistency criteria, then the control system may revert back to block 8022. The first consistency criteria may be a predefined criterion which indicates that the pressure data is relatively steady. For example, in some embodiments, a comparison between two consecutive moving average pressure samples may be made. The two consecutive moving average pressure samples may be the current sample moving average and the directly preceding sample's moving average value. The comparison may be based at least in part on the difference between the consecutive pressure sample moving average values. In specific examples, the difference or an absolute value of the difference may be determined in the comparison. Where a difference is calculated, the first consistency criteria may be deemed satisfied by the controller if the difference (or absolute value thereof) is nearly zero (e.g. less than 0.025-0.02 kPa). Alternatively, the criteria may be defined as a percentage of the measurable range of head heights.

If the data does conform to first consistency criteria, then the controller may require the pressure in the control chamber to remain stable in subsequent sampling. For example, the pressure difference may be required to remain consistently near zero for a number (e.g. 3-10) of subsequent moving average pressure samples. In certain embodiments, the control system may determine that pressure stability has been achieved if comparisons performed after each of five subsequent moving average pressure samples are collected indicate that pressure is steady.

In FIG. 82, the control system may initialize a counter in block 8032. The counter may be set to the desired number (e.g. 5) of moving average sample pressures required before a determination that the pressure is stable may be made. In block 8034, the control system may receive pressure data from one or more pressure sensor monitoring the control chamber, and in block 8036 the control system may increment the counter. In block 8038, the control system may determine whether the data conforms to a second consistency criteria. For example, a comparison value calculated between a new sample and the previous sample may be required to be with a range of about 0.00 kPa to 0.05 kPa (e.g. less than 0.03 kPa). If the data does not conform to the second consistency criteria, then the control system may revert back block 8022. If the data does conform to the second consistency criteria then the control system may determine if the counter is at or below preset limit in block 8040. If the counter is at or below the preset limit, the control system may revert back to block 8034. If the counter is above the preset limit then the control system may proceed to determine head height of a component of interest in block 8042.

As mentioned in relation to block 8014 of FIG. 81, when head height of the component of interest is determined, the determination may be made on an incomplete data set. It may be possible to characterize how the system behaves and, based at least in part on that characterization, generate one or more equations that can predict a final control chamber pressure from a data set which is cut off before a final, stabilized pressure is achieved. In certain embodiments, a head height determination conducted in this manner may take about 20%-15% or less of the time necessary to reach stabilized pressure. As setup of a therapy is generally performed as a user is readying for bed, minimizing the time required for setup is appreciated in the field as advantageous.

This may allow for rapid head height determinations, speeding up any pre-therapy checks in which head height is determined. It may also allow for head height determinations to be made during therapy with minimal impact on the therapy itself. Without significantly increasing setup or therapy time, this may also allow for a head height determination for a component reservoir of interest to be made redundantly as a self check or to generate an average of multiple readings which may afford greater accuracy.

To make a determination of head height with an incomplete data set, the control system may, for example, analyze data from at least one pressure sensor monitoring the control chamber for a number of expected features of a predefined feature set. These expected features and temporal characteristics related thereto (e.g. when they occur and/or the amount time between them) may be used to extrapolate a final, stabilized control chamber pressure once enough features have been detected. This extrapolated pressure may allow for a good estimation of the head height of the component of interest.

For example, in the system 10 shown in FIGS. 1-9, the system 10 may behave similarly to an under-dampened second order system when a head height determination is made. In such examples, the feature set may be informed by characteristics which would be expected in an ideal under dampened second order system. For example, the feature set may include an overshoot pressure peak and an undershoot pressure peak which is smaller in magnitude than the overshoot peak. The control system 16 of the cycler 14 may detect a pressure overshoot and undershoot peak in the control chamber after a pump chamber is placed into communication with the component of interest. Data related to these peaks may then be used to extrapolate the final chamber pressure thus significantly speeding the determination process.

The data may also be used to determine a characteristic of interest other than head height. For example, in certain embodiments, the temporal characteristics related to the feature set may be used as a measure of resistance in the tubing. This may allow for a determination of the length of the fluid line between the cassette and reservoir component of interest. Where line extensions accessories may be used, the number of line extension accessories in use may be determined based on temporal characteristics of the feature set. This type of determination may also allow for line extensions to be used on a wider variety of lines with a reduced impact on therapy time. For example, to increase patient comfort, pumping pressure to and from the patient may be adjusted to provide slower fluid transfer. The pumping pressure used may be selected based on the temporal characteristics to generate a desired pressure at the patient end of the line. This may allow pressure to be kept at or closer to a maximum pumping pressure as the resistance in the line will lead to a reduction in pressure at the patient end. Consequentially, an increase in fluid transfer time may be avoided when a patient line extension or extensions are in use. This may allow for longer dwell periods and more clearance of metabolic waste from the patient over the same programmed therapy time.

Temporal characteristics of the feature set may also be used to determine if a flow impedance is present in the flow path between the cassette and the reservoir component of interest. In certain embodiments, these temporal characteristics may be used to determine if an occlusion or partial occlusion is present. Alternatively, these temporal characteristics may be collected to aid in informing an occlusion or partial occlusion determination.

Figure 83:
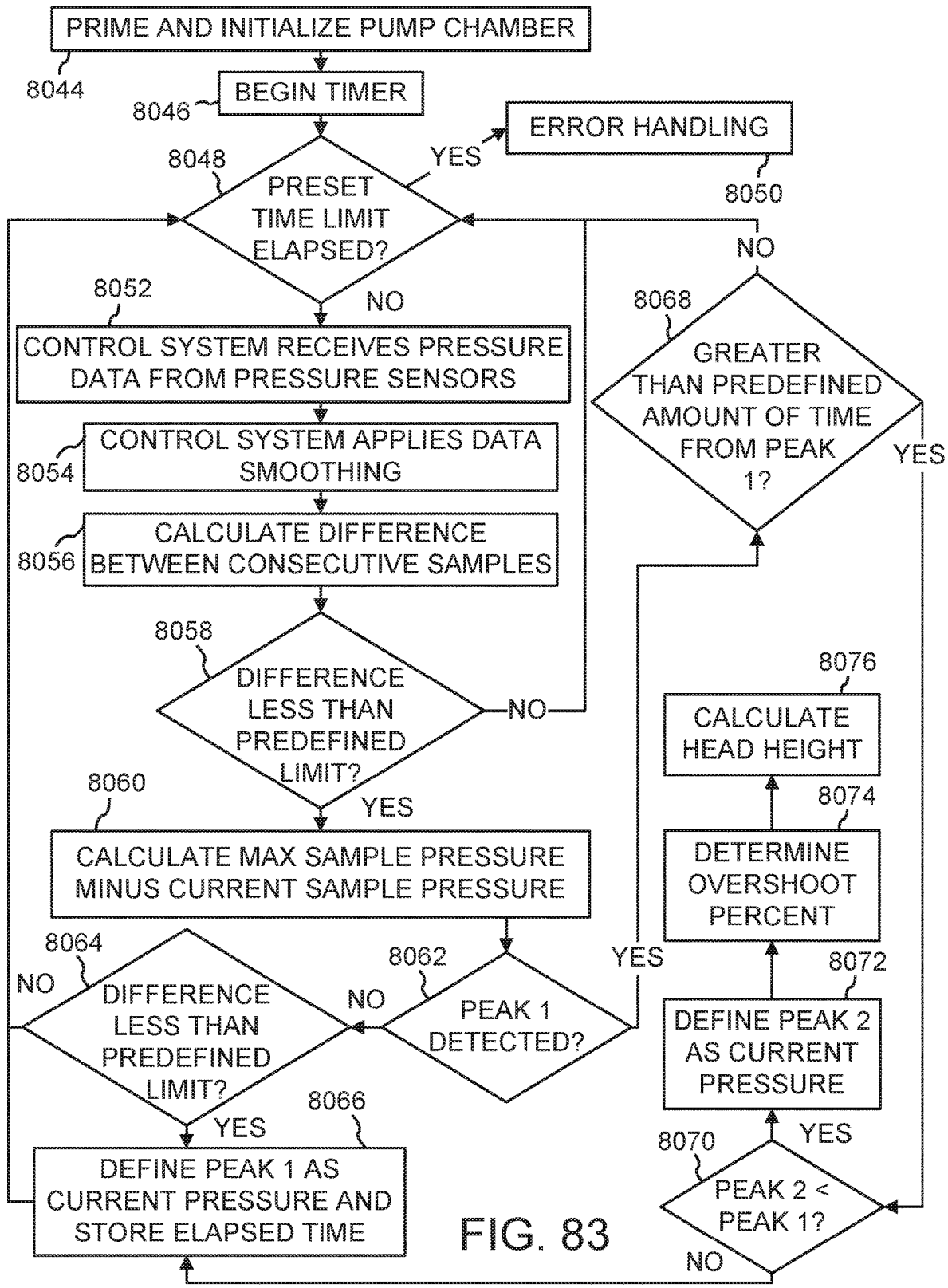
FIG. 83 shows a flowchart detailing a number of example actions which may be executed during a head height detection of a component of interest of the system.

FIG. 83 includes a flow diagram detailing a number of example actions which may be executed during a head height determination. In block 8044, a cassette is primed and the pump chamber sheeting may be placed in an initialized position. In block 8046 a timer may be started. The timer may set an amount of time during which it is expected that features of the feature set should be observed. The timer may be between 2-6 seconds (e.g. 3 seconds) in various embodiments. If it is determined, in block 8048, that the timer has elapsed, the control system may execute a predefined error handling protocol in block 8050. For example, the control system may generate an error signal or perform a retry of the head height determination while incrementing a retry counter (which may be limited by a retry cap).

When performing a head height detection, the control system can receive pressure data from at least one pressure sensor monitoring the control chamber in block 8052. In certain embodiments, data collected in an initial time window may not be used for analysis to minimize noise concerns. This time window may be up to about 1 second (e.g. ~0.3 seconds), though this value may vary from embodiment to embodiment. In block 8054, the control system may apply data smoothing to data received from the at least one pressure sensor. The data smoothing may be similar to that described in relation to block 8028 of FIG. 82. In block 8056, the control system may compare a number (e.g. 2) of consecutive moving average pressure samples to determine if a first condition exists. In the example embodiment shown in FIG. 83, the control system calculates the difference (or an absolute value thereof) between these moving average samples in block 8056. In block 8058, the system may determine if the first condition exists (e.g. if the difference is less than a predefined limit or not). The predefined limit may, for example, be between 0.005 and 0.04 kPa (e.g. 0.025 kPa). In the example in FIG. 83, if the difference is not less than the predefined limit, the control system may revert back to block 8048. If the difference is less than predefined limit the control system may compare a maximum value of the moving average sample window and the current moving average pressure sample to determine if a second condition exists. FIG. 83, for example, calculates a difference (or the absolute value of that difference) between the maximum moving average sample pressure and the current sample pressure in block 8060. In the example shown in FIG. 83, if a peak has not yet been detected in block 8062, the control system may determine if the difference is less than a second predefined limit in block 8064. The second predefined limit may be smaller than the first predefined limit described above in relation to block 8058. In some embodiments, if the difference is between about 0.000 kPa and 0.020 kPa (e.g., less than about 0.005 kPa), a first peak pressure may be set in block 8066. Where the system can be characterized as an under dampened second order system, the first peak may be an overshoot peak. This pressure peak may be set to the present moving average pressure sample or perhaps an average of the current moving average pressure sample and that directly preceding it. The time taken to reach the pressure overshoot may be also noted in block 8066. The control system may then revert back to block 8048. The control system may also revert back to block 8048 if the difference is not smaller than the second predefined limit in block 8064.

Once the first peak has been detected and control system reaches block 8062 again, the control system may proceed to block 8068. In block 8068, the control system may determine if the amount of time from the first pressure peak is greater than a predefined amount of time. This predefined amount of time may be an empirically determined amount of time which is expected before the next peak occurs. For an ideal under dampened second order system this amount of time should be about the same as the amount of time needed to reach the first peak. For example, the predefined amount of time may be set equal to the time required to reach the first peak less some value (e.g. 0.1-0.4 seconds) which may help account for any deviation from an ideal system. If the predefined amount of time has not yet elapsed, the control system may revert back to block 8048. When the predefined amount of time has elapsed, the control system may determine if the magnitude of the current pressure is greater than that detected for the first peak in block 8070. If the magnitude of the current pressure is greater than that detected in the first peak, the control system may return to block 8066 and reset the first peak as the current pressure. Again, the elapsed time may also be noted. If, however, the current pressure is lower in magnitude than the first peak pressure, the control system may define a second peak pressure as the current pressure in block 8072. The elapsed time before the detection of the second peak pressure may also be noted. In block 8074, the control system may determine an overshoot percent. The percent overshoot may be determined via an equation such as the following:

Percent Overshoot=$(1-(P_1/P_2)-\alpha)$

Where $P_1$ is the first peak pressure, $P_2$ is the second peak pressure and $\alpha$ is a correction factor which may be empirically determined. The correction factor may be used to adjust for any deviation from an ideal second order system.

In block 8076, the control system may calculate the head height. In some embodiments, head height itself may not be calculated, but a related value such as pressure due to head height may be calculated (or both may be calculated). This may be determined by predicting a final pressure which would have been present had the pressure been allowed to stabilize after detection of the peaks. The final pressure, $P_{Final}$, may be determined via and equation such as the following:

$P_{Final}=P_1/(1+\text{Percent Overshoot})$

The starting pressure of the pump chamber may then be subtracted from the final pressure to determine the pressure due to head height. If desired, this pressure may then be converted into a head height in units of distance based on acceleration due to gravity, density of the liquid, and the pressure value as described elsewhere herein.

Figure 84:
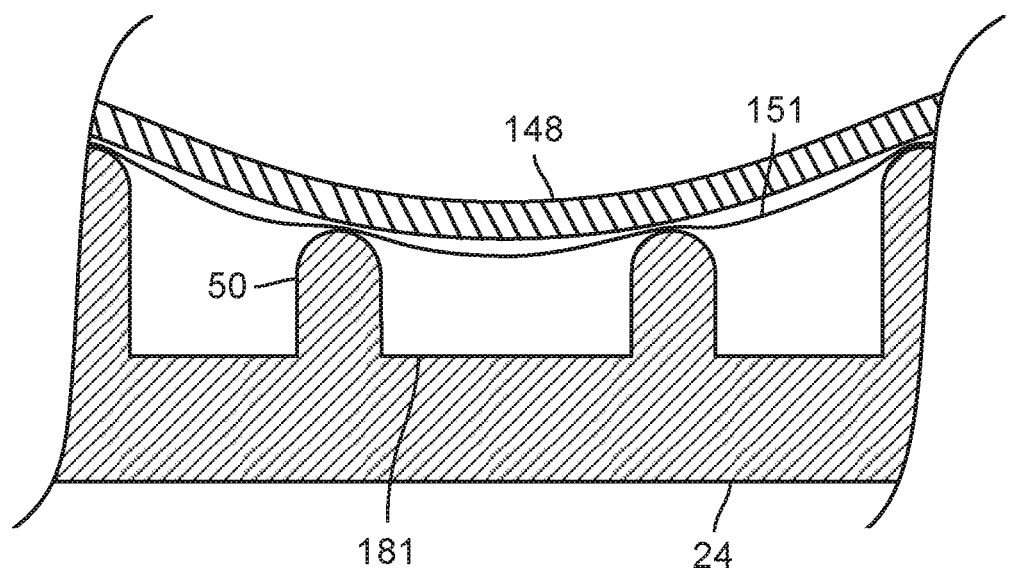
FIGS. 84 and 85 depict representational views of pump chambers after finishing delivery strokes to destinations at differing head heights.
Figure 85:
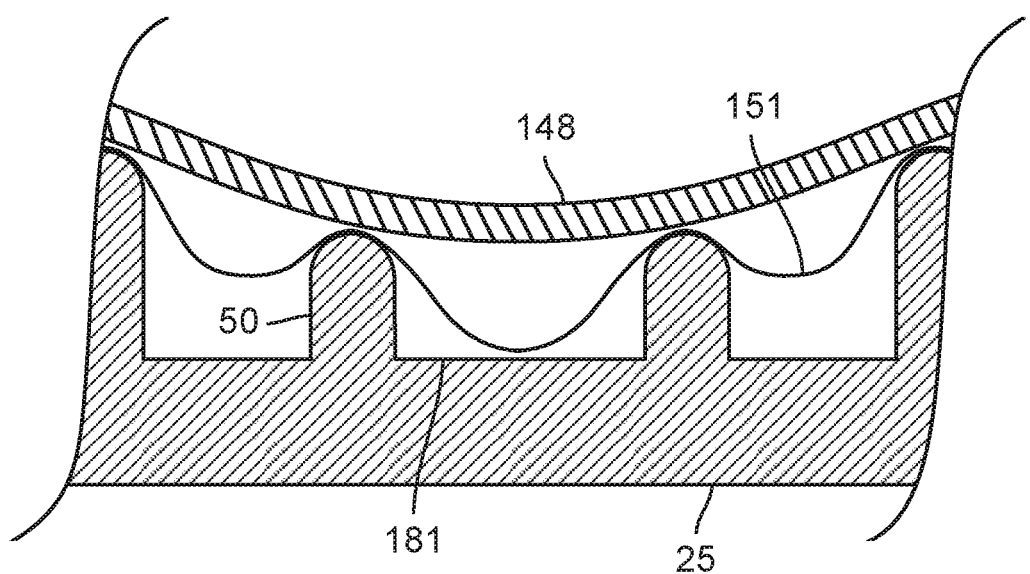
Figure 86:
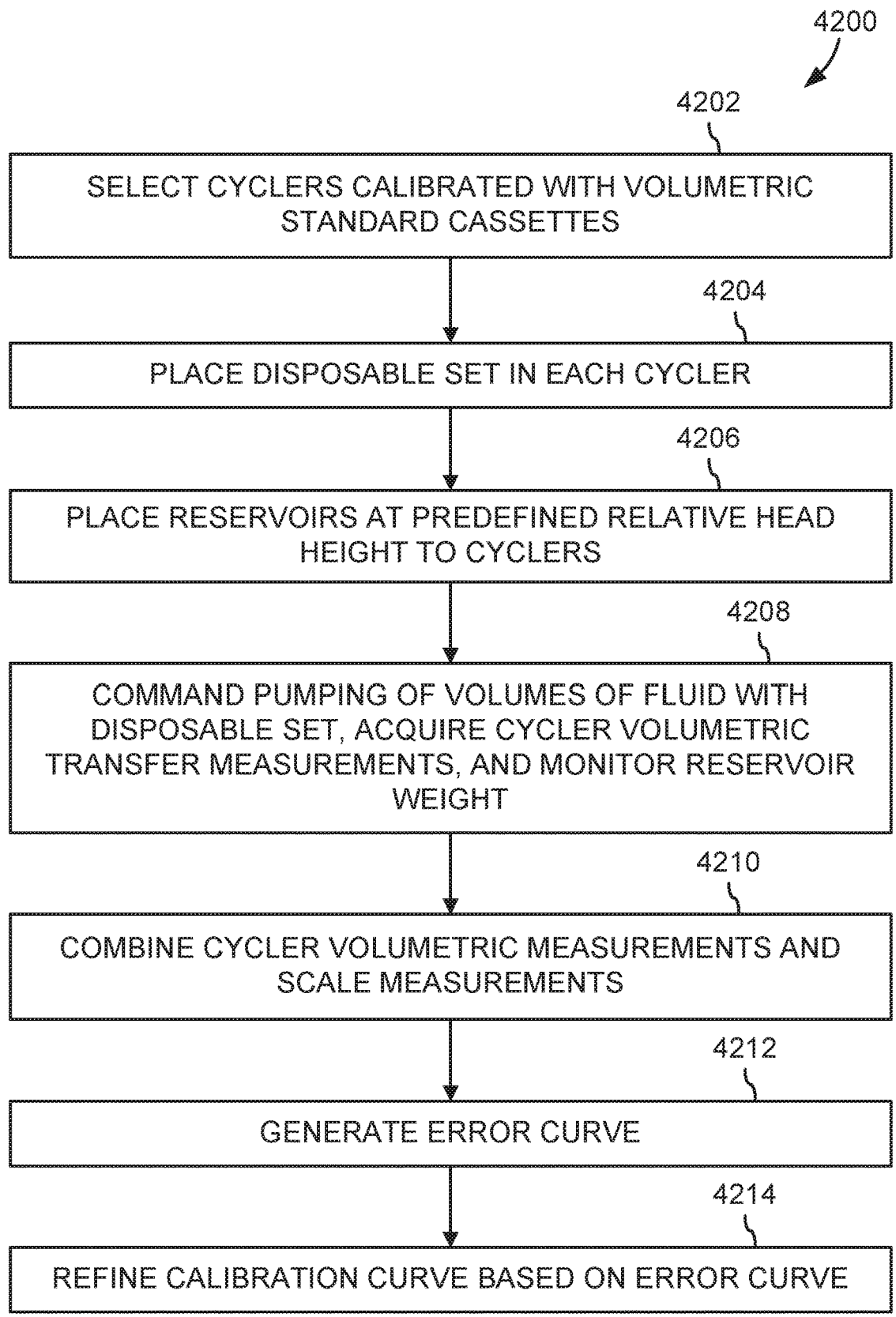
FIG. 86 depicts a flowchart detailing a number of actions which may be used to determine a calibration curve for a particular head height.

Referring now to FIG. 84-86, it has been observed that, in some embodiments, volumetric transfer measurement calibration with respect to the determined head height for a given source or destination may be desirable. Without being bound by any particular theory, it is possible that any air within a pump chamber may be under varying states of compression due to differences in source head height. This may have a small effect on volumetric measurements collected by a cycler 14. Additionally, the location of the pump sheeting 151 and gasket 148 may vary slightly depending on head height and this may affect volume measurement readings.

FIGS. 84 and 85 depict representational views of pump chambers 181 after finishing delivery strokes to destinations at differing head heights. For sake of explanation, the illustration depicts a large difference in pump sheeting 151 locations between FIG. 84 and FIG. 85. As shown in FIG. 84 when a cycler 14 finishes a deliver stroke to a destination at a certain elevated head height, the pump sheeting 151 of the cassette 24 sheeting 15 may substantially conform to the shape of the spacers 50 of the pump chamber 181. The gasket 148 may closely mimic or conform to the same contour assumed by the cassette sheeting 15. When completing a delivery stroke to a destination at an inferior relative head height (using substantially the same delivery pressure as in FIG. 84) the pump sheeting 151 may advance or bow into the gaps between spacers 50 of the pump chamber 181. The gasket 148 material, however, may not conform as tightly to the position of the pump sheeting 151 in this scenario. Similar, but generally opposite effects due to head height may be present on fill strokes. As illustrated above, at the end of the deliver stroke, there may be energy stored in non-ideal locations depending on the head height. During an FMS procedure (described in greater detail elsewhere herein), a control chamber 171 may typically be vented to atmosphere, charged with a predetermined pressure, and then equalized in pressure with a reference chamber volume. In the event that energy is stored in the system, there may be some slight movement in the pump sheeting 151 and/or gasket 148 during these pressure changes. This movement may be related to the amount of energy stored in the system at the end of the delivery stroke. As this slight movement may affect the volume of the control chamber 171, this may introduce some error into volumetric measurements collected by the cycler 14. Since this error would be predictably related to the head height, a calibration correction may be implemented based on the head height.

The calibration curve (e.g. any calibration curves described above) for a cycler 14 may, for example, be adjusted to a refined calibration curve to be used when transferring fluid to/from each source or destination based on its head height. Thus a different calibration curve may potentially be used for each source or destination in communication with a disposable pumping cassette 24.

Referring primarily to FIG. 86 a flowchart 4200 detailing a number of actions which may be used to determine a calibration curve for a particular head height is depicted. In block 4202, a number of cyclers 14 which have been calibrated with volumetric standard cassettes may be selected. These cyclers 14 may be chosen based on similar criteria to that described in relation to block 4172 of FIG. 77. In block 4204, a disposable set 24 may be placed in each cycler 14. Reservoirs associated with each of the cyclers 14 may be placed at a predefined head height relative to the cycler 14 in block 4206. In block 4208, a control system 16 of each cycler 14 may command pumping of volumes of fluid with the installed disposable set 24. The volumes pumped may be common for all cyclers 14 and may be pre-specified. The cycler 14 may take volumetric measurements of the fluid pumped in block 4208. A scale may also, in block 4208, be monitored to document consequent weight deltas as volumes of fluid are pumped through the disposable cassette 24 by the cycler 14.

In block 4210, the volumetric measurements collected from each cycler 14 and the associated scale data may be combined. For example, all raw data points may be combined together. These data points may be in pairs including a transfer volume measured by particular cyclers 14 and the corresponding measured volume displaced from the reservoir (e.g. converted from the weight delta on the scale using density). Alternatively, data collected from a particular cycler 14 may be analyzed and the outputs of the analysis of each individual cycler data set may be combined. For example, a correction curve for each cycler 14 at that predefined head height may be generated from the raw data associated with that cycler 14. Each of these correction curves may then be combined.

In block 4212, a single correction curve may be generated using the combined data. This correction curve may be used to refine the calibration curve generated using volumetric standard cassettes for each cycler 14 in block 4214. Thus, a refined calibration curve which takes into account error introduced due to source/destination head height 24 may be created. This curve may be used by the cycler 14 when transferring fluid to or from a location at this head height. Calibration curves for a number of head heights may be generated in the same manner. Additionally, at each head height, data sets may be collected for different pumping pressure pairs used by cyclers 14 as well as for positive and negative FMS measurements. Each data set may be used to create a specific refinement to the calibration curve. During therapy, the final calibration curve used may be chosen to match the detected head height, pumping pressure, and type of FMS measurement (positive or negative) being conducted.

Though other equations are possible, the final corrected value may be determined via a compound function. A first function may be applied to the raw control chamber volume measurement ($V_m$). A second function may then be applied to this result and the consequent value may further be feed into a third function to arrive at a determination for $V_{Final}$. For example, in some embodiments an equation such as:

$$V_{Final} = V_{HeadHeight}(V_{disposablecorrected}(V_{cyclercorrected}(V_m)))$$

may be used where $V_{cyclercorrected}$ is a function of the raw measured control chamber volume ($V_m$) which corrects for the particular cycler's 14 error contribution, $V_{disposablecorrected}$ is a function of the cycler corrected measurement volume corrected and corrects for disposable related error contribution and $V_{HeadHeight}$ is a function of the disposable corrected measurement volume and corrects for any head height related error contribution. Alternatively, $V_{disposablecorrected}$ may be a function of $V_{HeadHeight}$ as follows:

$$V_{Final} = V_{disposablecorrected}(V_{HeadHeight}(V_{cyclercorrected}(V_m))).$$

In other embodiments, $V_{Final}$ may be determined additively as described in relation to FIG. 76 with a head height correction being added into the equation to generate a sum equal to $V_{Final}$.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A fluid pumping system comprising:
   a pump;
   a fluid line state detector having a receptacle for retaining a fluid line, at least one light sensor, and at least one LED;
   a fluid transfer set including an output line configured to mate into the receptacle;
   at least one fluid source; and a controller in data communication with the fluid line state detector, the controller configured to power at least one of the at least one LED a plurality of times and monitor an output signal of the at least one light sensor when the outlet line is dry and installed in the receptacle to determine a dry tube light intensity value based upon a maximum light intensity value from the sensor over the plurality of times and at least one limit, the controller further configured to initiate operation of the pump, subsequent determination of the dry tube intensity value, to prime the output line with fluid from the at least one fluid source, and the controller further configured to power at least one of the at least one LED, monitor the output signal, and halt operation of the pump when the output signal indicates the light intensity value has dropped below a primed line threshold; wherein the primed line threshold is calculated by the controller based upon the dry tube intensity value.

2. The system of claim 1, wherein the primed line threshold is calculated by adding a constant to a percentage of the dry tube intensity value.

3. The system of claim 1, wherein the limit is a minimum value for the dry tube intensity value.

4. The system of claim 1, wherein system further comprises a displaced volume sensing assembly and the controller is configured to generate a notification when displaced volume sensing assembly indicates that the volume of fluid displaced before the light intensity value has dropped below a primed line threshold is greater than a predefined threshold.

5. The system of claim 4, wherein the controller is configured to continue to orchestrate pumping upon receipt of a user input from a user interface of the system indicating that the output line has yet to fully prime.

6. The system of claim 1, wherein a portion of the pump is included in the fluid transfer set.

7. The system of claim 1, wherein the at least one LED includes a first LED disposed at an non-parallel angle to the optical axis of the light sensor.

8. The system of claim 1, wherein the at least one LED includes a first LED, second LED, and a third LED.

9. The system of claim 8, wherein an axis of the second LED and an axis of the third LED are parallel to the optical axis of the light sensor.

10. A fluid pumping system comprising:
a pump;
a fluid line state detector having a receptacle, at least one sensor, and at least one illuminator;
a fluid transfer set including an output line configured to mate into the receptacle; and
a controller in data communication with the fluid line state detector, the controller configured to power at least one of the at least one illuminator and collect a number of output signal readings from the at least one sensor when the outlet line is installed in the receptacle and completely unprimed by the system to determine a dry tube light intensity value using a maximum light intensity value from the number of output signal readings, the controller further configured to govern operation of the pump to prime the output line with fluid from at least one fluid source after determination of the dry tube light intensity value, and the controller further configured to power at least one of the at least one illuminator, monitor the output signal, and halt operation of the pump when the output signal indicates the light intensity value has breached a primed line threshold which is dependent upon the dry tube intensity value.

11. The system of claim 10, wherein the primed line threshold is calculated by adding a constant to a percentage of the dry tube light intensity value.

12. The system of claim 10, wherein the maximum light intensity value is compared to a minimum value for the dry tube light intensity value and the dry tube light intensity value is set as the minimum value when the maximum light intensity value is below the minimum value.

13. The system of claim 10, wherein the system further comprises a displaced volume sensing assembly and the controller is further configured to generate a notification when the displaced volume sensing assembly indicates that the volume of fluid displaced is greater than a predefined threshold.

14. The system of claim 13, wherein the controller is configured to orchestrate reinitiation of pumping upon receipt of a user input from a user interface of the system indicating that the output line has yet to fully prime.

15. The system of claim 10, wherein a portion of the pump is included in the fluid transfer set.

16. The system of claim 10, wherein the at least one illuminator includes a first LED disposed at an angle other than parallel to the optical axis of the sensor.

17. The system of claim 16, wherein the at least one illuminator includes a second LED and a third LED an axis of the second LED and an axis of the third LED are parallel to the optical axis of the sensor.

18. A fluid pumping system comprising:
a pump;
a conduit state detector having a receptacle, at least one sensor, and at least one illuminator;
a fluid transfer set including an conduit configured to mate into the receptacle; and
a controller in data communication with the conduit state detector, the controller configured to power at least one of the at least one illuminator a plurality of times and monitor an output signal from the at least one sensor when the conduit is installed in the receptacle to determine an unprimed conduit light intensity value based on a maximum light intensity value from the output signal, the controller further configured to govern operation of the pump to transfer fluid from at least one fluid source into the conduit, and the controller further configured to power at least one of the at least one illuminator, monitor the output signal, and halt operation of the pump when the output signal indicates the light intensity value has dropped below a threshold which is calculated based upon the unprimed conduit light intensity value.

19. The system of claim 18, wherein the threshold is calculated by adding a constant to a percentage of the unprimed conduit light intensity value.

20. The system of claim 18, wherein the unprimed conduit light intensity value is determined by applying at least one limit to the maximum light intensity value.

21. The system of claim 18, wherein the system further comprises a displaced volume sensing assembly and the controller is further configured to generate a notification when the displaced volume sensing assembly indicates that the volume of fluid displaced is greater than a predefined threshold.

22. The system of claim 21, wherein the controller is configured to command additional pumping upon receipt of a user input from a user interface of the system indicating that the output line has yet to fully prime.

23. The system of claim 22, wherein the pump is a pneumatic diaphragm pump.

24. The system of claim 18, wherein a portion of the pump is included in the fluid transfer set.

25. The system of claim 18, wherein the at least one illuminator includes a first LED disposed at an angle other than parallel to the optical axis of the sensor.

26. The system of claim 25, wherein the at least one illuminator includes a second LED and a third LED an axis of the second LED and an axis of the third LED are disposed at a first side of the receptacle which his opposite of the sensor.

27. A fluid pumping system comprising:
a pump;
a conduit state detector having a receptacle, at least one sensor, and at least one illuminator;
a fluid transfer set including a conduit configured to mate into the receptacle; and
a controller in data communication with the conduit state detector, when the conduit is installed in the receptacle and prior to transfer of fluid into the conduit by the pump, the controller configured to power at least one of the at least one illuminator and monitor an output signal from the at least one sensor to determine an unprimed conduit light intensity value using a maximum light intensity value indicated by the output signal, the controller further configured to govern operation of the pump to transfer fluid from at least one fluid source into the conduit, and the controller further configured to power at least one of the at least one illuminator, monitor the output signal, and halt operation of the pump when the output signal indicates the light intensity value has dropped below a threshold which is calculated based upon the unprimed conduit light intensity value.

28. The system of claim 27, wherein the controller is further configured to power at least one of the at least one illuminator and monitor the output signal to confirm that the conduit is unprimed.

29. The system of claim 27, wherein the controller is configured to determine the unprimed conduit light intensity value by subjecting the maximum light intensity value to at least one limit.

* * * * *